US 011787800B2

(12) United States Patent
Ruppel et al.

(10) Patent No.: US 11,787,800 B2
(45) Date of Patent: Oct. 17, 2023

(54) BRD9 DEGRADERS AND USES THEREOF

(71) Applicant: Foghorn Therapeutics Inc., Cambridge, MA (US)

(72) Inventors: Sabine K. Ruppel, Cambridge, MA (US); Zhaoxia Yang, Belmont, MA (US); Jason T. Lowe, East Bridgewater, MA (US); Johannes H. Voigt, Cambridge, MA (US); Matthew Netherton, Cambridge, MA (US); Francois Brucelle, Belmont, MA (US)

(73) Assignee: Foghorn Therapeutics Inc., Cambridge, MA (US)

( * ) Notice: Subject to any disclaimer, the term of this patent is extended or adjusted under 35 U.S.C. 154(b) by 129 days.

(21) Appl. No.: 17/382,543

(22) Filed: Jul. 22, 2021

(65) Prior Publication Data
US 2022/0048906 A1 Feb. 17, 2022

Related U.S. Application Data

(60) Provisional application No. 63/058,249, filed on Jul. 29, 2020.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC ..................................... C07D 471/04
USPC ..................................... 514/210.16
See application file for complete search history.

(56) References Cited

U.S. PATENT DOCUMENTS

| | | | |
|---|---|---|---|
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,056,883 B2 | 6/2006 | Ito et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,205,103 B2 | 4/2007 | Emerson |
| 7,232,566 B2 | 6/2007 | June et al. |
| 9,271,978 B2 | 3/2016 | Liu et al. |
| 9,353,051 B2 | 5/2016 | Byrd et al. |
| 9,410,943 B2 | 8/2016 | Kadoch et al. |
| 10,105,420 B2 | 10/2018 | Kadoch et al. |
| 10,464,925 B2 | 11/2019 | Bradner et al. |
| 10,646,575 B2 | 5/2020 | Phillips et al. |
| 10,660,968 B2 | 5/2020 | Phillips et al. |
| 10,725,057 B2 | 7/2020 | Tojo et al. |
| 10,849,982 B2 | 12/2020 | Phillips et al. |
| 10,905,768 B1 | 2/2021 | Phillips et al. |
| 10,976,320 B2 | 4/2021 | Dykhuizen et al. |
| 11,185,592 B2 | 11/2021 | Phillips et al. |
| 11,414,416 B1 | 8/2022 | Ruppel et al. |
| 11,560,381 B1 | 1/2023 | Ruppel et al. |
| 2005/0079512 A1 | 4/2005 | Emerson et al. |
| 2006/0121005 A1 | 6/2006 | Berenson et al. |
| 2011/0053897 A1 | 3/2011 | Che et al. |
| 2011/0061116 A1 | 3/2011 | Haldar et al. |
| 2011/0201602 A1 | 8/2011 | Geuns-Meyer et al. |
| 2016/0058872 A1 | 3/2016 | Crew et al. |
| 2016/0200721 A1 | 7/2016 | Yukimasa et al. |
| 2016/0347708 A1 | 12/2016 | Ebright et al. |
| 2017/0014491 A1 | 1/2017 | Kadoch et al. |
| 2017/0050968 A1 | 2/2017 | Bennett et al. |
| 2017/0158709 A1 | 6/2017 | Boloor |
| 2017/0190686 A1 | 7/2017 | Tojo et al. |
| 2017/0340605 A1 | 11/2017 | Albrecht et al. |
| 2018/0044335 A1 | 2/2018 | Martin et al. |
| 2018/0085465 A1 | 3/2018 | Bradner et al. |
| 2018/0187614 A1 | 7/2018 | Dudar |
| 2018/0213422 A1 | 7/2018 | Kazmi et al. |
| 2018/0215766 A1 | 8/2018 | Bair et al. |
| 2018/0215866 A1 | 8/2018 | Zhao et al. |
| 2018/0328913 A1 | 11/2018 | Kadoch et al. |
| 2019/0076539 A1 | 3/2019 | Phillips et al. |
| 2019/0219562 A1 | 7/2019 | Matyskiela et al. |
| 2019/0247509 A1 | 8/2019 | Buckley et al. |
| 2019/0322683 A1 | 10/2019 | Chan et al. |
| 2020/0140456 A1 | 5/2020 | Phillips et al. |
| 2020/0206344 A1 | 7/2020 | Kadoch et al. |
| 2021/0009568 A1 | 1/2021 | Zhou et al. |
| 2021/0198256 A1 | 7/2021 | Nasveschuk et al. |
| 2021/0230190 A1 | 7/2021 | Ruppel et al. |
| 2022/0098190 A1 | 3/2022 | Ruppel et al. |
| 2022/0193205 A1 | 6/2022 | Zhou et al. |
| 2022/0289711 A1 | 9/2022 | Ruppel et al. |
| 2022/0315578 A1 | 10/2022 | Chen et al. |
| 2023/0065463 A1 | 3/2023 | Ruppel et al. |
| 2023/0066136 A1 | 3/2023 | Ruppel et al. |
| 2023/0077730 A1 | 3/2023 | Ruppel et al. |

FOREIGN PATENT DOCUMENTS

| | | |
|---|---|---|
| CN | 107056772 A | 8/2017 |
| CN | 108690020 A | 10/2018 |
| WO | WO-2017/197051 A1 | 11/2017 |
| WO | WO-2017/197056 A1 | 11/2017 |
| WO | WO-2017/223452 A1 | 12/2017 |

(Continued)

OTHER PUBLICATIONS

U.S. Appl. No. 17/245,379, Sandoval et al.

(Continued)

*Primary Examiner* — Niloofar Rahmani
(74) *Attorney, Agent, or Firm* — Clark & Elbing LLP

(57) ABSTRACT

The present invention relates to methods and compositions for the treatment of BAF-related disorders such as cancers and viral infections.

24 Claims, 14 Drawing Sheets

Specification includes a Sequence Listing.

(56) References Cited

FOREIGN PATENT DOCUMENTS

| WO | WO-2018/177297 A1 | 10/2018 |
| WO | WO-2019/099868 A2 | 5/2019 |
| WO | WO-2019/152437 A1 | 8/2019 |
| WO | WO-2019/195201 A1 | 10/2019 |
| WO | WO-2019/207538 A1 | 10/2019 |
| WO | WO-2020/051235 A1 | 3/2020 |
| WO | WO-2020/078933 A1 | 4/2020 |
| WO | WO-2020/132561 A1 | 6/2020 |
| WO | 2020160192 * | 8/2020 |
| WO | WO-2020/160192 A1 | 8/2020 |
| WO | WO-2020/160193 A2 | 8/2020 |
| WO | WO-2020/160198 A1 | 8/2020 |
| WO | WO-2020/239103 A1 | 12/2020 |
| WO | WO-2021/055295 A1 | 3/2021 |
| WO | WO-2021/178920 A1 | 9/2021 |

OTHER PUBLICATIONS

Baheti et al., "Excipients used in lyophilization of small molecules," J. Excipients and Food Chem. 1(1):41-54 (2010).
Brien et al, "Targeted degradation of BRD9 reverses oncogenic gene expression in synovial sarcoma," eLIFE. 7:e41305 (2018) (26 pages).
Börold et al., "BRD9 is a druggable component of interferon-stimulated gene expression and antiviral activity," EMBO Rep. 22(10):e52823 (Aug. 16, 2021) (18 pages).
Choi et al., "Correlation of computed tomography and positron emission tomography in patients with metastatic gastrointestinal stromal tumor treated at a single institution with imatinib mesylate: proposal of new computed tomography response criteria," J Clin Oncol. 25(13):1753-9 (May 1, 2007).
Crawford et al., "Inhibition of bromodomain-containing protein 9 for the prevention of epigenetically-defined drug resistance," Bioorg Med Chem Lett. 27(15):3534-41(2017).
Extended European Search Report for European Patent Application No. 20749033.5, dated Sep. 29, 2022 (5 pages).
Hay et al., "Design and synthesis of potent and selective inhibitors of BRD7 and BRD9 bromodomains," Med. Chem. Commun. 6:1381-86 (2015).
Hohmann et al., "Sensitivity and engineered resistance of myeloid leukemia cells to BRD9 inhibition," Nat Chem Biol. 12(9): 672-679 (2016) (12 pages).
Hu et al., "Genomic characterization of genes encoding histone acetylation modulator proteins identifies therapeutic targets for cancer treatment," Nat Commun. 10(1):733 (2019) (17 pages).
International Preliminary Report on Patentability for International Application No. PCT/US2020/015740, dated Jul. 27, 2021 (6 pages).
International Preliminary Report on Patentability for International Application No. PCT/US2020/044508, dated Feb. 10, 2022 (6 pages).
International Preliminary Report on Patentability for International Patent Application No. PCT/US2020/044043, dated Jan. 31, 2023 (7 pages).
International Search Report and Written Opinion for International Application No. PCT/US20/15740, dated Jun. 26, 2020 (11 pages).
International Search Report and Written Opinion for International Application No. PCT/US20/44043, dated Nov. 9, 2020 (15 pages).
International Search Report and Written Opinion for International Application No. PCT/US20/44508, dated Jan. 12, 2021 (9 pages).
International Search Report and Written Opinion for International Application No. PCT/US21/15630, dated Apr. 8, 2021 (8 pages).
International Search Report and Written Opinion for International Application No. PCT/US22/36252, dated Nov. 15, 2022 (15 pages).
International Search Report and Written Opinion for International Application No. PCT/US22/38641, dated Nov. 17, 2022 (10 pages).
International Search Report and Written Opinion for International Application No. PCT/US22/38668 dated Jan. 20, 2023 (11 pages).
International Search Report and Written Opinion for International Patent Application No. PCT/US21/15813, dated Apr. 6, 2021 (24 pages).
International Search Report and Written Opinion for International Patent Application No. PCT/US2022/028511, dated Aug. 1, 2022 (14 pages).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Kadoch et al., "Reversible Disruption of mSWI/SNF (BAF) Complexes by the SS18-SSX Oncogenic Fusion in Synovial Sarcoma," Cell. 153(1):71-85 (2013).
Kotla et al., "Mechanism of action of lenalidomide in hematological malignancies," J Hematol Oncol. 2:36 (Aug. 12, 2009) (10 pages).
Martin et al., "Structure-Based Design of an in Vivo Active Selective BRD9 Inhibitor," J Med Chem. 59(10):4462-75 (2016).
McBride et al., "Disruption of mammalian SWI/SNF and polycomb complexes in human sarcomas: mechanisms and therapeutic opportunities," J Pathol. 244(5): 638-649 (2018).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Muscal et al., "Plasma and cerebrospinal fluid pharmacokinetics of thalidomide and lenalidomide in nonhuman primates," Available in PMC Jun. 18, 2013. Published in final edited form as: Cancer Chemother Pharmacol. 69(4):943-7 (Apr. 2012) (10 pages).
Pan et al., "A major chromatin regulator determines resistance of tumor cells to T cell-mediated killing," Science. 359(6377):770-75 (2018) (11 pages).
Picaud et al., "9H-purine scaffold reveals induced-fit pocket plasticity of the BRD9 bromodomain," J Med Chem. 58(6):2718-36 (2015).
PubChem CID 68310947, "7-Methyl-4-phenyl-2H-isoquinolin-1-one," created Nov. 30, 2012 (8 pages).
Remillard et al., "Degradation of the BAF Complex Factor BRD9 by Heterobifunctional Ligands," Angew Chem Int Ed Engl. 56(21):5738-43 (2017) (7 pages).
Teuscher et al., "A Versatile Method to Determine the Cellular Bioavailability of Small-Molecule Inhibitors," J Med Chem. 60(1): 157-169 (2017).
Theodoulou et al., "Discovery of I-BRD9, a Selective Cell Active Chemical Probe for Bromodomain Containing Protein 9 Inhibition," J Med Chem. 59(4):1425-39 (2015).
Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).
Wang et al., "NMR Fragment Screening Hit Induces Plasticity of BRD7/9 Bromodomains," Chembiochem. 17(15):1456-63 (2016).
Zhu et al., "Targeting BRD9 for Cancer Treatment: A New Strategy," Onco Targets Ther. 13:13191-13200 (Dec. 24, 2020).
Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (2019).

* cited by examiner

SYO1

HS-SY-II

ASKA

RD

HCT116

Calu6

BRD9 DEGRADERS AND USES THEREOF

SEQUENCE LISTING

This application contains a Sequence Listing which has been submitted electronically in ASCII format and is hereby incorporated by reference in its entirety. Said ASCII copy, created on Jul. 29, 2020, is named 51121-053001_Sequence_Listing_07_29_20_ST25 and is 99,298 bytes in size.

BACKGROUND

Disorders can be affected by the BAF complex. BRD9 is a component of the BAF complex. The present invention relates to useful compositions and methods for the treatment of BAF complex-related disorders, such as cancer and infection.

SUMMARY

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents that reduce the levels and/or activity of BRD9 may provide new methods for the treatment of disease and disorders, such as cancer and infection. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Additionally, evidence suggests that the BAF complex is involved in cellular antiviral activities. Thus, agents that degrade BRD9 (e.g., compounds) are useful in the treatment of disorders (e.g., cancers or infections) related to BAF, BRD9, and/or SS18-SSX.

The present disclosure features compounds and methods useful for treating BAF-related disorders (e.g., cancer or infection).

In an aspect, the disclosure features a compound having the structure of Formula I:

$$\text{A-L-B} \qquad \text{Formula I,}$$

where

L has the structure of Formula II:

$$A^1\text{-}E^1\text{-}F\text{-}E^2\text{-}A^2, \qquad \text{Formula II}$$

$A^1$ is a bond between the linker and A;

$A^2$ is a bond between B and the linker;

each of $E^1$ and $E^2$ is, independently, absent, $CH_2$, O, or $NCH_3$; and

F is optionally substituted $C_3$-$C_{10}$ carbocyclylene or optionally substituted $C_2$-10 heterocyclylene;

B is a degradation moiety; and

A has the structure of Formula III:

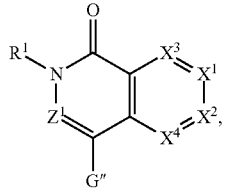

Formula III where $R^1$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;

$Z^1$ is $CR^2$ or N;

$R^2$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;

$X^1$ is N or CH, and $X^2$ is C—$R^{7''}$; or $X^1$ is C—$R^{7''}$, and $X^2$ is N or CH;

$R^{7''}$ is

optionally substituted $C_1$-$C_6$ alkyl, optionally substituted $C_1$-$C_6$ heteroalkyl, optionally substituted $C_1$-$C_6$ alkoxy, optionally substituted amino, optionally substituted sulfone, optionally substituted sulfonamide, optionally substituted carbocyclyl having 3 to 6 atoms, or optionally substituted heterocyclyl having 3 to 6 atoms;

$R^{7'}$ is H, optionally substituted $C_1$-$C_6$ alkyl, optionally substituted $C_1$-$C_6$ heteroalkyl, or optionally substituted $C_3$-$C_{10}$ carbocyclyl;

$X^3$ is N or CH;

$X^4$ is N or CH;

G''' is optionally substituted $C_3$-$C_{10}$ carbocyclyl, $C_2$-$C_9$ heterocyclyl, optionally substituted $C_6$-$C_{10}$ aryl, or optionally substituted $C_2$-$C_9$ heteroaryl;

G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and $A^1$ is a bond between A and the linker, where G''' is or R''' is or a pharmaceutically acceptable salt thereof.

In some embodiments, $R^1$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^1$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^1$ is H, optionally substituted $C_1$-$C_6$ alkyl, or optionally substituted $C_3$-$C_{10}$ carbocyclyl.

In some embodiments, $R^1$ is H. In some embodiments, $R^1$ is optionally substituted $C_1$-$C_6$ alkyl. In some embodiments, $R^1$ is optionally substituted $C_2$-$C_6$ alkenyl. In some embodiments, $R^1$ is optionally substituted $C_3$-$C_{10}$ carbocyclyl.

In some embodiments, optionally substituted $C_1$-$C_6$ alkyl is $C_1$-$C_6$ perfluoroalkyl.

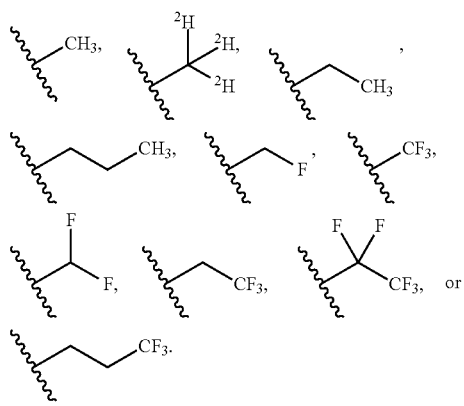

In some embodiments, $R^1$ is

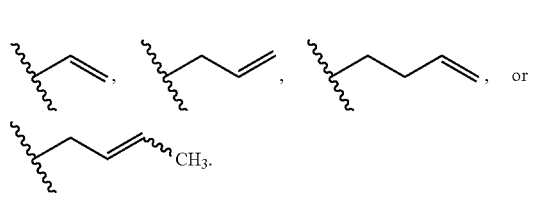

In some embodiments, $R^1$ is

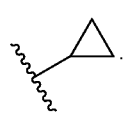

In some embodiments, $R^1$ is H,

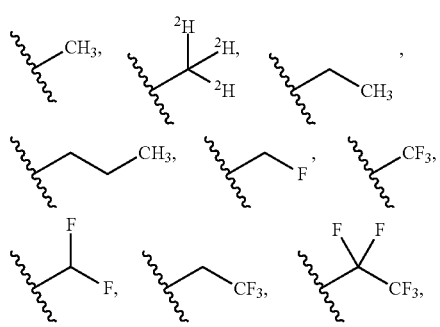

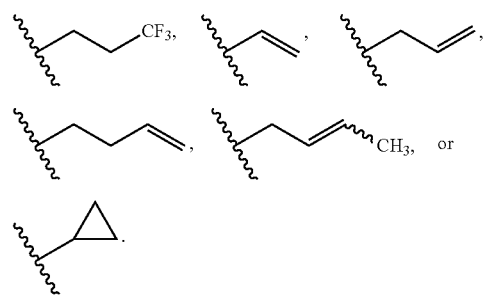

In some embodiments, $R^1$ is

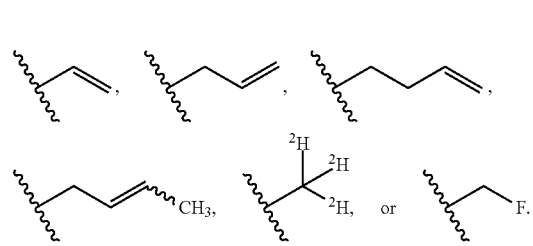

In some embodiments, $R^1$ is H,

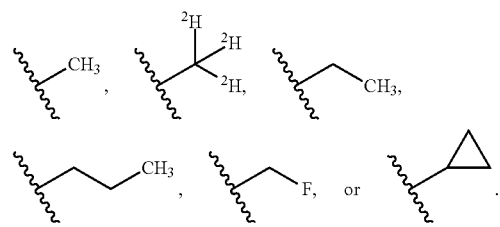

In some embodiments, $R^1$ is H,

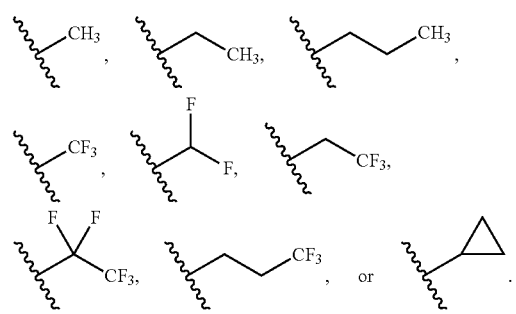

In some embodiments, $R^1$ is H,

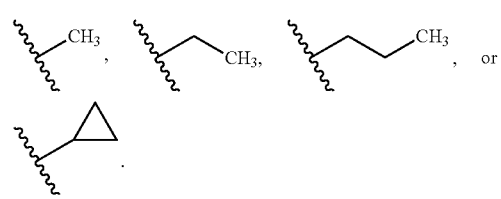

In some embodiments, $R^1$ is H or

In some embodiments, $R^1$ is H. In some embodiments, $R^1$ is

In some embodiments, $Z^1$ is $CR^2$. In some embodiments, $Z^1$ is N.

In some embodiments, $R^2$ is H, halogen, optionally substituted $C_1$-$C_6$ alkyl, optionally substituted $C_3$-$C_{10}$ carbocyclyl, or optionally substituted $C_6$-$C_{10}$ aryl.

In some embodiments, $R^2$ is H, halogen, or optionally substituted $C_1$-$C_6$ alkyl.

In some embodiments, $R^2$ is H, F, or

In some embodiments, $R^2$ is H. In some embodiments, $R^2$ is F. In some embodiments, $R^2$ is

In some embodiments, $R^{7''}$ is optionally substituted $C_1$-$C_6$ alkyl, optionally substituted $C_1$-$C_6$ heteroalkyl, optionally substituted $C_1$-$C_6$ alkoxy, optionally substituted carbocyclyl having 3 to 6 atoms, or optionally substituted heterocyclyl having 3 to 6 atoms. In some embodiments, $R^{7''}$ is optionally substituted $C_1$-$C_6$ alkyl, optionally substituted $C_1$-$C_6$ heteroalkyl, optionally substituted carbocyclyl having 3 to 6 atoms, or optionally substituted heterocyclyl having 3 to 6 atoms. In some embodiments, $R^{7''}$ is optionally substituted $C_1$-$C_6$ alkoxy or optionally substituted amino. In some embodiments, $R^{7''}$ is optionally substituted sulfone or optionally substituted sulfonamide.

In some embodiments, $R^{7''}$ is optionally substituted $C_1$-$C_6$ alkyl or optionally substituted carbocyclyl having 3 to 6 atoms. In some embodiments, $R^{7''}$ is optionally substituted $C_1$-$C_6$ heteroalkyl or optionally substituted heterocyclyl having 3 to 6 atoms. In some embodiments, $R^{7''}$ is optionally substituted $C_1$-$C_6$ alkyl or optionally substituted $C_1$-$C_6$ heteroalkyl.

In some embodiments, $R^{7''}$ is optionally substituted $C_1$-$C_6$ alkyl. In some embodiments, $R^{7''}$ is optionally substituted $C_1$-$C_6$ heteroalkyl. In some embodiments, $R^{7''}$ is optionally substituted $C_1$-$C_6$ alkoxy. In some embodiments, $R^{7''}$ is optionally substituted amino. In some embodiments, $R^{7''}$ is optionally substituted carbocyclyl having 3 to 6 atoms. In some embodiments, $R^{7''}$ is optionally substituted heterocyclyl having 3 to 6 atoms. In some embodiments, $R^{7''}$ is optionally substituted sulfone. In some embodiments, $R^{7''}$ is optionally substituted sulfonamide.

In some embodiments, $R^{7''}$ is optionally substituted $C_1$-$C_3$ alkyl. In some embodiments, $R^{7''}$ is optionally substituted $C_1$-$C_3$ heteroalkyl.

In some embodiments, $R^{7''}$ is

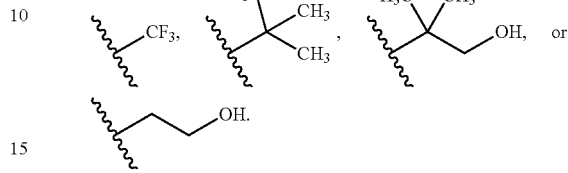

In some embodiments, $R^{7''}$ is —$NR^3R^4$ or —$OR^4$, where $R^3$ is H or optionally substituted $C_1$-$C_6$ alkyl, and $R^4$ is optionally substituted $C_1$-$C_6$ alkyl.

In some embodiments, $R^{7''}$ is —$NR^3R^4$. In some embodiments, $R^{7''}$ is —$OR^4$.

In some embodiments, $R^3$ is H. In some embodiments, $R^3$ is optionally substituted $C_1$-$C_6$ alkyl.

In some embodiments, $R^3$ is H and $R^4$ is methyl. In some embodiments, $R^3$ is methyl and $R^4$ is methyl.

In some embodiments, $R^{7''}$ is

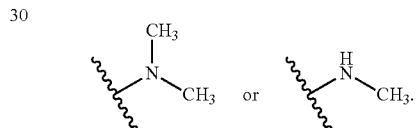

In some embodiments, $R^{7''}$ is

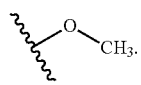

In some embodiments, $R^{7''}$ is optionally substituted carbocyclyl having 3 to 6 atoms or optionally substituted heterocyclyl having 3 to 6 atoms. In some embodiments, $R^{7''}$ is optionally substituted carbocyclyl having 3 to 6 atoms. In some embodiments, $R^{7''}$ is optionally substituted heterocyclyl having 3 to 6 atoms.

In some embodiments, $R^{7''}$ is carbocyclyl having 3 to 6 atoms or heterocyclyl having 3 to 6 atoms. In some embodiments, $R^{7''}$ is carbocyclyl having 3 to 6 atoms. In some embodiments, $R^{7''}$ is heterocyclyl having 3 to 6 atoms.

In some embodiments, $R^{7''}$ is

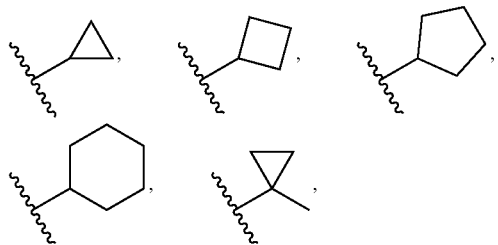

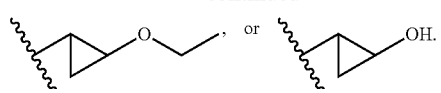
In some embodiments, R⁷‴ is
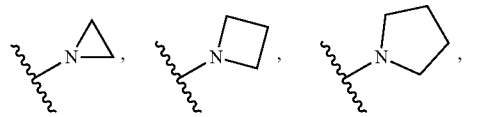
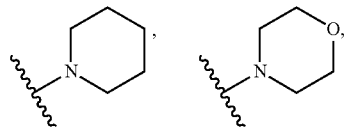
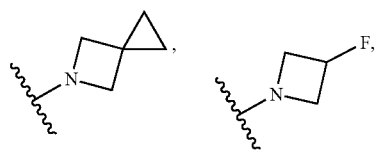
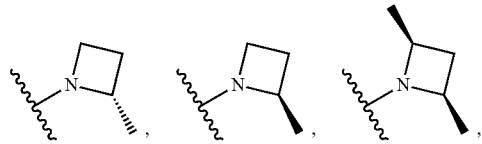
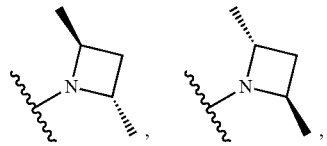
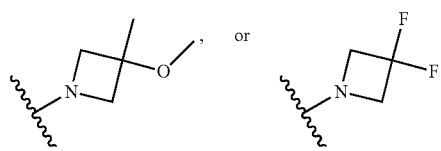
In some embodiments, R⁷‴ is
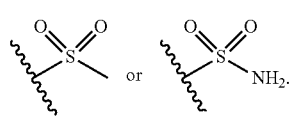
In some embodiments, R⁷‴ is
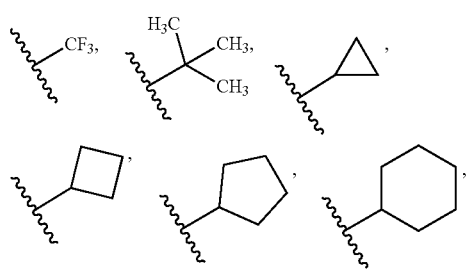
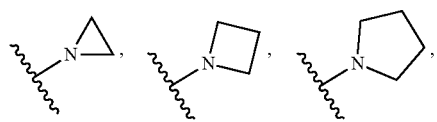
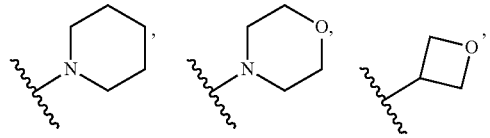
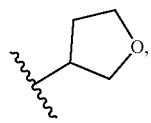
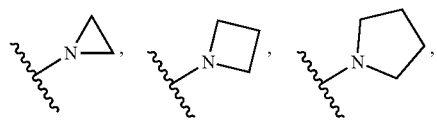
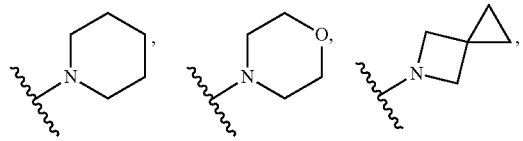
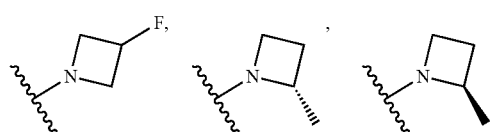
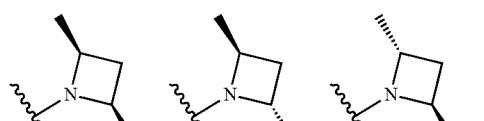
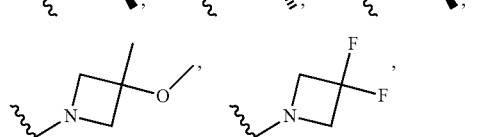
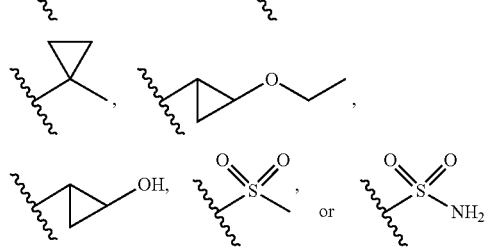
In some embodiments, R⁷‴ is
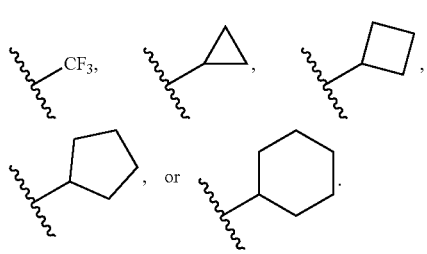

In some embodiments, $R^{7'''}$ is

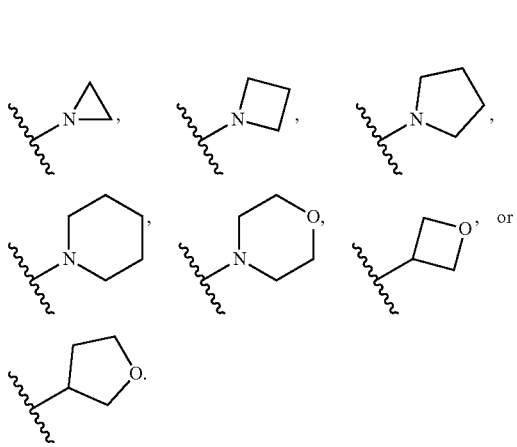

In some embodiments, $R^{7'''}$ is

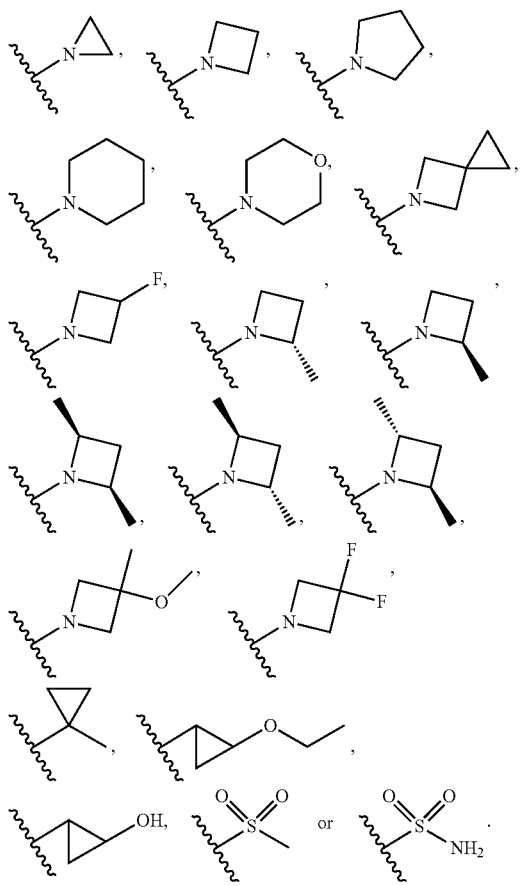

In some embodiments, $R^{7'''}$ is

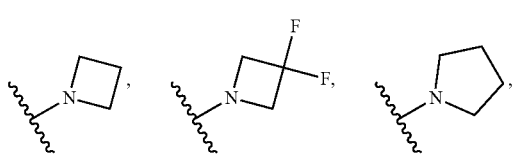

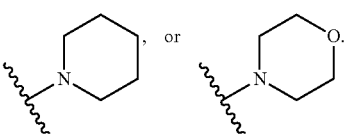

In some embodiments, $R^{7'''}$ is

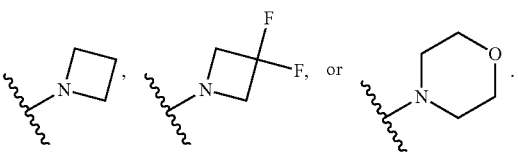 [SMILES: *N1CCC1 ; *N1CC(F)(F)C1 ; "or" ; *N1CCOCC1]

In some embodiments, $X^1$ is N and $X^2$ is $C-R^{7'''}$. In some embodiments, $X^1$ is OH and $X^2$ is $C-R^{7'''}$. In some embodiments, $X^1$ is $C-R^{7'''}$ and $X^2$ is N. In some embodiments, $X^1$ is $C-R^{7'''}$ and $X^2$ is OH.

In some embodiments, $X^1$ is N or CH, and $X^2$ is $C-NR^3R^4$, $C-OR^4$,

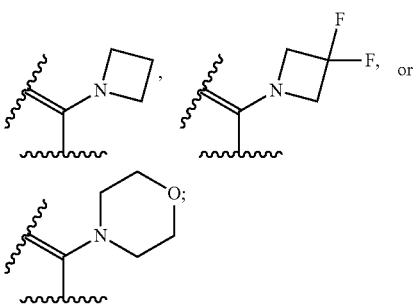

or $X^1$ is $C-NR^3R^4$, $C-OR^4$,

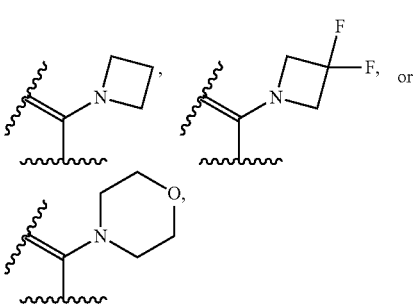

and $X^2$ is N or CH. In some embodiments, $X^1$ is N or CH, and $X^2$ is $C-NR^3R^4$,

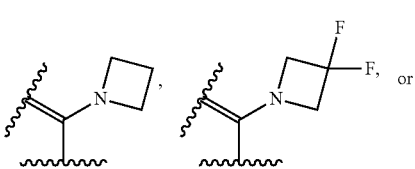

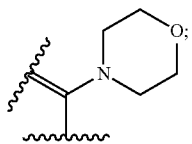

or $X^1$ is C—$NR^3R^4$,

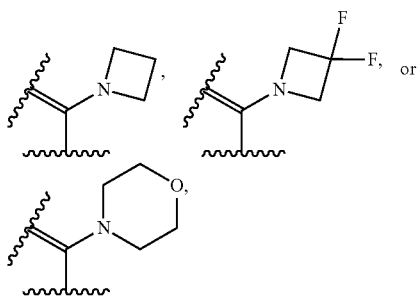

and $X^2$ is N or CH. In some embodiments, $X^1$ is N or CH, and $X^2$ is C—$NR^3R^4$ or

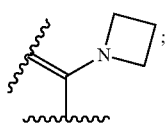

or $X^1$ is C—$NR^3R^4$ or

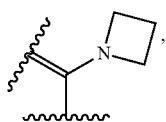 [SMILES: *C(=*)N1CCC1]

and $X^2$ is N or CH. In some embodiments, $X^1$ is N or CH, and $X^2$ is C—$NR^3R^4$ or

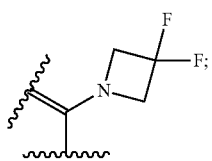 [SMILES: *C(=*)N1CC(F)(F)C1]

or $X^1$ is C—$NR^3R^4$ or

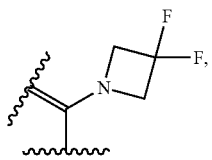

and $X^2$ is N or CH. In some embodiments, $X^1$ is N or CH, and $X^2$ is C—$NR^3R^4$ or

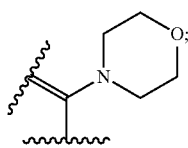

or $X^1$ is C—$NR^3R^4$ or

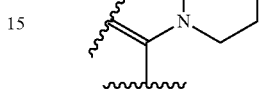

and $X^2$ is N or CH.

In some embodiments, $R^{7'''}$ is —$NR^3R^4$, —$OR^4$, or optionally substituted heterocyclyl having 3 to 6 atoms.

In some embodiments, $X^1$ is N and $X^2$ is C—$NR^3R^4$. In some embodiments, $X^1$ is C—$NR^3R^4$ and $X^2$ is N.

In some embodiments, $R^3$ is H. In some embodiments, $R^3$ is optionally substituted $C_1$-$C_6$ alkyl.

In some embodiments, $R^3$ is

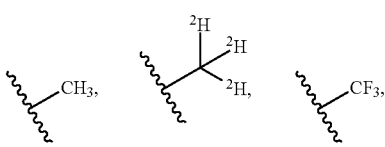

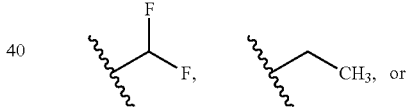

In some embodiments, $R^3$ is

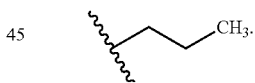

In some embodiments, $R^3$ is

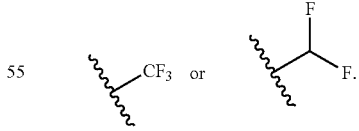

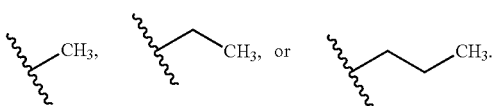

In some embodiments, $R^3$ is methyl, ethyl,

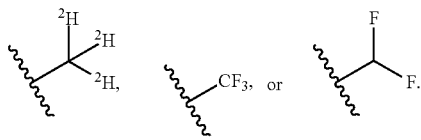

In some embodiments, $R^4$ is

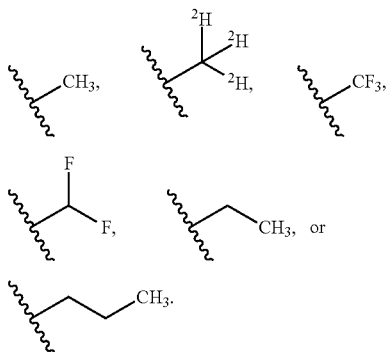

In some embodiments, $R^4$ is

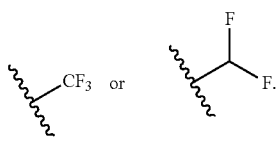

In some embodiments, $R^4$ is

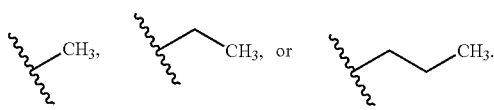

In some embodiments, $R^4$ is methyl, ethyl,

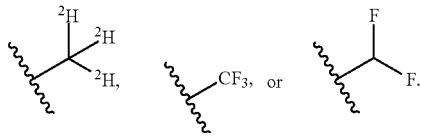

In some embodiments, $X^3$ is N. In some embodiments, $X^3$ is CH.

In some embodiments, $X^4$ is N. In some embodiments, $X^4$ is CH.

In some embodiments, $X^3$ is N and $X^4$ is N.
In some embodiments, $X^3$ is N and $X^4$ is CH.
In some embodiments, $X^3$ is CH and $X^4$ is N.
In some embodiments, $X^3$ is CH and $X^4$ is CH.

In some embodiments, G" is

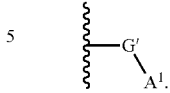

In some embodiments, G' is optionally substituted $C_3$-$C_{10}$ carbocyclylene or optionally substituted $C_2$-$C_9$ heterocyclylene. In some embodiments, G' is optionally substituted $C_6$-$C_{10}$ arylene or optionally substituted $C_2$-$C_9$ heteroarylene.

In some embodiments, G' is optionally substituted $C_3$-$C_{10}$ carbocyclylene. In some embodiments, G' is optionally substituted $C_6$-$C_{10}$ arylene. In some embodiments, G' is optionally substituted $C_2$-$C_9$ heterocyclylene. In some embodiments, G' is optionally substituted $C_2$-$C_9$ heteroarylene.

In some embodiments, G' is

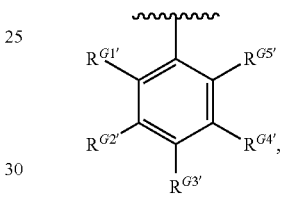

where each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G1'}$ and $R^{G2'}$, $R^{G2'}$ and $R^{G3'}$, $R^{G3'}$ and $R^{G4'}$, and/or $R^{G4'}$ and $R^{G5'}$, together with the carbon atoms to which each is attached, combine to form

and

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G1'}$, $R^{G2'}$, $R^{G3'}$, $R^{G4'}$, and $R^{G5'}$ is $A^1$, or

is substituted with $A^1$.

In some embodiments, each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G1'}$ and $R^{G2'}$, $R^{G2'}$ and $R^{G3'}$, $R^{G3'}$ and $R^{G4'}$, and/or $R^{G4'}$ and $R^{G5'}$, together with the carbon atoms to which each is attached, combine to form

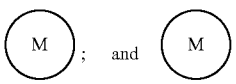

and is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G1'}$, $R^{G2'}$, $R^{G3'}$, $R^{G4'}$, and $R^{G5'}$ is $A^1$, or

is substituted with $A^1$.

In some embodiments, each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl; or $R^{G1'}$ and $R^{G2'}$, $R^{G2'}$ and $R^{G3'}$, $R^{G3'}$ and $R^{G4'}$, and/or $R^{G4'}$ and $R^{G5'}$, together with the carbon atoms to which each is attached, combine to form

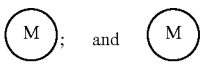

is optionally substituted $C_2$-$C_9$ heteroaryl or optionally substituted $C_2$-$C_9$ heterocyclyl, any of which is optionally substituted with $A^1$, where one of $R^{G1'}$, $R^{G2'}$, $R^{G3'}$, $R^{G4'}$ and $R^{G5'}$ is $A^1$, or

is substituted with $A^1$.

In some embodiments, each of $R^{G1'}$, $R^{G2'}$, $R^{G3'}$, $R^{G4'}$ and $R^{G5'}$ is, independently, H, $A^1$, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl.

In some embodiments, each of $R^{G1'}$, $R^{G2'}$, $R^{G3'}$, $R^{G4'}$, and $R^{G5'}$ is, independently, H, $A^1$, F, Cl,

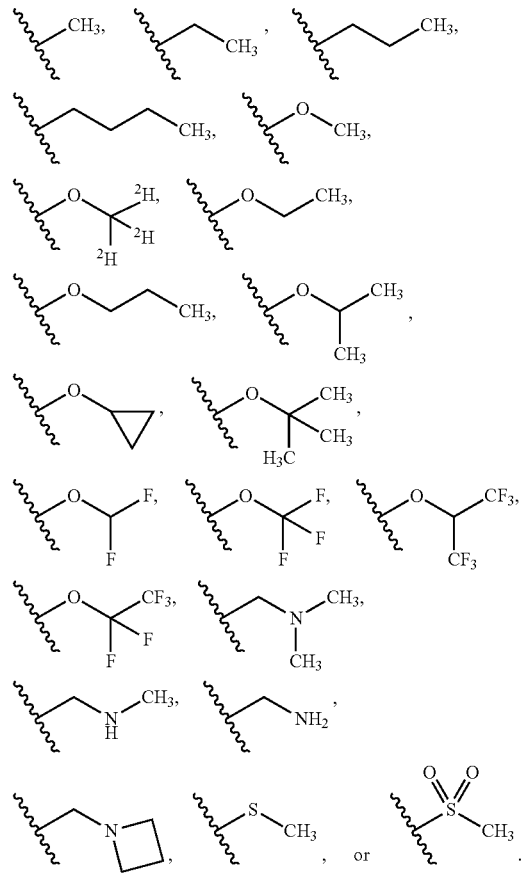

In some embodiments, each of $R^{G1'}$, $R^{G2'}$, $R^{G3'}$, $R^{G4'}$, and $R^{G5'}$ is, independently, H, $A^1$, F,

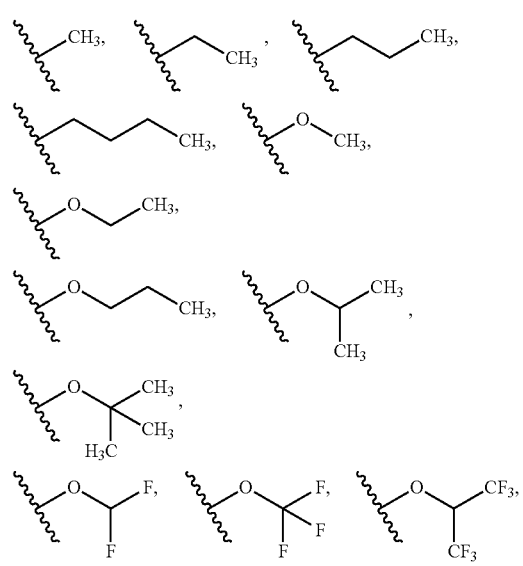

-continued

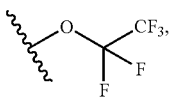

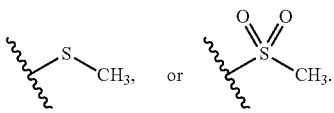

In some embodiments, each of $R^{G1'}$, $R^{G2'}$, $R^{G3'}$, $R^{G4'}$, and $R^{G5'}$ is, independently, H, $A^1$, F, Cl,

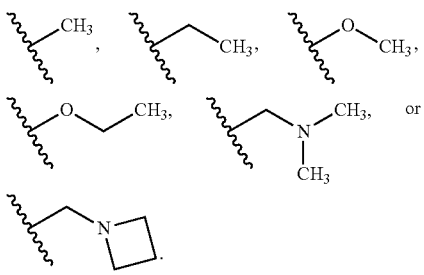

In some embodiments, $R^{G3'}$ is $A^1$.
In some embodiments, $R^{G1'}$ is H; $R^{G2'}$ is

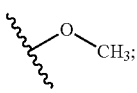

$R^{G3'}$ is $A^1$; $R^{G4'}$ is

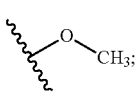

and $R^{G5'}$ is H. In some embodiments, $R^{G1'}$ is H; $R^{G2'}$ is

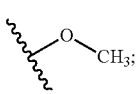

$R^{G3'}$ is $A^1$; $R^{G4'}$ is H; and $R^{G5'}$ is

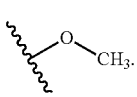

In some embodiments, $R^{G1'}$ is H; $R^{G2'}$ is

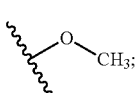

$R^{G3'}$ is $A^1$; $R^{G4'}$ is Cl or F; and $R^{G5'}$ is H. In some embodiments, $R^{G1'}$ is H; $R^{G2'}$ is

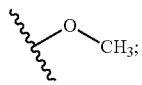

$R^{G3'}$ is $A^1$; $R^{G4'}$ is H; and $R^{G5'}$ is H. In some embodiments, $R^{G1'}$ is H; $R^{G2'}$ is

$R^{G3'}$ is $A^1$; $R^{G4'}$ is

and $R^{G5'}$ is H.

In some embodiments, $R^{G1'}$ and $R^{G2'}$, $R^{G2'}$ and $R^{G3'}$, $R^{G3'}$ and $R^{G4'}$, and/or $R^{G4'}$ and $R^{G5'}$ together with the carbon atoms to which each is attached, combine to form

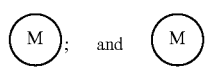

is optionally substituted $C_2$-$C_9$ heterocyclyl, which is optionally substituted with $A^1$, where one of $R^{G1'}$, $R^{G2'}$, $R^{G3'}$, $R^{G4'}$, and $R^{G5'}$ is $A^1$, or

is substituted with $A^1$. In some embodiments, $R^{G1'}$ and $R^{G2'}$, $R^{G2'}$ and $R^{G3'}$, $R^{G3'}$ and $R^{G4'}$, and/or $R^{G4'}$ and $R^{G5'}$, together with the carbon atoms to which each is attached, combine to form

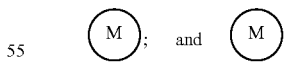

is optionally substituted $C_2$-$C_9$ heteroaryl, which is optionally substituted with $A^1$, where one of $R^{G1'}$, $R^{G2'}$, $R^{G3'}$, $R^{G4'}$, and $R^{G5'}$ is $A^1$, or

is substituted with $A^1$.

In some embodiments, G' is

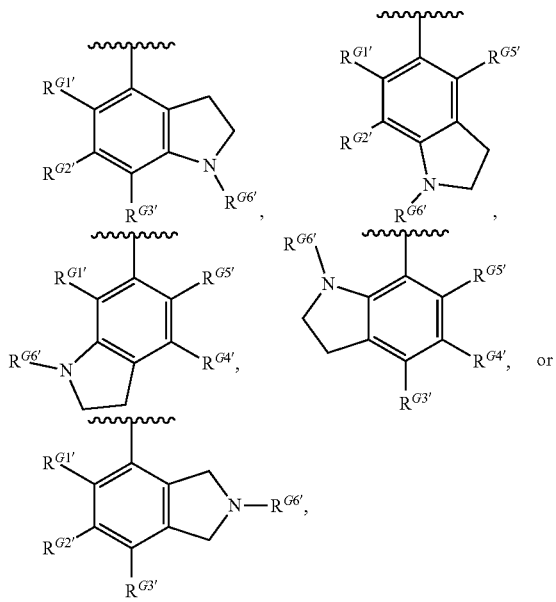

where $R^{G6'}$ is H, $A^1$, or optionally substituted $C_1$-$C_6$ alkyl.
In some embodiments, G' is

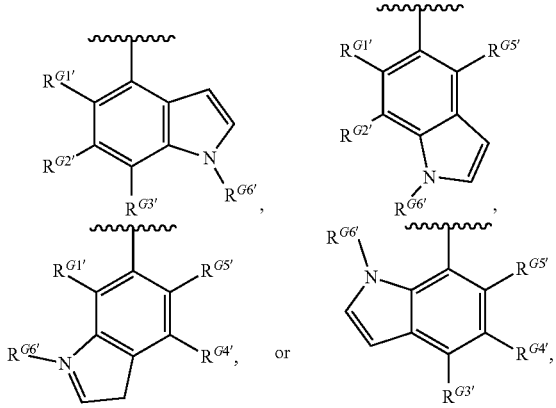

where $R^{G6'}$ is H, $A^1$, or optionally substituted $C_1$-$C_6$ alkyl.
In some embodiments, $R^{G1'}$ and $R^{G2'}$, $R^{G2'}$ and $R^{G3'}$, $R^{G3'}$ and $R^{G4'}$, and/or $R^{G4'}$ and $R^{G5}$, together with the carbon atoms to which each is attached, combine to form

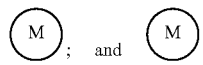; and 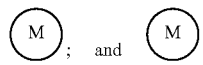

is optionally substituted $C_2$-$C_9$ heterocyclyl or optionally substituted $C_2$-$C_9$ heteroaryl, any of which is optionally substituted with $A^1$, where one of $R^{G1'}$, $R^{G2'}$, $R^{G3'}$, $R^{G4'}$, and $R^{G5'}$ is $A^1$, or

is substituted with $A^1$.

In some embodiments, G' is

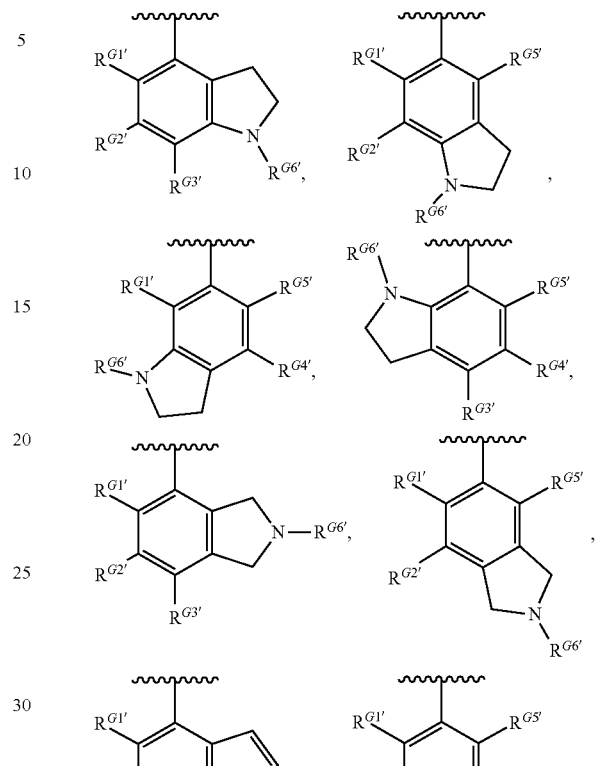

where $R^{G6'}$ is H, $A^1$, or optionally substituted $C_1$-$C_6$ alkyl.
In some embodiments, G' is

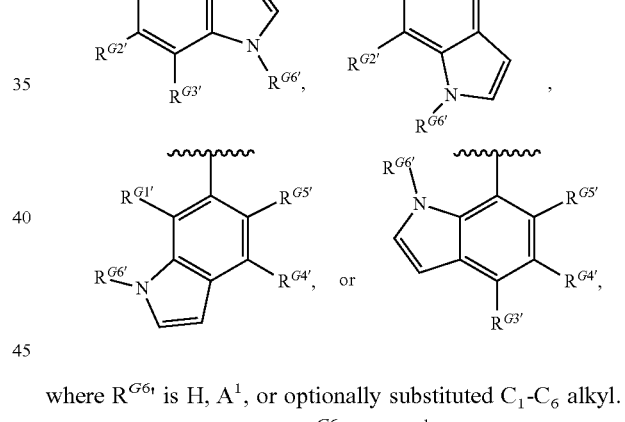

where $R^{G6'}$ is H, $A^1$, or optionally substituted $C_1$-$C_6$ alkyl.
In some embodiments, $R^{G6'}$ is H, $A^1$,

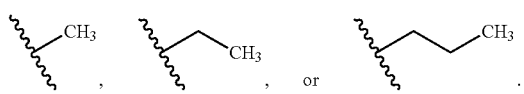

In some embodiments, $R^{G6'}$ is H, $A^1$, or

In some embodiments, $R^{G6'}$ is H or $A^1$.
In some embodiments, $R^{G6'}$ is H. In some embodiments, $R^{G6'}$ is $A^1$.

In some embodiments, $R^{G1'}$ is H, $A^1$, F,
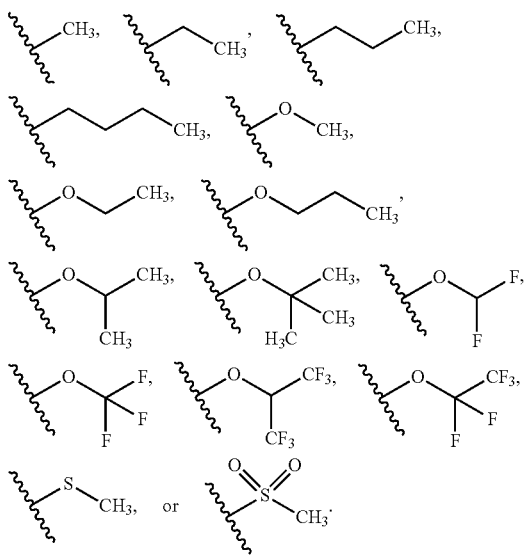
In some embodiments, $R^{G1'}$ is H.
In some embodiments, $R^{G2'}$ is H $A^1$, F,
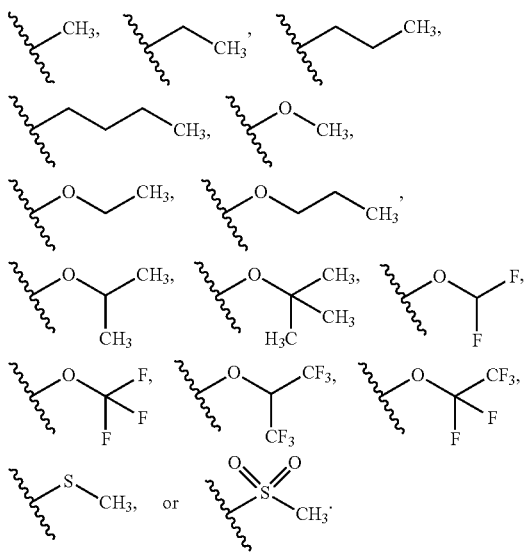
In some embodiments, $R^{G2'}$ is H.
In some embodiments, $R^{G3'}$ is H, $A^1$, F,
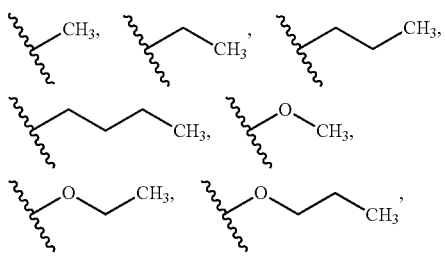
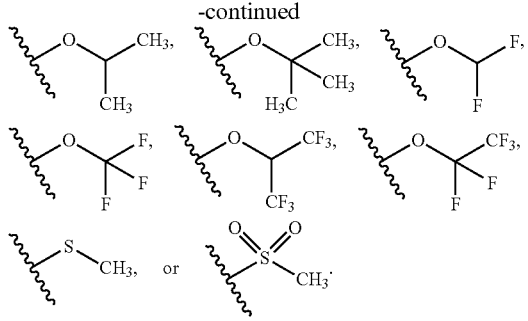
In some embodiments, $R^{G3'}$ is H.
In some embodiments, $R^{G4'}$ is H, $A^1$, F,
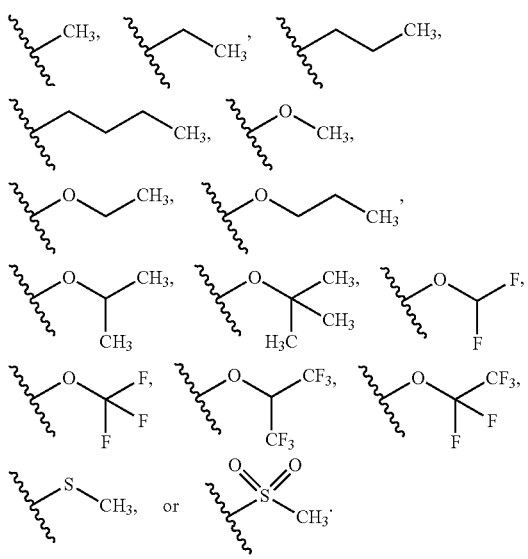
In some embodiments, $R^{G4'}$ is H.
In some embodiments, $R^{G5'}$ is H, $A^1$, F,
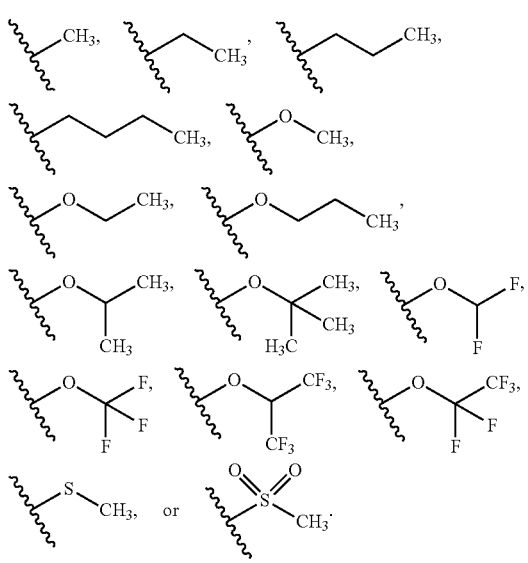
In some embodiments, $R^{G5'}$ is H.

In some embodiments, one or more of $R^{G1\prime}$, $R^{G2\prime}$, $R^{G3\prime}$, $R^{G4\prime}$, and $R^{G5\prime}$ is H. In some embodiments, two or more of $R^{G1\prime}$, $R^{G2\prime}$, $R^{G3\prime}$, $R^{G4\prime}$, and $R^{G5\prime}$ is H. In some embodiments, three or more of $R^{G1\prime}$, $R^{G2\prime}$, $R^{G3\prime}$, $R^{G4\prime}$ and $R^{G5\prime}$ is H.

In some embodiments, $R^{G1\prime}$ is $A^1$. In some embodiments, $R^{G2\prime}$ is $A^1$. In some embodiments, $R^{G3\prime}$ is $A^1$. In some embodiments, $R^{G4\prime}$ is $A^1$. In some embodiments, $R^{G5\prime}$ is $A^1$. In some embodiments,

is substituted with $A^1$.

In some embodiments, G' is

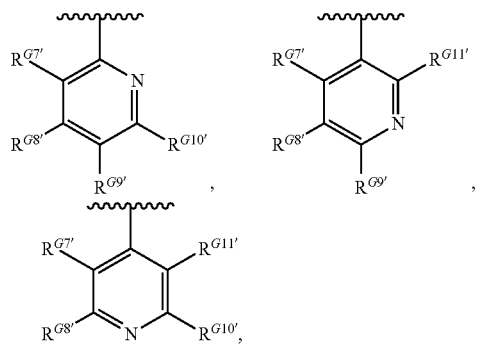

where each of $R^{G7\prime}$, $R^{G8\prime}$, $R^{G9\prime}$, $R^{G10\prime}$, and $R^{G11\prime}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G7\prime}$ and $R^{G8\prime}$, $R^{G8\prime}$ and $R^{G9\prime}$, $R^{G9\prime}$ and $R^{G10\prime}$, and/or $R^{G10\prime}$ and $R^{G11\prime}$, together with the carbon atoms to which each is attached, combine to form

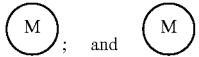

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^1$, where one of $R^{G7\prime}$, $R^{G8\prime}$, $R^{G9\prime}$, $R^{G10\prime}$, and $R^{G11\prime}$ is $A^1$; or

is substituted with $A^1$.

In some embodiments, each of $R^{G7\prime}$, $R^{G8\prime}$, $R^{G9\prime}$, $R^{G10\prime}$, and $R^{G11\prime}$ is, independently, H, $A^1$, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl; or $R^{G7\prime}$ and $R^{G8\prime}$, $R^{G8\prime}$ and $R^{G9\prime}$, $R^{G9\prime}$ and $R^{G10\prime}$, and/or $R^{G10\prime}$ and $R^{G11\prime}$, together with the carbon atoms to which each is attached, combine to form

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^1$, where one of $R^{G7\prime}$, $R^{G8\prime}$, $R^{G9\prime}$, $R^{G10\prime}$, and $R^{G11\prime}$ is $A^1$; or

is substituted with $A^1$.

In some embodiments, each of $R^{G7\prime}$, $R^{G8\prime}$, $R^{G9\prime}$, $R^{G10\prime}$, and $R^{G11\prime}$ is, independently, H, $A^1$, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl.

In some embodiments, each of $R^{G7\prime}$, $R^{G8\prime}$, $R^{G9\prime}$, $R^{G10\prime}$, and $R^{G11\prime}$ is, independently, H, $A^1$, F, Cl,

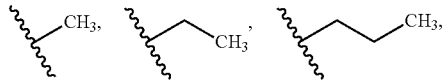

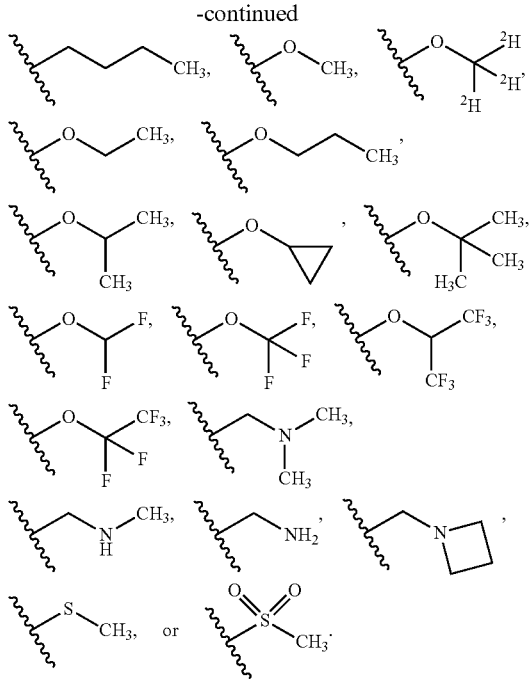

In some embodiments, $R^{G8'}$ is

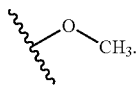

In some embodiments, G' is

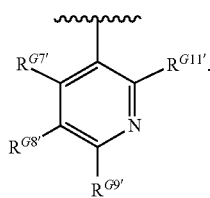

In some embodiments, $R^{G7'}$ is H; $R^{G8'}$ is

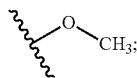

$R^{G9'}$ is $A^1$; and $R^{G11'}$ is H.

In some embodiments, G' is

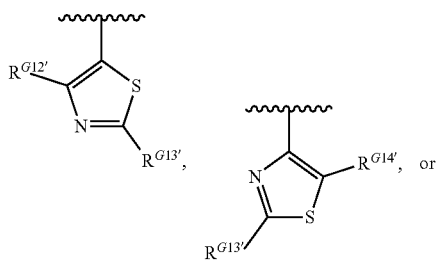

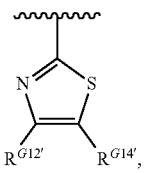

where each of $R^{G12'}$, $R^{G13'}$, and $R^{G14'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G12'}$ and $R^{G14'}$, together with the carbon atoms to which each is attached, combine to form

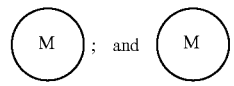

is optionally substituted $C_6$-$C_1$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G12'}$, $R^{G13'}$, and $R^{G14'}$ is $A^1$; or

is substituted with $A^1$.

In some embodiments, each of $R^{G12'}$, $R^{G13'}$ and $R^{G14'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G12'}$ and $R^{G14'}$, together with the carbon atoms to which each is attached, combine to form

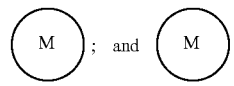

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G12'}$, $R^{G13'}$, and $R^{G14'}$ is $A^1$; or

is substituted with $A^1$.

In some embodiments, $R^{7'''}$ is

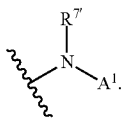

In some embodiments, $R^{7'}$ is H, optionally substituted $C_1$-$C_6$ alkyl, or optionally substituted $C_3$-$C_{10}$ carbocyclyl. In some embodiments, $R^{7'}$ is H or optionally substituted $C_1$-$C_6$ alkyl.

In some embodiments, $R^{7'}$ is H,

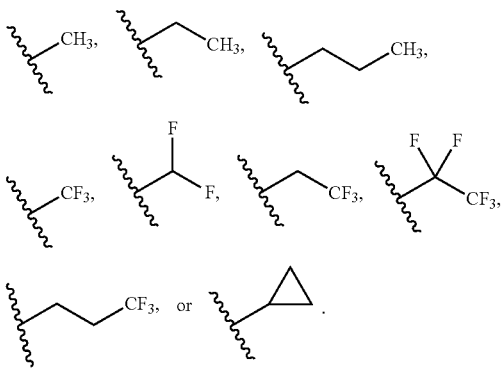

In some embodiments, $R^{7'}$ is H or

In some embodiments, $R^{7'}$ is H. In some embodiments, $R^{7'}$ is

In some embodiments, G" is optionally substituted $C_3$-$C_{10}$ carbocyclyl or optionally substituted $C_2$-$C_9$ heterocyclyl. In some embodiments, G" is optionally substituted $C_6$-$C_{10}$ aryl or optionally substituted $C_2$-$C_9$ heteroaryl.

In some embodiments, G" is optionally substituted $C_3$-$C_{10}$ carbocyclyl. In some embodiments, G is optionally substituted $C_6$-$C_{10}$ aryl. In some embodiments, G is optionally substituted $C_2$-$C_9$ heterocyclyl. G" is optionally substituted $C_2$-$C_9$ heteroaryl.

In some embodiments, G" is

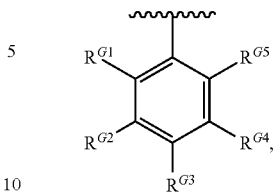

where
each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl.

In some embodiments, each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl.

In some embodiments, each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl; or $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heteroaryl or optionally substituted $C_2$-$C_9$ heterocyclyl.

In some embodiments, each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl.

In some embodiments, each of $R^{G1}$, $R^{G2}$, $R^{G3}$, $R^{G4}$, and $R^{G5}$ is, independently, H, F, Cl,

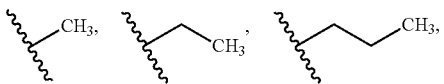

-continued

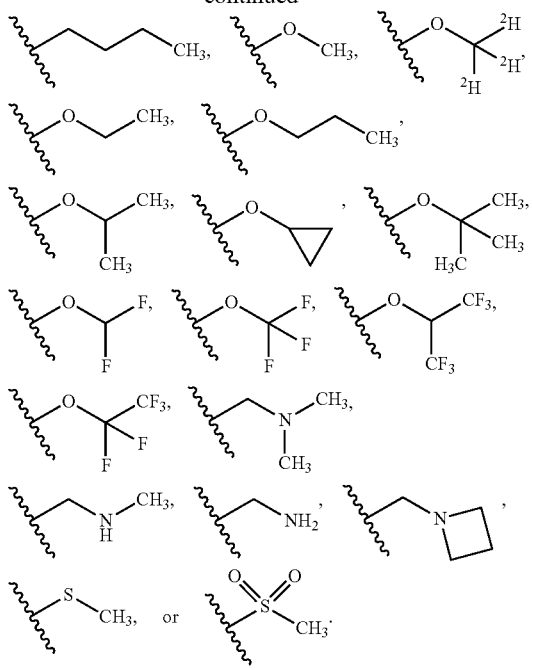

In some embodiments, each of $R^{G1}$, $R^{G2}$, $R^{G3}$, $R^{G4}$, and $R^{G5}$ is, independently, H, F,

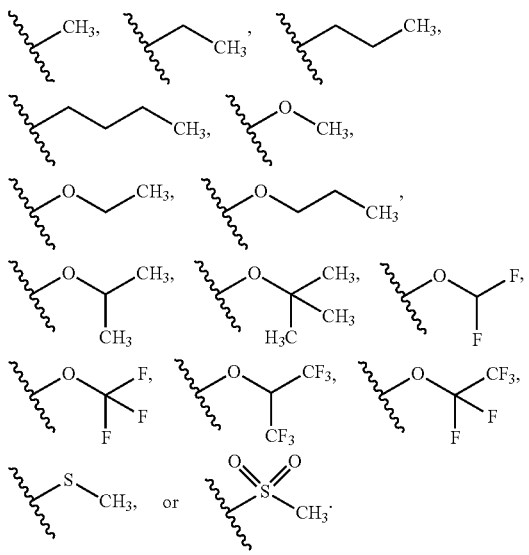

In some embodiments, each of $R^{G1}$, $R^{G2}$, $R^{G3}$, $R^{G4}$, and $R^{G5}$ is, independently, H, F, Cl,

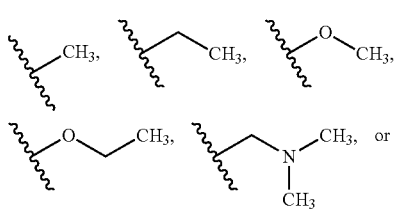

-continued

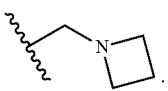

In some embodiments, $R^{G1}$ is H; $R^{G2}$

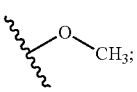

$R^{G3}$ is

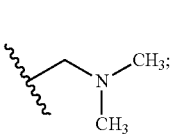

$R^{G4}$ is

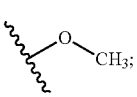

and $R^{G5}$ is H. In some embodiments, $R^{G1}$ is H; $R^{G2}$ is

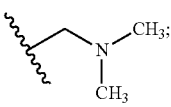

$R^{G3}$ is

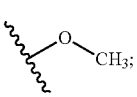

$R^{G4}$ is H; and $R^{G5}$ is

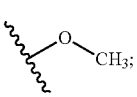

In some embodiments, $R^{G1}$ is H; $R^{G2}$ is

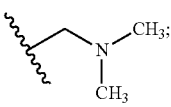

$R^{G3}$ is

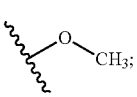

$R^{G4}$ is Cl or F; and $R^{G5}$ is H. In some embodiments, $R^{G1}$ is H; $R^{G2}$ is

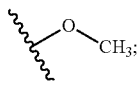

$R^{G3}$ is

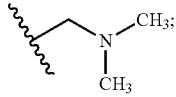

$R^{G4}$ is H; and $R^{G5}$ is H.

In some embodiments, $R^{G1}$ is H; $R^{G2}$ is

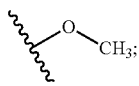

$R^{G3}$ is

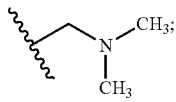

$R^{G4}$ is

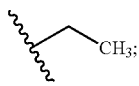

and $R^{G5}$ is H.

In some embodiments, $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heteroaryl or optionally substituted $C_2$-$C_9$ heterocyclyl.

In some embodiments, $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heterocyclyl. In some embodiments, $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heteroaryl.

In some embodiments, $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heterocyclyl. In some embodiments, $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_2$-$C_9$ heteroaryl.

In some embodiments, G" is

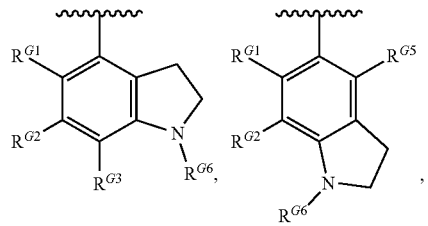

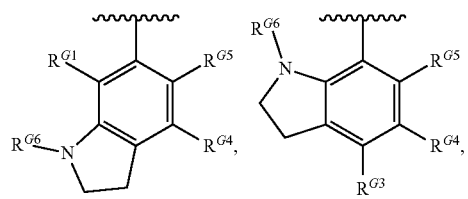

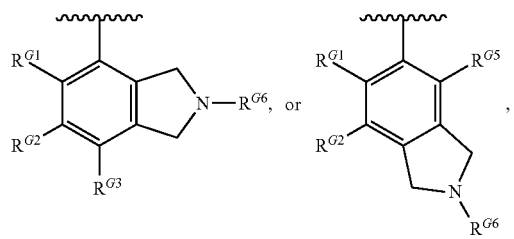

where $R^{G6}$ is H or optionally substituted $C_1$-$C_6$ alkyl. In some embodiments G" is

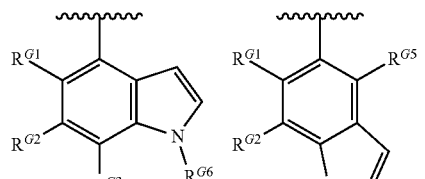

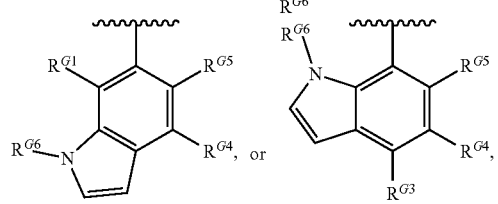

where $R^{G6}$ is H or optionally substituted $C_1$-$C_6$ alkyl.

In some embodiments, G" is

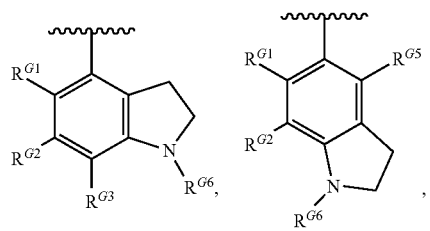

-continued
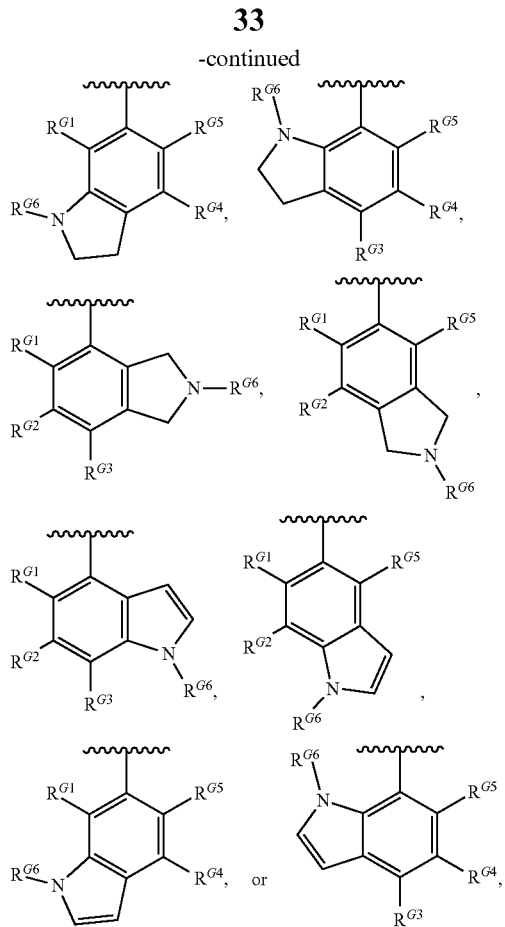
where $R^{G6}$ is H or optionally substituted $C_1$-$C_6$ alkyl.
In some embodiments, $R^{G6}$ is H,
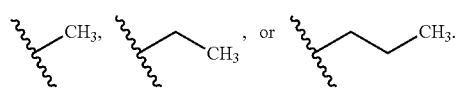
In some embodiments, $R^{G6}$ is H or
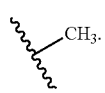
In some embodiments, $R^{G6}$ is H.
In some embodiments, $R^{G1}$ is H, F,
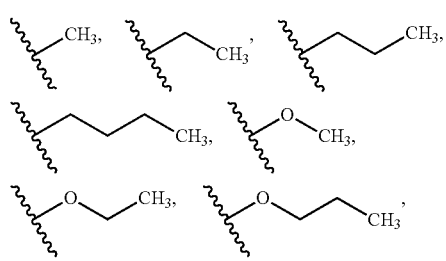
In some embodiments, $R^{G1}$ is H.
In some embodiments, $R^{G2}$ is H, F,
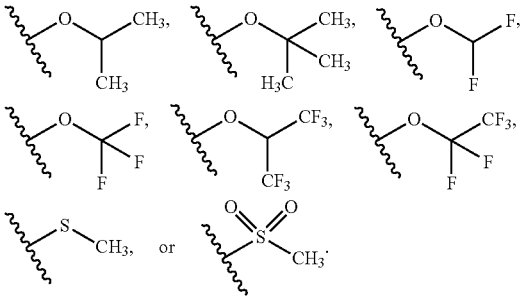
In some embodiments, $R^{G2}$ is H.
In some embodiments, $R^{G3}$ is H, F,
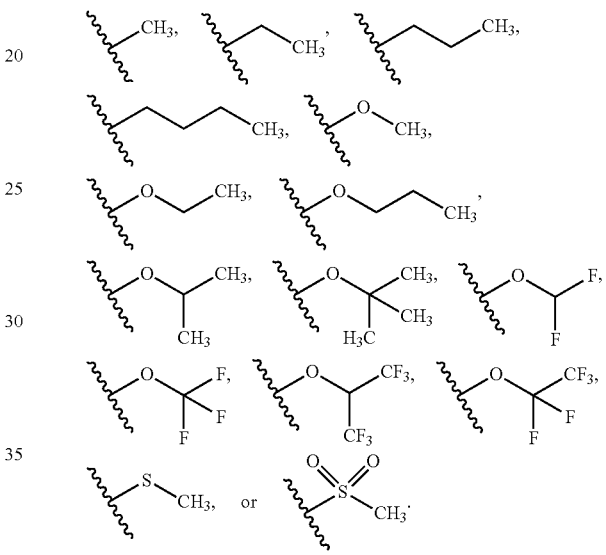
In some embodiments, $R^{G3}$ is H.

In some embodiments, $R^{G4}$ is H, F,

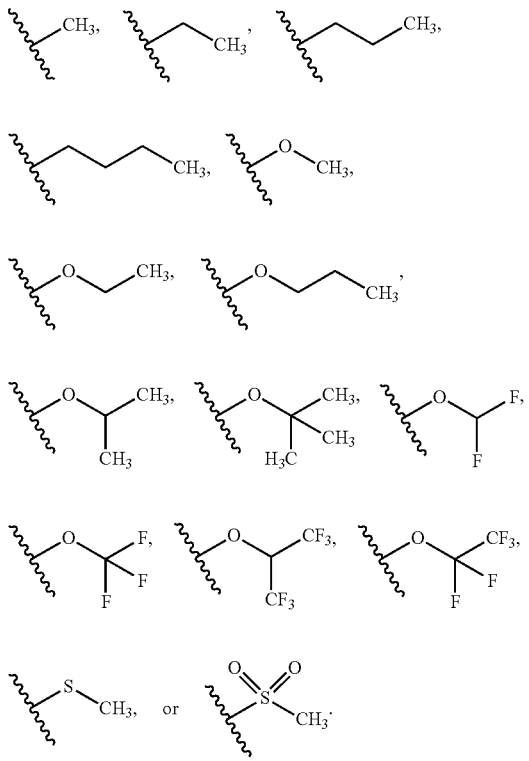

In some embodiments, $R^{G4}$ is H.

In some embodiments, $R^{G5}$ is H, F,

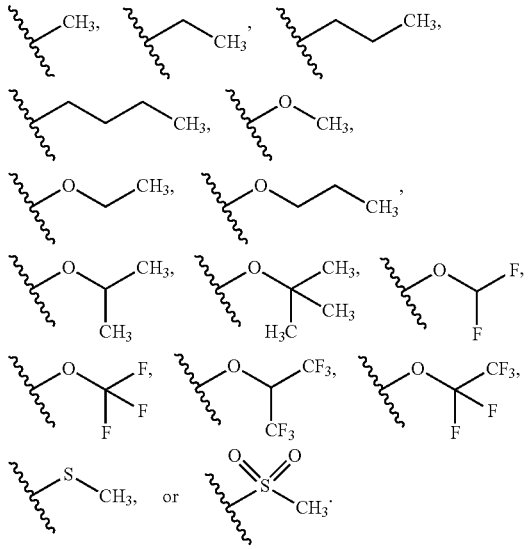

In some embodiments, $R^{G5}$ is H.

In some embodiments, one or more of $R^{G1}$, $R^{G2}$, $R^{G3}$, $R^{G4}$, and $R^{G5}$ is H. In some embodiments, two or more of $R^{G1}$, $R^{G2}$, $R^{G3}$, $R^{G4}$ and $R^{G5}$ is H. In some embodiments, three or more of $R^{G1}$, $R^{G2}$, $R^{G3}$, $R^{G4}$, and $R^{G5}$ is H. In some embodiments, each of $R^{G1}$, $R^{G2}$, $R^{G3}$, $R^{G4}$, and $R^{G5}$ is H.

In some embodiments, G" is

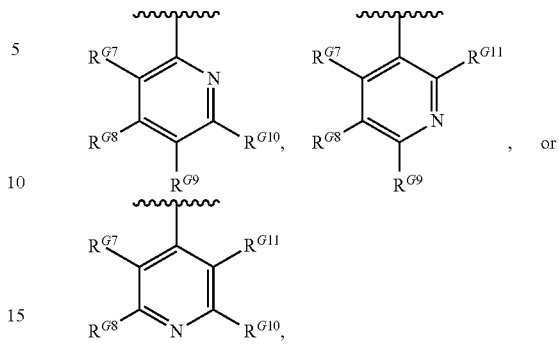

where each of $R^{G7}$, $R^{G8}$, $R^{G9}$, $R^{G10}$, and $R^{G11}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G7}$ and $R^{G8}$, $R^{G8}$ and $R^{G9}$, $R^{G9}$ and $R^{G10}$, and/or $R^{G10}$ and $R^{G11}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl.

In some embodiments, each of $R^{G7}$, $R^{G8}$, $R^{G9}$, $R^{G10}$, and $R^{G11}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{G7}$ and $R^{G8}$, $R^{G8}$ and $R^{G9}$, $R^{G9}$ and $R^{G10}$, and/or $R^{G10}$ and $R^{G11}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl.

In some embodiments, each of $R^{G7}$, $R^{G8}$, $R^{G9}$, $R^{G10}$, and $R^{G11}$ is, independently, H, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl; or $R^{G7}$ and $R^{G8}$, $R^{G8}$ and $R^{G9}$, $R^{G9}$ and $R^{G10}$, and/or $R^{G10}$ and $R^{G11}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl.

In some embodiments, each of $R^{G7}$, $R^{G8}$, $R^{G9}$, $R^{G10}$, and $R^{G11}$ is, independently, H, halogen, optionally substituted $C_1$-$C_6$ alkyl, optionally substituted $C_1$-$C_6$ heteroalkyl, optionally substituted —O—$C_3$-$C_6$ carbocyclyl, or optionally substituted —$C_1$-$C_3$ alkyl-$C_2$-$C_5$ heterocyclyl.

In some embodiments, each of $R^{G7}$, $R^{G8}$, $R^{G9}$, $R^{G10}$, and $R^{G11}$ is, independently, H, F, Cl

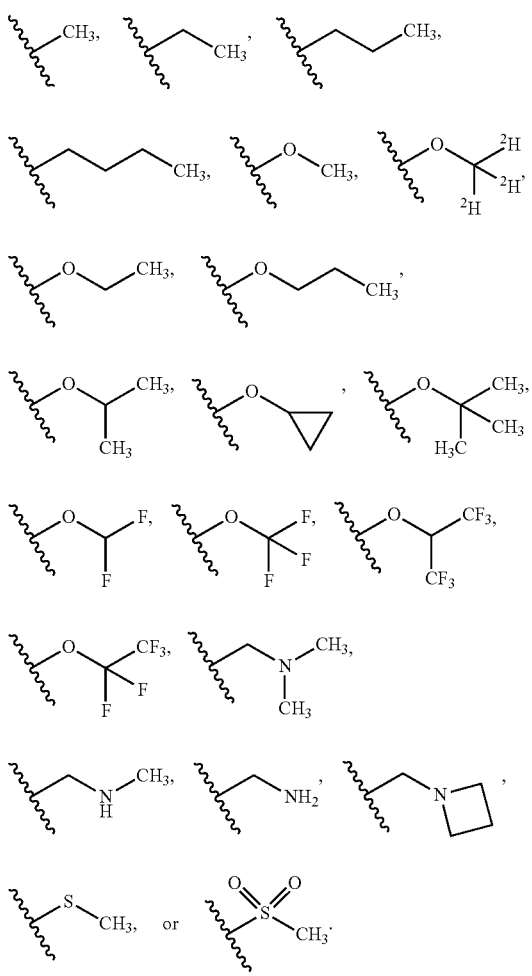

In some embodiments, $R^{G8}$ is

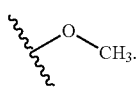

In some embodiments, G" is

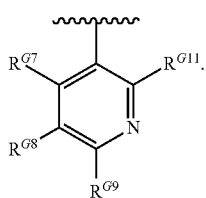

In some embodiments, $R^{G7}$ is H; $R^{G8}$ is

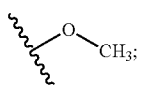

$R^{G9}$ is H; and $R^{G11}$ is H.

In some embodiments, G" is

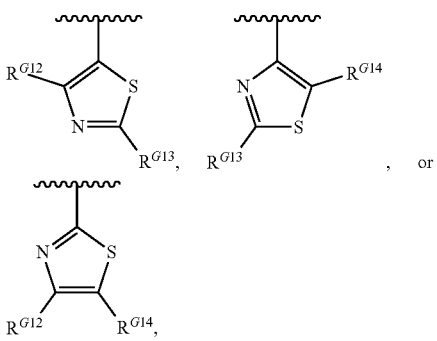

where each of $R^{G12}$, $R^{G13}$, and $R^{G14}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G12}$ and $R^{G14}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl.

In some embodiments, each of $R^{G12}$, $R^{G13}$, and $R^{G14}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{G12}$ and $R^{G14}$, together with the carbon atoms to which each is attached combine to form optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl.

In some embodiments, A has the structure of Formula IIIa:

Formula IIIa

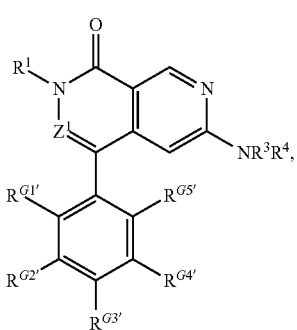

or a pharmaceutically acceptable salt thereof.

In some embodiments, A has the structure of Formula IIIb:

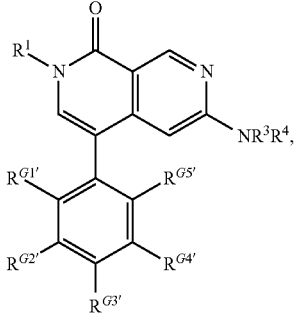

Formula IIIb or a pharmaceutically acceptable salt thereof.

In some embodiments, A has the structure of Formula IIIc:

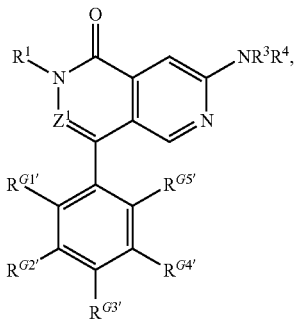

Formula IIIc or a pharmaceutically acceptable salt thereof.

In some embodiments, A has the structure of Formula IIId:

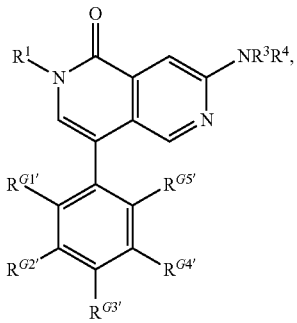

Formula IIId or a pharmaceutically acceptable salt thereof.

In some embodiments, A has the structure of Formula IIIe:

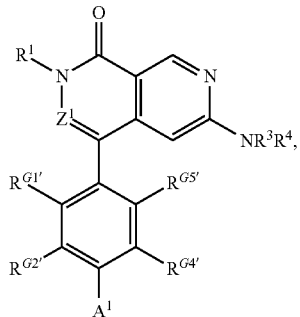

Formula IIIe or a pharmaceutically acceptable salt thereof.

In some embodiments, A has the structure of Formula IIIf:

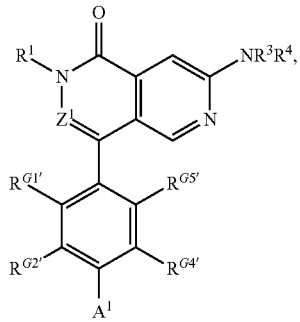

Formula IIIf or a pharmaceutically acceptable salt thereof.

In some embodiments, A has the structure of Formula IIIg:

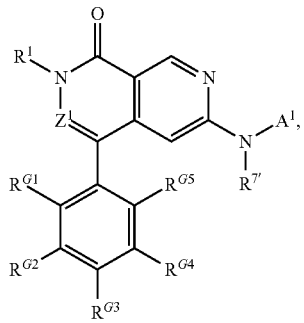

Formula IIIg or a pharmaceutically acceptable salt thereof.

In some embodiments, A has the structure of Formula IIIh:

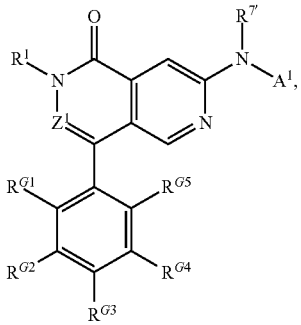
Formula IIIh or a pharmaceutically acceptable salt thereof.

In some embodiments, A has the structure of Formula IIIi:

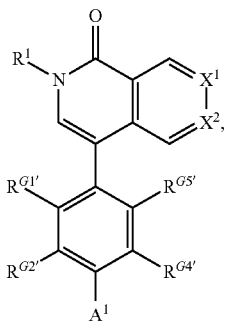
Formula IIIi or a pharmaceutically acceptable salt thereof.

In some embodiments, A has the structure of Formula IIIj:

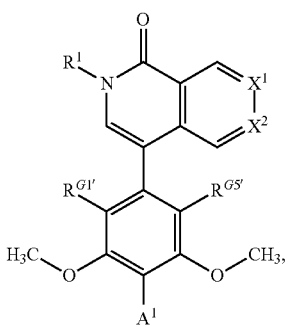
Formula IIIj or a pharmaceutically acceptable salt thereof.

In some embodiments, A has the structure of Formula IIIk:

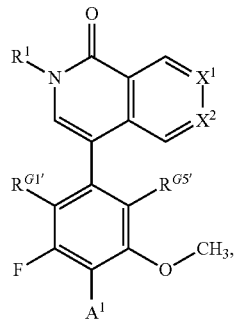
Formula IIIk or a pharmaceutically acceptable salt thereof.

In some embodiments, A has the structure of Formula IIIm:

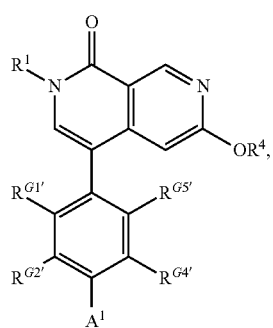
Formula IIIm or a pharmaceutically acceptable salt thereof.

In some embodiments, A has the structure of Formula IIIn:

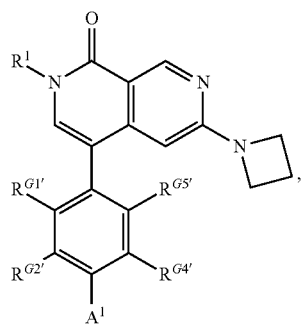
Formula IIIn or a pharmaceutically acceptable salt thereof.

In some embodiments, A has the structure of Formula IIIo:

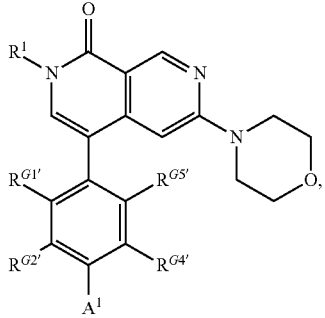

Formula IIIo or a pharmaceutically acceptable salt thereof.

In some embodiments, A has the structure of Formula IIIp:

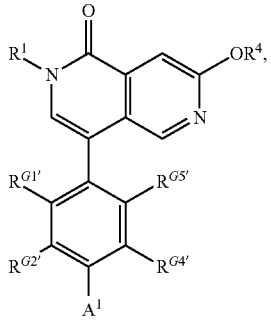

Formula IIIp or a pharmaceutically acceptable salt thereof.

In some embodiments, A has the structure of Formula IIIq:

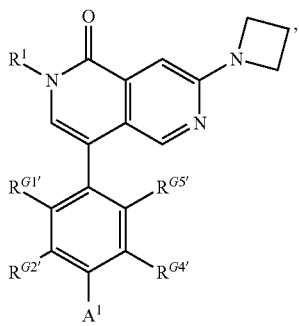

Formula IIIq or a pharmaceutically acceptable salt thereof.

In some embodiments, A has the structure of Formula IIIr:

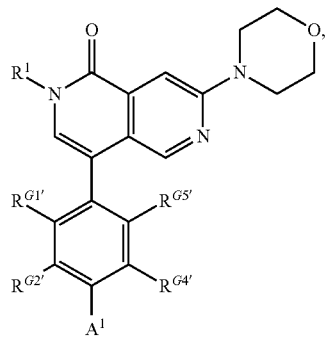

Formula IIIr or a pharmaceutically acceptable salt thereof.

In some embodiments, A has the structure of Formula IIIs:

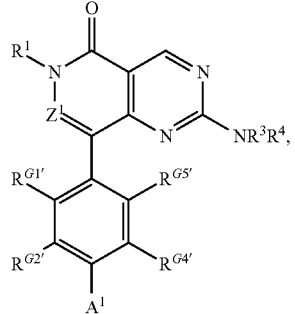

Formula IIIs or a pharmaceutically acceptable salt thereof.

In some embodiments, A has the structure of Formula IIIt:

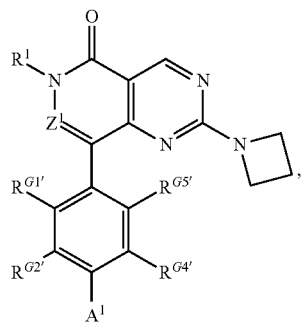

Formula IIIt or a pharmaceutically acceptable salt thereof.

In some embodiments, A has the structure of Formula IIIu:

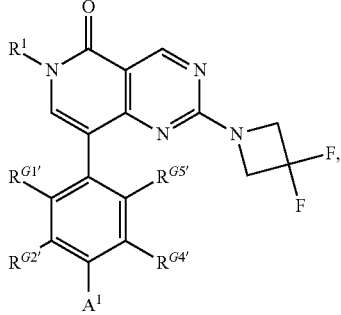

Formula IIIu or a pharmaceutically acceptable salt thereof.

In some embodiments, A has the structure of Formula IIIy:

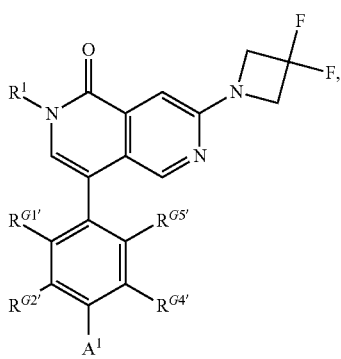

Formula IIIv or a pharmaceutically acceptable salt thereof.

In some embodiments, the degradation moiety is a ubiquitin ligase binding moiety.

In some embodiments, the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

In some embodiments, the degradation moiety is a ubiquitin ligase binding moiety.

In some embodiments, the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

In some embodiments, the degradation moiety has the structure of Formula A:

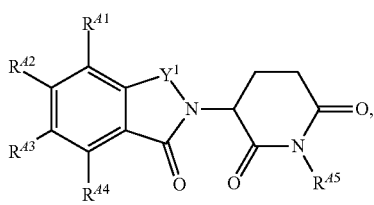

Formula A where
$Y^1$ is

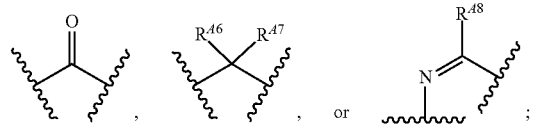

$R^{45}$ is H, optionally substituted $C_1$-$C_6$ alkyl, or optionally substituted $C_1$-$C_6$ heteroalkyl;

$R^{46}$ is H or optionally substituted $C_1$-$C_6$ alkyl; and $R^{47}$ is H or optionally substituted $C_1$-$C_6$ alkyl; or $R^{46}$ and $R^{47}$, together with the carbon atom to which each is bound, combine to form optionally substituted $C_3$-$C_6$ carbocyclyl or optionally substituted $C_2$-$C_5$ heterocyclyl; or $R^{46}$ and $R^{47}$, together with the carbon atom to which each is bound, combine to form optionally substituted $C_3$-$C_6$ carbocyclyl or optionally substituted $C_2$-$C_5$ heterocyclyl;

$R^{48}$ is H, optionally substituted $C_1$-$C_6$ alkyl, or optionally substituted $C_1$-$C_6$ heteroalkyl;

each of $R^{41}$, $R^{42}$, $R^{43}$, and $R^{44}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{41}$ and $R^{42}$, $R^{42}$ and $R^{43}$, and/or $R^{43}$ and $R^{44}$, together with the carbon atoms to which each is attached, combine to form

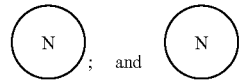

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{41}$, $R^{42}$, $R^{43}$, and $R^{44}$ is $A^2$, or

is substituted with $A^2$, or a pharmaceutically acceptable salt thereof.

In some embodiments, each of $R^{41}$, $R^{42}$, $R^{43}$, and $R^{44}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{41}$ and $R^{42}$, $R^{42}$ and $R^{43}$ and/or $R^{43}$ and $R^{44}$, together with the carbon atoms to which each is attached, combine to form

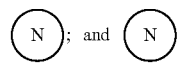

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{41}$, $R^{42}$, $R^{43}$ and $R^{44}$ is $A^2$, or

is substituted with $A^2$, or a pharmaceutically acceptable salt thereof.

In some embodiments, each of $R^{41}$, $R^{42}$, $R^{43}$, and $R^{44}$ is, H, $A^2$, halogen, optionally substituted $C_1$-$C_6$ alkyl, optionally substituted $C_1$-$C_6$ heteroalkyl, optionally substituted —O—$C_3$-$C_6$ carbocyclyl, hydroxyl, optionally substituted amino; or $R^{41}$ and $R^{42}$, $R^{42}$ and $R^{43}$, or $R^{43}$ and $R^{44}$, together with the carbon atoms to which each is attached, combine to form

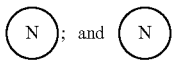

is optionally substituted $C_2$-$C_9$ heterocyclyl, which is optionally substituted with $A^2$, where one of $R^{41}$, $R^{42}$, $R^{43}$ and $R^{44}$ is $A^2$, or

is substituted with $A^2$.

In some embodiments, each of $R^{41}$, $R^{42}$, $R^{43}$, and $R^{44}$ is, independently, H, $A^2$, F,

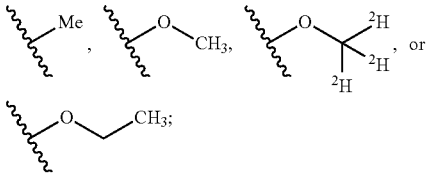

or $R^{41}$ and $R^{42}$, $R^{42}$ and $R^{43}$, $R^{43}$ and $R^{44}$, together with the carbon atoms to which each is attached, combine to form

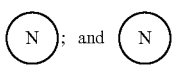

is optionally substituted $C_2$-$C_9$ heterocyclyl, which is optionally substituted with $A^2$, where one of $R^{41}$, $R^{42}$, $R^{43}$, and $R^{44}$ is $A^2$, or

is substituted with $A^2$.

In some embodiments, $R^{41}$ is $A^2$. In some embodiments, $R^{42}$ is $A^2$. In some embodiments, $R^{43}$ is $A^2$.

In some embodiments, $R^{44}$ is $A^2$. In some embodiments, $R^{45}$ is $A^2$.

In some embodiments, $R^{45}$ is H or optionally substituted $C_1$-$C_6$ alkyl.

In some embodiments, $R^{45}$ is H or

In some embodiments, $R^{45}$ is H. In some embodiments, $R^{45}$ is

In some embodiments, $Y^1$ is or

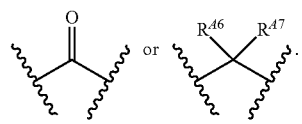

In some embodiments, $Y^1$ is

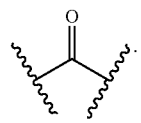

In some embodiments, $Y^1$ is

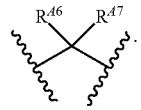

In some embodiments, each of $R^{46}$ and $R^{47}$ is, independently, H, F,

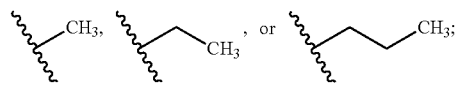

or $R^{46}$ and $R^{47}$, together with the carbon atom to which each is bound, combine to form

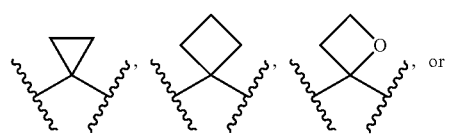

-continued

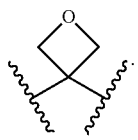

In some embodiments, $R^{46}$ is H and $R^{47}$ is H.

In some embodiments, $Y^1$ is

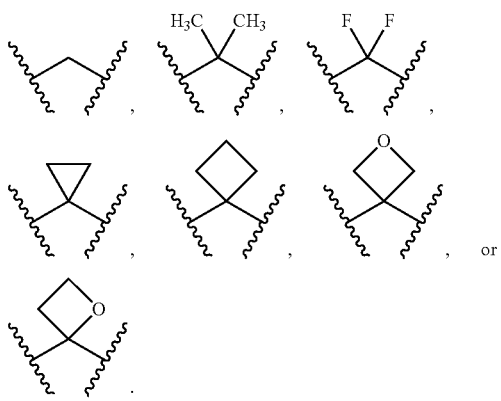

In some embodiments, $Y^1$ is

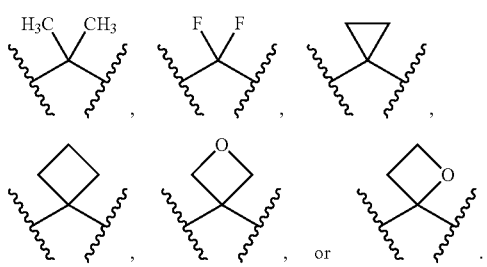

In some embodiments, $Y^1$ is

In some embodiments, the structure of Formula A has the structure of Formula A1:

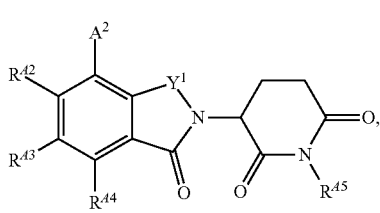

Formula A1 or a pharmaceutically acceptable salt thereof.

In some embodiments, the structure of Formula A has the structure of Formula A2:

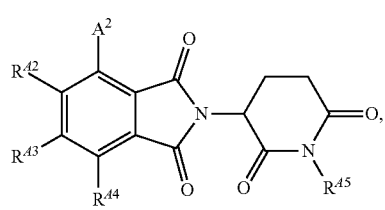

Formula A2 or a pharmaceutically acceptable salt thereof.

In some embodiments, the structure of Formula A has the structure of Formula A3:

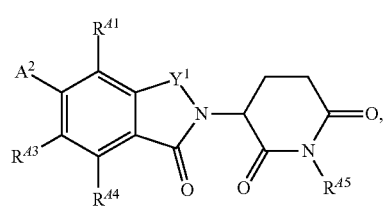

Formula A3 or a pharmaceutically acceptable salt thereof.

In some embodiments, the structure of Formula A has the structure of Formula A4:

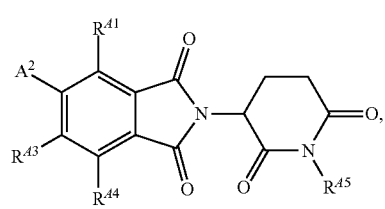

Formula A4 or a pharmaceutically acceptable salt thereof.

In some embodiments, the structure of Formula A has the structure of Formula A5:

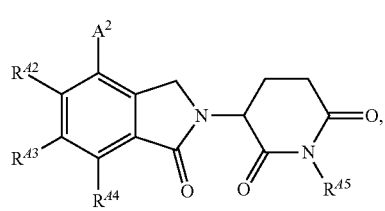

Formula A5 or a pharmaceutically acceptable salt thereof.

In some embodiments, the structure of Formula A has the structure of Formula A6:

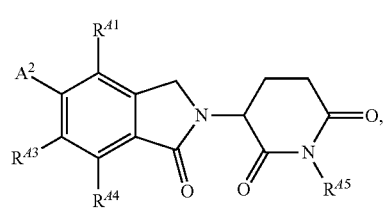

Formula A6 or a pharmaceutically acceptable salt thereof.

In some embodiments, the structure of Formula A has the structure of Formula A7:

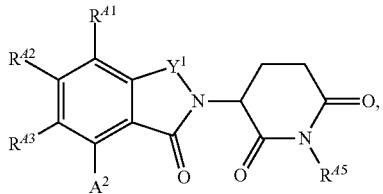

Formula A7 or a pharmaceutically acceptable salt thereof.

In some embodiments, the structure of Formula A has the structure of Formula A8:

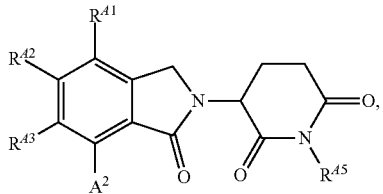

Formula A8 or a pharmaceutically acceptable salt thereof.

In some embodiments, the structure of Formula A has the structure of Formula A9:

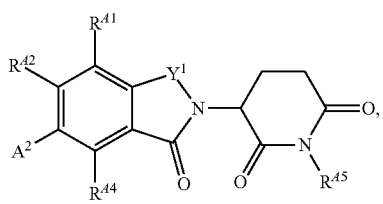

Formula A9 or a pharmaceutically acceptable salt thereof.

In some embodiments, the structure of Formula A has the structure of Formula A10:

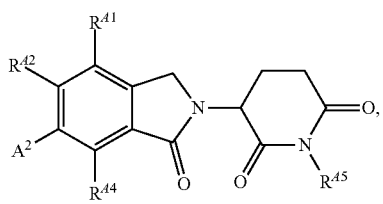

Formula A10 or a pharmaceutically acceptable salt thereof.

In some embodiments, wherein the structure of Formula A is

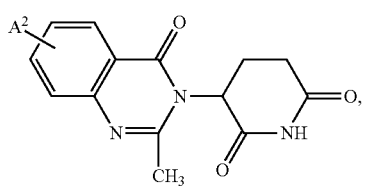

-continued

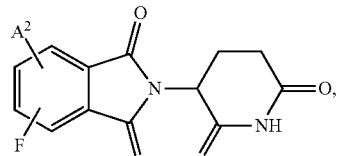

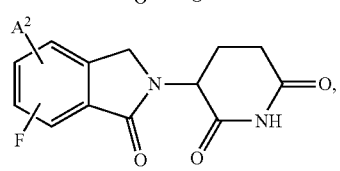

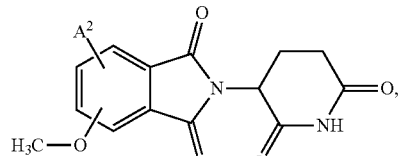

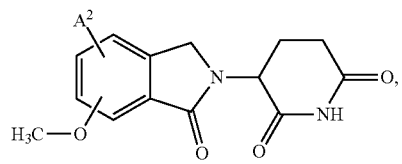

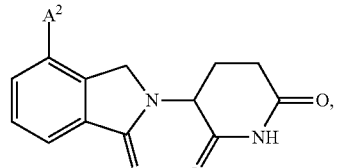

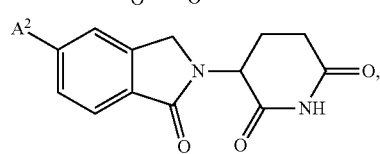

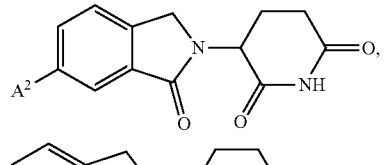

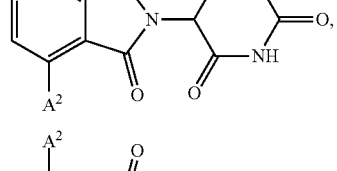

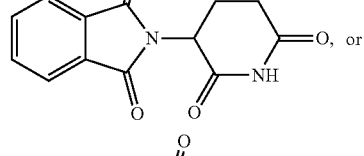

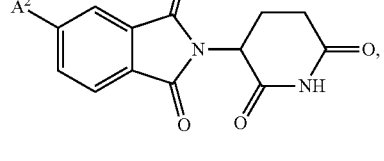

or derivative or analog thereof.

In some embodiments, the structure of Formula A is

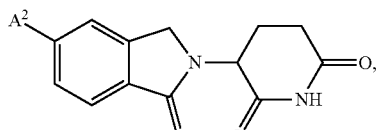

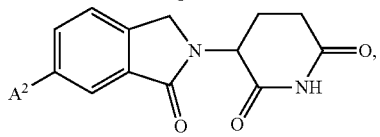

or

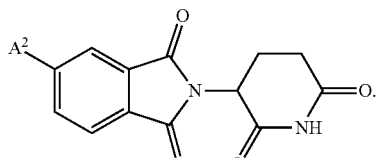

In some embodiments, the structure of Formula A is

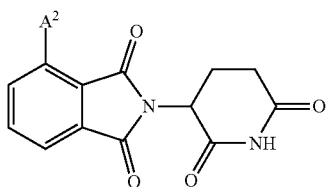

or

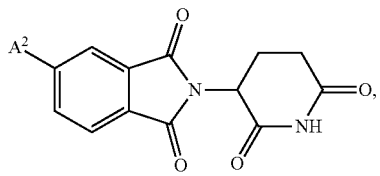

or derivative or analog thereof.

In some embodiments, the linker has the structure of Formula II:

$$A^1\text{-}E^1\text{-}F\text{-}E^2\text{-}A^2,  \quad \text{Formula II}$$

$A^1$ is a bond between the linker and A;

$A^2$ is a bond between B and the linker;

each of $E^1$ and $E^2$ is, independently, absent, $CH_2$, O, or $NCH_3$; and

F has the structure:

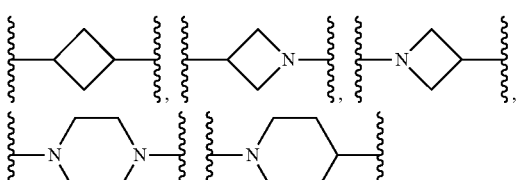

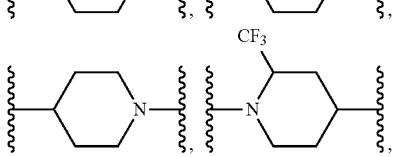

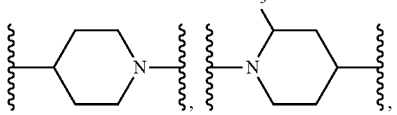

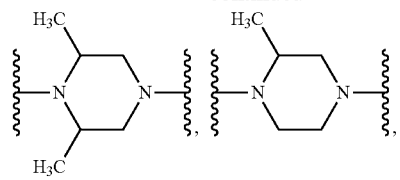

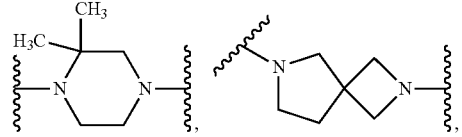

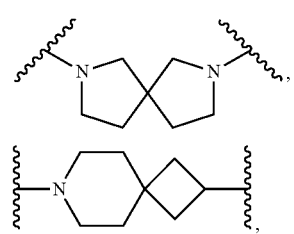

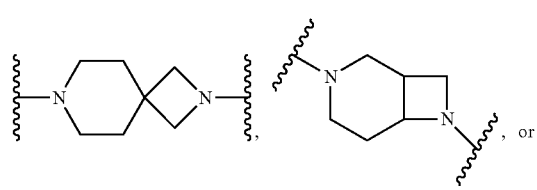

In some embodiments, $E^1$ is absent. In some embodiments, $E^1$ is $CH_2$. In some embodiments, $E^1$ is O. In some embodiments, $E^1$ is $NCH_3$.

In some embodiments, $E^2$ is absent. In some embodiments, $E^2$ is $CH_2$. In some embodiments, $E^2$ is O. In some embodiments, $E^2$ is $NCH_3$.

In some embodiments, the linker comprises the structure:

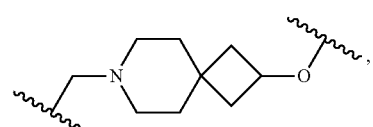

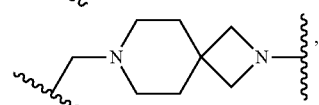

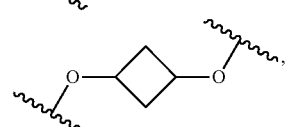

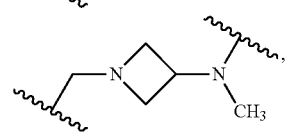

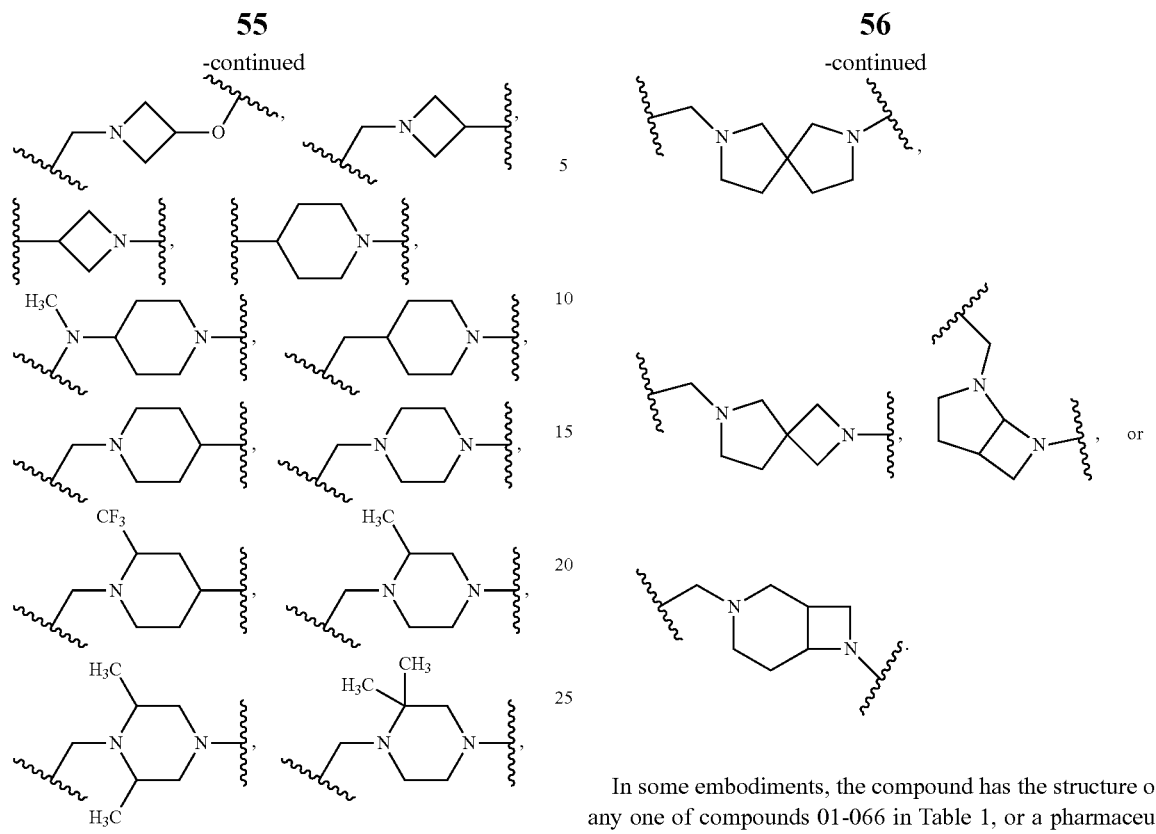
In some embodiments, the compound has the structure of any one of compounds 01-066 in Table 1, or a pharmaceutically acceptable salt thereof.
TABLE 1
| Compounds D1-D184 of the Disclosure | |
|---|---|
| Compound No. | Structure |
| D1 | |
| D2 | |

TABLE 1-continued
Compounds D1-D184 of the Disclosure
| Compound No. | Structure |
| --- | --- |
| D3 | 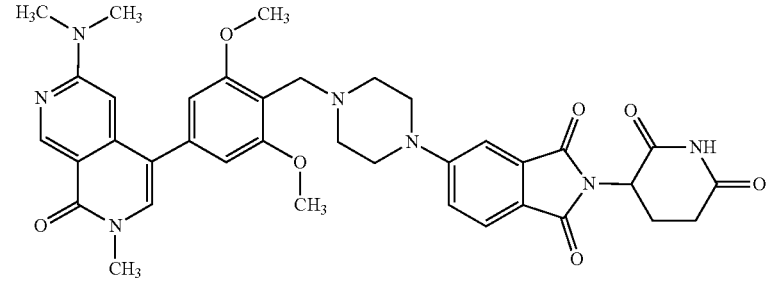 [SMILES: COc1cc(-c2cn(C)c(=O)c3cnc(N(C)C)cc23)cc(OC)c1CN1CCC(c2ccc3c(c2)C(=O)N(C2CCC(=O)NC2=O)C3=O)CC1] |
| D4 | 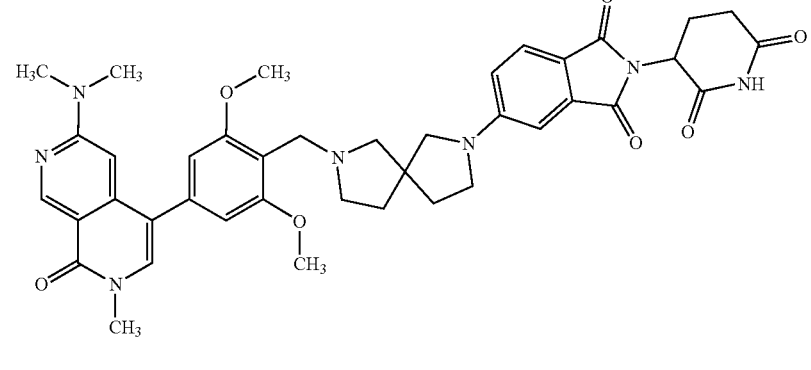 |
| D5 | 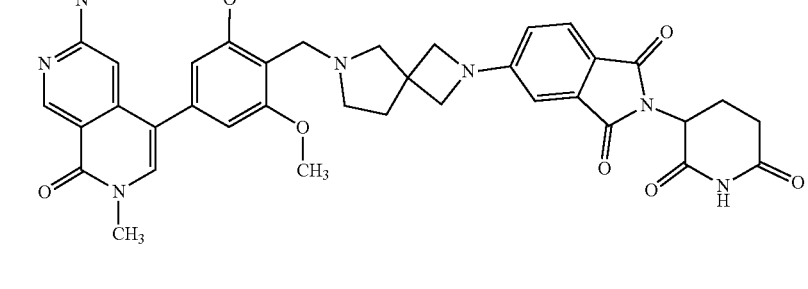 |
| D6 | 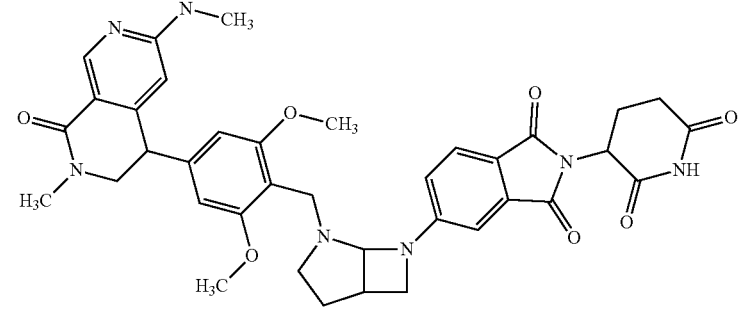 |

TABLE 1-continued

Compounds D1-D184 of the Disclosure

| Compound No. | Structure |
| --- | --- |
| D7 | (structure) |
| D8 | (structure) |
| D9 | (structure) |
| D10 | (structure) |
| D11 | (structure) |

TABLE 1-continued

Compounds D1-D184 of the Disclosure

| Compound No. | Structure |
| --- | --- |
| D12 | 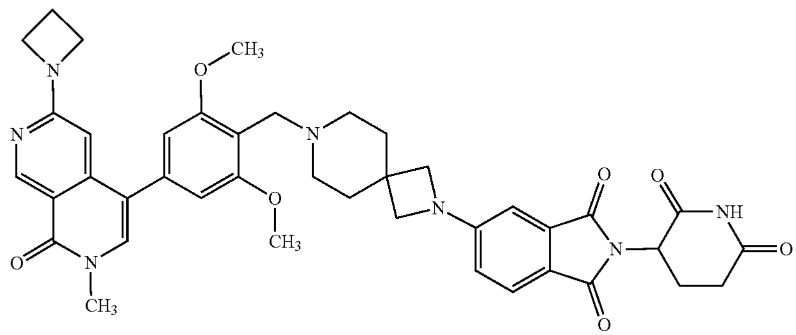 [SMILES: COc1cc(-c2cn(C)c(=O)c3cnc(N4CCC4)cc23)cc(OC)c1CN1CCC2(CC1)CN(c1ccc3c(c1)C(=O)N(C1CCC(=O)NC1=O)C3=O)C2] |
| D13 | 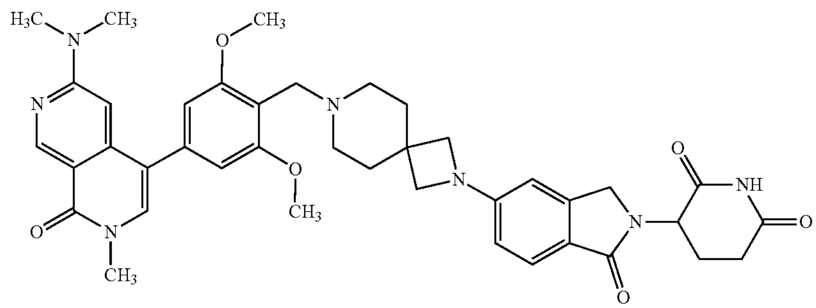 [SMILES: COc1cc(-c2cn(C)c(=O)c3cnc(N(C)C)cc23)cc(OC)c1CN1CCC2(CC1)CN(c1ccc3c(c1)CN(C1CCC(=O)NC1=O)C3=O)C2] |
| D14 | 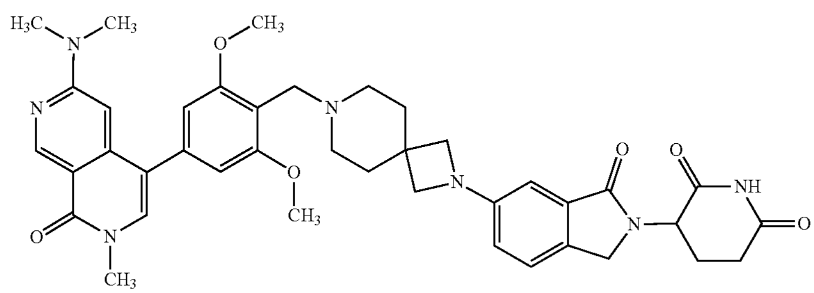 [SMILES: COc1cc(-c2cn(C)c(=O)c3cnc(N(C)C)cc23)cc(OC)c1CN1CCC2(CC1)CN(c1ccc3c(c1)C(=O)N(C1CCC(=O)NC1=O)C3)C2] |
| D15 | 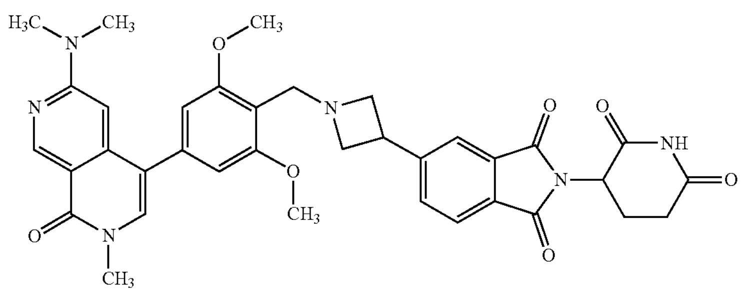 [SMILES: COc1cc(-c2cn(C)c(=O)c3cnc(N(C)C)cc23)cc(OC)c1CN1CC(c2ccc3c(c2)C(=O)N(C2CCC(=O)NC2=O)C3=O)C1] |
| D16 | 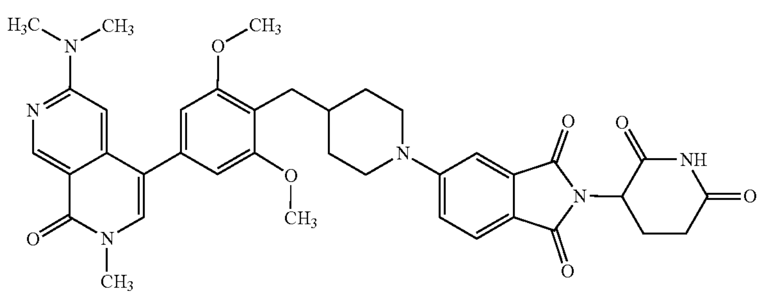 |

TABLE 1-continued
Compounds D1-D184 of the Disclosure
| Compound No. | Structure |
| --- | --- |
| D17 | 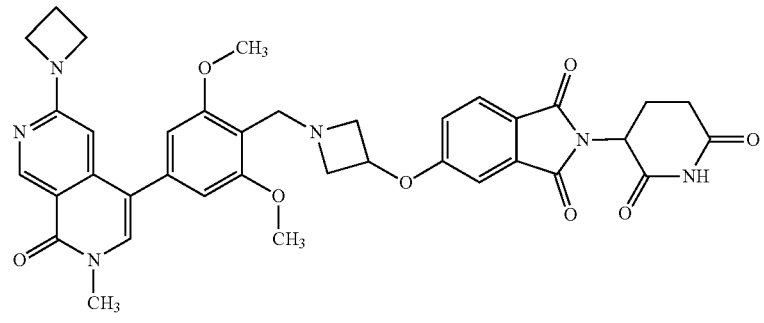 [SMILES: COc1cc(-c2cn(C)c(=O)c3cnc(N4CCC4)cc23)cc(OC)c1CN1CC(Oc2ccc3c(c2)C(=O)N(C2CCC(=O)NC2=O)C3=O)C1] |
| D18 | 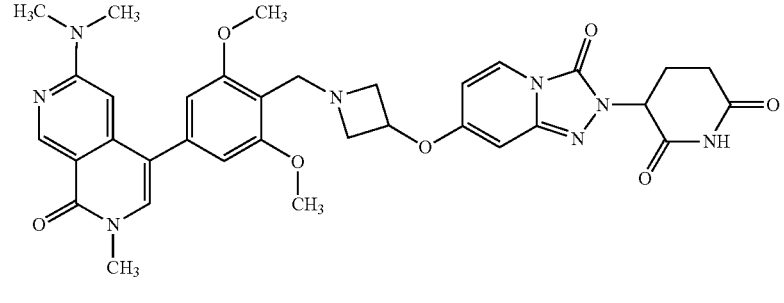 [SMILES: COc1cc(-c2cn(C)c(=O)c3cnc(N(C)C)cc23)cc(OC)c1CN1CC(Oc2ccn3c(=O)n(C4CCC(=O)NC4=O)nc3c2)C1] |
| D19 | 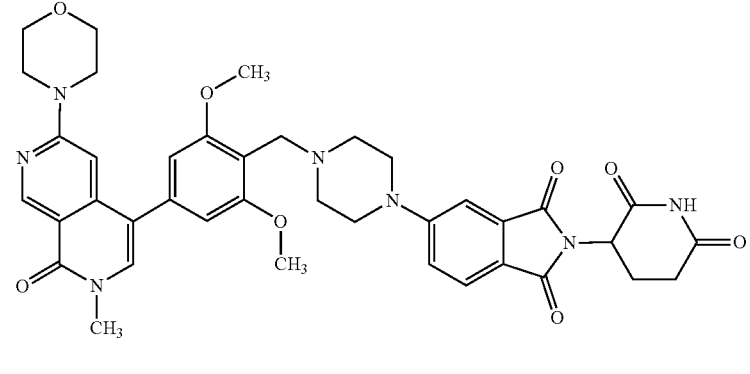 [SMILES: COc1cc(-c2cn(C)c(=O)c3cnc(N4CCOCC4)cc23)cc(OC)c1CN1CCN(c2ccc3c(c2)C(=O)N(C2CCC(=O)NC2=O)C3=O)CC1] |
| D20 | 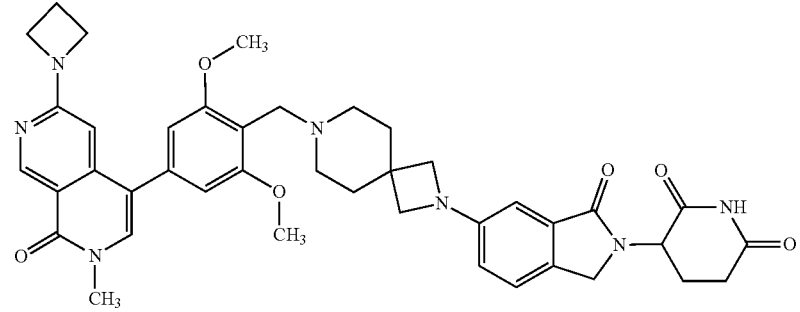 [SMILES: COc1cc(-c2cn(C)c(=O)c3cnc(N4CCC4)cc23)cc(OC)c1CN1CCC2(CC1)CN(c1ccc3c(c1)C(=O)N(C1CCC(=O)NC1=O)C3)C2] |

TABLE 1-continued

Compounds D1-D184 of the Disclosure

| Compound No. | Structure |
|---|---|
| D21 | 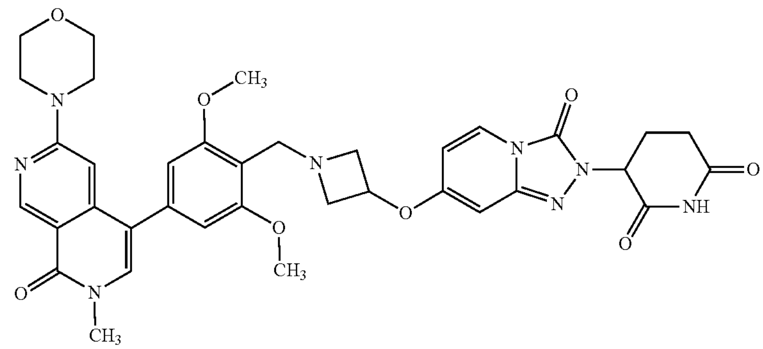 [SMILES: COc1cc(-c2cn(C)c(=O)c3cnc(N4CCOCC4)cc23)cc(OC)c1CN1CC(Oc2ccn3c(=O)n(C4CCC(=O)NC4=O)nc3c2)C1] |
| D22 | 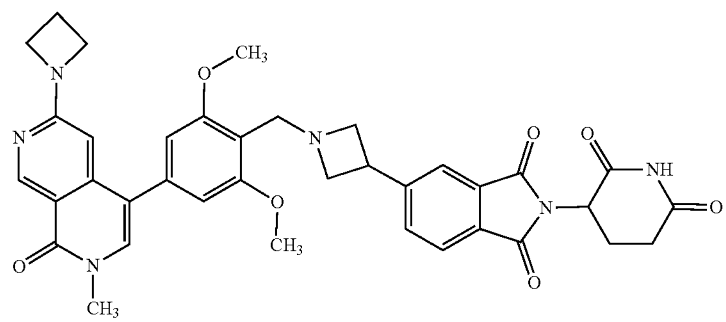 [SMILES: COc1cc(-c2cn(C)c(=O)c3cnc(N4CCC4)cc23)cc(OC)c1CN1CC(c2ccc3c(c2)C(=O)N(C2CCC(=O)NC2=O)C3=O)C1] |
| D23 | 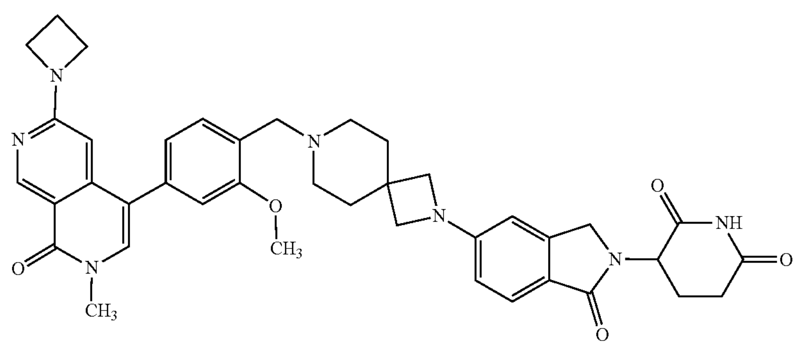 [SMILES: COc1cc(-c2cn(C)c(=O)c3cnc(N4CCC4)cc23)ccc1CN1CCC2(CC1)CN(c1ccc3c(c1)CN(C1CCC(=O)NC1=O)C3=O)C2] |
| D24 | 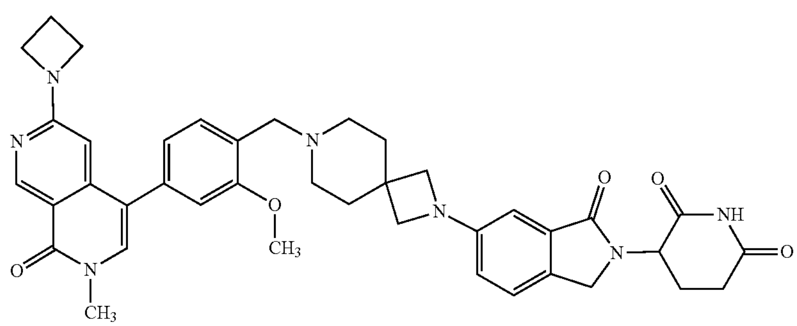 [SMILES: COc1cc(-c2cn(C)c(=O)c3cnc(N4CCC4)cc23)ccc1CN1CCC2(CC1)CN(c1ccc3c(c1)C(=O)N(C1CCC(=O)NC1=O)C3)C2] |

TABLE 1-continued
Compounds D1-D184 of the Disclosure
| Compound No. | Structure |
| --- | --- |
| D25 | 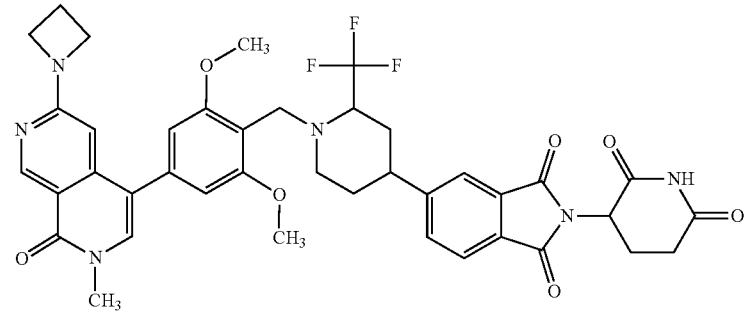 [SMILES: COc1cc(-c2cn(C)c(=O)c3cnc(N4CCC4)cc23)cc(OC)c1CN1CCC(c2ccc3c(c2)C(=O)N(C2CCC(=O)NC2=O)C3=O)CC1C(F)(F)F] |
| D26 | 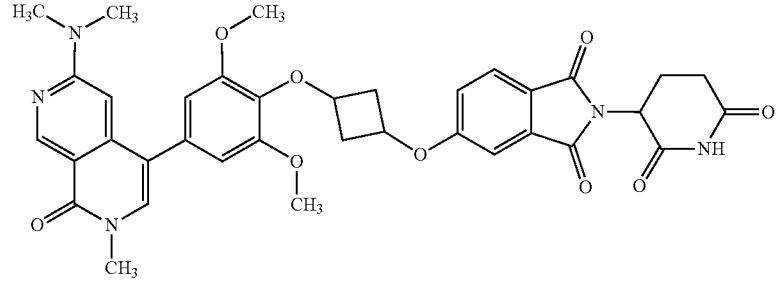 [SMILES: COc1cc(-c2cn(C)c(=O)c3cnc(N(C)C)cc23)cc(OC)c1OC1CC(Oc2ccc3c(c2)C(=O)N(C2CCC(=O)NC2=O)C3=O)C1] |
| D27 | 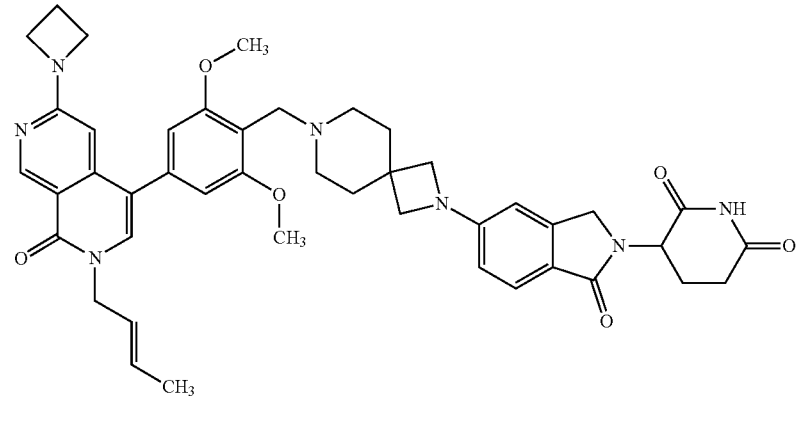 [SMILES: C/C=C/Cn1cc(-c2cc(OC)c(CN3CCC4(CC3)CN(c3ccc5c(c3)CN(C3CCC(=O)NC3=O)C5=O)C4)c(OC)c2)c2cc(N3CCC3)ncc2c1=O] |
| D28 | 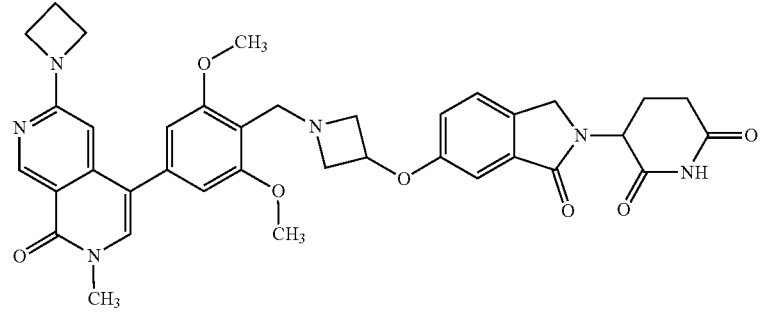 [SMILES: COc1cc(-c2cn(C)c(=O)c3cnc(N4CCC4)cc23)cc(OC)c1CN1CC(Oc2ccc3c(c2)C(=O)N(C2CCC(=O)NC2=O)C3)C1] |

TABLE 1-continued

Compounds D1-D184 of the Disclosure

| Compound No. | Structure |
| --- | --- |
| D29 | 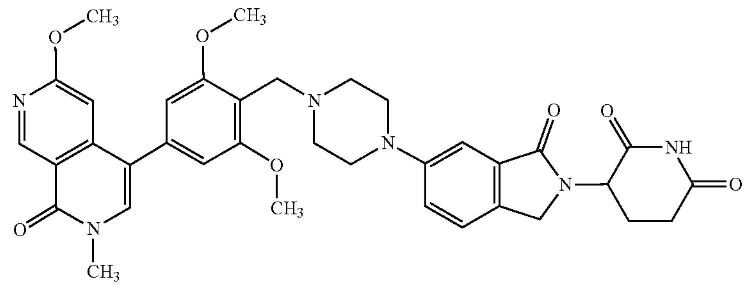 [SMILES: COc1cc2c(-c3cc(OC)c(CN4CCN(c5ccc6c(c5)C(=O)N(C5CCC(=O)NC5=O)C6)CC4)c(OC)c3)cn(C)c(=O)c2cn1] |
| D30 | 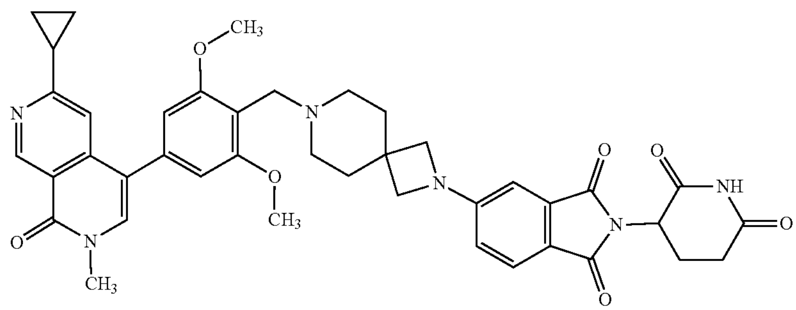 [SMILES: COc1cc(-c2cn(C)c(=O)c3cnc(C4CC4)cc23)cc(OC)c1CN1CCC2(CC1)CN(c1ccc3c(c1)C(=O)N(C1CCC(=O)NC1=O)C3=O)C2] |
| D31 | 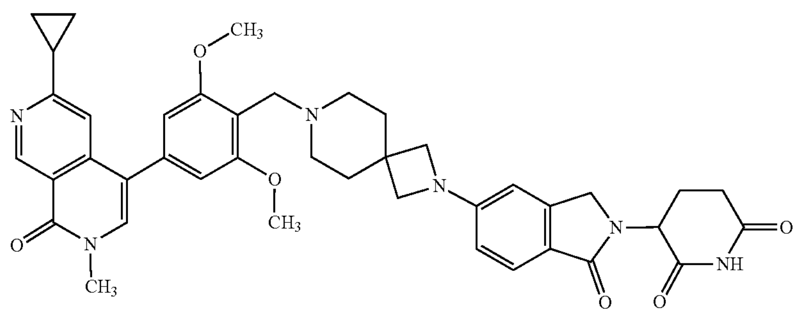 [SMILES: COc1cc(-c2cn(C)c(=O)c3cnc(C4CC4)cc23)cc(OC)c1CN1CCC2(CC1)CN(c1ccc3c(c1)CN(C1CCC(=O)NC1=O)C3=O)C2] |
| D32 | 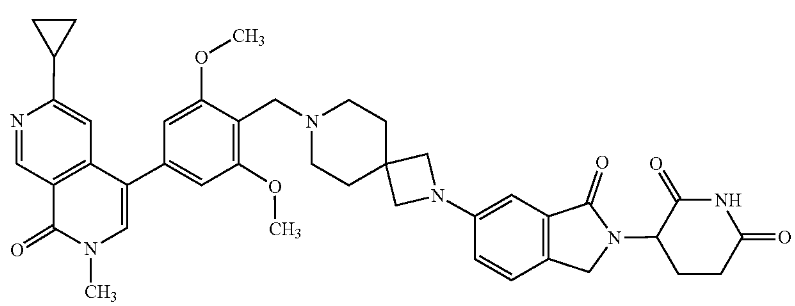 [SMILES: COc1cc(-c2cn(C)c(=O)c3cnc(C4CC4)cc23)cc(OC)c1CN1CCC2(CC1)CN(c1ccc3c(c1)C(=O)N(C1CCC(=O)NC1=O)C3)C2] |
| D33 | 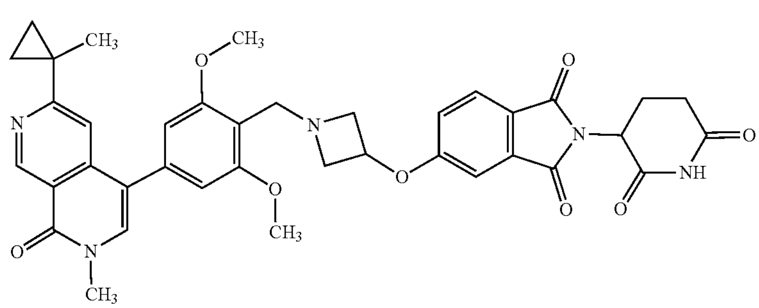 [SMILES: COc1cc(-c2cn(C)c(=O)c3cnc(C4(C)CC4)cc23)cc(OC)c1CN1CC(Oc2ccc3c(c2)C(=O)N(C2CCC(=O)NC2=O)C3=O)C1] |

TABLE 1-continued
Compounds D1-D184 of the Disclosure
| Compound No. | Structure |
| --- | --- |
| D34 | 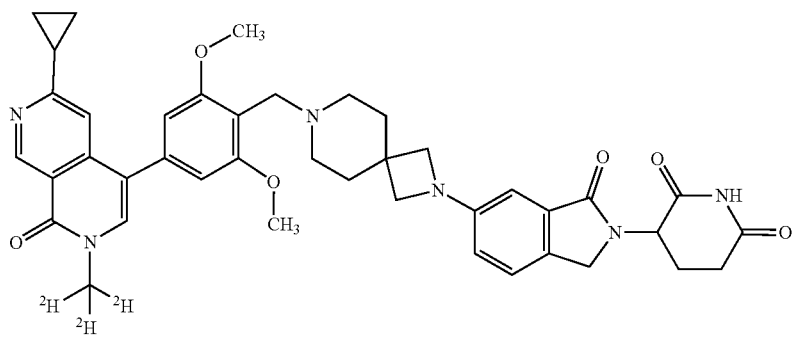 [SMILES: [2H]C([2H])([2H])n1cc(-c2cc(OC)c(CN3CCC4(CC3)CN(c3ccc5c(c3)C(=O)N(C3CCC(=O)NC3=O)C5)C4)c(OC)c2)c2cc(C3CC3)ncc2c1=O] |
| D35 | 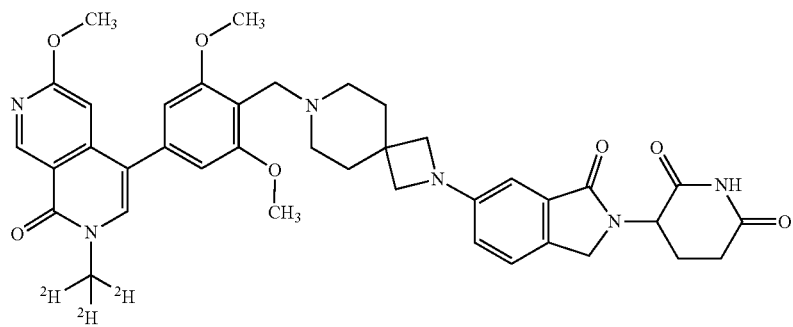 [SMILES: [2H]C([2H])([2H])n1cc(-c2cc(OC)c(CN3CCC4(CC3)CN(c3ccc5c(c3)C(=O)N(C3CCC(=O)NC3=O)C5)C4)c(OC)c2)c2cc(OC)ncc2c1=O] |
| D36 | 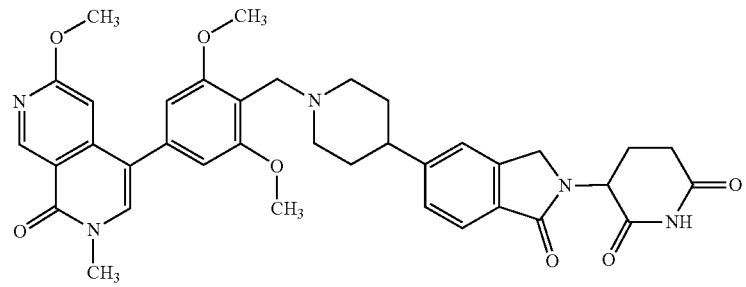 [SMILES: COc1cc2c(-c3cc(OC)c(CN4CCC(c5ccc6c(c5)CN(C5CCC(=O)NC5=O)C6=O)CC4)c(OC)c3)cn(C)c(=O)c2cn1] |
| D37 | 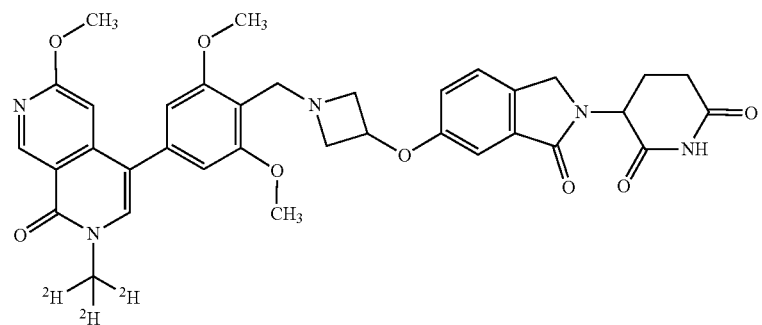 [SMILES: [2H]C([2H])([2H])n1cc(-c2cc(OC)c(CN3CC(Oc4ccc5c(c4)C(=O)N(C4CCC(=O)NC4=O)C5)C3)c(OC)c2)c2cc(OC)ncc2c1=O] |

TABLE 1-continued

Compounds D1-D184 of the Disclosure

| Compound No. | Structure |
|---|---|
| D38 | (structure) |
| D39 | (structure) |
| D40 | (structure) |
| D41 | (structure) |

TABLE 1-continued
Compounds D1-D184 of the Disclosure
| Compound No. | Structure |
|---|---|
| D42 | 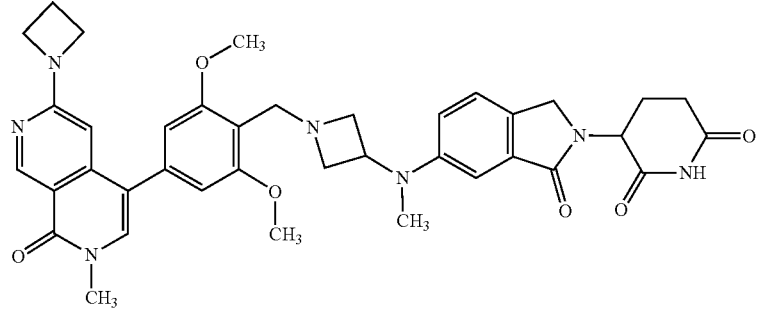 [SMILES: COc1cc(-c2cn(C)c(=O)c3cnc(N4CCC4)cc23)cc(OC)c1CN1CC(N(C)c2ccc3c(c2)C(=O)N(C2CCC(=O)NC2=O)C3)C1] |
| D43 | 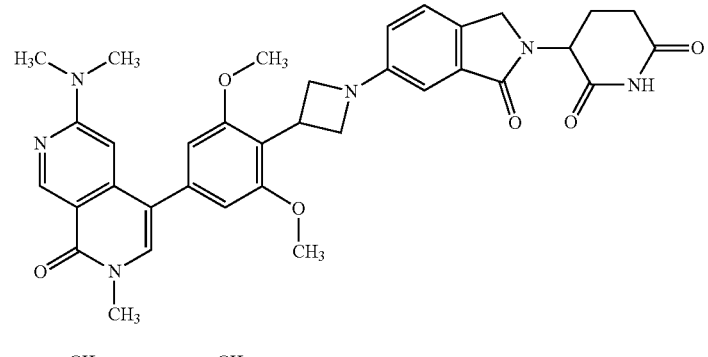 |
| D44 | 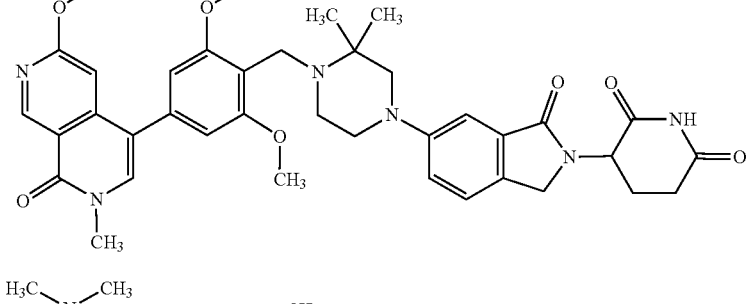 |
| D45 | 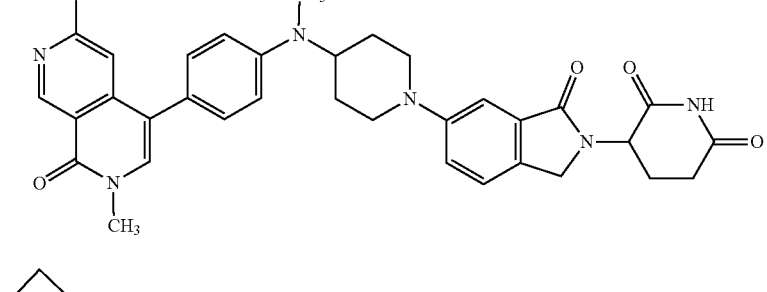 |
| D46 | 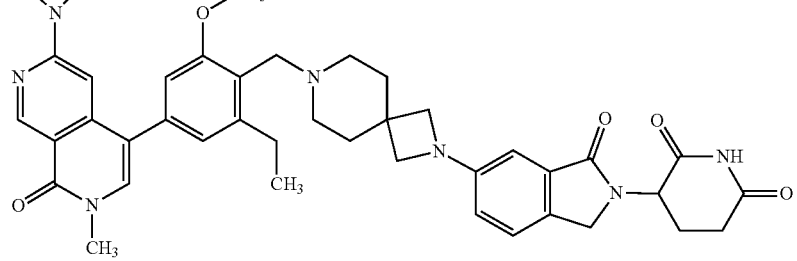 |

TABLE 1-continued

Compounds D1-D184 of the Disclosure

| Compound No. | Structure |
| --- | --- |
| D47 | 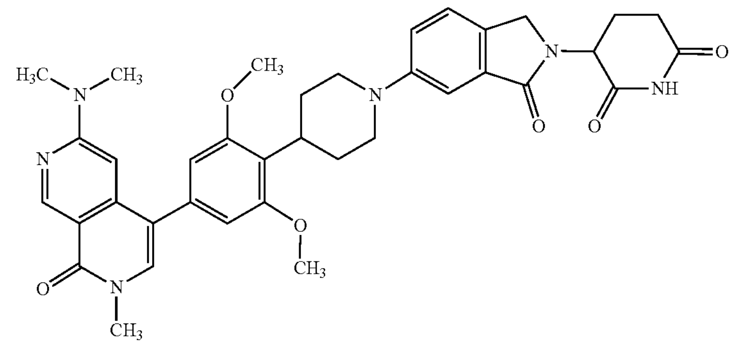 [SMILES: COc1cc(-c2cn(C)c(=O)c3cnc(N(C)C)cc23)cc(OC)c1C1CCN(c2ccc3c(c2)C(=O)N(C2CCC(=O)NC2=O)C3)CC1] |
| D48 | 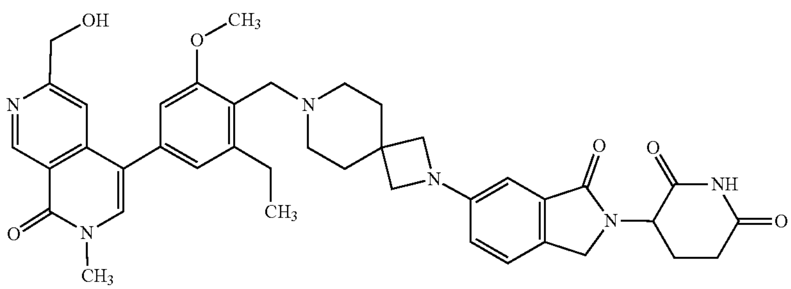 [SMILES: CCc1cc(-c2cn(C)c(=O)c3cnc(CO)cc23)cc(OC)c1CN1CCC2(CC1)CN(c1ccc3c(c1)C(=O)N(C1CCC(=O)NC1=O)C3)C2] |
| D49 | 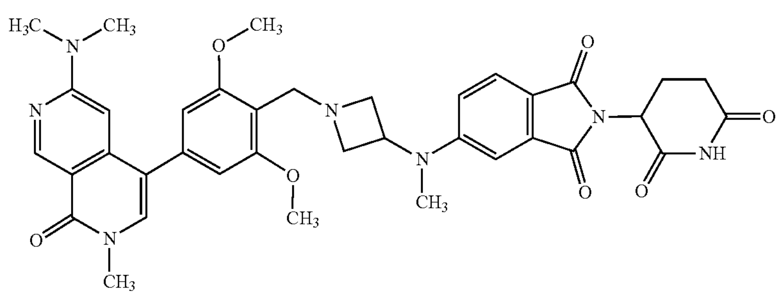 [SMILES: COc1cc(-c2cn(C)c(=O)c3cnc(N(C)C)cc23)cc(OC)c1CN1CC(N(C)c2ccc3c(c2)C(=O)N(C2CCC(=O)NC2=O)C3=O)C1] |
| D50 | 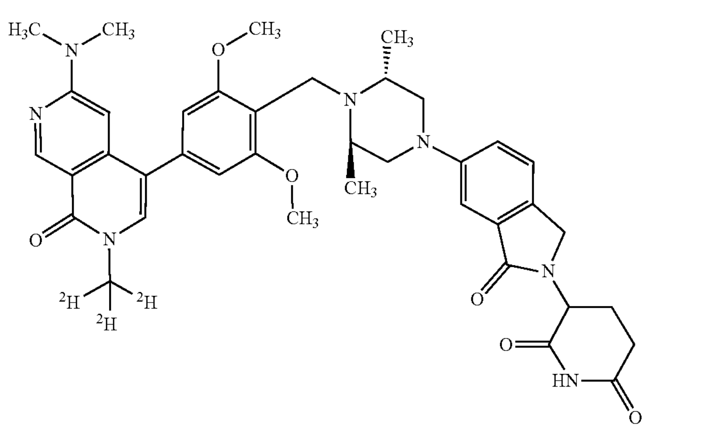 [SMILES: [2H]C([2H])([2H])n1cc(-c2cc(OC)c(CN3[C@H](C)CN(c4ccc5c(c4)C(=O)N(C4CCC(=O)NC4=O)C5)C[C@H]3C)c(OC)c2)c2cc(N(C)C)ncc2c1=O] |

TABLE 1-continued

Compounds D1-D184 of the Disclosure

| Compound No. | Structure |
| --- | --- |
| D51 | 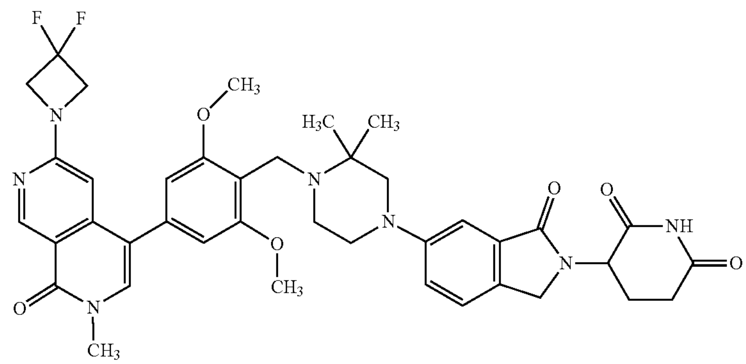 [SMILES: COc1cc(-c2cn(C)c(=O)c3cnc(N4CC(F)(F)C4)cc23)cc(OC)c1CN1CCN(c2ccc3c(c2)C(=O)N(C2CCC(=O)NC2=O)C3)CC1(C)C] |
| D52 | 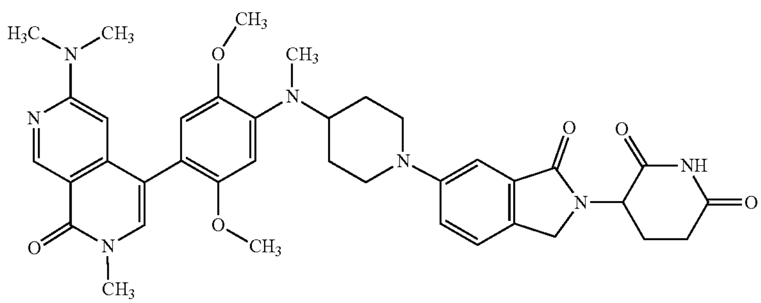 [SMILES: COc1cc(N(C)C2CCN(c3ccc4c(c3)C(=O)N(C3CCC(=O)NC3=O)C4)CC2)c(OC)cc1-c1cn(C)c(=O)c2cnc(N(C)C)cc12] |
| D53 | 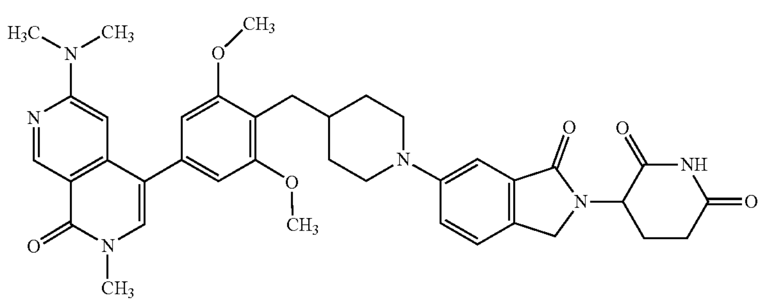 [SMILES: COc1cc(-c2cn(C)c(=O)c3cnc(N(C)C)cc23)cc(OC)c1CC1CCN(c2ccc3c(c2)C(=O)N(C2CCC(=O)NC2=O)C3)CC1] |
| D54 | 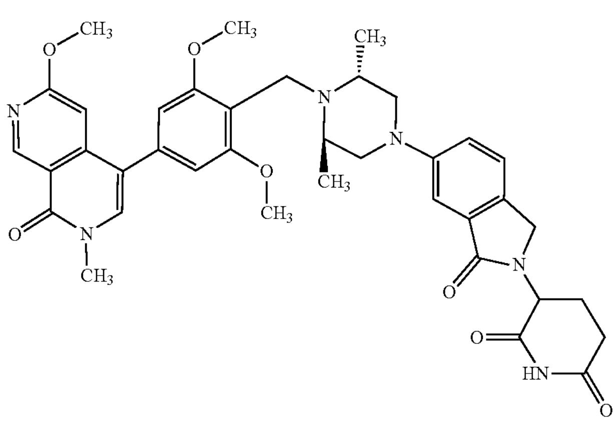 [SMILES: COc1cc2c(-c3cc(OC)c(CN4[C@H](C)CN(c5ccc6c(c5)C(=O)N(C5CCC(=O)NC5=O)C6)C[C@H]4C)c(OC)c3)cn(C)c(=O)c2cn1] |

TABLE 1-continued

Compounds D1-D184 of the Disclosure

| Compound No. | Structure |
| --- | --- |
| D55 | 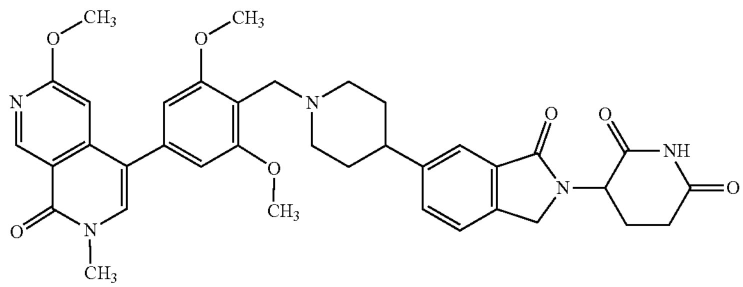 [SMILES: COc1cc2c(-c3cc(OC)c(CN4CCC(c5ccc6c(c5)C(=O)N(C5CCC(=O)NC5=O)C6)CC4)c(OC)c3)cn(C)c(=O)c2cn1] |
| D56 | 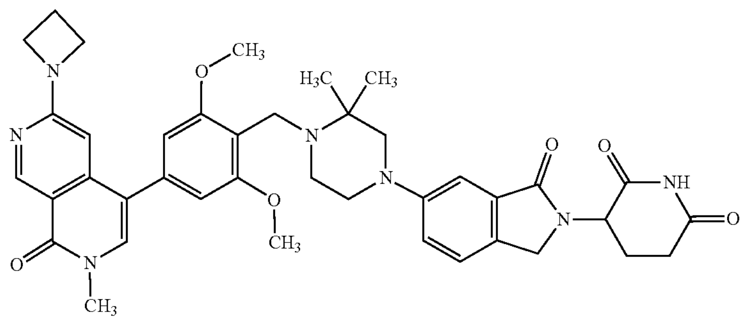 [SMILES: COc1cc(-c2cn(C)c(=O)c3cnc(N4CCC4)cc23)cc(OC)c1CN1CCN(c2ccc3c(c2)C(=O)N(C2CCC(=O)NC2=O)C3)CC1(C)C] |
| D57 | 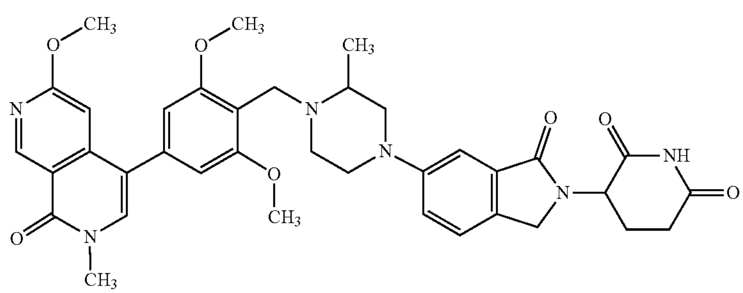 [SMILES: COc1cc2c(-c3cc(OC)c(CN4CCN(c5ccc6c(c5)C(=O)N(C5CCC(=O)NC5=O)C6)CC4C)c(OC)c3)cn(C)c(=O)c2cn1] |
| D58 | 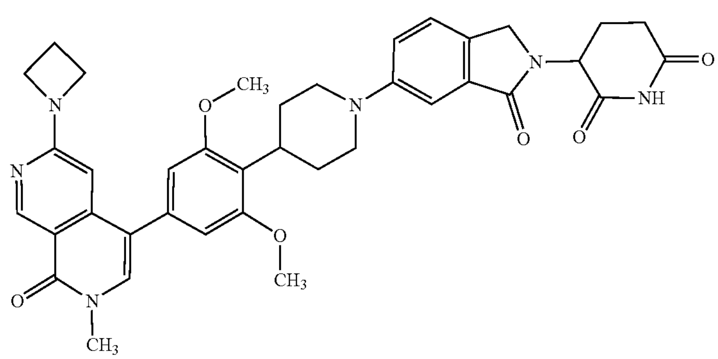 [SMILES: COc1cc(-c2cn(C)c(=O)c3cnc(N4CCC4)cc23)cc(OC)c1C1CCN(c2ccc3c(c2)C(=O)N(C2CCC(=O)NC2=O)C3)CC1] |

TABLE 1-continued
Compounds D1-D184 of the Disclosure
| Compound No. | Structure |
|---|---|
| D59 | 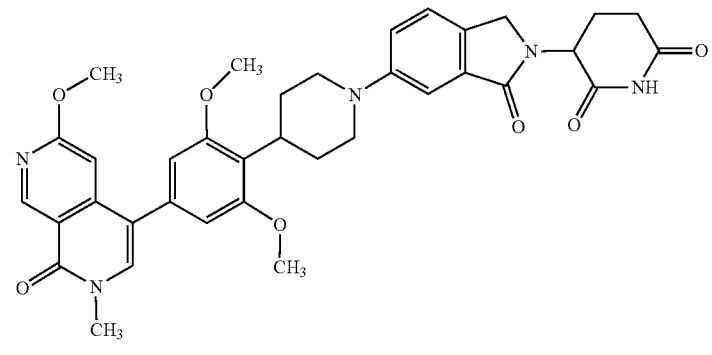 [SMILES: COc1cc2c(-c3cc(OC)c(C4CCN(c5ccc6c(c5)C(=O)N(C5CCC(=O)NC5=O)C6)CC4)c(OC)c3)cn(C)c(=O)c2cn1] |
| D60 | 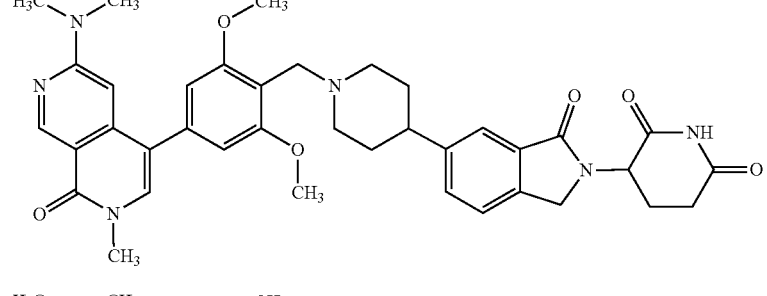 |
| D61 | 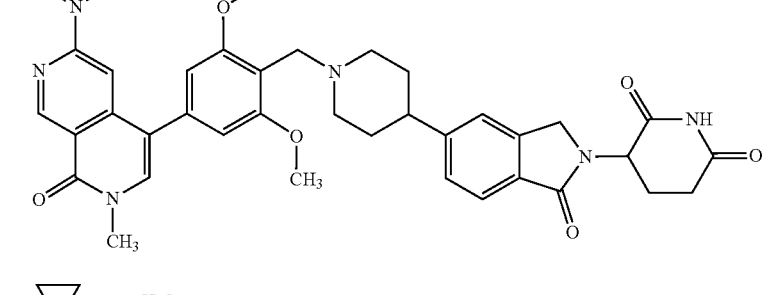 |
| D62 | 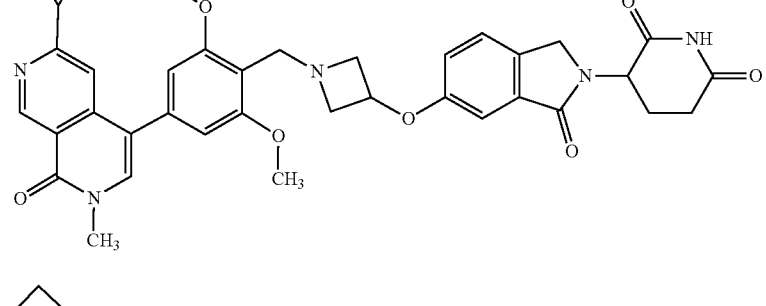 |
| D63 | 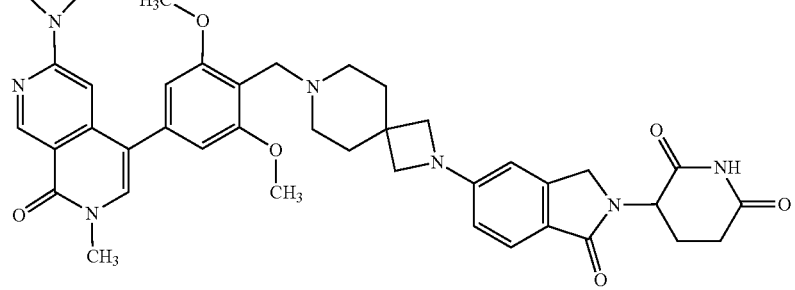 |

TABLE 1-continued

Compounds D1-D184 of the Disclosure

| Compound No. | Structure |
| --- | --- |
| D64 | 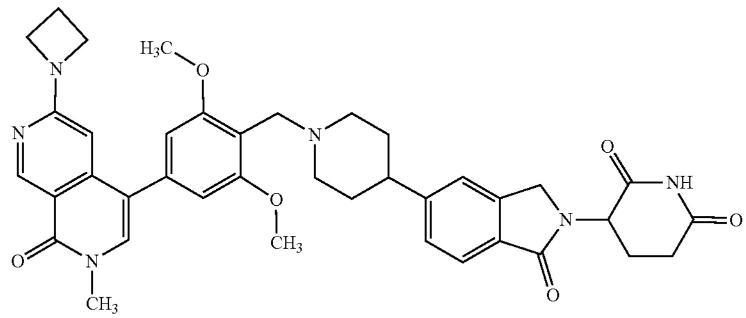 [SMILES: COc1cc(-c2cn(C)c(=O)c3cnc(N4CCC4)cc23)cc(OC)c1CN1CCC(c2ccc3c(c2)CN(C2CCC(=O)NC2=O)C3=O)CC1] |
| D65 | 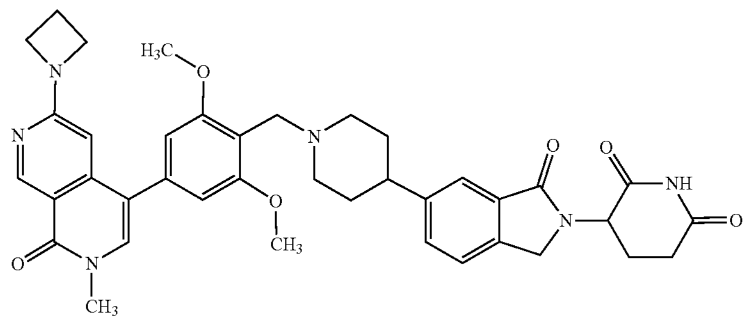 [SMILES: COc1cc(-c2cn(C)c(=O)c3cnc(N4CCC4)cc23)cc(OC)c1CN1CCC(c2ccc3c(c2)C(=O)N(C2CCC(=O)NC2=O)C3)CC1] |
| D66 | 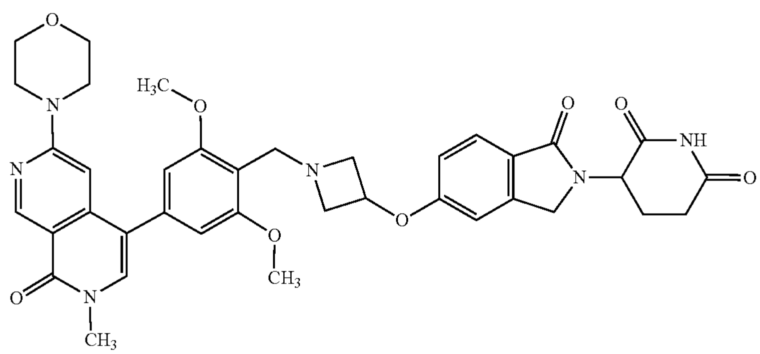 [SMILES: COc1cc(-c2cn(C)c(=O)c3cnc(N4CCOCC4)cc23)cc(OC)c1CN1CC(Oc2ccc3c(c2)CN(C2CCC(=O)NC2=O)C3=O)C1] |

In another aspect, the disclosure features a pharmaceutical composition including any of the foregoing compounds, or pharmaceutically acceptable salts thereof, and a pharmaceutically acceptable excipient.

In an aspect, the disclosure features a method of inhibiting the level and/or activity of BRD9 in a cell, the method involving contacting the cell with an effective amount of any of the foregoing compounds, or pharmaceutically acceptable salts thereof, or a pharmaceutical composition thereof.

In another aspect, the disclosure features a method of reducing the level and/or activity of BRD9 in a cell, the method involving contacting the cell with an effective amount of any of the foregoing compounds, or pharmaceutically acceptable salts thereof, or a pharmaceutical composition thereof.

In some embodiments, the cell is a cancer cell.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), lung cancer (e.g., non-small cell lung cancer (e.g., squamous or adenocarcinoma)), stomach cancer, or breast cancer. In some embodiments, the cancer is sarcoma (e.g., synovial sarcoma or Ewing's sarcoma). In some embodiments, the sarcoma is synovial sarcoma.

In an aspect, the disclosure features a method of treating a BAF complex-related disorder in a subject in need thereof, the method involving administering to the subject an effective amount of any of the foregoing compounds, or pharmaceutically acceptable salts thereof, or a pharmaceutical composition thereof. In some embodiments, the BAF complex-related disorder is cancer. In some embodiments, the BAF complex-related disorder is infection.

In another aspect, the disclosure features a method of treating an SS18-SSX fusion protein-related disorder in a subject in need thereof, the method involving administering to the subject an effective amount of any of the foregoing compounds, or pharmaceutically acceptable salts thereof, or a pharmaceutical composition thereof. In some embodiments, the SS18-SSX fusion protein-related disorder is cancer. In some embodiments, the SS18-SSX fusion protein-related disorder is infection. In some embodiments of any of the foregoing methods, the SS18-SSX fusion protein is a SS18-SSX1 fusion protein, a SS18-SSX2 fusion protein, or a SS18-SSX4 fusion protein.

In yet another aspect, the disclosure features a method of treating a BRD9-related disorder in a subject in need thereof, the method involving administering to the subject an effective amount of any of the foregoing compounds, or pharmaceutically acceptable salts thereof, or a pharmaceutical composition thereof. In some embodiments, the BRD9-related disorder is cancer. In some embodiments, the BRD9-related disorder is infection.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments, the infection is viral infection (e.g., an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)); Flaviviridae family (e.g. hepatitis C virus (HCV)); Adenoviridae family (e.g. Human Adenovirus); Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvirus K*, CMV, varicella-zoster virus); Papillomaviridae family (e.g. Human Papillomavirus (HPV, HPV E1)); Parvoviridae family (e.g. Parvovirus B19); Polyomaviridae family (e.g. JC virus and BK virus); Paramyxoviridae family (e.g. Measles virus); or Togaviridae family (e.g. Rubella virus)). In some embodiments, the disorder is Coffin Siris, Neurofibromatosis (e.g., NF-1, NF-2, or Schwannomatosis), or Multiple Meningioma. In an aspect, the disclosure features a method of treating a cancer in a subject in need thereof, the method including administering to the subject an effective amount of any of the foregoing compounds, or pharmaceutically acceptable salts thereof, or any of the foregoing pharmaceutical compositions.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In another aspect, the disclosure features a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvirus K*, CMV, varicella-zoster virus), Papillomaviridae family (e.g. Human Papillomavirus (HPV, HPV E1)), Parvoviridae family (e.g. Parvovirus B19), Polyomaviridae family (e.g. JC virus and BK virus), Paramyxoviridae family (e.g. Measles virus), Togaviridae family (e.g. Rubella virus).

In another embodiment of any of the foregoing methods, the method further includes administering to the subject an additional anticancer therapy (e.g., chemotherapeutic or cytotoxic agent or radiotherapy).

In particular embodiments, the additional anticancer therapy is: a chemotherapeutic or cytotoxic agent (e.g., doxorubicin or ifosfamide), a differentiation-inducing agent (e.g., retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having anticancer activity can be found in L. Brunton, B. Chabner and B. Knollman (eds).

Goodman and Gilman's The Pharmacological Basis of Therapeutics, Twelfth Edition, 2011, McGraw Hill Companies, New York, NY.

In particular embodiments, the compound of the invention and the additional anticancer therapy and any of the foregoing compounds or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The term "aliphatic," as used herein, refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$, or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic," as used herein, refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, and alkyl-O-haloalkyl.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms). An "alkylene" is a divalent alkyl group.

The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms). An "alkenylene" is a divalent alkenyl group.

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms). An "alkynylene" is a divalent alkynyl group.

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the compounds described herein can be an unsubstituted amino (i.e., —NH$_2$) or a substituted amino (i.e., —N(R$^{N1}$)$_2$).

The term "aryl," as used herein, refers to an aromatic mono- or polycarbocyclic radical of, e.g., 6 to 12, carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as C$_1$-C$_6$ alkyl C$_6$-C$_{10}$ aryl, C$_1$-C$_{10}$ alkyl C$_6$-C$_{10}$ aryl, or C$_1$-C$_{20}$ alkyl C$_6$-C$_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —N$_3$ group.

The term "bridged cyclyl," as used herein, refers to a bridged polycyclic group of 5 to 20 atoms, containing from 1 to 3 bridges. Bridged cyclyl includes bridged carbocyclyl (e.g., norbornyl) and bridged heterocyclyl (e.g., 1,4-diazabicyclo[2.2.2]octane).

The term "cyano," as used herein, represents a —CN group.

The term "carbocyclyl," as used herein, refers to a non-aromatic C$_3$-C$_{12}$, monocyclic or polycyclic (e.g., bicyclic or tricyclic) structure in which the rings are formed by carbon atoms. Carbocyclyl structures include cycloalkyl groups (e.g., cyclohexyl) and unsaturated carbocyclyl radicals (e.g., cyclohexenyl). Polycyclic carbocyclyl includes spirocyclic carbocyclyl, bridged carbocyclyl, and fused carbocyclyl. A "carbocyclylene" is a divalent carbocyclyl group.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The terms "halo" or "halogen," as used herein, mean a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers to alkyl-O— (e.g., methoxy and ethoxy), and an "alkylamino" which, as used herein, refers to —N(alkyl)R$^{Na}$, where R$^{Na}$ is H or alkyl (e.g., methylamino). A "heteroalkylene" is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers to alkenyl-O—. A "heteroalkenylene" is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers to alkynyl-O—. A "heteroalkynylene" is a divalent heteroalkynyl group.

The term "heteroaryl," as used herein, refers to an aromatic monocyclic or polycyclic structure of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as C$_1$-C$_6$ alkyl C$_2$-C$_9$ heteroaryl, C$_1$-C$_{10}$ alkyl C$_2$-C$_9$ heteroaryl, or C$_1$-C$_{20}$ alkyl C$_2$-C$_9$ heteroaryl). In some embodiments, the alkyl and the heteroaryl each can be further substituted with 1, 2, 3, or 4 substituent groups as defined herein for the respective groups.

The term "heterocyclyl," as used herein, refers a monocyclic or polycyclic radical (e.g., bicyclic or tricyclic) having 3 to 12 atoms having at least one non-aromatic ring containing 1, 2, 3, or 4 ring atoms selected from N, O, or S, and no aromatic ring containing any N, O, or S atoms. Polycyclic heterocyclyl includes spirocyclic heterocyclyl, bridged heterocyclyl, and fused heterocyclyl. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl. A "heterocyclylene" is a divalent heterocyclyl group.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as C$_1$-C$_6$ alkyl C$_2$-C$_9$ heterocyclyl, C$_1$-C$_{10}$ alkyl C$_2$-C$_9$ heterocyclyl, or C$_1$-C$_{20}$ alkyl C$_2$-C$_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "imine," as used herein, represents =NR$^N$ group, where R$^N$ is, e.g., H or alkyl.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH$_2$ or mono- or dialkyl amino), azido, cyano, nitro, oxo, sulfonyl, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds described herein (e.g., compounds of the invention) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein (e.g., the compounds of the invention) may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "adult soft tissue sarcoma" refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi's sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

The term "antisense," as used herein, refers to a nucleic acid comprising a polynucleotide that is sufficiently complementary to all or a portion of a gene, primary transcript, or processed mRNA, so as to interfere with expression of the endogenous gene (e.g., BRD9). "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other.

The term "antisense nucleic acid" includes single-stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity (e.g., 80%, 85%, 86%, 87%, 88%, 89%, 90%, 91%, 92%, 93%, 94%, 95%, 96%, 97%, 98%, 99%, 99.9% identity, or more) with the targeted polypeptide sequence (e.g., a BRD9 polypeptide sequence). The antisense nucleic acid can be complementary to an entire coding strand, or to only a portion thereof. In some embodiments, an antisense nucleic acid molecule is antisense to a "coding region" of the coding strand of a nucleotide sequence. The term "coding region" refers to the region of the nucleotide sequence comprising codons that are translated into amino acid residues. In some embodiments, the antisense nucleic acid molecule is antisense to a "noncoding region" of the coding strand of a nucleotide sequence. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of mRNA, or can be antisense to only a portion of the coding or noncoding region of an mRNA. For example, the antisense oligonucleotide can be complementary to the region surrounding the translation start site. An antisense oligonucleotide can be, for example, about 5, 10, 15, 20, 25, 30, 35, 40, 45, or 50 nucleotides in length.

As used herein, the term "BAF complex" refers to the BRG1- or HRBM-associated factors complex in a human cell.

As used herein, the term "BAF complex-related disorder" refers to a disorder that is caused or affected by the level and/or activity of a BAF complex.

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term "cancer" refers to a condition caused by the proliferation of malignant neoplastic cells, such as tumors, neoplasms, carcinomas, sarcomas, leukemias, and lymphomas.

As used herein, the term "BRD9" refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence corresponding to positions 863735-892803 in RefSeq sequence NC_000005.10 of GRCh38.p13 (RefSeq assembly accession No. GCF_000001405.39). The term "BRD9" also refers to natural variants of the wild-type BRD9 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9, which is set forth in SEQ ID NO: 1.

As used herein, the term "BRD9-related disorder" refers to a disorder that is caused or affected by the level and/or activity of BRD9. The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

A "compound of the present invention" and similar terms as used herein, whether explicitly noted or not, refers to compounds useful for treating BAF-related disorders (e.g., cancer or infection) described herein, including, e.g., compounds of Formula I (e.g., a compound of Table 1), as well as salts (e.g., pharmaceutically acceptable salts), solvates, hydrates, stereoisomers (including atropisomers), and tautomers thereof. Those skilled in the art will appreciate that certain compounds described herein can exist in one or more different isomeric (e.g., stereoisomers, geometric isomers, atropisomers, and tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination. Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

As used herein, the term "degrader" refers to a small molecule compound including a degradation moiety, wherein the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

As used herein, the terms "effective amount," "therapeutically effective amount," and "a "sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

The term "inhibitory RNA agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein, or RNA) is down-regulated. Generally, an interfering RNA ("iRNA") is a double-stranded short-interfering RNA (siRNA), short hairpin RNA (shRNA), or single-stranded micro-RNA (miRNA) that results in catalytic degradation of specific mRNAs, and also can be used to lower or inhibit gene expression.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

The terms "miRNA" and "microRNA" refer to an RNA agent, preferably a single-stranded agent, of about 10-50 nucleotides in length, preferably between about 15-25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer ortholog or homolog capable of processing dsRNA structures into siRNAs, miRNAs, siRNA-like or miRNA-like molecules. The term microRNA ("miRNA") is used interchangeably with the term "small temporal RNA" ("stRNA") based on the fact that naturally-occurring miRNAs have been found to be expressed in a temporal fashion (e.g., during development).

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity.

Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

The terms "short interfering RNA" and "siRNA" (also known as "small interfering RNAs") refer to an RNA agent, preferably a double-stranded agent, of about 10-50 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the term "SS18-SSX fusion protein-related disorder" refers to a disorder that is caused or affected by the level and/or activity of SS18-SSX fusion protein.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
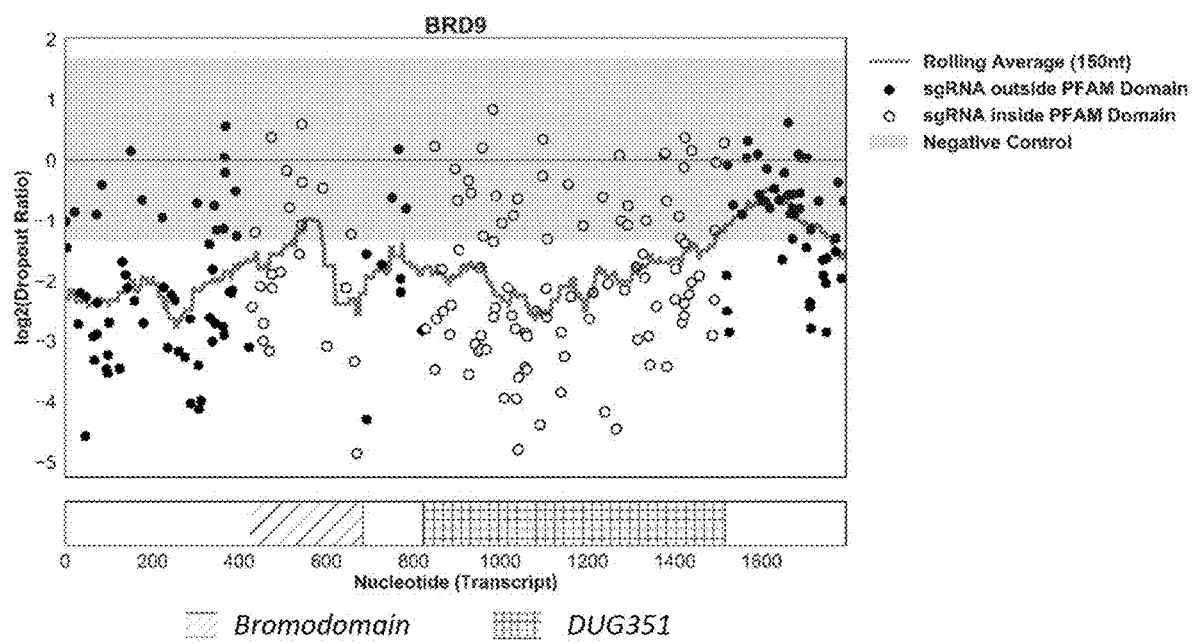
FIG. 1 is a series of graphs illustrating the effect of specific guide RNA (sgRNA) targeting of the BRD9 BAF complex subunit on synovial sarcoma cell growth. The Y-axis indicated the dropout ratio. The X-axis indicates the nucleotide position of the BRD9 gene. The grey box indicates the range of the negative control sgRNAs in the screen. The SYO1 cell line carries SS18-SSX2 fusion protein. The breakpoint joining the N-terminal region of SS18 to the C-terminal region of SSX2 are indicated by the black lines in their respective panel. The linear protein sequence is show with BRD9 PFAM domains annotated from the PFAM database.

The present disclosure features compositions and methods useful for the treatment of BAF-related disorders (e.g., cancer and infection). The disclosure further features compositions and methods useful for inhibition of the level and/or activity of BRD9, e.g., for the treatment of disorders such as cancer (e.g., sarcoma) and infection (e.g., viral infection), e.g., in a subject in need thereof.

Compounds

Compounds described herein reduce the level of an activity related to BRD9, or a related downstream effect, or reduce the level of BRD9 in a cell or subject. Exemplary compounds described herein have the structure according to Formula I.

Formula I is:

A-L-B    Formula I where

L has the structure of Formula II:

$A^1-E^1-F-E^2-A^2$,    Formula II $A^1$ is a bond between the linker and A;
$A^2$ is a bond between B and the linker;
each of $E^1$ and $E^2$ is, independently, absent, $CH_2$, O, or $NCH_3$; and
F is optionally substituted $C_3-C_{10}$ carbocyclylene or optionally substituted $C_{2-10}$ heterocyclylene;
B is a degradation moiety; and A has the structure of Formula III:

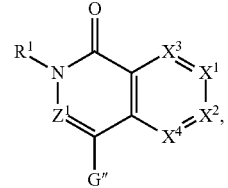

Formula III where
$R^1$ is H, optionally substituted $C_1-C_6$ alkyl, optionally substituted $C_2-C_6$ alkenyl, optionally substituted $C_1-C_6$ heteroalkyl, or optionally substituted $C_3-C_{10}$ carbocyclyl;
$Z^1$ is $CR^2$ or N;
$R^2$ is H, halogen, optionally substituted $C_1-C_6$ alkyl, optionally substituted $C_1-C_6$ heteroalkyl, optionally substituted $C_3-C_{10}$ carbocyclyl, optionally substituted $C_2-C_9$ heterocyclyl, optionally substituted $C_6-C_{10}$ aryl, or optionally substituted $C_2-C_9$ heteroaryl;
$X^1$ is N or CH, and $X^2$ is C—$R^{7'''}$; or $X^1$ is C—$R^{7'''}$, and $X^2$ is N or CH;
$R^{7'''}$ is

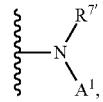

optionally substituted $C_1-C_6$ alkyl, optionally substituted $C_1-C_6$ heteroalkyl, optionally substituted $C_1-C_6$ alkoxy, optionally substituted amino, optionally substituted sulfone, optionally substituted sulfonamide, optionally substituted carbocyclyl having 3 to 6 atoms, or optionally substituted heterocyclyl having 3 to 6 atoms;
$R^{7'}$ is H, optionally substituted $C_1-C_6$ alkyl, optionally substituted $C_1-C_6$ heteroalkyl, or optionally substituted $C_3-C_{10}$ carbocyclyl;
$X^3$ is N or CH;
$X^4$ is N or CH;
G" is

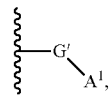

optionally substituted $C_3-C_{10}$ carbocyclyl, $C_2-C_9$ heterocyclyl, optionally substituted $C_6-C_{10}$ aryl, or optionally substituted $C_2-C_9$ heteroaryl;
G' is optionally substituted $C_3-C_{10}$ carbocyclylene, $C_2-C_9$ heterocyclylene, optionally substituted $C_6-C_{10}$ arylene, or optionally substituted $C_2-C_9$ heteroarylene; and
$A^1$ is a bond between A and the linker,
where G" is

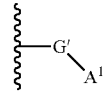

or R⁷‴ is

or a pharmaceutically acceptable salt thereof.

In some embodiments, the compound has the structure of any one of compounds D1-D66 in Table 1, or a pharmaceutically acceptable salt thereof.

Other embodiments, as well as exemplary methods for the synthesis of production of these compounds, are described herein.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Preferably, the methods of the inventions include an oral administration of a compound of the invention to a subject in need thereof. In some embodiments, methods of the invention are particularly preferred for subjects suffering from a sarcoma (e.g., synovial sarcoma). In some embodiments, methods of the invention are particularly preferred for subjects suffering from a breast cancer. In some embodiments, methods of the invention are particularly preferred for subjects suffering from a lung cancer (e.g., non-small cell lung cancer). In some embodiments, methods of the invention are particularly preferred for subjects suffering from an ovarian cancer. In some embodiments, methods of the invention are particularly preferred for subjects suffering from acute myeloid leukemia (AML).

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; Ionidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18:233a (1999), and Douillard et al., *Lancet* 355(9209):1041-1047 (2000).

In some embodiments, the second therapeutic agent is a DNA damaging agent (e.g., a platinum-based antineoplastic agent, topoisomerase inhibitors, PARP inhibitors, alkylating antineoplastic agents, and ionizing radiation).

Examples of platinum-based antineoplastic agent that may be used as a second therapeutic agent in the compositions and methods of the invention are cisplatin, carboplatin, oxaliplatin, dicycloplatin, eptaplatin, lobaplatin, miriplatin, nedaplatin, triplatin tetranitrate, phenanthrilplatin, picoplatin, and satraplatin. In some embodiments, the second therapeutic agent is cisplatin and the treated cancer is a testicular cancer, ovarian cancer, or a bladder cancer (e.g., advanced bladder cancer). In some embodiments, the second therapeutic agent is carboplatin and the treated cancer is an ovarian cancer, lung cancer, head and neck cancer, brain cancer, or neuroblastoma. In some embodiments, the second therapeutic agent is oxaliplatin and the treated cancer is a colorectal cancer. In some embodiments, the second therapeutic agent is dicycloplatin and the treated cancer is a non-small cell ung cancer or prostate cancer. In some embodiments, the second therapeutic agent is eptaplatin and the treated cancer is a gastric cancer. In some embodiments, the second therapeutic agent is lobaplatin and the treated cancer is a breast cancer. In some embodiments, the second therapeutic agent is miriplatin and the treated cancer is a hepatocellular carcinoma. In some embodiments, the second therapeutic agent is nedaplatin and the treated cancer is a nasopharyngeal carcinoma, esophageal cancer, squamous cell carcinoma, or cervical cancer. In some embodiments, the second therapeutic agent is triplatin tetranitrate and the treated cancer is a lung cancer (e.g., small cell lung cancer) or pancreatic cancer. In some embodiments, the second therapeutic agent is picoplatin and the treated cancer is a lung cancer (e.g., small cell lung cancer), prostate cancer, bladder cancer, or colorectal cancer. In some embodiments, the second therapeutic agent is satrapltin and the treated cancer is a prostate cancer, breast cancer, or lung cancer.

Examples of topoisomerase inhibitors that may be used as a second therapeutic agent in the compositions and methods of the invention are etoposide, teniposide, doxorubicin, daunorubicin, mitoxantrone, amsacrine, ellipticine, irinotecan, topotecan, camptothecin, and diflomotecan. In some embodiments, the second therapeutic agent is etoposide and the treated cancer is a lung cancer (e.g., small cell lung cancer) or testicular cancer. In some embodiments, the second therapeutic agent is teniposide and the treated cancer is an acute lymphoblastic leukemia (e.g., childhood acute lymphoblastic leukemia). In some embodiments, the second therapeutic agent is doxorubicin and the treated cancer is an acute lymphoblastic leukemia, acute myeloblastic leukemia, Hodgkin lymphoma, Non-Hodgkin lymphoma, breast cancer, Wilm's tumor, neuroblastoma, soft tissue sarcoma, bone sarcomas, ovarian carcinoma, transitional cell bladder carcinoma, thyroid carcinoma, gastric carcinoma, or bronchogenic carcinoma. In some embodiments, the second therapeutic agent is daunorubicin and the treated cancer is an acute lymphoblastic leukemia or acute myeloid leukemia. In some embodiments, the second therapeutic agent is mitoxantrone and the treated cancer is a prostate cancer or acute nonlymphocytic leukemia. In some embodiments, the second therapeutic agent is amsacrine and the treated cancer is a leukemia (e.g., acute adult leukemia). In some embodiments, the second therapeutic agent is irinotecan and the treated cancer is a colorectal cancer. In some embodiments, the second therapeutic agent is topotecan and the treated cancer is a lung cancer (e.g., small cell lung cancer). In some embodiments, the second therapeutic agent is diflomotecan and the treated cancer is a lung cancer (e.g., small cell lung cancer).

Examples of alkylating antineoplastic agents that may be used as a second therapeutic agent in the compositions and methods of the invention are cyclophosphamide, uramustine, melphalan, chlorambucil, ifosfamide, bendamustine, carmustine, lomustine, chlorozotocin, fotemustine, nimustine, ranimustine, busulfan, improsulfan, piposulfan, chlornaphazine, cholophosphamide, estramustine, mechlorethamine, mechlorethamine oxide hydrochloride, novembichin, phenesterine, prednimustine, trofosfamide, procarbazine, altretamine, dacarbazine, mitozolomide, and temozolomide. In some embodiments, the second therapeutic agent is cyclophosphamide and the treated cancer is a Non-Hodgking lymphoma. In some embodiments, the second therapeutic agent is melphalan and the treated cancer is a multiple myeloma, ovarian cancer, or melanoma. In some embodiments, the second therapeutic agent is chlorambucil and the treated cancer is a chronic lymphatic leukemia, malignant lymphoma (e.g., lymphosarcoma, giant follicular lymphoma, or Hodgkin's lymphoma). In some embodiments, the second therapeutic agent is ifosfamide and the treated cancer is a testicular cancer. In some embodiments, the second therapeutic agent is bendamustine and the treated cancer is a chronic lymphocytic leukemia or non-Hodgkin lymphoma. In some embodiments, the second therapeutic agent is carmustine and the treated cancer is a brain cancer (e.g., glioblastoma, brainstem glioma, medulloblastoma, astrocytoma, ependymoma, or a metastatic brain tumor), multiple myeloma, Hodgkin's disease, or Non-Hodgkin's lymphoma. In some embodiments, the second therapeutic agent is lomustine and the treated cancer is a brain cancer or Hodgkin's lymphoma. In some embodiments, the second therapeutic agent is fotemustine and the treated cancer is a melanoma. In some embodiments, the second therapeutic agent is nimustine and the treated cancer is a brain cancer. In some embodiments, the second therapeutic agent is ranimustine and the treated cancer is a chronic myelogenous leukemia or polycythemia vera. In some embodiments, the second therapeutic agent is busulfan and the treated cancer is a chronic myelogenous leukemia. In some embodiments, the second therapeutic agent is improsulfan and the treated cancer is a sarcoma. In some embodiments, the second therapeutic agent is estramustine and the treated cancer is a prostate cancer (e.g., prostate carcinoma). In some embodiments, the second therapeutic agent is mechlomethamine and the treated cancer is a cutaneous T-cell lymphoma. In some embodiments, the second therapeutic agent is trofosfamide and the treated cancer is a sarcoma (e.g., soft tissue sarcoma). In some embodiments, the second therapeutic agent is procarbazine and the treated cancer is a Hodgkin's disease. In some embodiments, the second therapeutic agent is altretamine and the treated cancer is an ovarian cancer. In some embodiments, the second therapeutic agent is dacarbazine and the treated cancer is a melanoma, Hodgkin's lymphoma, or sarcoma. In some embodiments, the second therapeutic agent is temozolomide and the treated cancer is a brain cancer (e.g., astrocytoma or glioblastoma) or lung cancer (e.g., small cell lung cancer).

Examples of PARP inhibitors that may be used as a second therapeutic agent in the compositions and methods of the invention are niraparib, olaparib, rucaparib, talazoparib, veliparib, pamiparib, CK-102, or E7016. Advantageously, the compounds of the invention and a DNA damaging agent may act synergistically to treat cancer. In some embodiments, the second therapeutic agent is niraparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is olaparib and the treated cancer is a lung cancer (e.g., small cell lung cancer), ovarian cancer (e.g., BRCA mutated ovarian cancer), breast cancer (e.g., BRCA mutated breast cancer), fallopian tube cancer (e.g., BRCA mutated fallopian tube cancer), primary peritoneal cancer (e.g., BRCA mutated primary peritoneal cancer), prostate cancer (e.g., castration-resistant prostate cancer), or pancreatic cancer (e.g., pancreatic adenocarcinoma). In some embodiments, the second therapeutic agent is rucaparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is talazoparib and the treated cancer is a breast cancer (e.g., BRCA mutated breast cancer). In some embodiments, the second therapeutic agent is veliparib and the treated cancer is a lung cancer (e.g., non-small cell lung cancer), malenoma, breast cancer, ovarian cancer, prostate cancer, or brain cancer. In some embodiments, the second therapeutic agent is pamiparib and the treated cancer is an ovarian cancer. In some embodiments, the second therapeutic agent is CK-102 and the treated cancer is a lung cancer (e.g., non-small cell lung cancer). In some embodiments, the second therapeutic agent is E7016 and the treated cancer is a melanoma.

Without wishing to be bound by theory, the synergy between the compounds of the invention and DNA damaging agents may be attributed to the necessity of BRD9 for DNA repair; inhibition of BRD9 may sensitize cancer (e.g., cancer cell or cancer tissue) to DNA damaging agents.

In some embodiments, the second therapeutic agent is a JAK inhibitor (e.g., JAK1 inhibitor). Non-limiting examples of JAK inhibitors that may be used as a second therapeutic agent in the compositions and methods of the invention include tofacitinib, ruxolitinib, oclacitinib, baricitinib, peficitinib, fedratinib, upadacitinib, filgotinib, cerdulatinib, gandotinib, lestaurtinib, momelotinib, pacritinib, abrocitinib, solcitinib, itacitinib, or SHRO302. Without wishing to be bound by theory, the synergy between the compounds of the invention and JAK inhibitors may be inhibitor of SAGA complex to their combined effect of downregulating Foxp3+ Treg cells. In some embodiments, the second therapeutic agent is ruxolitinib and the treated cancer is a myeloproliferative neoplasm (e.g., polycythemia or myelofibrosis), ovarian cancer, breast cancer, pancreatic cancer. In some embodiments, the second therapeutic agent is fedratinib and the treated cancer is a myeloproliferative neoplasm (e.g., myelofibrosis). In some embodiments, the second therapeutic agent is cerdulatinib and the treated cancer is a lymphoma (e.g., peripheral T-cell lymphoma). In some embodiments, the second therapeutic agent is gandotinib and the treated cancer is a myeloproliferative neoplasm (e.g., polycythemia or myelofibrosis). In some embodiments, the second therapeutic agent is lestaurtinib and the treated cancer is a myeloproliferative neoplasm (e.g., polycythemia or myelofibrosis), leukemia (e.g., acute myelogenous leukemia), pancreatic cancer, prostate cancer, or neuroblastoma. In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma). In some embodiments, the second therapeutic agent is momelotinib and the treated cancer is a myeloproliferative neoplasm (e.g., polycythemia or myelofibrosis). In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma).

In some embodiments, the second therapeutic agent is an inhibitor of SAGA complex or a component thereof. A SAGA complex inhibitor may be, e.g., an inhibitory antibody or small molecule inhibitor of CCDC101, Tada2B, Tada3, Usp22, Tada1, Taf61, Supt5, Supt20, or a combination thereof. Without wishing to be bound by theory, the synergy between the compounds of the invention and inhibitors of SAGA complex may be attributed to their combined effect of downregulating Foxp3+ Treg cells.

In some embodiments, the second therapeutic agent is a therapeutic agent which is a biologic such a cytokine (e.g., interferon or an interleukin (e.g., IL-2)) used in cancer treatment. In some embodiments the biologic is an antiangiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab);
XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the second therapeutic agent is ipilimumab and the treated cancer is a melanoma, kidney cancer, lung cancer (e.g., non-small cell lung cancer or small cell lung cancer), or prostate cancer. In some embodiments, the second therapeutic agent is tremelimumab and the treated cancer is a melanoma, mesothelioma, or lung cancer (e.g., non-small cell lung cancer). In some embodiments, the second therapeutic agent is nivolumab and the treated cancer is a melanoma, lung cancer (e.g., non-small cell lung cancer or small cell lung cancer), kidney cancer, Hodgkin lymphoma, head and neck cancer (e.g., squamous cell carcinoma of the head and neck), urothelial carcinoma, hepatocellular carcinoma, or colorectal cancer. In some embodiments, the second therapeutic agent is pembrolizumab and the treated cancer is a melanoma, lung cancer (e.g., non-small cell lung cancer or small cell lung cancer), Hodgkin lymphoma, head and neck cancer (e.g., squamous cell carcinoma of the head and neck), primary mediastinal large B-cell lymphoma, urothelial carcinoma, hepatocellular carcinoma, microsatellite instability-high cancer, gastric cancer, esophageal cancer, cervical cancer, Merkel cell carcinoma, kidney carcinoma, or endometrial carcinoma. In some embodiments, the second therapeutic agent is MPDL3280A and the treated cancer is a lung cancer (e.g., non-small cell lung cancer or small cell lung cancer), urothelial carcinoma, hepatocellular carcinoma, or breast cancer. In some embodiments, the second therapeutic agent is MED14736 and the treated cancer is a lung cancer (e.g., non-small cell lung cancer or small cell lung cancer) or urothelial carcinoma. In some embodiments, the second therapeutic agent is MSB0010718C and the treated cancer is a urothelial carcinoma. In some embodiments, the second therapeutic agent is MSB0010718C and the treated cancer is a melanoma, lung cancer (e.g., non-small cell lung cancer), colorectal cancer, kidney cancer, ovarian cancer, pancreatic cancer, gastric cancer, and breast cancer.

Advantageously, the compounds of the invention and a checkpoint inhibitor may act synergistically to treat cancer.

Without wishing to be bound by theory, the synergy between the compounds of the invention and checkpoint inhibitors may be attributed to the checkpoint inhibitor efficacy enhancement associated with the BRD9 inhibition-induced downregulation of Foxp3+ Treg cells.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg.

Alternatively, the dosage amount can be calculated using the body weight of the patient. For example, the dose of a compound, or pharmaceutical composition thereof, administered to a patient may range from 0.1-100 mg/kg.

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Example 1—High Density Tiling sgRNA Screen Against Human BAF Complex Subunits in Synovial Sarcoma Cell Line SYO1

The following example shows that BRD9 sgRNA inhibits cell growth in synovial sarcoma cells.

Procedure: To perform high density sgRNA tiling screen, an sgRNA library against BAF complex subunits was custom synthesized at Cellecta (Mountain View, CA). Sequences of DNA encoding the BRD9-targeting sgRNAs used in this screen are listed in Table 2. Negative and positive control sgRNA were included in the library. Negative controls consisted of 200 sgRNAs that do not target human genome. The positive controls are sgRNAs targeting essential genes (CDC16, GTF2B, HSPA5, HSPA9, PAFAH1B1, PCNA, POLR2L, RPL9, and SF3A3). DNA sequences encoding all positive and negative control sgRNAs are listed in Table 3. Procedures for virus production, cell infection, and performing the sgRNA screen were previously described (Tsherniak et al, Cell 170:564-576 (2017); Munoz et al, Cancer Discovery 6:900-913 (2016)). For each sgRNA, 50 counts were added to the sequencing counts and for each time point the resulting counts were normalized to the total number of counts. The log 2 of the ratio between the counts (defined as dropout ratio) at day 24 and day 1 post-infection was calculated. For negative control sgRNAs, the 2.5 and 97.5 percentile of the log 2 dropout ratio of all non-targeting sgRNAs was calculated and considered as background (grey box in the graph). Protein domains were obtained from PFAM regions defined for the UNIPROT identifier: Q9H8M2.

Results: As shown in FIG. 1, targeted inhibition of the GBAF complex component BRD9 by sgRNA resulted in growth inhibition of the SYO1 synovial sarcoma cell line. sgRNAs against other components of the BAF complexes resulted in increased proliferation of cells, inhibition of cell growth, or had no effect on SYO1 cells. These data show that targeting various subunits of the GBAF complex represents a therapeutic strategy for the treatment of synovial sarcoma.

TABLE 2

BRD9 sgRNA Library

| SEQ ID NO | Nucleic Acid Sequence |
|---|---|
| 203 | CAAGAAGCACAAGAAGCACA |
| 204 | CTTGTGCTTCTTGCCCATGG |
| 205 | CTTCTTGTGCTTCTTGCCCA |
| 206 | ACAAGAAGCACAAGGCCGAG |
| 207 | CTCGTAGGACGAGCGCCACT |
| 208 | CGAGTGGCGCTCGTCCTACG |
| 209 | GAGTGGCGCTCGTCCTACGA |
| 210 | AGGCTTCTCCAGGGGCTTGT |
| 211 | AGATTATGCCGACAAGCCCC |
| 212 | ACCTTCAGGACTAGCTTTAG |
| 213 | AGCTTTAGAGGCTTCTCCAG |
| 214 | CTAGCTTTAGAGGCTTCTCC |
| 215 | TAGCTTTAGAGGCTTCTCCA |
| 216 | CTAAAGCTAGTCCTGAAGGT |
| 217 | GCCTCTAAAGCTAGTCCTGA |
| 218 | CTTCACTTCCTCCGACCTTC |
| 219 | AAGCTAGTCCTGAAGGTCGG |
| 220 | AGTGAAGTGACTGAACTCTC |
| 221 | GTGACTGAACTCTCAGGATC |
| 222 | ATAGTAACTGGAGTCGTGGC |
| 223 | CATCATAGTAACTGGAGTCG |
| 224 | TGACCTGTCATCATAGTAAC |
| 225 | ACTCCAGTTACTATGATGAC |
| 226 | CTTTGTGCCTCTCTCGCTCA |
| 227 | GGTCAGACCATGAGCGAGAG |
| 228 | GAAGAAGAAGAAGTCCGAGA |
| 229 | GTCCAGATGCTTCTCCTTCT |
| 230 | GTCCGAGAAGGAGAAGCATC |
| 231 | GGAGAAGCATCTGGACGATG |
| 232 | TGAGGAAAGAAGGAAGCGAA |
| 233 | ATCTGGACGATGAGGAAAGA |

TABLE 2-continued

BRD9 sgRNA Library

| SEQ ID NO | Nucleic Acid Sequence |
|---|---|
| 234 | AGAAGAAGCGGAAGCGAGAG |
| 235 | GAAGAAGCGGAAGCGAGAGA |
| 236 | CCGCCCAGGAAGAGAAGAAG |
| 237 | AGAGAGGGAGCACTGTGACA |
| 238 | AGGGAGCACTGTGACACGGA |
| 239 | GAGGGAGCACTGTGACACGG |
| 240 | GCACTGTGACACGGAGGGAG |
| 241 | GAGGCTGACGACTTTGATCC |
| 242 | AGGCTGACGACTTTGATCCT |
| 243 | TCCACCTCCACCTTCTTCCC |
| 244 | CGACTTTGATCCTGGGAAGA |
| 245 | CTTTGATCCTGGGAAGAAGG |
| 246 | TGATCCTGGGAAGAAGGTGG |
| 247 | TCCTGGGAAGAAGGTGGAGG |
| 248 | CGGACTGGCCGATCTGGGGG |
| 249 | ACGCTCGGACTGGCCGATCT |
| 250 | AGGTGGAGCCGCCCCCAGAT |
| 251 | CGCTCGGACTGGCCGATCTG |
| 252 | GCTCGGACTGGCCGATCTGG |
| 253 | CACGCTCGGACTGGCCGATC |
| 254 | TGTGTCCGGCACGCTCGGAC |
| 255 | CTGGCTGTGTCCGGCACGCT |
| 256 | ATCGGCCAGTCCGAGCGTGC |
| 257 | CACCCTTGCCTGGCTGTGTC |
| 258 | CGAGCGTGCCGGACACAGCC |
| 259 | TGTTCCAGGAGTTGCTGAAT |
| 260 | CACACCTATTCAGCAACTCC |
| 261 | GCTGGCGGAGGAAGTGTTCC |
| 262 | TTTACCTCTGAAGCTGGCGG |
| 263 | CCCCGGTTTACCTCTGAAGC |
| 264 | ACTTCCTCCGCCAGCTTCAG |
| 265 | CAGGAAAAGCAAAAAATCCA |
| 266 | GCTTTCAGAAAAGATCCCCA |
| 267 | AGGAAAAGCAAAAATCCAT |
| 268 | GGAAAAGCAAAAATCCATG |
| 269 | GGAGCAATTGCATCCGTGAC |
| 270 | GTCACGGATGCAATTGCTCC |
| 271 | TTTATTATCATTGAATATCC |
| 272 | AATGATAATAAAACATCCCA |
| 273 | ATAAAACATCCCATGGATTT |
| 274 | TTCATGGTGCCAAAATCCAT |
| 275 | TTTCATGGTGCCAAAATCCA |
| 276 | TAATGAATACAAGTCAGTTA |
| 277 | CAAGTCAGTTACGGAATTTA |
| 278 | ATAATGCAATGACATACAAT |
| 279 | AACTTGTAGTACACGGTATC |
| 280 | CTTCGCCAACTTGTAGTACA |
| 281 | AGATACCGTGTACTACAAGT |
| 282 | GCGAAGAAGATCCTTCACGC |
| 283 | TCATCTTAAAGCCTGCGTGA |
| 284 | TTCTCAGCAGGCAGCTCTTT |
| 285 | CAATGAAGATACAGCTGTTG |
| 286 | ACTGGTACAACTTCAGGGAC |
| 287 | CTTGTACTGGTACAACTTCA |
| 288 | ACTTGTACTGGTACAACTTC |
| 289 | TTGGCAGTTTCTACTTGTAC |
| 290 | TACCTGATAACTTCTCTACT |
| 291 | AGCCGAGTAGAGAAGTTATC |
| 292 | AGCTGCATGTTTGAGCCTGA |
| 293 | GCTGCATGTTTGAGCCTGAA |
| 294 | AAGCTGCAGGCATTCCCTTC |
| 295 | GGTACTGTCCGTCAAGCTGC |
| 296 | AGGGAATGCCTGCAGCTTGA |
| 297 | CTTGACGGACAGTACCGCAG |
| 298 | CGCCAGCACGTGCTCCTCTG |
| 299 | TACCGCAGAGGAGCACGTGC |
| 300 | AGAGGAGCACGTGCTGGCGC |
| 301 | GGAGCACGTGCTGGCGCTGG |
| 302 | AGCACGCAGCTGACGAAGCT |
| 303 | GCACGCAGCTGACGAAGCTC |
| 304 | CAGCTGACGAAGCTCGGGAC |
| 305 | AAGCTCGGGACAGGATCAAC |
| 306 | CCTTGCCGCCTGGGAGGAAC |
| 307 | AGGATCAACCGGTTCCTCCC |
| 308 | ATCAACCGGTTCCTCCCAGG |
| 309 | GCACTACCTTGCCGCCTGGG |

TABLE 2-continued

BRD9 sgRNA Library

| SEQ ID NO | Nucleic Acid Sequence |
|---|---|
| 310 | AGAGCACTACCTTGCCGCCT |
| 311 | CCGGTTCCTCCCAGGCGGCA |
| 312 | TCCTCTTCAGATAGCCCATC |
| 313 | ATGGGCTATCTGAAGAGGAA |
| 314 | GGGCTATCTGAAGAGGAACG |
| 315 | TGGGCTATCTGAAGAGGAAC |
| 316 | TATCTGAAGAGGAACGGGGA |
| 317 | ATCTGAAGAGGAACGGGGAC |
| 318 | TGTTGACCACGCTGTAGAGC |
| 319 | GCTCTACAGCGTGGTCAACA |
| 320 | CGGGAGCCTGCTCTACAGCG |
| 321 | CGTGGTCAACACGGCCGAGC |
| 322 | CCCACCATCAGCGTCCGGCT |
| 323 | ACGGCCGAGCCGGACGCTGA |
| 324 | GGGCACCCACCATCAGCGTC |
| 325 | GCCGAGCCGGACGCTGATGG |
| 326 | CCATGTCCGTGTTGCAGAGG |
| 327 | CCGAGCCGGACGCTGATGGT |
| 328 | CGAGCTCAAGTCCACCGGGT |
| 329 | GCGAGCTCAAGTCCACCGGG |
| 330 | AGAGCGAGCTCAAGTCCACC |
| 331 | GAGAGCGAGCTCAAGTCCAC |
| 332 | GAAGCCTGGGAGTAGCTTAC |
| 333 | CTCTCCAGTAAGCTACTCCC |
| 334 | AGCCCAGCGTGGTGAAGCCT |
| 335 | AAGCCCAGCGTGGTGAAGCC |
| 336 | ACTCCCAGGCTTCACCACGC |
| 337 | CTCCCAGGCTTCACCACGCT |
| 338 | CTCGTCTTTGAAGCCCAGCG |
| 339 | CACTGGAGAGAAAGGTGACT |
| 340 | GCACTGGAGAGAAAGGTGAC |
| 341 | AGTAGTGGCACTGGAGAGAA |
| 342 | CGAAAGCGCAGTAGTGGCAC |
| 343 | CTGCATCGAAAGCGCAGTAG |
| 344 | ATGCAGAATAATTCAGTATT |
| 345 | AGTATTTGGCGACTTGAAGT |
| 346 | CGACTTGAAGTCGGACGAGA |
| 347 | GAGCTGCTCTACTCAGCCTA |
| 348 | CACGCCTGTCTCATCTCCGT |
| 349 | TCAGCCTACGGAGATGAGAC |
| 350 | CAGGCGTGCAGTGTGCGCTG |
| 351 | CCGCGGCCCCTCTAGCCTGC |
| 352 | CATCCTTCACAAACTCCTGC |
| 353 | TAGCCTGCAGGAGTTTGTGA |
| 354 | CAGGAGTTTGTGAAGGATGC |
| 355 | AGGAGTTTGTGAAGGATGCT |
| 356 | TGGGAGCTACAGCAAGAAAG |
| 357 | GAGCTACAGCAAGAAAGTGG |
| 358 | GAAAGTGGTGGACGACCTCC |
| 359 | CGCCTGTGATCTGGTCCAGG |
| 360 | CTCCGCCTGTGATCTGGTCC |
| 361 | GACCTCCTGGACCAGATCAC |
| 362 | CTCCTGGACCAGATCACAGG |
| 363 | GCTGGAAGAGCGTCCTAGAG |
| 364 | TGCAGCCCACCTGCTTCAGC |
| 365 | GACGCTCTTCCAGCTGAAGC |
| 366 | CTCTTCCAGCTGAAGCAGGT |
| 367 | GCTCTTCCAGCTGAAGCAGG |
| 368 | CCTCCAGATGAAGCCAAGGT |
| 369 | GCTTCATCTGGAGGCTTCAT |
| 370 | GGCTTCATCTGGAGGCTTCA |
| 371 | CTTACCTTGGCTTCATCTGG |
| 372 | AAACTTACCTTGGCTTCATC |
| 373 | GAAGCCTCCAGATGAAGCCA |
| 374 | TCCTAGGGTGTCCCCAACCT |
| 375 | CCTAGGGTGTCCCCAACCTG |
| 376 | GTGTCTGTCTCCACAGGTTG |
| 377 | TGTGTCTGTCTCCACAGGTT |
| 378 | CCACAGGTTGGGGACACCCT |
| 379 | AGAGCTGCTGCTGTCTCCTA |
| 380 | CAGAGCTGCTGCTGTCTCCT |
| 381 | AGACAGCAGCAGCTCTGTTC |
| 382 | ATCCACAGAAACGTCGGGAT |
| 383 | GAGATATCCACAGAAACGTC |
| 384 | GGAGATATCCACAGAAACGT |
| 385 | GTCCTATCCCGACGTTTCTG |

TABLE 2-continued

BRD9 sgRNA Library

| SEQ ID NO | Nucleic Acid Sequence |
|---|---|
| 386 | TCTCCATGCTCAGCTCTCTG |
| 387 | CTCACCCAGAGAGCTGAGCA |
| 388 | ATCTCCATGCTCAGCTCTCT |
| 389 | TATCTCCATGCTCAGCTCTC |
| 390 | ATGTCCTGTTTACACAGGGA |
| 391 | TTACACAGGGAAGGTGAAGA |
| 392 | AGTTCAAATGGCTGTCGTCA |
| 393 | TGACGACAGCCATTTGAACT |
| 394 | AAGTTCAAATGGCTGTCGTC |
| 395 | TCGTCTCATCCAAGTTCAAA |
| 396 | TGAGACGACGAAGCTCCTGC |
| 397 | GTGCTTCGTGCAGGTCCTGC |
| 398 | GCAGGACCTGCACGAAGCAC |
| 399 | GCTCCGCCTGTGCTTCGTGC |
| 400 | GGACCTGCACGAAGCACAGG |
| 401 | CACGAAGCACAGGCGGAGCG |
| 402 | AGGCGGAGCGCGGCGGCTCT |
| 403 | AGGGAGCTGAGGTTGGACGA |
| 404 | GTTGGACAGGGAGCTGAGGT |
| 405 | AGGCGTTGGACAGGGAGCTG |
| 406 | CCCTCTCGGAGGCGTTGGAC |
| 407 | CCTCTCGGAGGCGTTGGACA |
| 408 | CTGGTCCCTCTCGGAGGCGT |
| 409 | CCCTGTCCAACGCCTCCGAG |

TABLE 2-continued

BRD9 sgRNA Library

| SEQ ID NO | Nucleic Acid Sequence |
|---|---|
| 410 | CCTGTCCAACGCCTCCGAGA |
| 411 | GTGGTGCTGGTCCCTCTCGG |
| 412 | CAGGTGGTGCTGGTCCCTCT |
| 413 | GCATCTCACCCAGGTGGTGC |
| 414 | CGAGAGGGACCAGCACCACC |
| 415 | GAGAGGGACCAGCACCACCT |
| 416 | GTGGGGCATCTCACCCAGG |
| 417 | CCCCGACACTCAGGCGAGAA |
| 418 | TCCCCGACACTCAGGCGAGA |
| 419 | AGCCCTTCTCGCCTGAGTGT |
| 420 | CTGGCTGCTCCCCGACACTC |
| 421 | CCCTTCTCGCCTGAGTGTCG |
| 422 | GCCCTTCTCGCCTGAGTGTC |
| 423 | TAGGGGTCGTGGGTGACGTC |
| 424 | AAGAAACTCATAGGGGTCGT |
| 425 | GAAGAAACTCATAGGGGTCG |
| 426 | GAGACTGAAGAAACTCATAG |
| 427 | GGAGACTGAAGAAACTCATA |
| 428 | TGGAGACTGAAGAAACTCAT |
| 429 | TCTTCAGTCTCCAGAGCCTG |
| 430 | TTGGCAGAGGCCGCAGGCTC |
| 431 | TAGGTCTTGGCAGAGGCCGC |
| 432 | CTAGAGTTAGGTCTTGGCAG |
| 433 | GGTGGTCTAGAGTTAGGTCT |

TABLE 3

Control sgRNA Library

| SEQ ID NO. | gRNA Label | Gene | Nucleic Acid Sequence |
|---|---|---|---|
| 434 | 1\|sg_Non_Targeting_Human_0001\|Non_Targeting_Human | Non_Targeting_Human | GTAGCGAACGTGTCCGGCGT |
| 435 | 1\|sg_Non_Targeting_Human_0002\|Non_Targeting_Human | Non_Targeting_Human | GACCGGAACGATCTCGCGTA |
| 436 | 1\|sg_Non_Targeting_Human_0003\|Non_Targeting_Human | Non_Targeting_Human | GGCAGTCGTTCGGTTGATAT |
| 437 | 1\|sg_Non_Targeting_Human_0004\|Non_Targeting_Human | Non_Targeting_Human | GCTTGAGCACATACGCGAAT |

TABLE 3-continued

Control sgRNA Library

| SEQ ID NO. | gRNA Label | Gene | Nucleic Acid Sequence |
|---|---|---|---|
| 438 | 1\|sg_Non_Targeting_Human_0005\|Non_Targeting_Human | Non_Targeting_Human | GTGGTAGAATAACGTATTAC |
| 439 | 1\|sg_Non_Targeting_Human_0006\|Non_Targeting_Human | Non_Targeting_Human | GTCATACATGGATAAGGCTA |
| 440 | 1\|sg_Non_Targeting_Human_0007\|Non_Targeting_Human | Non_Targeting_Human | GATACACGAAGCATCACTAG |
| 441 | 1\|sg_Non_Targeting_Human_0008\|Non_Targeting_Human | Non_Targeting_Human | GAACGTTGGCACTACTTCAC |
| 442 | 1\|sg_Non_Targeting_Human_0009\|Non_Targeting_Human | Non_Targeting_Human | GATCCATGTAATGCGTTCGA |
| 443 | 1\|sg_Non_Targeting_Human_0010\|Non_Targeting_Human | Non_Targeting_Human | GTCGTGAAGTGCATTCGATC |
| 444 | 1\|sg_Non_Targeting_Human_0011\|Non_Targeting_Human | Non_Targeting_Human | GTTCGACTCGCGTGACCGTA |
| 445 | 1\|sg_Non_Targeting_Human_0012\|Non_Targeting_Human | Non_Targeting_Human | GAATCTACCGCAGCGGTTCG |
| 446 | 1\|sg_Non_Targeting_Human_0013\|Non_Targeting_Human | Non_Targeting_Human | GAAGTGACGTCGATTCGATA |
| 447 | 1\|sg_Non_Targeting_Human_0014\|Non_Targeting_Human | Non_Targeting_Human | GCGGTGTATGACAACCGCCG |
| 448 | 1\|sg_Non_Targeting_Human_0015\|Non_Targeting_Human | Non_Targeting_Human | GTACCGCGCCTGAAGTTCGC |
| 449 | 1\|sg_Non_Targeting_Human_0016\|Non_Targeting_Human | Non_Targeting_Human | GCAGCTCGTGTGTCGTACTC |
| 450 | 1\|sg_Non_Targeting_Human_0017\|Non_Targeting_Human | Non_Targeting_Human | GCGCCTTAAGAGTACTCATC |
| 451 | 1\|sg_Non_Targeting_Human_0018\|Non_Targeting_Human | Non_Targeting_Human | GAGTGTCGTCGTTGCTCCTA |
| 452 | 1\|sg_Non_Targeting_Human_0019\|Non_Targeting_Human | Non_Targeting_Human | GCAGCTCGACCTCAAGCCGT |
| 453 | 1\|sg_Non_Targeting_Human_0020\|Non_Targeting_Human | Non_Targeting_Human | GTATCCTGACCTACGCGCTG |
| 454 | 1\|sg_Non_Targeting_Human_0021\|Non_Targeting_Human | Non_Targeting_Human | GTGTATCTCAGCACGCTAAC |
| 455 | 1\|sg_Non_Targeting_Human_0022\|Non_Targeting_Human | Non_Targeting_Human | GTCGTCATACAACGGCAACG |
| 456 | 1\|sg_Non_Targeting_Human_0023\|Non_Targeting_Human | Non_Targeting_Human | GTCGTGCGCTTCCGGCGGTA |

TABLE 3-continued

Control sgRNA Library

| SEQ ID NO. | gRNA Label | Gene | Nucleic Acid Sequence |
|---|---|---|---|
| 457 | 1\|sg_Non_Targeting_Human_0024\|Non_Targeting_Human | Non_Targeting_Human | GCGGTCCTCAGTAAGCGCGT |
| 458 | 1\|sg_Non_Targeting_Human_0025\|Non_Targeting_Human | Non_Targeting_Human | GCTCTGCTGCGGAAGGATTC |
| 459 | 1\|sg_Non_Targeting_Human_0026\|Non_Targeting_Human | Non_Targeting_Human | GCATGGAGGAGCGTCGCAGA |
| 460 | 1\|sg_Non_Targeting_Human_0027\|Non_Targeting_Human | Non_Targeting_Human | GTAGCGCGCGTAGGAGTGGC |
| 461 | 1\|sg_Non_Targeting_Human_0028\|Non_Targeting_Human | Non_Targeting_Human | GATCACCTGCATTCGTACAC |
| 462 | 1\|sg_Non_Targeting_Human_0029\|Non_Targeting_Human | Non_Targeting_Human | GCACACCTAGATATCGAATG |
| 463 | 1\|sg_Non_Targeting_Human_0030\|Non_Targeting_Human | Non_Targeting_Human | GTTGATCAACGCGCTTCGCG |
| 464 | 1\|sg_Non_Targeting_Human_0031\|Non_Targeting_Human | Non_Targeting_Human | GCGTCTCACTCACTCCATCG |
| 465 | 1\|sg_Non_Targeting_Human_0032\|Non_Targeting_Human | Non_Targeting_Human | GCCGACCAACGTCAGCGGTA |
| 466 | 1\|sg_Non_Targeting_Human_0033\|Non_Targeting_Human | Non_Targeting_Human | GGATACGGTGCGTCAATCTA |
| 467 | 1\|sg_Non_Targeting_Human_0034\|Non_Targeting_Human | Non_Targeting_Human | GAATCCAGTGGCGGCGACAA |
| 468 | 1\|sg_Non_Targeting_Human_0035\|Non_Targeting_Human | Non_Targeting_Human | GCACTGTCAGTGCAACGATA |
| 469 | 1\|sg_Non_Targeting_Human_0036\|Non_Targeting_Human | Non_Targeting_Human | GCGATCCTCAAGTATGCTCA |
| 470 | 1\|sg_Non_Targeting_Human_0037\|Non_Targeting_Human | Non_Targeting_Human | GCTAATATCGACACGGCCGC |
| 471 | 1\|sg_Non_Targeting_Human_0038\|Non_Targeting_Human | Non_Targeting_Human | GGAGATGCATCGAAGTCGAT |
| 472 | 1\|sg_Non_Targeting_Human_0039\|Non_Targeting_Human | Non_Targeting_Human | GGATGCACTCCATCTCGTCT |
| 473 | 1\|sg_Non_Targeting_Human_0040\|Non_Targeting_Human | Non_Targeting_Human | GTGCCGAGTAATAACGCGAG |
| 474 | 1\|sg_Non_Targeting_Human_0041\|Non_Targeting_Human | Non_Targeting_Human | GAGATTCCGATGTAACGTAC |
| 475 | 1\|sg_Non_Targeting_Human_0042\|Non_Targeting_Human | Non_Targeting_Human | GTCGTCACGAGCAGGATTGC |

TABLE 3-continued

Control sgRNA Library

| SEQ ID NO. | gRNA Label | Gene | Nucleic Acid Sequence |
|---|---|---|---|
| 476 | 1\|sg_Non_Targeting_Human_0043\|Non_Targeting_Human | Non_Targeting_Human | GCGTTAGTCACTTAGCTCGA |
| 477 | 1\|sg_Non_Targeting_Human_0044\|Non_Targeting_Human | Non_Targeting_Human | GTTCACACGGTGTCGGATAG |
| 478 | 1\|sg_Non_Targeting_Human_0045\|Non_Targeting_Human | Non_Targeting_Human | GGATAGGTGACCTTAGTACG |
| 479 | 1\|sg_Non_Targeting_Human_0046\|Non_Targeting_Human | Non_Targeting_Human | GTATGAGTCAAGCTAATGCG |
| 480 | 1\|sg_Non_Targeting_Human_0047\|Non_Targeting_Human | Non_Targeting_Human | GCAACTATTGGAATACGTGA |
| 481 | 1\|sg_Non_Targeting_Human_0048\|Non_Targeting_Human | Non_Targeting_Human | GTTACCTTCGCTCGTCTATA |
| 482 | 1\|sg_Non_Targeting_Human_0049\|Non_Targeting_Human | Non_Targeting_Human | GTACCGAGCACCACAGGCCG |
| 483 | 1\|sg_Non_Targeting_Human_0050\|Non_Targeting_Human | Non_Targeting_Human | GTCAGCCATCGGATAGAGAT |
| 484 | 1\|sg_Non_Targeting_Human_0051\|Non_Targeting_Human | Non_Targeting_Human | GTACGGCACTCCTAGCCGCT |
| 485 | 1\|sg_Non_Targeting_Human_0052\|Non_Targeting_Human | Non_Targeting_Human | GGTCCTGTCGTATGCTTGCA |
| 486 | 1\|sg_Non_Targeting_Human_0053\|Non_Targeting_Human | Non_Targeting_Human | GCCGCAATATATGCGGTAAG |
| 487 | 1\|sg_Non_Targeting_Human_0054\|Non_Targeting_Human | Non_Targeting_Human | GCGCACGTATAATCCTGCGT |
| 488 | 1\|sg_Non_Targeting_Human_0055\|Non_Targeting_Human | Non_Targeting_Human | GTGCACAACACGATCCACGA |
| 489 | 1\|sg_Non_Targeting_Human_0056\|Non_Targeting_Human | Non_Targeting_Human | GCACAATGTTGACGTAAGTG |
| 490 | 1\|sg_Non_Targeting_Human_0057\|Non_Targeting_Human | Non_Targeting_Human | GTAAGATGCTGCTCACCGTG |
| 491 | 1\|sg_Non_Targeting_Human_0058\|Non_Targeting_Human | Non_Targeting_Human | GTCGGTGATCCAACGTATCG |
| 492 | 1\|sg_Non_Targeting_Human_0059\|Non_Targeting_Human | Non_Targeting_Human | GAGCTAGTAGGACGCAAGAC |
| 493 | 1\|sg_Non_Targeting_Human_0060\|Non_Targeting_Human | Non_Targeting_Human | GTACGTGGAAGCTTGTGGCC |
| 494 | 1\|sg_Non_Targeting_Human_0061\|Non_Targeting_Human | Non_Targeting_Human | GAGAACTGCCAGTTCTCGAT |

TABLE 3-continued

Control sgRNA Library

| SEQ ID NO. | gRNA Label | Gene | Nucleic Acid Sequence |
|---|---|---|---|
| 495 | 1\|sg_Non_Targeting_Human_0062\|Non_Targeting_Human | Non_Targeting_Human | GCCATTCGGCGCGGCACTTC |
| 496 | 1\|sg_Non_Targeting_Human_0063\|Non_Targeting_Human | Non_Targeting_Human | GCACACGACCAATCCGCTTC |
| 497 | 1\|sg_Non_Targeting_Human_0064\|Non_Targeting_Human | Non_Targeting_Human | GAGGTGATCGATTAAGTACA |
| 498 | 1\|sg_Non_Targeting_Human_0065\|Non_Targeting_Human | Non_Targeting_Human | GTCACTCGCAGACGCCTAAC |
| 499 | 1\|sg_Non_Targeting_Human_0066\|Non_Targeting_Human | Non_Targeting_Human | GCGCTACGGAATCATACGTT |
| 500 | 1\|sg_Non_Targeting_Human_0067\|Non_Targeting_Human | Non_Targeting_Human | GGTAGGACCTCACGGCGCGC |
| 501 | 1\|sg_Non_Targeting_Human_0068\|Non_Targeting_Human | Non_Targeting_Human | GAACTGCATCTTGTTGTAGT |
| 502 | 1\|sg_Non_Targeting_Human_0069\|Non_Targeting_Human | Non_Targeting_Human | GATCCTGATCCGGCGGCGCG |
| 503 | 1\|sg_Non_Targeting_Human_0070\|Non_Targeting_Human | Non_Targeting_Human | GGTATGCGCGATCCTGAGTT |
| 504 | 1\|sg_Non_Targeting_Human_0071\|Non_Targeting_Human | Non_Targeting_Human | GCGGAGCTAGAGAGCGGTCA |
| 505 | 1\|sg_Non_Targeting_Human_0072\|Non_Targeting_Human | Non_Targeting_Human | GAATGGCAATTACGGCTGAT |
| 506 | 1\|sg_Non_Targeting_Human_0073\|Non_Targeting_Human | Non_Targeting_Human | GTATGGTGAGTAGTCGCTTG |
| 507 | 1\|sg_Non_Targeting_Human_0074\|Non_Targeting_Human | Non_Targeting_Human | GTGTAATTGCGTCTAGTCGG |
| 508 | 1\|sg_Non_Targeting_Human_0075\|Non_Targeting_Human | Non_Targeting_Human | GGTCCTGGCGAGGAGCCTTG |
| 509 | 1\|sg_Non_Targeting_Human_0076\|Non_Targeting_Human | Non_Targeting_Human | GAAGATAAGTCGCTGTCTCG |
| 510 | 1\|sg_Non_Targeting_Human_0077\|Non_Targeting_Human | Non_Targeting_Human | GTCGGCGTTCTGTTGTGACT |
| 511 | 1\|sg_Non_Targeting_Human_0078\|Non_Targeting_Human | Non_Targeting_Human | GAGGCAAGCCGTTAGGTGTA |
| 512 | 1\|sg_Non_Targeting_Human_0079\|Non_Targeting_Human | Non_Targeting_Human | GCGGATCCAGATCTCATTCG |
| 513 | 1\|sg_Non_Targeting_Human_0080\|Non_Targeting_Human | Non_Targeting_Human | GGAACATAGGAGCACGTAGT |

TABLE 3-continued

Control sgRNA Library

| SEQ ID NO. | gRNA Label | Gene | Nucleic Acid Sequence |
|---|---|---|---|
| 514 | 1\|sg_Non_Targeting_Human_0081\|Non_Targeting_Human | Non_Targeting_Human | GTCATCATTATGGCGTAAGG |
| 515 | 1\|sg_Non_Targeting_Human_0082\|Non_Targeting_Human | Non_Targeting_Human | GCGACTAGCGCCATGAGCGG |
| 516 | 1\|sg_Non_Targeting_Human_0083\|Non_Targeting_Human | Non_Targeting_Human | GGCGAAGTTCGACATGACAC |
| 517 | 1\|sg_Non_Targeting_Human_0084\|Non_Targeting_Human | Non_Targeting_Human | GCTGTCGTGTGGAGGCTATG |
| 518 | 1\|sg_Non_Targeting_Human_0085\|Non_Targeting_Human | Non_Targeting_Human | GCGGAGAGCATTGACCTCAT |
| 519 | 1\|sg_Non_Targeting_Human_0086\|Non_Targeting_Human | Non_Targeting_Human | GACTAATGGACCAAGTCAGT |
| 520 | 1\|sg_Non_Targeting_Human_0087\|Non_Targeting_Human | Non_Targeting_Human | GCGGATTAGAGGTAATGCGG |
| 521 | 1\|sg_Non_Targeting_Human_0088\|Non_Targeting_Human | Non_Targeting_Human | GCCGACGGCAATCAGTACGC |
| 522 | 1\|sg_Non_Targeting_Human_0089\|Non_Targeting_Human | Non_Targeting_Human | GTAACCTCTCGAGCGATAGA |
| 523 | 1\|sg_Non_Targeting_Human_0090\|Non_Targeting_Human | Non_Targeting_Human | GACTTGTATGTGGCTTACGG |
| 524 | 1\|sg_Non_Targeting_Human_0091\|Non_Targeting_Human | Non_Targeting_Human | GTCACTGTGGTCGAACATGT |
| 525 | 1\|sg_Non_Targeting_Human_0092\|Non_Targeting_Human | Non_Targeting_Human | GTACTCCAATCCGCGATGAC |
| 526 | 1\|sg_Non_Targeting_Human_0093\|Non_Targeting_Human | Non_Targeting_Human | GCGTTGGCACGATGTTACGG |
| 527 | 1\|sg_Non_Targeting_Human_0094\|Non_Targeting_Human | Non_Targeting_Human | GAACCAGCCGGCTAGTATGA |
| 528 | 1\|sg_Non_Targeting_Human_0095\|Non_Targeting_Human | Non_Targeting_Human | GTATACTAGCTAACCACACG |
| 529 | 1\|sg_Non_Targeting_Human_0096\|Non_Targeting_Human | Non_Targeting_Human | GAATCGGAATAGTTGATTCG |
| 530 | 1\|sg_Non_Targeting_Human_0097\|Non_Targeting_Human | Non_Targeting_Human | GAGCACTTGCATGAGGCGGT |
| 531 | 1\|sg_Non_Targeting_Human_0098\|Non_Targeting_Human | Non_Targeting_Human | GAACGGCGATGAAGCCAGCC |
| 532 | 1\|sg_Non_Targeting_Human_0099\|Non_Targeting_Human | Non_Targeting_Human | GCAACCGAGATGAGAGGTTC |

TABLE 3-continued

Control sgRNA Library

| SEQ ID NO. | gRNA Label | Gene | Nucleic Acid Sequence |
|---|---|---|---|
| 533 | 1\|sg_Non_Targeting_Human_0100\|Non_Targeting_Human | Non_Targeting_Human | GCAAGATCAATATGCGTGAT |
| 534 | 1\|sg_Non_Targeting_Human_GA_0101\|Non_Targeting_Human | Non_Targeting_Human | ACGGAGGCTAAGCGTCGCAA |
| 535 | 1\|sg_Non_Targeting_Human_GA_0102\|Non_Targeting_Human | Non_Targeting_Human | CGCTTCCGCGGCCCGTTCAA |
| 536 | 1\|sg_Non_Targeting_Human_GA_0103\|Non_Targeting_Human | Non_Targeting_Human | ATCGTTTCCGCTTAACGGCG |
| 537 | 1\|sg_Non_Targeting_Human_GA_0104\|Non_Targeting_Human | Non_Targeting_Human | GTAGGCGCGCCGCTCTCTAC |
| 538 | 1\|sg_Non_Targeting_Human_GA_0105\|Non_Targeting_Human | Non_Targeting_Human | CCATATCGGGGCGAGACATG |
| 539 | 1\|sg_Non_Targeting_Human_GA_0106\|Non_Targeting_Human | Non_Targeting_Human | TACTAACGCCGCTCCTACAG |
| 540 | 1\|sg_Non_Targeting_Human_GA_0107\|Non_Targeting_Human | Non_Targeting_Human | TGAGGATCATGTCGAGCGCC |
| 541 | 1\|sg_Non_Targeting_Human_GA_0108\|Non_Targeting_Human | Non_Targeting_Human | GGGCCCGCATAGGATATCGC |
| 542 | 1\|sg_Non_Targeting_Human_GA_0109\|Non_Targeting_Human | Non_Targeting_Human | TAGACAACCGCGGAGAATGC |
| 543 | 1\|sg_Non_Targeting_Human_GA_0110\|Non_Targeting_Human | Non_Targeting_Human | ACGGGCGGCTATCGCTGACT |
| 544 | 1\|sg_Non_Targeting_Human_GA_0111\|Non_Targeting_Human | Non_Targeting_Human | CGCGGAAATTTTACCGACGA |
| 545 | 1\|sg_Non_Targeting_Human_GA_0112\|Non_Targeting_Human | Non_Targeting_Human | CTTACAATCGTCGGTCCAAT |
| 546 | 1\|sg_Non_Targeting_Human_GA_0113\|Non_Targeting_Human | Non_Targeting_Human | GCGTGCGTCCCGGGTTACCC |
| 547 | 1\|sg_Non_Targeting_Human_GA_0114\|Non_Targeting_Human | Non_Targeting_Human | CGGAGTAACAAGCGGACGGA |
| 548 | 1\|sg_Non_Targeting_Human_GA_0115\|Non_Targeting_Human | Non_Targeting_Human | CGAGTGTTATACGCACCGTT |
| 549 | 1\|sg_Non_Targeting_Human_GA_0116\|Non_Targeting_Human | Non_Targeting_Human | CGACTAACCGGAAACTTTTT |
| 550 | 1\|sg_Non_Targeting_Human_GA_0117\|Non_Targeting_Human | Non_Targeting_Human | CAACGGGTTCTCCCGGCTAC |
| 551 | 1\|sg_Non_Targeting_Human_GA_0118\|Non_Targeting_Human | Non_Targeting_Human | CAGGAGTCGCCGATACGCGT |

TABLE 3-continued

Control sgRNA Library

| SEQ ID NO. | gRNA Label | Gene | Nucleic Acid Sequence |
|---|---|---|---|
| 552 | 1\|sg_Non_Targeting_Human_GA_0119\|Non_Targeting_Human | Non_Targeting_Human | TTCACGTCGTCTCGCGACCA |
| 553 | 1\|sg_Non_Targeting_Human_GA_0120\|Non_Targeting_Human | Non_Targeting_Human | GTGTCGGATTCCGCCGCTTA |
| 554 | 1\|sg_Non_Targeting_Human_GA_0121\|Non_Targeting_Human | Non_Targeting_Human | CACGAACTCACACCGCGCGA |
| 555 | 1\|sg_Non_Targeting_Human_GA_0122\|Non_Targeting_Human | Non_Targeting_Human | CGCTAGTACGCTCCTCTATA |
| 556 | 1\|sg_Non_Targeting_Human_GA_0123\|Non_Targeting_Human | Non_Targeting_Human | TCGCGCTTGGGTTATACGCT |
| 557 | 1\|sg_Non_Targeting_Human_GA_0124\|Non_Targeting_Human | Non_Targeting_Human | CTATCTCGAGTGGTAATGCG |
| 558 | 1\|sg_Non_Targeting_Human_GA_0125\|Non_Targeting_Human | Non_Targeting_Human | AATCGACTCGAACTTCGTGT |
| 559 | 1\|sg_Non_Targeting_Human_GA_0126\|Non_Targeting_Human | Non_Targeting_Human | CCCGATGGACTATACCGAAC |
| 560 | 1\|sg_Non_Targeting_Human_GA_0127\|Non_Targeting_Human | Non_Targeting_Human | ACGTTCGAGTACGACCAGCT |
| 561 | 1\|sg_Non_Targeting_Human_GA_0128\|Non_Targeting_Human | Non_Targeting_Human | CGCGACGACTCAACCTAGTC |
| 562 | 1\|sg_Non_Targeting_Human_GA_0129\|Non_Targeting_Human | Non_Targeting_Human | GGTCACCGATCGAGAGCTAG |
| 563 | 1\|sg_Non_Targeting_Human_GA_0130\|Non_Targeting_Human | Non_Targeting_Human | CTCAACCGACCGTATGGTCA |
| 564 | 1\|sg_Non_Targeting_Human_GA_0131\|Non_Targeting_Human | Non_Targeting_Human | CGTATTCGACTCTCAACGCG |
| 565 | 1\|sg_Non_Targeting_Human_GA_0132\|Non_Targeting_Human | Non_Targeting_Human | CTAGCCGCCCAGATCGAGCC |
| 566 | 1\|sg_Non_Targeting_Human_GA_0133\|Non_Targeting_Human | Non_Targeting_Human | GAATCGACCGACACTAATGT |
| 567 | 1\|sg_Non_Targeting_Human_GA_0134\|Non_Targeting_Human | Non_Targeting_Human | ACTTCAGTTCGGCGTAGTCA |
| 568 | 1\|sg_Non_Targeting_Human_GA_0135\|Non_Targeting_Human | Non_Targeting_Human | GTGCGATGTCGCTTCAACGT |
| 569 | 1\|sg_Non_Targeting_Human_GA_0136\|Non_Targeting_Human | Non_Targeting_Human | CGCCTAATTTCCGGATCAAT |
| 570 | 1\|sg_Non_Targeting_Human_GA_0137\|Non_Targeting_Human | Non_Targeting_Human | CGTGGCCGGAACCGTCATAG |

TABLE 3-continued

Control sgRNA Library

| SEQ ID NO. | gRNA Label | Gene | Nucleic Acid Sequence |
|---|---|---|---|
| 571 | 1\|sg_Non_Targeting_Human_GA_0138\|Non_Targeting_Human | Non_Targeting_Human | ACCCTCCGAATCGTAACGGA |
| 572 | 1\|sg_Non_Targeting_Human_GA_0139\|Non_Targeting_Human | Non_Targeting_Human | AAACGGTACGACAGCGTGTG |
| 573 | 1\|sg_Non_Targeting_Human_GA_0140\|Non_Targeting_Human | Non_Targeting_Human | ACATAGTCGACGGCTCGATT |
| 574 | 1\|sg_Non_Targeting_Human_GA_0141\|Non_Targeting_Human | Non_Targeting_Human | GATGGCGCTTCAGTCGTCGG |
| 575 | 1\|sg_Non_Targeting_Human_GA_0142\|Non_Targeting_Human | Non_Targeting_Human | ATAATCCGGAAACGCTCGAC |
| 576 | 1\|sg_Non_Targeting_Human_GA_0143\|Non_Targeting_Human | Non_Targeting_Human | CGCCGGGCTGACAATTAACG |
| 577 | 1\|sg_Non_Targeting_Human_GA_0144\|Non_Targeting_Human | Non_Targeting_Human | CGTCGCCATATGCCGGTGGC |
| 578 | 1\|sg_Non_Targeting_Human_GA_0145\|Non_Targeting_Human | Non_Targeting_Human | CGGGCCTATAACACCATCGA |
| 579 | 1\|sg_Non_Targeting_Human_GA_0146\|Non_Targeting_Human | Non_Targeting_Human | CGCCGTTCCGAGATACTTGA |
| 580 | 1\|sg_Non_Targeting_Human_GA_0147\|Non_Targeting_Human | Non_Targeting_Human | CGGGACGTCGCGAAAATGTA |
| 581 | 1\|sg_Non_Targeting_Human_GA_0148\|Non_Targeting_Human | Non_Targeting_Human | TCGGCATACGGGACACACGC |
| 582 | 1\|sg_Non_Targeting_Human_GA_0149\|Non_Targeting_Human | Non_Targeting_Human | AGCTCCATCGCCGCGATAAT |
| 583 | 1\|sg_Non_Targeting_Human_GA_0150\|Non_Targeting_Human | Non_Targeting_Human | ATCGTATCATCAGCTAGCGC |
| 584 | 1\|sg_Non_Targeting_Human_GA_0151\|Non_Targeting_Human | Non_Targeting_Human | TCGATCGAGGTTGCATTCGG |
| 585 | 1\|sg_Non_Targeting_Human_GA_0152\|Non_Targeting_Human | Non_Targeting_Human | CTCGACAGTTCGTCCCGAGC |
| 586 | 1\|sg_Non_Targeting_Human_GA_0153\|Non_Targeting_Human | Non_Targeting_Human | CGGTAGTATTAATCGCTGAC |
| 587 | 1\|sg_Non_Targeting_Human_GA_0154\|Non_Targeting_Human | Non_Targeting_Human | TGAACGCGTGTTTCCTTGCA |
| 588 | 1\|sg_Non_Targeting_Human_GA_0155\|Non_Targeting_Human | Non_Targeting_Human | CGACGCTAGGTAACGTAGAG |
| 589 | 1\|sg_Non_Targeting_Human_GA_0156\|Non_Targeting_Human | Non_Targeting_Human | CATTGTTGAGCGGGCGCGCT |

TABLE 3-continued

Control sgRNA Library

| SEQ ID NO. | gRNA Label | Gene | Nucleic Acid Sequence |
|---|---|---|---|
| 590 | 1\|sg_Non_Targeting_Human_GA_0157\|Non_Targeting_Human | Non_Targeting_Human | CCGCTATTGAAACCGCCCAC |
| 591 | 1\|sg_Non_Targeting_Human_GA_0158\|Non_Targeting_Human | Non_Targeting_Human | AGACACGTCACCGGTCAAAA |
| 592 | 1\|sg_Non_Targeting_Human_GA_0159\|Non_Targeting_Human | Non_Targeting_Human | TTTACGATCTAGCGGCGTAG |
| 593 | 1\|sg_Non_Targeting_Human_GA_0160\|Non_Targeting_Human | Non_Targeting_Human | TTCGCACGATTGCACCTTGG |
| 594 | 1\|sg_Non_Targeting_Human_GA_0161\|Non_Targeting_Human | Non_Targeting_Human | GGTTAGAGACTAGGCGCGCG |
| 595 | 1\|sg_Non_Targeting_Human_GA_0162\|Non_Targeting_Human | Non_Targeting_Human | CCTCCGTGCTAACGCGGACG |
| 596 | 1\|sg_Non_Targeting_Human_GA_0163\|Non_Targeting_Human | Non_Targeting_Human | TTATCGCGTAGTGCTGACGT |
| 597 | 1\|sg_Non_Targeting_Human_GA_0164\|Non_Targeting_Human | Non_Targeting_Human | TACGCTTGCGTTTAGCGTCC |
| 598 | 1\|sg_Non_Targeting_Human_GA_0165\|Non_Targeting_Human | Non_Targeting_Human | CGCGGCCCACGCGTCATCGC |
| 599 | 1\|sg_Non_Targeting_Human_GA_0166\|Non_Targeting_Human | Non_Targeting_Human | AGCTCGCCATGTCGGTTCTC |
| 600 | 1\|sg_Non_Targeting_Human_GA_0167\|Non_Targeting_Human | Non_Targeting_Human | AACTAGCCCGAGCAGCTTCG |
| 601 | 1\|sg_Non_Targeting_Human_GA_0168\|Non_Targeting_Human | Non_Targeting_Human | CGCAAGGTGTCGGTAACCCT |
| 602 | 1\|sg_Non_Targeting_Human_GA_0169\|Non_Targeting_Human | Non_Targeting_Human | CTTCGACGCCATCGTGCTCA |
| 603 | 1\|sg_Non_Targeting_Human_GA_0170\|Non_Targeting_Human | Non_Targeting_Human | TCCTGGATACCGCGTGGTTA |
| 604 | 1\|sg_Non_Targeting_Human_GA_0171\|Non_Targeting_Human | Non_Targeting_Human | ATAGCCGCCGCTCATTACTT |
| 605 | 1\|sg_Non_Targeting_Human_GA_0172\|Non_Targeting_Human | Non_Targeting_Human | GTCGTCCGGGATTACAAAAT |
| 606 | 1\|sg_Non_Targeting_Human_GA_0173\|Non_Targeting_Human | Non_Targeting_Human | TAATGCTGCACACGCCGAAT |
| 607 | 1\|sg_Non_Targeting_Human_GA_0174\|Non_Targeting_Human | Non_Targeting_Human | TATCGCTTCCGATTAGTCCG |
| 608 | 1\|sg_Non_Targeting_Human_GA_0175\|Non_Targeting_Human | Non_Targeting_Human | GTACCATACCGCGTACCCTT |

TABLE 3-continued

Control sgRNA Library

| SEQ ID NO. | gRNA Label | Gene | Nucleic Acid Sequence |
|---|---|---|---|
| 609 | 1\|sg_Non_Targeting_Human_GA_0176\|Non_Targeting_Human | Non_Targeting_Human | TAAGATCCGCGGGTGGCAAC |
| 610 | 1\|sg_Non_Targeting_Human_GA_0177\|Non_Targeting_Human | Non_Targeting_Human | GTAGACGTCGTGAGCTTCAC |
| 611 | 1\|sg_Non_Targeting_Human_GA_0178\|Non_Targeting_Human | Non_Targeting_Human | TCGCGGACATAGGGCTCTAA |
| 612 | 1\|sg_Non_Targeting_Human_GA_0179\|Non_Targeting_Human | Non_Targeting_Human | AGCGCAGATAGCGCGTATCA |
| 613 | 1\|sg_Non_Targeting_Human_GA_0180\|Non_Targeting_Human | Non_Targeting_Human | GTTCGCTTCGTAACGAGGAA |
| 614 | 1\|sg_Non_Targeting_Human_GA_0181\|Non_Targeting_Human | Non_Targeting_Human | GACCCCCGATAACTTTTGAC |
| 615 | 1\|sg_Non_Targeting_Human_GA_0182\|Non_Targeting_Human | Non_Targeting_Human | ACGTCCATACTGTCGGCTAC |
| 616 | 1\|sg_Non_Targeting_Human_GA_0183\|Non_Targeting_Human | Non_Targeting_Human | GTACCATTGCCGGCTCCCTA |
| 617 | 1\|sg_Non_Targeting_Human_GA_0184\|Non_Targeting_Human | Non_Targeting_Human | TGGTTCCGTAGGTCGGTATA |
| 618 | 1\|sg_Non_Targeting_Human_GA_0185\|Non_Targeting_Human | Non_Targeting_Human | TCTGGCTTGACACGACCGTT |
| 619 | 1\|sg_Non_Targeting_Human_GA_0186\|Non_Targeting_Human | Non_Targeting_Human | CGCTAGGTCCGGTAAGTGCG |
| 620 | 1\|sg_Non_Targeting_Human_GA_0187\|Non_Targeting_Human | Non_Targeting_Human | AGCACGTAATGTCCGTGGAT |
| 621 | 1\|sg_Non_Targeting_Human_GA_0188\|Non_Targeting_Human | Non_Targeting_Human | AAGGCGCGCGAATGTGGCAG |
| 622 | 1\|sg_Non_Targeting_Human_GA_0189\|Non_Targeting_Human | Non_Targeting_Human | ACTGCGGAGCGCCCAATATC |
| 623 | 1\|sg_Non_Targeting_Human_GA_0190\|Non_Targeting_Human | Non_Targeting_Human | CGTCGAGTGCTCGAACTCCA |
| 624 | 1\|sg_Non_Targeting_Human_GA_0191\|Non_Targeting_Human | Non_Targeting_Human | TCGCAGCGGCGTGGGATCGG |
| 625 | 1\|sg_Non_Targeting_Human_GA_0192\|Non_Targeting_Human | Non_Targeting_Human | ATCTGTCCTAATTCGGATCG |
| 626 | 1\|sg_Non_Targeting_Human_GA_0193\|Non_Targeting_Human | Non_Targeting_Human | TGCGGCGTAATGCTTGAAAG |
| 627 | 1\|sg_Non_Targeting_Human_GA_0194\|Non_Targeting_Human | Non_Targeting_Human | CGAACTTAATCCCGTGGCAA |

TABLE 3-continued

Control sgRNA Library

| SEQ ID NO. | gRNA Label | Gene | Nucleic Acid Sequence |
|---|---|---|---|
| 628 | 1\|sg_Non_Targeting_Human_GA_0195\|Non_Targeting_Human | Non_Targeting_Human | GCCGTGTTGCTGGATACGCC |
| 629 | 1\|sg_Non_Targeting_Human_GA_0196\|Non_Targeting_Human | Non_Targeting_Human | TACCCTCCGGATACGGACTG |
| 630 | 1\|sg_Non_Targeting_Human_GA_0197\|Non_Targeting_Human | Non_Targeting_Human | CCGTTGGACTATGGCGGGTC |
| 631 | 1\|sg_Non_Targeting_Human_GA_0198\|Non_Targeting_Human | Non_Targeting_Human | GTACGGGGCGATCATCCACA |
| 632 | 1\|sg_Non_Targeting_Human_GA_0199\|Non_Targeting_Human | Non_Targeting_Human | AAGAGTAGTAGACGCCCGGG |
| 633 | 1\|sg_Non_Targeting_Human_GA_0200\|Non_Targeting_Human | Non_Targeting_Human | AAGAGCGAATCGATTTCGTG |
| 634 | 3\|sg_hCDC16_CC_1\|CDC16 | CDC16 | TCAACACCAGTGCCTGACGG |
| 635 | 3\|sg_hCDC16_CC_2\|CDC16 | CDC16 | AAAGTAGCTTCACTCTCTCG |
| 636 | 3\|sg_hCDC16_CC_3\|CDC16 | CDC16 | GAGCCAACCAATAGATGTCC |
| 637 | 3\|sg_hCDC16_CC_4\|CDC16 | CDC16 | GCGCCGCCATGAACCTAGAG |
| 638 | 3\|sg_hGTF2B_CC_1\|GTF2B | GTF2B | ACAAAGGTTGGAACAGAACC |
| 639 | 3\|sg_hGTF2B_CC_2\|GTF2B | GTF2B | GGTGACCGGGTTATTGATGT |
| 640 | 3\|sg_hGTF2B_CC_3\|GTF2B | GTF2B | TTAGTGGAGGACTACAGAGC |
| 641 | 3\|sg_hGTF2B_CC_4\|GTF2B | GTF2B | ACATATAGCCCGTAAAGCTG |
| 642 | 3\|sg_hHSPA5_CC_1\|HSPA5 | HSPA5 | CGTTGGCGATGATCTCCACG |
| 643 | 3\|sg_hHSPA5_CC_2\|HSPA5 | HSPA5 | TGGCCTTTTCTACCTCGCGC |
| 644 | 3\|sg_hHSPA5_CC_3\|HSPA5 | HSPA5 | AATGGAGATACTCATCTGGG |
| 645 | 3\|sg_hHSPA5_CC_4\|HSPA5 | HSPA5 | GAAGCCCGTCCAGAAAGTGT |
| 646 | 3\|sg_hHSPA9_CC_1\|HSPA9 | HSPA9 | CAATCTGAGGAACTCCACGA |
| 647 | 3\|sg_hHSPA9_CC_2\|HSPA9 | HSPA9 | AGGCTGCGGCGCCCACGAGA |
| 648 | 3\|sg_hHSPA9_CC_3\|HSPA9 | HSPA9 | ACTTTGACCAGGCCTTGCTA |
| 649 | 3\|sg_hHSPA9_CC_4\|HSPA9 | HSPA9 | ACCTTCCATAACTGCCACGC |
| 650 | 3\|sg_hPAFAH1B1_CC_1\|PAFAH1B1 | PAFAH1B1 | CGAGGCGTACATACCCAAGG |
| 651 | 3\|sg_hPAFAH1B1_CC_2\|PAFAH1B1 | PAFAH1B1 | ATGGTACGGCCAAATCAAGA |
| 652 | 3\|sg_hPAFAH1B1_CC_3\|PAFAH1B1 | PAFAH1B1 | TCTTGTAATCCCATACGCGT |
| 653 | 3\|sg_hPAFAH1B1_CC_4\|PAFAH1B1 | PAFAH1B1 | ATTCACAGGACACAGAGAAT |
| 654 | 3\|sg_hPCNA_CC_1\|PCNA | PCNA | CCAGGGCTCCATCCTCAAGA |
| 655 | 3\|sg_hPCNA_CC_2\|PCNA | PCNA | TGAGCTGCACCAAAGAGACG |
| 656 | 3\|sg_hPCNA_CC_3\|PCNA | PCNA | ATGTCTGCAGATGTACCCCT |
| 657 | 3\|sg_hPCNA_CC_4\|PCNA | PCNA | CGAAGATAACGCGGATACCT |

TABLE 3-continued

Control sgRNA Library

| SEQ ID NO. | gRNA Label | Gene | Nucleic Acid Sequence |
|---|---|---|---|
| 658 | 3\|sg_hPOLR2L_CC_1\|POLR2L | POLR2L | GCTGCAGGCCGAGTACACCG |
| 659 | 3\|sg_hPOLR2L_CC_2\|POLR2L | POLR2L | ACAAGTGGGAGGCTTACCTG |
| 660 | 3\|sg_hPOLR2L_CC_3\|POLR2L | POLR2L | GCAGCGTACAGGGATGATCA |
| 661 | 3\|sg_hPOLR2L_CC_4\|POLR2L | POLR2L | GCAGTAGCGCTTCAGGCCCA |
| 662 | 3\|sg_hRPL9_CC_1\|RPL9 | RPL9 | CAAATGGTGGGGTAACAGAA |
| 663 | 3\|sg_hRPL9_CC_2\|RPL9 | RPL9 | GAAAGGAACTGGCTACCGTT |
| 664 | 3\|sg_hRPL9_CC_3\|RPL9 | RPL9 | AGGGCTTCCGTTACAAGATG |
| 665 | 3\|sg_hRPL9_CC_4\|RPL9 | RPL9 | GAACAAGCAACACCTAAAAG |
| 666 | 3\|sg_hSF3A3_CC_1\|SF3A3 | SF3A3 | TGAGGAGAAGGAACGGCTCA |
| 667 | 3\|sg_hSF3A3_CC_2\|SF3A3 | SF3A3 | GGAAGAATGCAGAGTATAAG |
| 668 | 3\|sg_hSF3A3_CC_3\|SF3A3 | SF3A3 | GGAATTTGAGGAACTCCTGA |
| 669 | 3\|sg_hSF3A3_CC_4\|SF3A3 | SF3A3 | GCTCACCGGCCATCCAGGAA |
| 670 | 3\|sg_hSF3B3_CC_1\|SF3B3 | SF3B3 | ACTGGCCAGGAACGATGCGA |
| 671 | 3\|sg_hSF3B3_CC_2\|SF3B3 | SF3B3 | GCAGCTCCAAGATCTTCCCA |
| 672 | 3\|sg_hSF3B3_CC_3\|SF3B3 | SF3B3 | GAATGAGTACACAGAACGGA |
| 673 | 3\|sg_hSF3B3_CC_4\|SF3B3 | SF3B3 | GGAGCAGGACAAGGTCGGGG |

Example 2—BRD9 Degrader Depletes BRD9 Protein

The following example demonstrates the depletion of the BRD9 protein in synovial sarcoma cells treated with a BRD9 degrader.

Procedure: Cells were treated with DMSO or the BRD9 degrader, Compound A (also known as dBRD9, see Remillard et al, *Angew. Chem. Int. Ed. Engl.* 56(21):5738-5743 (2017); see structure of Compound 1 below), for indicated doses and timepoints.

(Compound A)

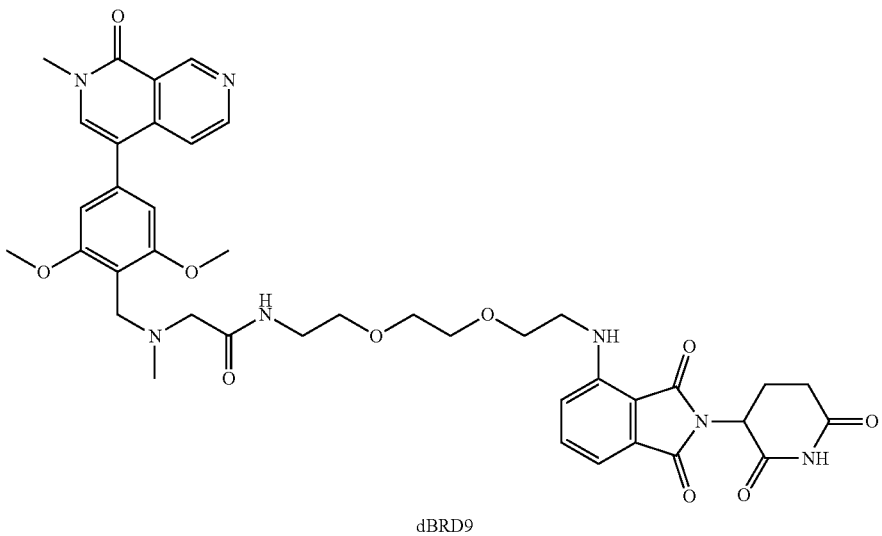

dBRD9

Figure 2:
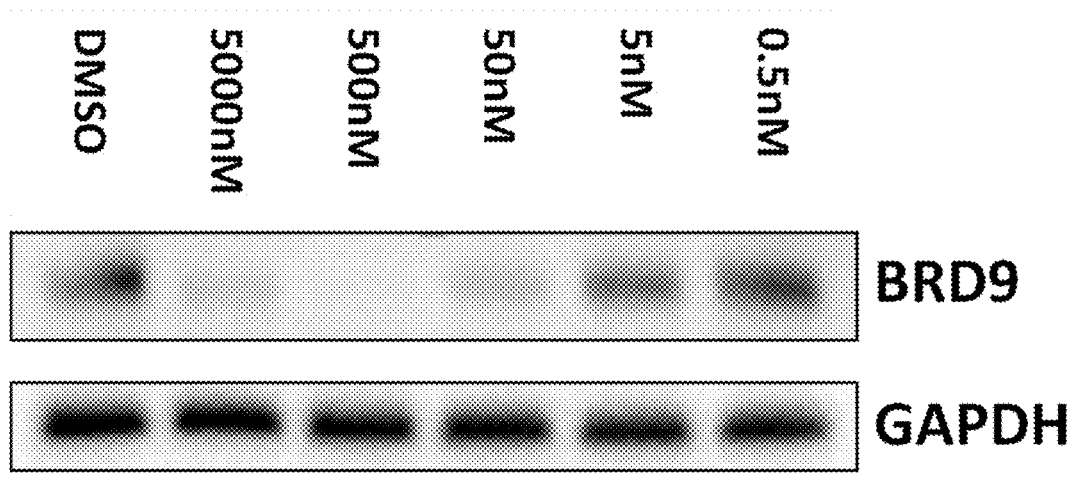
FIG. 2 is an image illustrating dose dependent depletion of BRD9 levels in a synovial sarcoma cell line (SYO1) in the presence of a BRD9 degrader.
Figure 3:
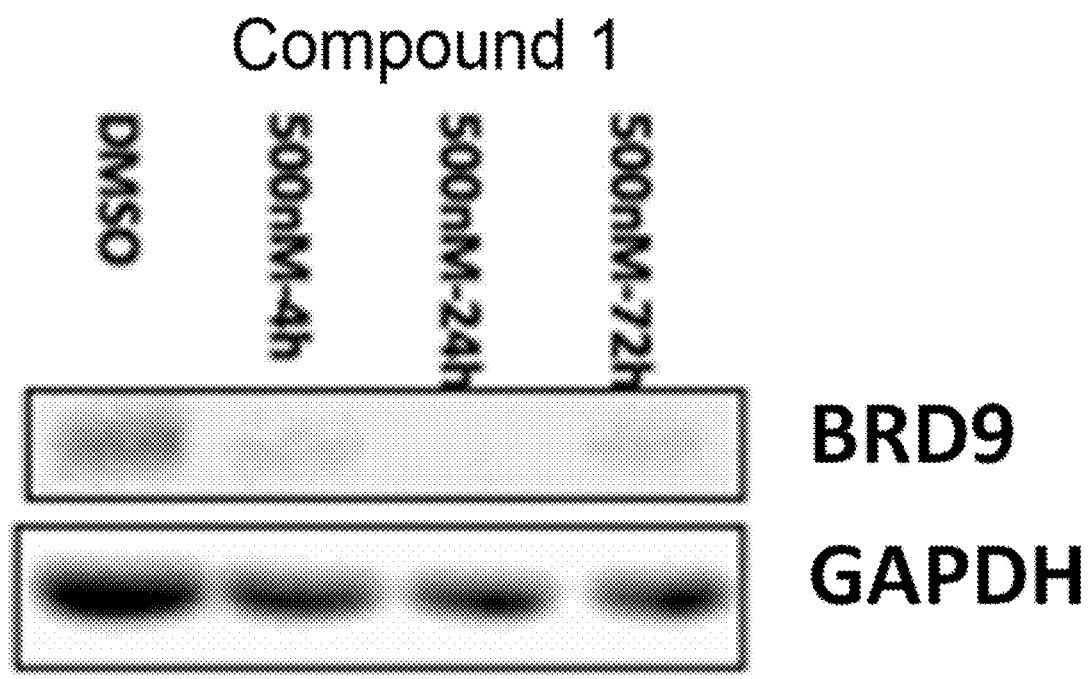
FIG. 3 is an image illustrating sustained suppression of BRD9 levels in a synovial sarcoma cell line (SYO1) in the presence of a BRD9 degrader over 72 hours.
Figure 4:
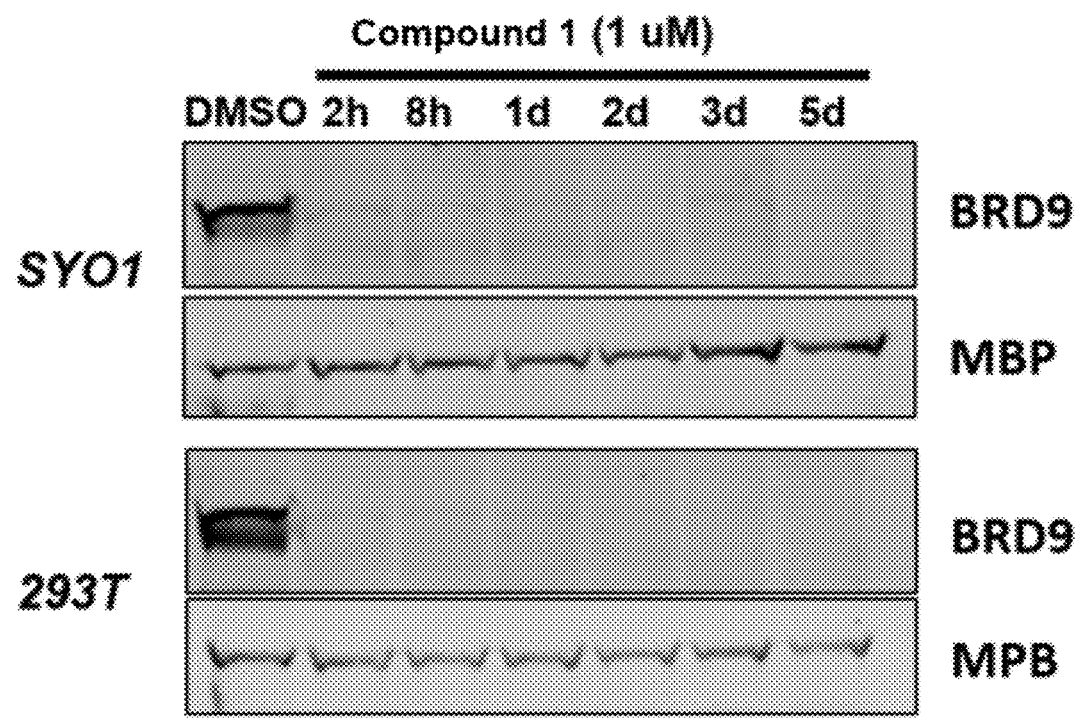
FIG. 4 is an image illustrating sustained suppression of BRD9 levels in two cell lines (293T and SYO1) in the presence of a BRD9 degrader over 5 days.

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 minutes, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C. Membranes were washed three times for 10 min and incubated with anti-mouse or anti-rabbit antibodies conjugated with either horseradish peroxidase (HRP, FIGS. 2-3) or IRDye (FIG. 4, 1:20,000, LI-COR) for at least 1 h. Blots were washed with TBST three times and developed with either the ECL system according to the manufacturer's protocols (FIGS. 2-3) or scanned on an Odyssey CLx Imaging system (FIG. 4).

Results: Treatment of SYO1 synovial sarcoma cells with the BRD9 degrader Compound A results in dose dependent (FIG. 2) and time dependent (FIG. 3) depletion of BRD9 in the cells. Further, as shown in FIG. 4, the depletion of BRD9 by Compound 1 is replicated in a non-synovial sarcoma cell line (293T) and may be sustained for at least 5 days.

Example 3—Inhibition of Growth of Synovial Cell Lines by BRD9 Inhibitors and BRD9 Degraders The following example demonstrates that BRD9 degraders and inhibitors selectively inhibit growth of synovial sarcoma cells.

Figure 5:
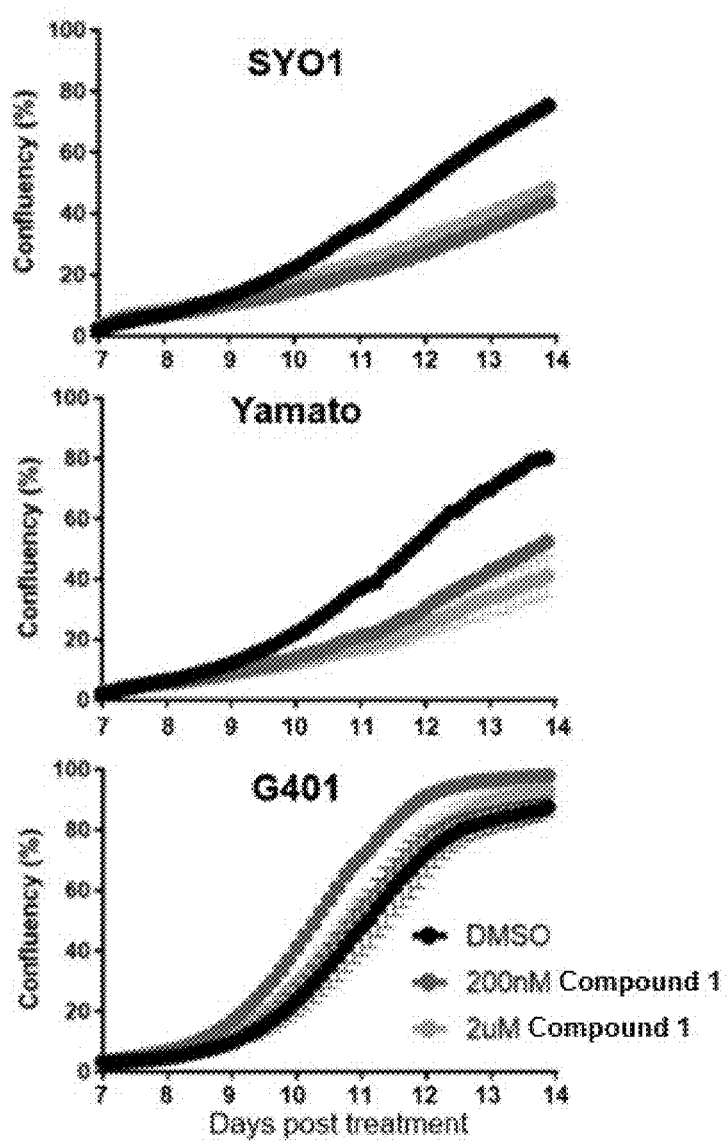
FIG. 5 is an image illustrating sustained suppression of BRD9 levels in synovial sarcoma cell lines (SYO1 and Yamato) in the presence of a BRD9 degrader over 7 days compared to the levels in cells treated with CRISPR reagents.

Procedures:

Cells were treated with DMSO or the BRD9 degrader, Compound A, at indicated concentrations, and proliferation was monitored from day 7 to day 14 by measuring confluency overtime using an IncuCyte live cell analysis system (FIG. 5). Growth medium and compounds were refreshed every 3-4 days.

Cells were seeded into 12-well plates and treated with DMSO, 1 µM BRD9 inhibitor, Compound B (also known as BI-7273, see Martin et al, *J Med Chem.* 59(10):4462-4475 (2016); see structure of Compound B below), or 1 µM BRD9 degrader, Compound A.

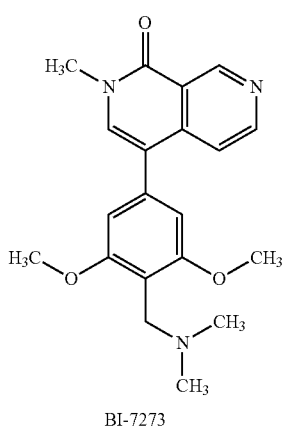

(Compound B)

BI-7273

Figure 6:
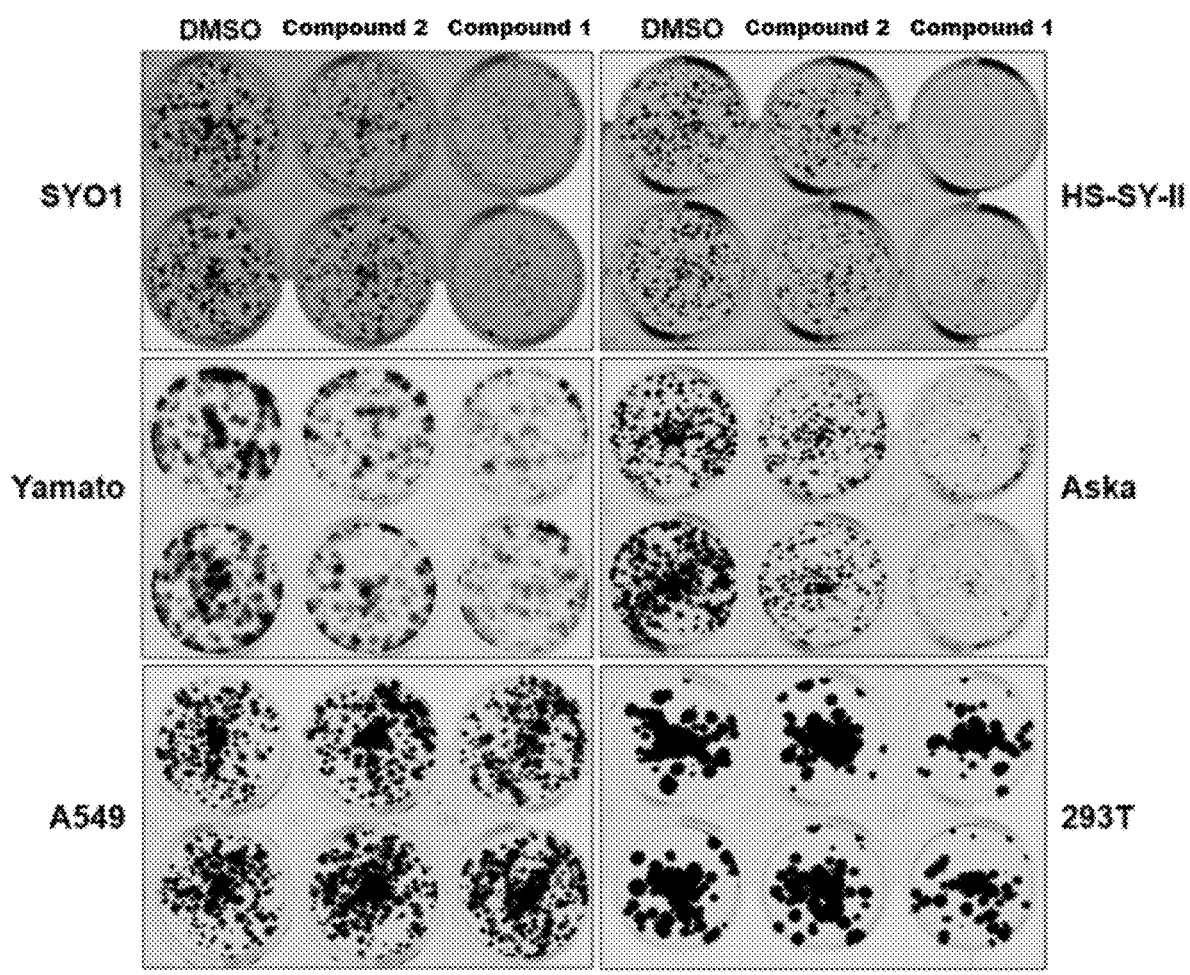
FIG. 6 is an image illustrating the effect on cell growth of six cell lines (SYO1, Yamato, A549, HS-SY-II, ASKA, and 293T) in the presence of a BRD9 degrader and a BRD9 inhibitor.

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1 L) for 30 min followed by 3× washes with water and drying the plates for at least 24 h at room temperature. Subsequently plates were scanned on an Odyssey CLx Imaging system (FIG. 6).

Figure 7:
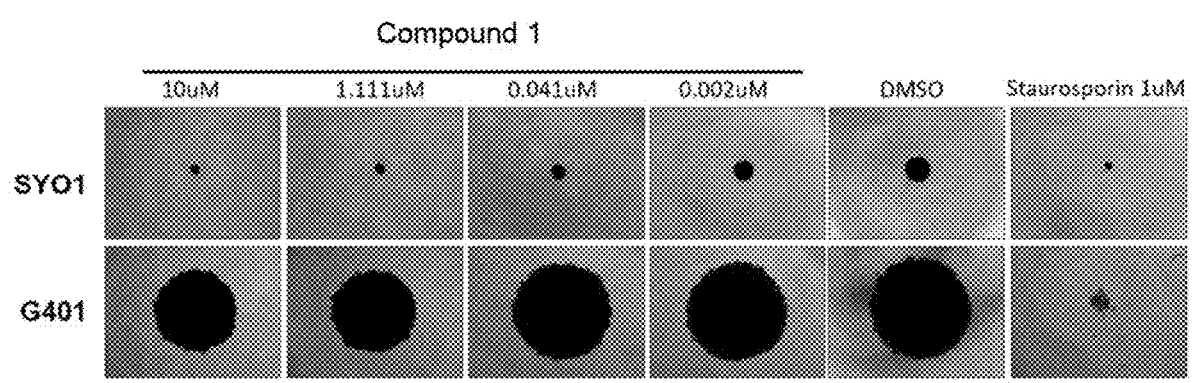
FIG. 7 is an image illustrating the effect on cell growth of two cell lines (SYO1 and G401) in the presence of a BRD9 degrader.

Cells were seeded into 96-well ultra low cluster plate (Costar, #7007) in 200 µL complete media and treated at day 2 with DMSO, Staurosporin, or BRD9 degarder, Compound 1, at indicated doses (FIG. 7). Media and compounds were changed every 5 d and cell colonies were imaged at day 14.

Results: As shown in FIGS. 5, 6, and 7, treatment of synovial sarcoma cell lines (SYO1, Yamato, HS-SY-II, and ASKA) with a BRD9 inhibitor, Compound B, or a BRD9 degrader, Compound A, results in inhibition of the growth of the cells, but does not result in inhibition of the growth of non-synovial control cancer cell lines (293T, A549, G401).

Example 4—Selective Inhibition of Growth of Synovial Cell Lines by BRD9 Degraders and BRD9 Binders The following example demonstrates that BRD9 degraders and binders selectively inhibit growth of synovial sarcoma cells.

Procedure: Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 µL of 0.005% (w/v) crystal violet solution in 25% (v/v) methanol for at least 1 hour at room temperature. Subsequently plates were scanned on an Odyssey CLx Imaging system.

Figure 8:
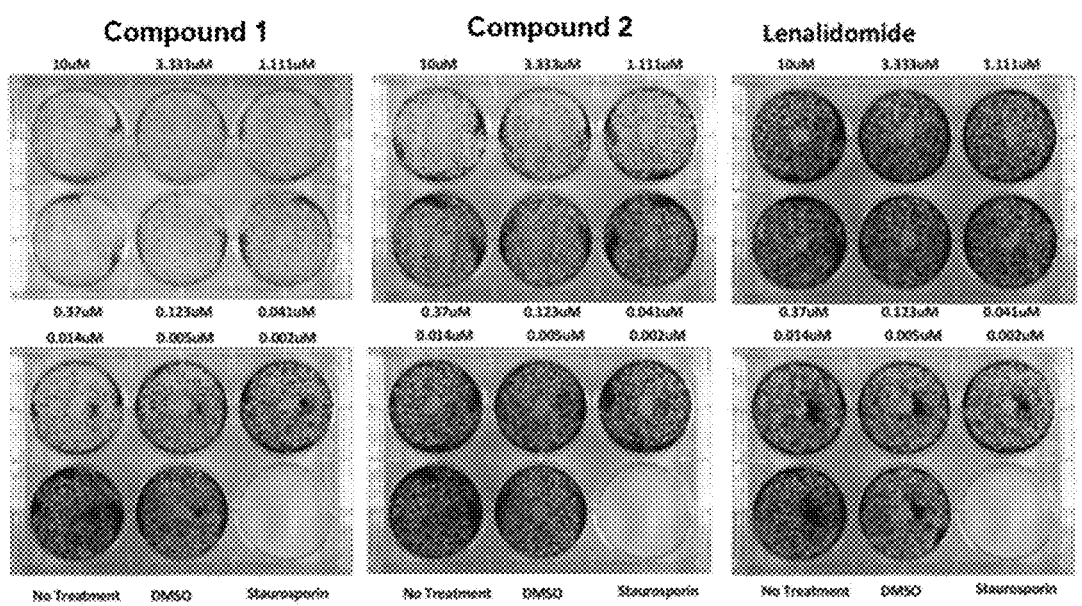
FIG. 8 is an image illustrating the effect on cell growth of three synovial sarcoma cell lines (SYO1, HS-SY-II, and ASKA) in the presence of a BRD9 degrader, BRD9 binder and E3 ligase binder.
Figure 8:
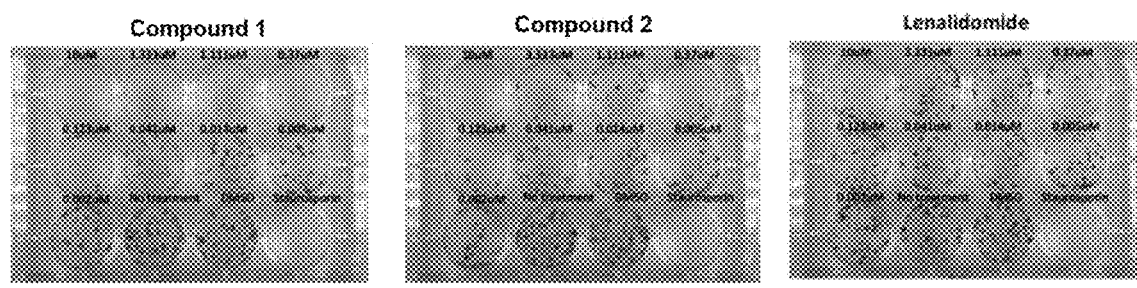
Figure 8:
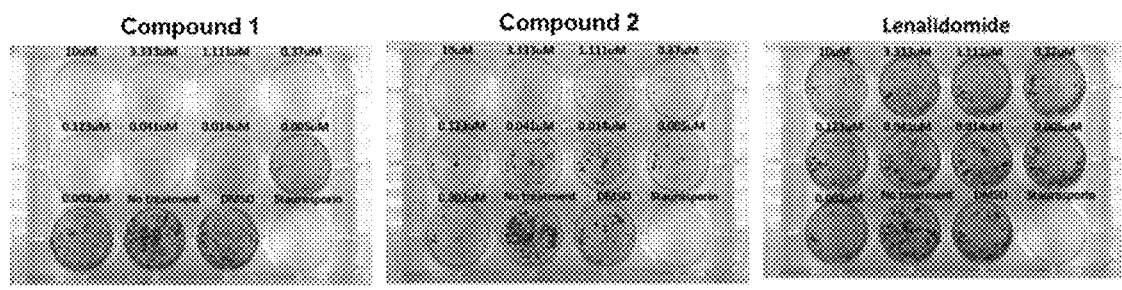
Figure 9:
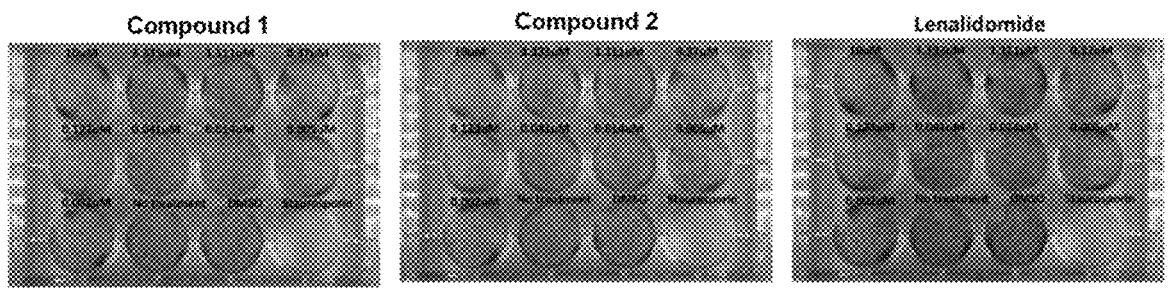
FIG. 9 is an image illustrating the effect on cell growth of three non-synovial sarcoma cell lines (RD, HCT116, and Calu6) in the presence of a BRD9 degrader, BRD9 binder and E3 ligase binder.
Figure 9:
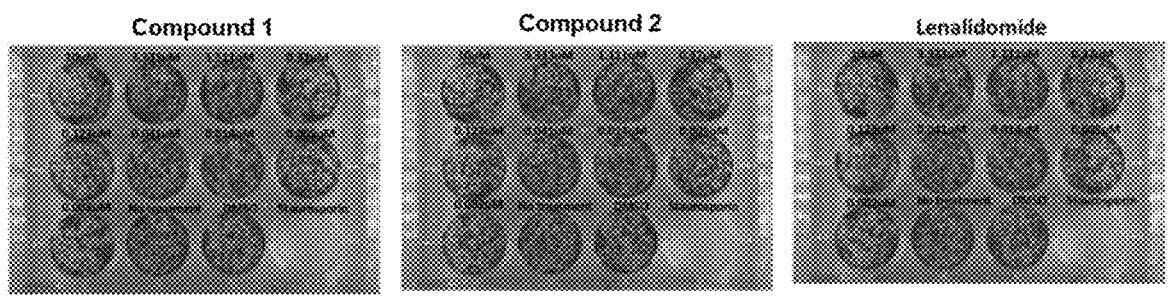
Figure 9:
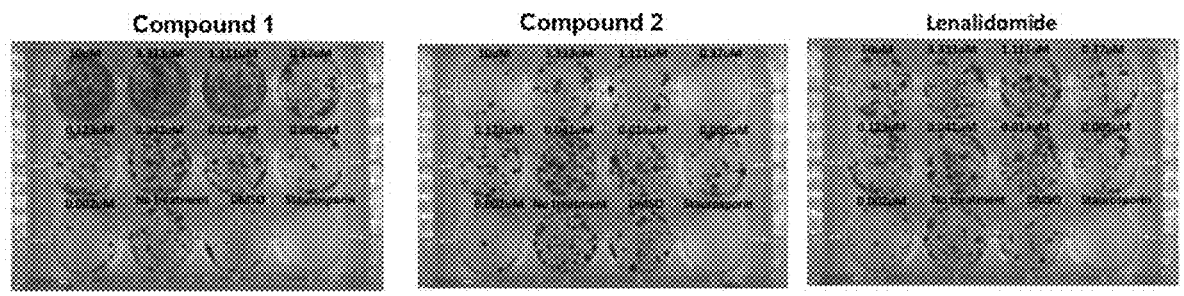
Figure 10:
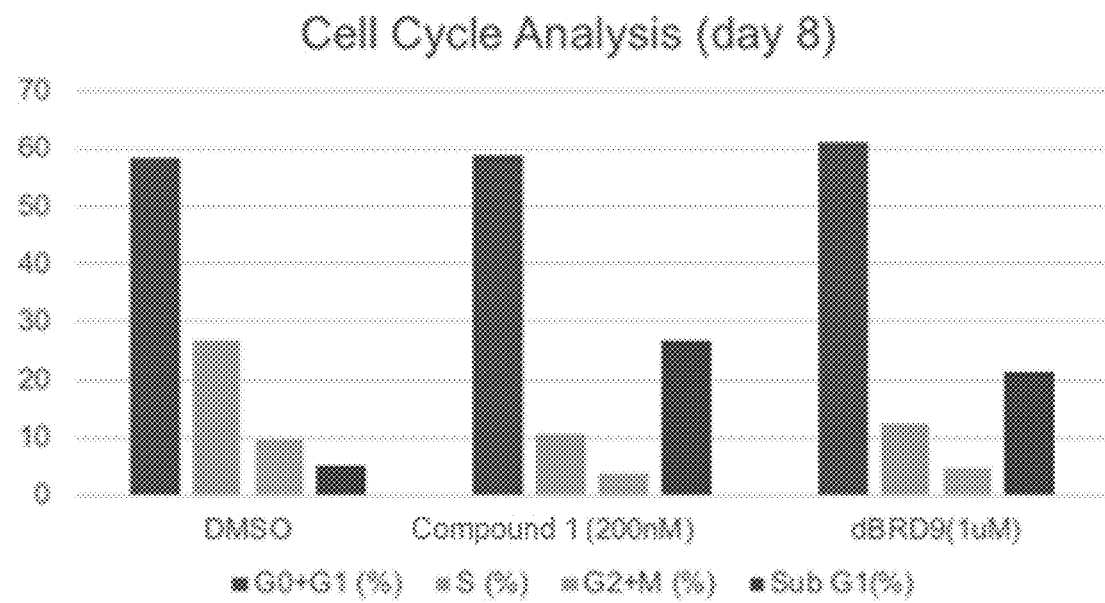
FIG. 10 is a graph illustrating the percentage of SYO1 in various cell cycle phases following treatment with DMSO, Compound 1 at 200 nM, or Compound 1 at 1 µM for 8 or 13 days.
Figure 10:
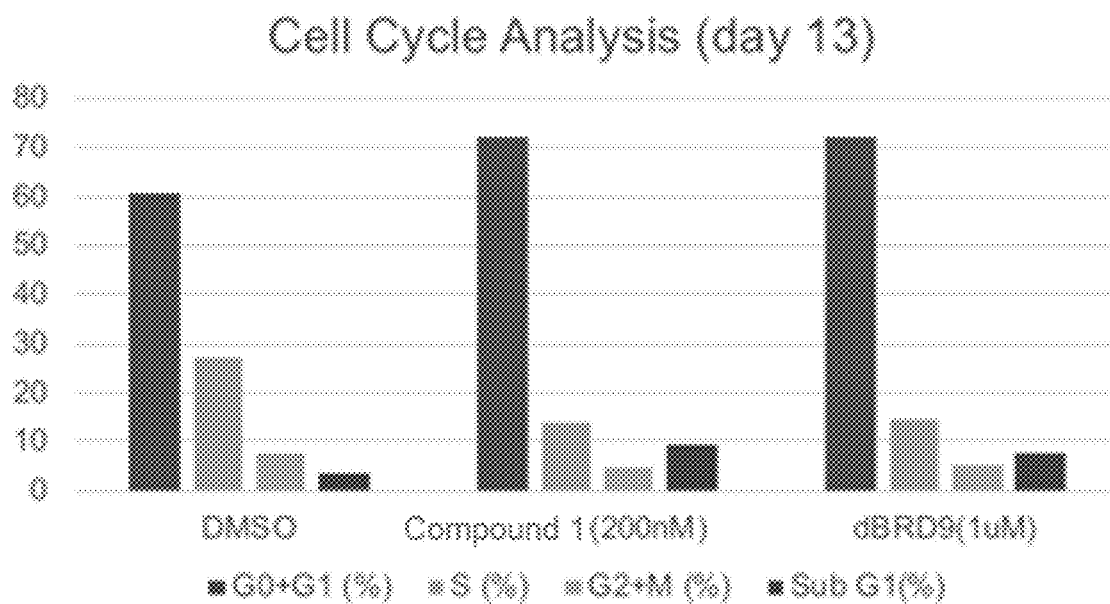
Figure 11:
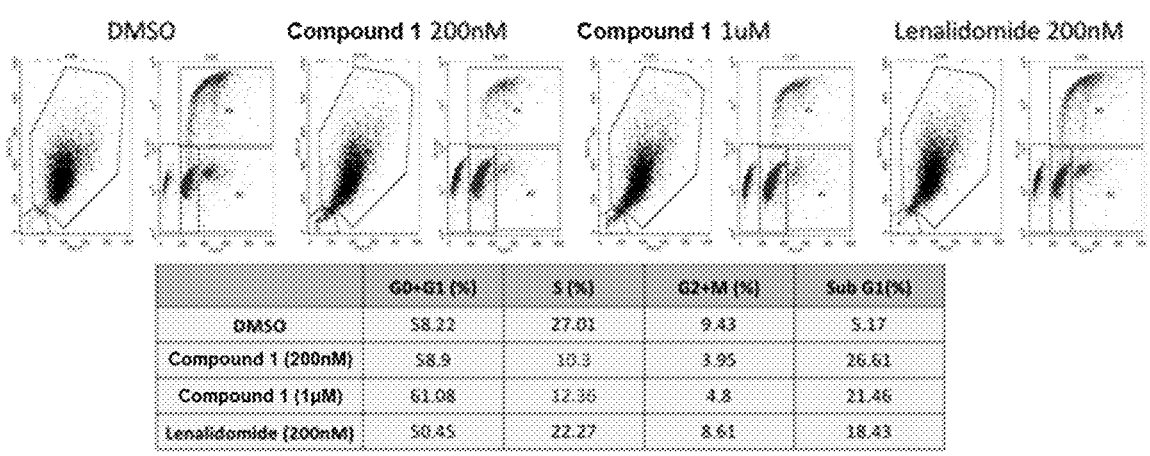
FIG. 11 is a series of contour plots illustrating the percentage of SYO1 cells in various cell cycle phases following treatment with DMSO, Compound 1 at 200 nM, Compound 1 at 1 µM, or lenalidomide at 200 nM for 8 days. Numerical values corresponding to each contour plot are found in the table below.
Figure 12:
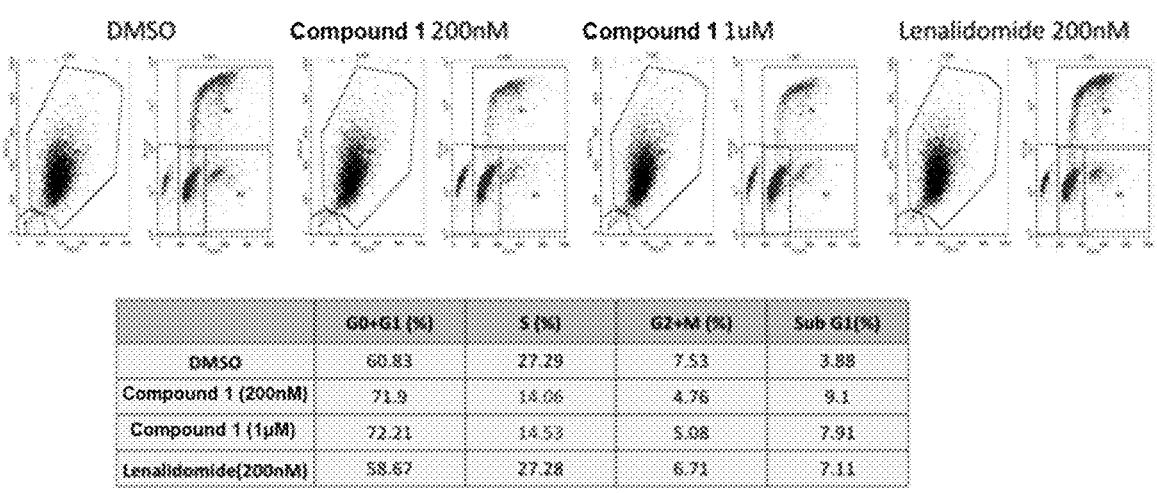
FIG. 12 is a series of contour plots illustrating the percentage of SYO1 cells in various cell cycle phases following treatment with DMSO, Compound 1 at 200 nM, Compound 1 at 1 µM, or lenalidomide at 200 nM for 13 days. Numerical values corresponding to each contour plot are found in the table below.
Figure 13:
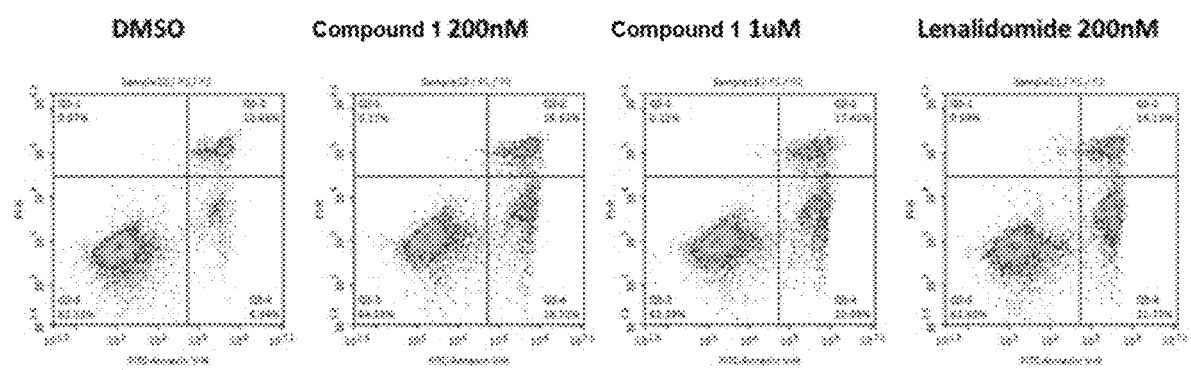
FIG. 13 is a series of contour plots illustrating the percentage of early- and late-apoptotic SYO1 cells following treatment with DMSO, Compound 1 at 200 nM, Compound 1 at 1 µM, or lenalidomide at 200 nM for 8 days. Numerical values corresponding to each contour plot are found in the table below.

Results: As shown in FIGS. 8 and 9, treatment of synovial sarcoma cell lines (SYO1, HS-SY-II, and ASKA) with Compound A or Compound B resulted in inhibition of the growth of the cells, but did not result in inhibition of the growth of non-synovial control cancer cell lines (RD, HCT116, and Calu6). Overall, Compound A showed most significant growth inhibition in all synovial cell lines.

Example 5—Inhibition of Cell Growth in Synovial Sarcoma Cells

The following example shows that BRD9 degraders inhibit cell growth and induce apoptosis in synovial sarcoma cells.

Procedure: SYO1 cells were treated for 8 or 13 days with DMSO, a BRD9 degrader (Compound A) at 200 nM or 1 µM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma A9210). Assays were performed according to the manufacturer's protocol.

Results: As shown in FIGS. 10-13, treatment with Compound A for 8 or 13 days resulted in reduced numbers of cells in the S-phase of the cell cycle as compared to DMSO and lenalidomide. Treatment with Compound A for 8 days also resulted in increased numbers of early- and late-apoptotic cells as compared to DMSO controls.

Example 6—Composition for SS18-SSX1-BAF

The following example shows the identification of BRD9 as a component of SS18-SSX containing BAF complexes.

Procedure: A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 14:
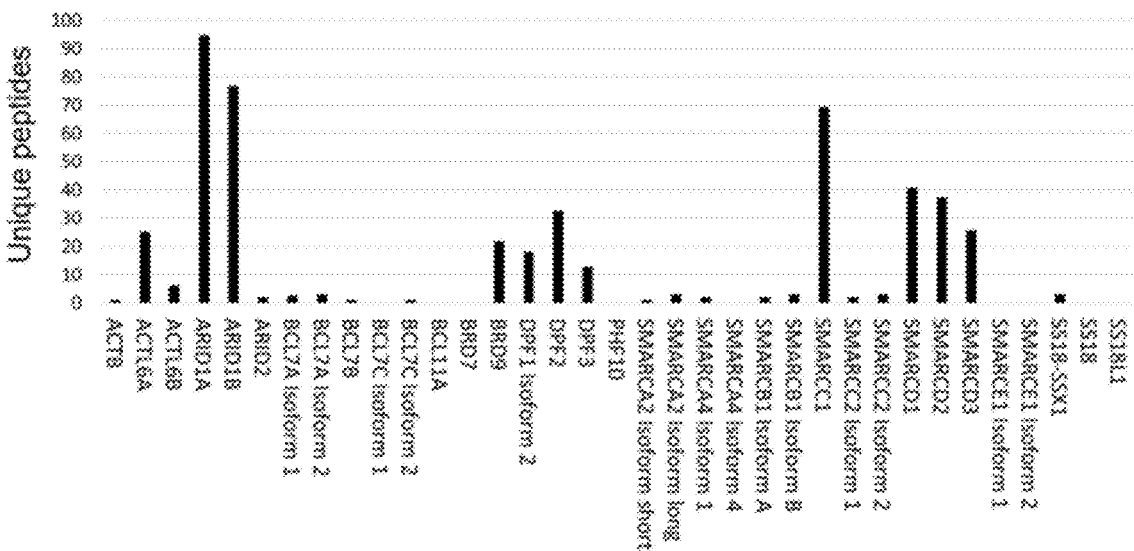
FIG. 14 is a graph illustrating the proteins present in BAF complexes including the SS18-SSX fusion protein.

Results: As shown in FIG. 14, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 7—Preparation of 4-[10-(5-[4-[(dimethyl-amino)methyl]-3,5-dimethoxyphenyl]-7-methyl-8-oxo-2,7-naphthyridin-3-yl)-4,7-dioxa-1,10-diazaundecan-1-yl]-2-(2,6-dioxopiperidin-3-yl)isoindole-1,3-dione (Compound C)

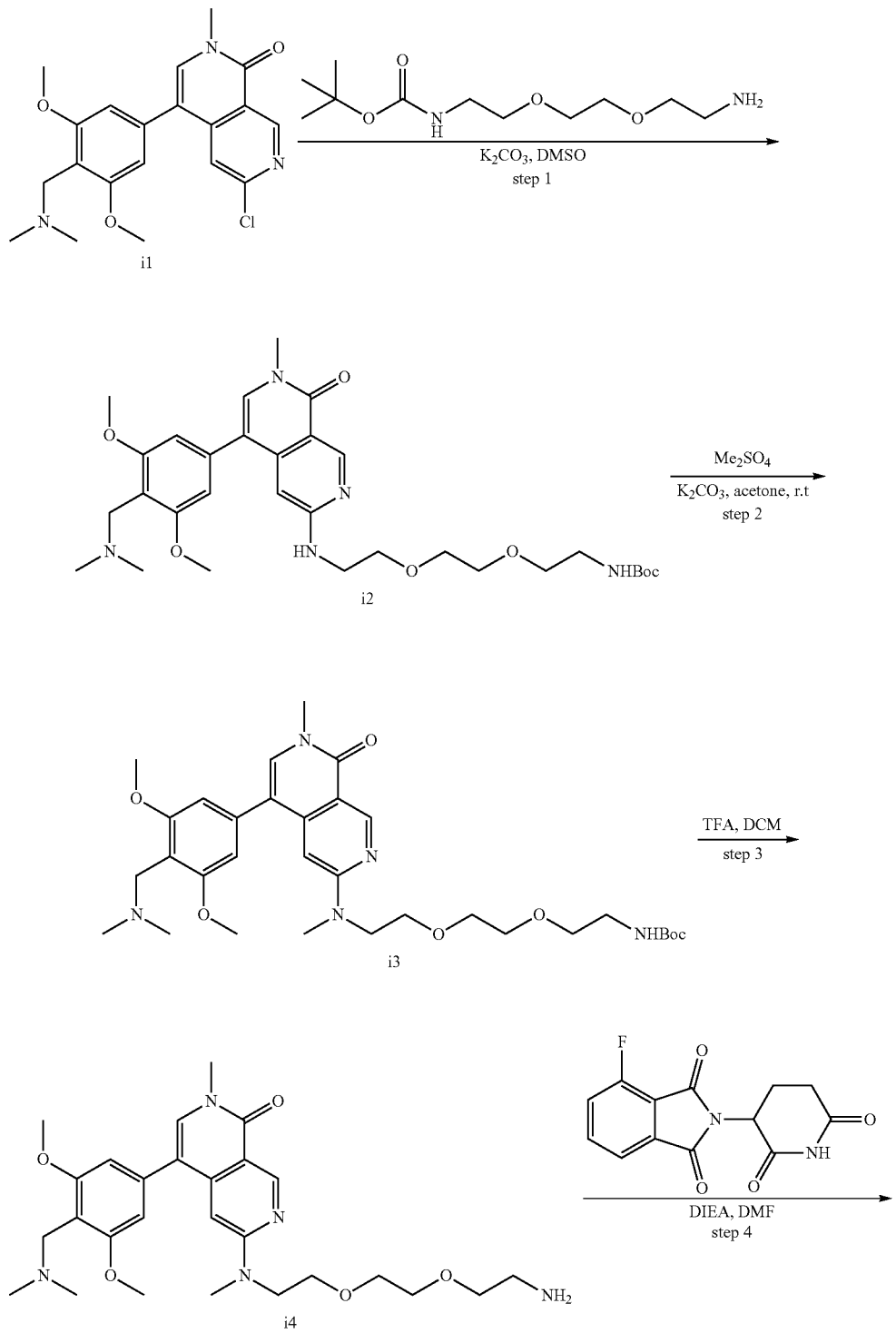

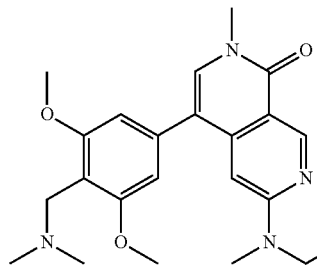

Compound C

Step 1: preparation of tert-butyl N-[2-(2-[2-[(5-[4-[(dimethylamino)methyl]-3,5-dimethoxyphenyl]-7-methyl-8-oxo-2,7-naphthyridin-3-yl)amino]ethoxy]ethoxy)ethyl]carbamate (i2)

Step 2: Preparation of tert-butyl N-[2-(2-[2-[(5-[4-[(dimethylamino)methyl]-3,5-dimethoxyphenyl]-7-methyl-8-oxo-2,7-naphthyridin-3-yl)(methyl)amino]ethoxy]ethoxy)ethyl]carbamate (i3)

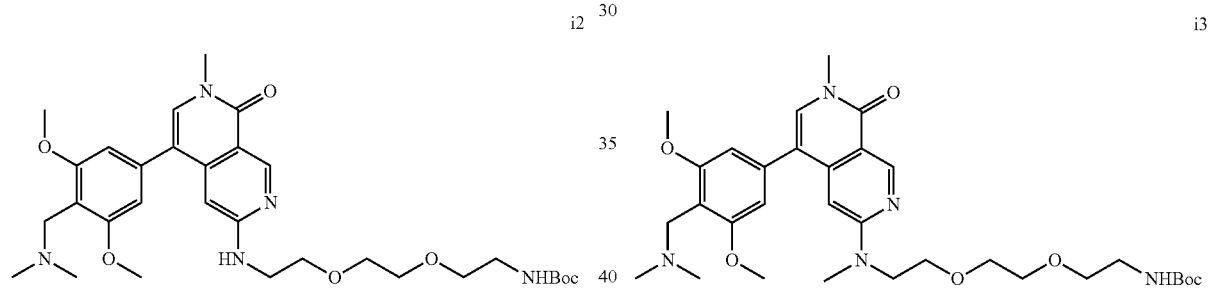

i2 i3

To a stirred solution of 6-chloro-4-[4-[(dimethylamino)methyl]-3,5-dimethoxyphenyl]-2-methyl-2,7-naphthyridin-1-one (335.0 mg, 0.864 mmol, 1.00 equiv) and tert-butyl N-[2-[2-(2-aminoethoxy)ethoxy]ethyl]carbamate (643.4 mg, 2.591 mmol, 3.00 equiv) in DMSO (2 mL) was added $K_2CO_3$ (238.7 mg, 1.727 mmol, 2.00 equiv) at room temperature. The resulting mixture was stirred overnight at 130 degrees C. The mixture was allowed to cool down to room temperature. The resulting mixture was filtered, and the filter cake was washed with $CH_2Cl_2$ (2×3 mL). The filtrate was concentrated under reduced pressure. The residue was purified by reverse flash chromatography (conditions: column, 018 silica gel; Mobile Phase A: Water/0.05% TEA, Mobile Phase B: ACN; Flow rate: 50 mL/min; Gradient: 0% B to 40% B in 15 min; detector, 254 nm) to afford tert-butyl N-[2-(2-[2-[(5-[4-[(dimethylamino)methyl]-3,5-dimethoxyphenyl]-7-methyl-8-oxo-2,7-naphthyridin-3-yl)amino]ethoxy]ethoxy) ethyl]carbamate (380 mg, 73.36%) as a yellow oil. LCMS (ESI) m/z: [M+H]$^+$=600.

To a stirred solution/mixture of tert-butyl N-[2-(2-[2-[(5-[4-[(dimethylamino)methyl]-3,5-dimethoxyphenyl]-7-methyl-8-oxo-2,7-naphthyridin-3-yl)amino]ethoxy]ethoxy)ethyl]carbamate (190.0 mg, 0.317 mmol, 1.00 equiv) and $K_2CO_3$ (87.6 mg, 0.634 mmol, 2 equiv) in acetone (3 mL) was added dimethyl sulfate (44.0 mg, 0.348 mmol, 1.10 equiv) at room temperature. The resulting mixture was stirred overnight at room temperature. The reaction was quenched with water at room temperature. The aqueous layer was extracted with $CH_2Cl_2$/isopropanol (3×5 mL). The combined organic layers were washed with brine (1×10 mL) and dried over anhydrous $Na_2SO_4$. After filtration, the filtrate was concentrated under reduced pressure to afford tert-butyl N-[2-(2-[2-[(5-[4-[(dimethylamino)methyl]-3,5-dimethoxyphenyl]-7-methyl-8-oxo-2,7-naphthyridin-3-yl)(methyl)amino]ethoxy]ethoxy)ethyl]carbamate (95.00 mg, 48.86%) as a yellow oil. The crude product was used in the next step directly without further purification. LCMS (ESI) m/z: [M+H]$^+$=614.

Step 3: Preparation of 3,3,3-trifluoropropanoic acid; 6-([2-[2-(2-aminoethoxy)ethoxy]ethyl](methyl) amino)-4-[4-[(dimethylamino)methyl]-3,5-dimethoxyphenyl]-2-methyl-2,7-naphthyridin-1-one (i4)

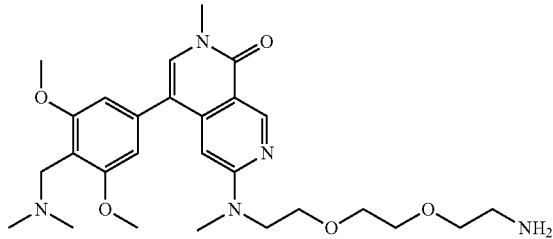

i4

To a stirred solution of tert-butyl N-[2-(2-[2-[(5-[4-[(dimethylamino)methyl]-3,5-dimethoxyphenyl]-7-methyl-8-oxo-2,7-naphthyridin-3-yl)(methyl)amino]ethoxy]ethoxy)ethyl]carbamate (75.00 mg, 0.122 mmol, 1.00 equiv) in dichloromethane (3 mL) was added TFA (1 mL) dropwise at room temperature. The resulting mixture was concentrated under vacuum to afford 3,3,3-trifluoropropanoic acid; 6-([2-[2-(2-amino ethoxy)ethoxy]ethyl](methyl)amino)-4-[4-[(dimethylamino)methyl]-3,5-dimethoxyphenyl]-2-methyl-2,7-naphthyridin-1-one (103 mg, crude) as yellow oil. The crude product was used in the next step directly without further purification. LCMS (ESI) m/z: [M+H]$^+$=514.

Step 4: Preparation of 4-[10-(5-[4-[(dimethylamino) methyl]-3,5-dimethoxyphenyl]-7-methyl-8-oxo-2,7-naphthyridin-3-yl)-4,7-dioxa-1,10-diazaundecan-1-yl]-2-(2,6-dioxopiperidin-3-yl)isoindole-1,3-dione (Compound C)

To a stirred solution of 6-([2-[2-(2-aminoethoxy)ethyl](methyl)amino)-4-[4-[(dimethylamino) methyl]-3,5-dimethoxyphenyl]-2-methyl-2,7-naphthyridin-1-one (68.00 mg, 0.132 mmol, 1.00 equiv) in DMF (1 mL) was added 2-(2,6-dioxopiperidin-3-yl)-4-fluoroisoindole-1,3-dione (34.6 mg, 0.125 mmol, 0.95 equiv) and DIEA (85.6 mg, 0.662 mmol, 5.00 equiv) at room temperature. The resulting mixture was stirred for overnight at 80 degrees C. The crude product was purified by Prep-HPLC (conditions: Xselect CSH F-Phenyl OBD Column 19*150 mm 5um; Mobile Phase A: Water (0.1% FA), Mobile Phase B: ACN; Flow rate: 25 mL/min; Gradient: 9 B to 19 B in 12 min; 254 nm; Rt: 12.63 minutes) to afford 4-[10-(5-[4-[(dimethylamino) methyl]-3,5-dimethoxyphenyl]-7-methyl-8-oxo-2,7-naphthyridin-3-yl)-4,7-dioxa-1,10-diazaundecan-1-yl]-2-(2,6-dioxopiperidin-3-yl)isoindole-1,3-dione (3.2 mg, 3.14%) as a yellow solid. $^1$H NMR (400 MHz, Methanol-d4) δ 8.96 (s, 1H), 7.54-7.46 (m, 2H), 6.99 (dd, J=15.8, 7.7 Hz, 2H), 6.84 (s, 2H), 6.74 (s, 1H), 4.96-4.94 (m, 1H), 4.57 (s, 2H), 3.97 (s, 6H), 3.77-3.69 (m, 8H), 3.59-3.53 (m, 5H), 3.41 (t, J=5.2 Hz, 2H), 3.17-3.11 (m, 9H), 2.83-2.53 (m, 3H), 2.04-1.95 (m, 1H). LCMS (ESI) m/z: [M+H]$^+$=770.50.

Example 8—Preparation of Compounds D32-D184

In analogous procedures to those described for Compound C in the example above, compounds D1-D59 were prepared using the appropriate starting materials.

Compound C

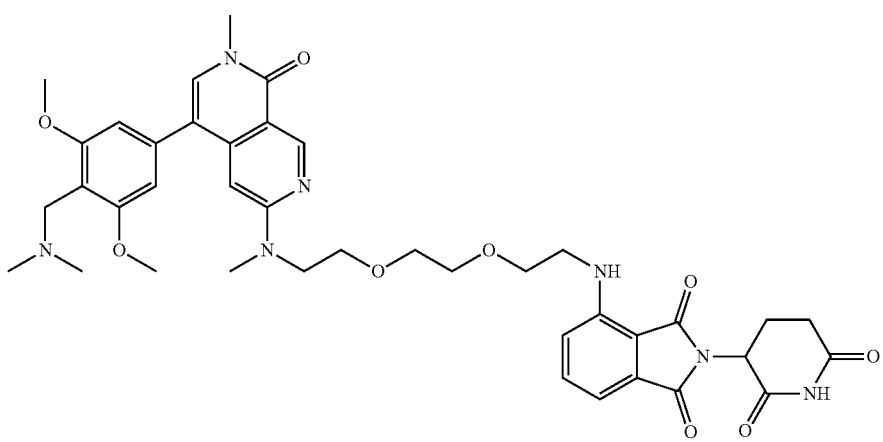

TABLE 4

| Compound No. | LCMS | ¹H NMR |
|---|---|---|
| D1 | 749.74 | |
| D2 | 734.71 | ¹H NMR (400 MHz, DMSO-d6) δ 11.11 (s, 1H), 9.45 (s, 1H), 8.72 (d, J = 5.7 Hz, 1H), 7.97 (s, 1H), 7.86 (s, 1H), 7.55 (d, J = 5.7 Hz, 1H), 6.84 (s, 2H), 5.14 (d, J = 13.2 Hz, 1H), 4.98 (s, 2H), 4.35 (s, 2H), 3.91-3.71 (m, 6H), 3.59 (s, 3H), 3.03-2.78 (m, 1H), 2.73 (s, 2H), 2.67-2.49 (m, 1H), 2.05 (s, 2H). |
| D3 | 694.5 | |
| D4 | 734.26 | |
| D5 | 720.54 | |
| D6 | 706.65 | |
| D7 | 720.4 | |
| D8 | 681.35 | ¹H NMR (300 MHz, DMSO-d6) δ 11.13 (s, 1H), 9.04 (s, 1H), 8.17 (s, 1H, FA), 7.86-7.80 (m, 1H), 7.59 (s, 1H), 7.29-7.23 (m, 2H), 6.77 (s, 2H), 6.47 (s, 1H), 5.12 (dd, J = 12.9, 5.3 Hz, 1H), 4.95 (t, J = 5.5 Hz, 1H), 3.81 (s, 6H), 3.75-3.69 (m, 4H), 3.48 (s, 3H), 3.15-3.11 (m, 2H), 3.06 (s, 6H), 2.91-2.84 (m, 1H), 2.65-2.55 (m, 2H), 2.07-1.99 (m, 1H). |
| D9 | 693.3 | ¹H NMR (300 MHz, DMSO-d6) δ 11.12 (s, 1H), 9.04 (s, 1H), 8.17 (s, 1H, FA), 7.88-7.73 (m, 3H), 7.60 (s, 1H), 6.78 (s, 2H), 6.50 (s, 1H), 5.14 (dd, J = 12.9, 5.3 Hz, 1H), 3.84 (s, 6H), 3.65 (s, 2H), 3.49 (s, 3H), 3.08 (s, 6H), 3.02 (d, J = 11.3 Hz, 2H), 2.97-2.70 (m, 3H), 2.63-2.55 (m, 1H), 2.30-2.20 (m, 2H), 2.10-2.00 (m, 1H), 1.83-1.63 (m, 4H). |
| D10 | 680.2 | ¹H NMR (300 MHz, DMSO-d6) δ 10.97 (s, 1H), 9.04 (s, 1H), 7.60 (s, 1H), 7.42 (d, J = 8.5 Hz, 1H), 7.26 (dd, J = 8.5, 2.3 Hz, 1H), 7.15 (d, J = 2.3 Hz, 1H), 6.79 (s, 2H), 6.50 (s, 1H), 5.09 (dd, J = 13.2, 5.0 Hz, 1H), 4.41-4.14 (m, 2H), 3.84 (s, 6H), 3.67 (s, 2H), 3.48 (s, 3H), 3.19 (s, 4H), 3.08 (s, 6H), 2.91 (ddd, J = 17.9, 13.6, 5.5 Hz, 1H), 2.65 (s, 4H), 2.48-2.24 (m, 2H), 2.06-1.92 (m, 1H). |
| D11 | 680.3 | ¹H NMR (300 MHz, DMSO-d6) δ 10.94 (s, 1H), 9.04 (s, 1H), 7.60 (s, 1H), 7.52 (d, J = 8.7 Hz, 1H), 7.05 (d, J = 7.9 Hz, 2H), 6.79 (s, 2H), 6.50 (s, 1H), 5.05 (dd, J = 13.3, 5.1 Hz, 1H), 4.40-4.10 (m, 2H), 3.84 (s, 6H), 3.65 (s, 2H), 3.48 (s, 3H), 3.33-3.20 (m, 4H), 3.08 (s, 6H), 2.96-2.83 (m, 1H), 2.59 (d, J = 14.6 Hz, 4H), 2.45-2.25 (m, 2H), 1.95 (dd, J = 12.1, 6.5 Hz, 1H). |
| D12 | 746.2 | ¹H NMR (400 MHz, Methanol-d4) δ 8.99-8.94 (m, 1H), 7.67 (d, J = 8.3 Hz, 1H), 7.59 (s, 1H), 6.88 (s, 2H), 6.87 (d, J = 2.0 Hz, 1H), 6.75-6.68 (m, 1H), 6.38 (d, J = 1.8 Hz, 1H), 5.12-5.02 (m, 1H), 4.44 (s, 2H), 4.23 (t, J = 7.6 Hz, 4H), 3.99 (s, 8H), 3.87 (s, 2H), 3.60 (s, 4H), 3.34 (s, 1H), 3.31-3.19 (m, 2H), 2.95-2.81 (m, 1H), 2.81-2.64 (m, 2H), 2.60-2.48 (m, 2H), 2.30 (d, J = 14.4 Hz, 2H), 2.21-2.07 (m, 3H). |
| D13 | 720.45 | ¹H NMR (400 MHz, DMSO-d6) δ 10.90 (s, 1H), 9.01 (s, 1H), 8.17 (s, 1H), 7.51 (d, J = 37.4 Hz, 1H), 6.74 (s, 2H), 6.65-6.35 (m, 3H), 5.01 (dd, J = 13.3, 5.1 Hz, 1H), 4.37-3.99 (m, 2H), 3.80 (s, 5H), 3.59 (s, 3H), 3.54 (s, 2H), 3.46 (s, 2H), 3.15 (s, 1H), 3.05 (s, 5H), 2.58 (s, 1H), 2.45-2.39 (m, 5H), 2.39-2.27 (m, 1H), 1.93 (ddq, J = 10.4, 5.4, 3.2, 2.6 Hz, 1H), 1.71 (t, J = 5.4 Hz, 4H). |
| D14 | 720.52 | ¹H NMR (400 MHz, DMSO-d6) δ 10.93 (s, 1H), 9.02 (s, 1H), 8.12 (s, 1H), 7.57 (s, 1H), 7.36 (d, J = 8.2 Hz, 1H), 6.80 (s, 2H), 6.67 (d, J = 7.5 Hz, 2H), 6.47 (s, 1H), 5.05 (dd, J = 13.3, 5.1 Hz, 1H), 4.37-4.07 (m, 2H), 3.84 (s, 7H), 3.60 (s, 4H), 3.47 (s, 3H), 3.06 (s, 6H), 2.97-2.84 (m, 1H), 2.81 (d, J = 25.0 Hz, 0H), 2.69-2.52 (m, 1H), 2.42-2.26 (m, 1H), 2.05-1.92 (m, 1H), 1.85 (s, 4H). |
| D15 | 665.55 | ¹H NMR (400 MHz, Methanol-d4) δ 8.97 (d, J = 0.8 Hz, 1H), 7.73 (d, J = 9.2 Hz, 1H), 7.59 (s, 1H), 7.20 (d, J = 6.5 Hz, 2H), 6.88 (s, 2H), 6.39 (s, 1H), 5.14 (dd, J = 13.3, 5.1 Hz, 1H), 4.46 (d, J = 7.1 Hz, 4H), 4.23 (t, J = 7.6 Hz, 4H), 3.98 (s, 6H), 3.86-3.63 (m, 6H), 3.60 (s, 4H), 3.58-3.46 (m, 3H), 3.31-3.24 (m, 3H), 2.99-2.86 (m, 1H), 2.84-2.75 (m, 1H), 2.60-2.42 (m, 5H), 2.18 (d, J = 16.2 Hz, 3H). |
| D16 | 693.35 | ¹H NMR (400 MHz, DMSO-d6) δ 11.09 (s, 1H), 9.04 (s, 1H), 7.64 (d, J = 9.0 Hz, 1H), 7.58 (d, J = 2.7 Hz, 1H), 7.14 (d, J = 7.2 Hz, 2H), 6.76 (s, 2H), 6.49 (s, 1H), 5.06 (dd, J = 12.9, 5.4 Hz, 1H), 3.97 (d, J = 13.3 Hz, 1H), 3.82 (s, 6H), 3.76 (d, J = 13.1 Hz, 1H), 3.48 (s, 3H), 3.06 (s, 7H), 2.95-2.82 (m, 2H), 2.71-2.54 (m, 4H), 2.01 (d, J = 12.7 Hz, 1H), 1.85 (s, 1H), 1.72 (d, J = 11.2 Hz, 2H), 1.35 (tt, J = 33.0, 18.0 Hz, 2H). |
| D17 | 693.1 | ¹H NMR (300 MHz, DMSO-d6) δ 11.12 (s, 1H), 9.01 (s, 1H), 7.88-7.79 (m, 1H), 7.60 (s, 1H), 7.27 (d, 2H), 6.74 (s, 2H), 6.18 (s, 1H), 5.12-4.96 (m, 2H), 3.99 (t, 4H), 3.82 (s, 6H), 3.78-3.70 (m, 3H), 3.48 (s, 4H), 3.24-3.13 (m, 2H), 2.97-2.80 (m, 1H), 2.66-2.62 (m, 1H), 2.61-2.54 (m, 1H), 2.30-2.28 (m, 2H), 2.10-1.92 (m, 1H). |

TABLE 4-continued

| Compound No. | LCMS | 1H NMR |
|---|---|---|
| D18 | 669.15 | 1H NMR (400 MHz, DMSO-d6) δ 11.09 (s, 1H), 9.04 (s, 1H), 8.16 (s, 1H, FA), 7.82 (dd, J = 7.5, 0.9 Hz, 1H), 7.59 (s, 1H), 6.76 (s, 2H), 6.46 (s, 1H), 6.38-6.30 (m, 2H), 5.29 (dd, J = 12.5, 5.2 Hz, 1H), 4.76 (t, J = 5.6 Hz, 1H), 3.81 (s, 6H), 3.76-3.63 (m, 4H), 3.48 (s, 3H), 3.10 (dd, J = 8.2, 4.8 Hz, 2H), 3.06 (s, 6H), 2.97-2.83 (m, 1H), 2.68-2.59 (m, 1H), 2.48-2.37 (m, 1H), 2.27-2.07 (m, 1H). |
| D19 | 736.35 | 1H NMR (400 MHz, DMSO-d6) δ 11.11 (s, 1H), 9.52 (s, 1H, TFA), 9.09 (s, 1H), 7.78 (d, J = 8.4 Hz, 1H), 7.65 (s, 1H), 7.49 (d, J = 2.3 Hz, 1H), 7.35 (dd, J = 8.6, 2.3 Hz, 1H), 6.90 (s, 2H), 6.67 (s, 1H), 5.10 (dd, J = 13.0, 5.3 Hz, 1H), 4.42-4.31 (m, 2H), 4.20 (d, J = 12.6 Hz, 2H), 3.92 (s, 6H), 3.70 (t, J = 4.8 Hz, 5H), 3.63-3.55 (m, 8H), 3.32 (h, J = 11.6, 10.4 Hz, 4H), 2.90 (ddd, J = 17.4, 14.0, 5.4 Hz, 1H), 2.65-2.54 (m, 2H), 2.07-2.00 (m, 1H). |
| D20 | 732.5 | 1H NMR (300 MHz, DMSO-d6) δ 10.97 (s, 1H), 9.02 (s, 1H), 8.24 (s, 1H, FA), 7.61 (s, 1H), 7.37 (d, J = 8.1 Hz, 1H), 6.78-6.63 (m, 4H), 6.21 (s, 1H), 5.09 (dd, J = 13.2, 5.1 Hz, 1H), 4.35-4.15 (m, 2H), 4.01 (t, J = 7.3 Hz, 4H), 3.82 (s, 6H), 3.58-3.48 (m, 8H), 2.97-2.85 (m, 1H), 2.67-2.55 (m, 2H), 2.42-2.26 (m, 7H), 1.98 (d, J = 12.6 Hz, 1H), 1.80-1.62 (m, 4H). |
| D21 | 711.3 | 1H NMR (300 MHz, DMSO-d6) δ 11.09 (s, 1H), 9.07 (s, 1H), 8.19 (s, 0.6H, FA), 7.87-7.78 (m, 1H), 7.63 (s, 1H), 6.74 (s, 2H), 6.63 (s, 1H), 6.40-6.29 (m, 2H), 5.29 (dd, J = 12.5, 5.2 Hz, 1H), 4.76 (t, J = 5.5 Hz, 1H), 3.81 (s, 6H), 3.68-3.57 (m, 8H), 3.52-3.50 (m, 7H), 3.10 (t, J = 6.4 Hz, 2H), 2.99-2.81 (m, 1H), 2.66-2.50 (m, 1H), 2.49-2.38 (m, 1H), 2.16-2.08 (m, 1H). |
| D22 | 677.35 | 1H NMR (400 MHz, DMSO-d6) δ 11.14 (s, 1H), 9.01 (s, 1H), 8.18 (s, 1H, FA), 7.90-7.82 (m, 2H), 7.81-7.74 (m, 1H), 7.62 (s, 1H), 6.75 (s, 2H), 6.19 (s, 1H), 5.15 (dd, J = 12.8, 5.4 Hz, 1H), 3.99 (t, J = 7.4 Hz, 4H), 3.83 (s, 6H), 3.79-3.60 (m, 6H), 3.48 (s, 3H), 3.26 (s, 1H), 2.98-2.80 (m, 1H), 2.66-2.52 (m, 2H), 2.33 (m, J = 7.2 Hz, 2H), 2.10-2.01 (m, 1H). |
| D23 | 702.46 | |
| D24 | 702.46 | 1H NMR (400 MHz, DMSO-d6) δ 10.92 (s, 1H), 8.99 (s, 1H), 8.17 (s, 1H), 7.59-7.46 (m, 1H), 7.37 (dd, J = 18.7, 7.8 Hz, 2H), 7.17-6.87 (m, 2H), 6.67 (d, J = 8.1 Hz, 2H), 5.05 (dd, J = 13.3, 5.2 Hz, 1H), 4.39-4.05 (m, 2H), 4.07-3.89 (m, 5H), 3.82 (d, J = 7.8 Hz, 4H), 3.58 (s, 3H), 3.47 (d, J = 16.6 Hz, 5H), 2.97-2.79 (m, 1H), 2.67-2.51 (m, 2H), 2.45-2.26 (m, 9H), 2.08-1.88 (m, 2H), 1.77 (d, J = 5.4 Hz, 5H). |
| D25 | 773.42 | |
| D26 | 805.4 | 1H NMR (300 MHz, DMSO-d6) δ 11.07 (s, 1H), 10.20-9.86 (m, 1H), 9.30-9.10 (m, 1H), 9.02 (s, 1H), 7.84 (dd, J = 7.8, 4.2 Hz, 1H), 7.63 (d, J = 2.1 Hz, 1H), 6.87 (s, 2H), 6.80-6.68 (m, 1H), 6.35 (d, J = 5.7 Hz, 1H), 6.23 (s, 5.7 Hz, 1H), 5.27 (dd, J = 12.3, 5.1 Hz, 1H), 4.22 (d, J = 3.6 Hz, 2H), 4.10-3.96 (m, 6H), 3.90 (s, 6H), 3.65-3.52 (m, 2H), 3.50-3.34 (m, 5H), 3.30-3.10 (m, 6H), 3.08-2.80 (m, 2H), 2.75-2.60 (m, 1H), 2.50-2.42 (m, 2H), 2.42-2.28 (m, 2H), 2.20-2.08 (m, 1H), 1.96-1.70 (m, 3H), 1.70-1.40 (m, 4H). |
| D27 | 747.25 | 1H NMR (400 MHz, DMSO-d6) δ 10.96 (s, 1H), 9.01 (s, 1H), 8.19 (s, 1H, FA salt), 7.60 (s, 1H), 7.52 (d, J = 9.1 Hz, 1H), 7.08-7.01 (m, 2H), 6.74 (s, 2H), 6.19 (s, 1H), 5.05 (dd, J = 13.3, 5.1 Hz, 1H), 4.33 (d, J = 16.9 Hz, 1H), 4.20 (d, J = 16.9 Hz, 1H), 4.00 (t, J = 7.4 Hz, 4H), 3.82 (s, 6H), 3.68 (s, 2H), 3.48 (s, 3H), 3.30-3.25 (m, 6H), 3.05 (t, J = 6.5 Hz, 2H), 2.97-2.80 (m, 2H), 2.63-2.54 (m, 1H), 2.44-2.26 (m, 7H), 2.00-1.92 (m, 1H). |
| D28 | 639.2 | 1H NMR (400 MHz, DMSO-d6) δ 11.08 (s, 1H), 9.02 (s, 1H), 7.63 (d, J = 8.6 Hz, 1H), 7.58 (s, 1H), 7.31 (d, J = 2.4 Hz, 1H), 7.04 (dd, J = 8.7, 2.4 Hz, 1H), 6.80 (s, 2H), 6.44 (s, 1H), 5.05 (dd, J = 12.9, 5.4 Hz, 1H), 4.68 (s, 2H), 3.88 (s, 6H), 3.46 (s, 3H), 3.13 (s, 3H), 3.05 (s, 6H), 2.95-2.82 (m, 1H), 2.63-2.56 (m, 1H), 2.55 (s, 1H), 2.06-1.95 (m, 1H). |
| D29 | 667.30 | 1H NMR (300 MHz, DMSO-d6) δ 10.98 (s, 1H), 9.16 (s, 1H), 7.75 (s, 1H), 7.42 (d, J = 8.5 Hz, 1H), 7.26 (d, J = 8.8 Hz, 1H), 7.17-7.11 (m, 1H), 6.78 (s, 1H), 6.74 (s, 2H), 5.10 (dd, J = 13.2, 5.2 Hz, 1H), 4.34 (d, J = 16.7 Hz, 1H), 4.20 (d, J = 16.9 Hz, 1H), 3.94 (s, 3H), 3.83 (s, 6H), 3.68-3.61 (m, 2H), 3.54 (s, 3H), 3.19-3.12 (m, 4H), 2.74 (d, J = 1.9 Hz, 1H), 2.65-2.58 (m, 5H), 2.38 (d, J = 8.0 Hz, 1H), 2.30-2.25 (m, 1H). |
| D30 | 731.20 | 1H NMR (400 MHz, DMSO-d6) δ 11.08 (s, 1H), 9.28 (s, 1H), 8.23 (s, 1H, FA), 7.80 (s, 1H), 7.64 (d, J = 8.3 Hz, 1H), 7.44 (s, 1H), 6.81-6.72 (m, 3H), 6.65 (dd, J = 8.3, 2.1 Hz, 1H), 5.06 (dd, J = 12.9, 5.4 Hz, 1H), 3.83 (s, 6H), 3.74 (s, 4H), 3.56 (d, J = 5.4 Hz, 5H), 2.95-2.82 (m, 1H), 2.55 (s, 3H), 2.44 (s, 3H), 2.27 (tt, J = 7.8, 3.9 Hz, 1H), 2.06-1.97 (m, 1H), 1.74 (t, J = 5.4 Hz, 4H), 1.06-0.94 (m, 4H). |

TABLE 4-continued

| Compound No. | LCMS | ¹H NMR |
|---|---|---|
| D31 | 717.25 | ¹H NMR (400 MHz, DMSO-d6) δ 10.95 (s, 1H), 9.28 (s, 1H), 8.21 (s, 1H, FA), 7.80 (s, 1H), 7.53-7.42 (m, 2H), 6.75 (s, 2H), 6.54-6.44 (m, 2H), 5.04 (dd, J = 13.2, 5.1 Hz, 1H), 4.36-4.13 (m, 2H), 3.83 (s, 6H), 3.63 (s, 4H), 3.56 (s, 5H), 2.90 (ddd, J = 17.0, 13.6, 5.4 Hz, 1H), 2.55 (s, 3H), 2.45 (s, 2H), 2.40-2.30 (m, 1H), 2.27 (td, J = 7.8, 3.9 Hz, 1H), 2.05-1.85 (m, 1H), 1.74 (t, J = 5.4 Hz, 4H), 1.06-0.94 (m, 4H). |
| D32 | 717.25 | ¹H NMR (400 MHz, DMSO-d6) δ 10.98 (s, 1H), 9.29 (s, 1H), 8.15 (s, 1H, FA), 7.81 (s, 1H), 7.44 (s, 1H), 7.38 (d, J = 8.1 Hz, 1H), 6.78 (s, 2H), 6.70 (d, J = 7.9 Hz, 2H), 5.08 (dd, J = 13.3, 5.1 Hz, 1H), 4.36-4.15 (m, 2H), 3.86 (s, 6H), 3.76 (s, 2H), 3.61 (s, 4H), 3.57 (s, 4H), 2.98-2.84 (m, 1H), 2.71-2.65 (m, 2H), 2.60 (d, J = 16.6 Hz, 2H), 2.38 (dd, J = 13.3, 4.5 Hz, 1H), 2.30-2.21 (m, 1H), 1.98 (d, J = 13.1 Hz, 1H), 1.83 (s, 4H), 1.05-0.96 (m, 4H). |
| D33 | 692.15 | ¹H NMR (300 MHz, DMSO-d6) δ 11.13 (s, 1H), 9.30 (s, 1H), 7.85 (d, J = 9.0 Hz, 2H), 7.52 (s, 1H), 7.28 (d, J = 7.9 Hz, 2H), 6.82 (s, 2H), 5.24-5.05 (m, 1H), 5.00 (s, 1H), 4.00-3.67 (m, 10H), 3.58 (s, 3H), 3.32-3.27 (m, 2H), 3.02-2.78 (m, 1H), 2.67-2.54 (m, 2H), 2.14-1.97 (m, 1H), 1.40 (s, 3H), 1.33-1.20 (m, 2H), 0.96-0.80 (m, 2H). |
| D34 | 720.35 | ¹H NMR (300 MHz, DMSO-d6) δ 10.98 (s, 1H), 9.29 (s, 1H), 8.14 (s, 1H, FA), 7.80 (s, 1H), 7.44 (s, 1H), 7.38 (d, J = 7.9 Hz, 1H), 6.75 (s, 2H), 6.69 (d, J = 8.1 Hz, 2H), 5.09 (dd, J = 13.2, 5.2 Hz, 1H), 4.41-4.06 (m, 2H), 3.84 (s, 6H), 3.59 (s, 6H), 2.95-2.84 (m, 1H), 2.64-2.61 (m, 2H), 2.42-2.34 (m, 4H), 2.05-1.92 (m, 2H), 1.76 (s, 4H), 1.01 (s, 4H). |
| D35 | 710.35 | ¹H NMR (300 MHz, Methanol-d4) δ 9.26 (s, 1H), 7.58 (s, 1H), 7.42 (d, J = 8.2 Hz, 1H), 6.89 (d, J = 4.7 Hz, 3H), 6.85-6.79 (m, 2H), 5.15 (dd, J = 13.2, 5.1 Hz, 1H), 4.49-4.32 (m, 4H), 4.00 (d, J = 7.0 Hz, 9H), 3.87 (s, 2H), 3.74 (s, 2H), 3.64-3.52 (m, 2H), 3.29-3.19 (m, 2H), 3.01-2.86 (m, 1H), 2.85-2.74 (m, 1H), 2.60-2.41 (m, 1H), 2.36-2.25 (m, 2H), 2.24-2.04 (m, 3H). |
| D36 | 666.30 | ¹H NMR (300 MHz, Methanol-d4) δ 9.25 (s, 1H), 8.56 (d, 1H, FA), 7.79 (d, J = 7.9 Hz, 1H), 7.58 (s, 1H), 7.54 (s, 1H), 7.48 (d, J = 8.1 Hz, 1H), 6.94-6.78 (m, 3H), 5.17 (dd, J = 13.3, 5.1 Hz, 1H), 4.51 (d, J = 5.0 Hz, 2H), 4.37-4.24 (m, 2H), 4.01 (s, 3H), 3.97 (s, 6H), 3.65 (s, 3H), 3.57 (d, J = 12.0 Hz, 2H), 3.16-2.97 (m, 3H), 2.97-2.86 (m, 1H), 2.86-2.75 (m, 1H), 2.51 (qd, J = 13.1, 4.7 Hz, 1H), 2.27-2.15 (m, 1H), 2.15-2.03 (m, 4H). |
| D37 | 657.35 | ¹H NMR (300 MHz, Methanol-d4) δ 7.70 (s, 1H), 6.04 (d, J = 9.4 Hz, 2H), 5.76-5.64 (m, 2H), 5.31 (s, 2H), 5.25 (s, 1H), 3.75-3.57 (m, 2H), 3.25-3.19 (m, 2H), 3.15-3.05 (m, 2H), 3.00-2.89 (m, 2H), 2.89-2.75 (m, 2H), 2.50-2.34 (m, 9H), 1.45-1.20 (m, 2H), 1.08-0.89 (m, 1H), 0.73-0.59 (m, 1H). |
| D38 | 657.30 | ¹H NMR (300 MHz, DMSO-d6) δ 11.00 (s, 1H), 10.29 (s, 1H, TFA), 9.17 (s, 1H), 7.77-7.66 (m, 2H), 7.24-6.99 (m, 2H), 6.80 (d, J = 30.9 Hz, 3H), 5.33-5.02 (m, 2H), 4.81-4.55 (m, 2H), 4.55-4.13 (m, 6H), 4.00-3.82 (m, 9H), 3.02-2.85 (m, 1H), 2.63 (s, 1H), 2.44-2.31 (m, 1H), 2.08-1.93 (m, 1H). |
| D39 | 667.35 | ¹H NMR (300 MHz, Methanol-d4) δ 9.39 (s, 1H), 7.72 (s, 1H), 7.63-7.57 (m, 1H), 7.38 (d, J = 4.4 Hz, 1H), 7.32-7.19 (m, 2H), 6.89 (s, 2H), 5.17 (dd, J = 13.4, 5.2 Hz, 2H), 4.83-4.74 (m, 1H), 4.67 (d, J = 15.1 Hz, 2H), 4.51-4.30 (m, 4H), 3.98 (d, J = 16.9 Hz, 6H), 3.79-3.54 (m, 1H), 3.01-2.77 (m, 2H), 2.60-2.45 (m, 1H), 2.25-2.13 (m, 2H), 1.11 (d, J = 8.9 Hz, 4H). |
| D40 | 698.35 | ¹H NMR (400 MHz, Methanol-d4) δ 9.25 (s, 1H), 8.55 (s, 1H, FA), 7.58 (s, 1H), 7.52 (d, J = 8.2 Hz, 1H), 7.39 (s, 1H), 7.37 (s, 1H), 6.88 (s, 2H), 6.83 (s, 1H), 5.16 (dd, J = 13.4, 5.1 Hz, 1H), 4.60 (d, J = 13.5 Hz, 1H), 4.52-4.37 (m, 3H), 4.00 (d, J = 7.0 Hz, 9H), 3.89-3.85 (m, 2H), 3.64-3.59 (m, 2H), 3.48-3.33 (m, 2H), 2.95-2.86 (m, 1H), 2.81 (d, J = 17.2 Hz, 1H), 2.59-2.44 (m, 1H), 2.23-2.16 (m, 1H), 1.62 (d, J = 6.4 Hz, 6H). |
| D41 | 708.45 | ¹H NMR (300 MHz, Methanol-d4) δ 9.16 (s, 1H), 8.56 (s, 1H, FA), 7.51 (d, J = 9.0 Hz, 1H), 7.44 (s, 1H), 7.35 (d, J = 7.1 Hz, 2H), 6.88 (s, 2H), 6.52 (s, 1H), 5.16 (dd, J = 13.2, 5.1 Hz, 1H), 4.64 (s, 2H), 4.52-4.35 (m, 2H), 4.25 (br s, 2H), 3.97 (s, 6H), 3.68-3.54 (m, 4H), 3.45-3.37 (m, 2H), 3.14 (s, 7H), 3.03-2.73 (m, 2H), 2.59-2.43 (m, 1H), 2.27-2.14 (m, 1H), 1.63 (s, 6H). |
| D42 | 692.20 | ¹H NMR (300 MHz, Methanol-d4) δ 9.09 (d, J = 3.5 Hz, 1H), 8.56 (s, 1H), 7.67-7.37 (m, 2H), 7.21 (dd, J = 8.4, 2.3 Hz, 1H), 7.11 (s, 1H), 6.85 (s, 2H), 6.18 (s, 1H), 5.15 (dd, J = 13.3, 5.1 Hz, 1H), 4.55-4.26 (m, 7H), 4.15-4.00 (m, 6H), 3.94 (s, 6H), 3.58 (d, J = 1.3 Hz, 3H), 2.96 (s, 3H), 2.95-2.87 (m, 1H), 2.85-2.73 (m, 1H), 2.55-2.29 (m, 3H), 2.25-2.12 (m, 1H). |

TABLE 4-continued

| Compound No. | LCMS | ¹H NMR |
| --- | --- | --- |
| D43 | 637.15 | ¹H NMR (300 MHz, Methanol-d4) δ 9.14 (d, J = 0.7 Hz, 1H), 7.46-7.36 (m, 2H), 6.94 (d, J = 2.1 Hz, 1H), 6.86 (dd, J = 8.2, 2.2 Hz, 1H), 6.73 (s, 2H), 6.52 (d, J = 0.8 Hz, 1H), 5.15 (dd, J = 13.2, 5.2 Hz, 1H), 4.55-4.33 (m, 5H), 4.14-4.00 (m, 2H), 3.80 (s, 6H), 3.58 (s, 3H), 3.12 (s, 6H), 2.98-2.86 (m, 1H), 2.85-2.76 (m, 1H), 2.57-2.44 (m, 1H), 2.24-2.13 (m, 1H). |
| D44 | 695.35 | ¹H NMR (400 MHz, Methanol-d4) δ 9.26 (s, 1H), 8.56 (s, 0.49H, FA), 7.57 (s, 1H), 7.50 (d, J = 8.2 Hz, 1H), 7.35 (d, J = 8.3 Hz, 2H), 6.83 (d, J = 5.9 Hz, 3H), 5.16 (dd, J = 13.4, 5.2 Hz, 1H), 4.46-4.39 (m, 2H), 4.28-4.11 (m, 2H), 4.01 (s, 3H), 3.96 (s, 6H), 3.65 (s, 4H), 3.42-3.36 (m, 2H), 3.30-3.18 (m, 3H), 2.95-2.89 (m, 1H), 2.83-2.77 (m, 1H), 2.54-2.47 (m, 1H), 2.22-2.16 (m, 1H), 1.62 (s, 6H). |
| D45 | 634.30 | ¹H NMR (400 MHz, DMSO-d6) δ 10.98 (s, 1H), 9.02 (s, 1H), 7.45 (d, J = 8.4 Hz, 1H), 7.36 (s, 1H), 7.34-7.25 (m, 3H), 7.21 (d, J = 2.4 Hz, 1H), 7.00-6.92 (m, 2H), 6.39 (s, 1H), 5.11 (dd, J = 13.3, 5.1 Hz, 1H), 4.40-4.15 (m, 2H), 4.03-3.81 (m, 3H), 3.46 (s, 3H), 3.06 (s, 6H), 2.99-2.85 (m, 3H), 2.78 (s, 3H), 2.70-2.58 (m, 1H), 2.44-2.32 (m, 1H), 2.05-1.95 (m, 1H), 1.97-1.80 (m, 2H), 1.75 (d, J = 12.0 Hz, 2H). |
| D46 | 730.45 | ¹H NMR (300 MHz, DMSO-d6) δ 10.98 (s, 1H), 9.03 (s, 1H), 8.70 (s, 1H, TFA salt), 7.59 (s, 1H), 7.42 (d, J = 8.8 Hz, 1H), 7.08 (s, 2H), 6.75-6.67 (m, 2H), 6.17 (s, 1H), 5.08 (dd, J = 13.2, 5.0 Hz, 1H), 4.34 (s, 2H), 4.31 (s, 1H), 4.20 (d, J = 16.7 Hz, 1H), 4.01 (t, J = 7.4 Hz, 4H), 3.93 (s, 3H), 3.79 (s, 2H), 3.65 (s, 2H), 3.50 (s, 3H), 3.45-3.34 (m, 2H), 3.33-3.15 (m, 2H), 2.88-2.75 (m, 3H), 2.66-2.54 (m, 1H), 2.44-2.30 (m, 3H), 2.20-2.09 (m, 2H), 2.08-1.94 (m, 3H), 1.22 (t, J = 7.4 Hz, 3H). |
| D47 | 665.30 | ¹H NMR (400 MHz, DMSO-d6) δ 10.98 (s, 1H), 9.04 (s, 1H), 7.57 (s, 1H), 7.45 (d, J = 8.4 Hz, 1H), 7.36-7.29 (m, 1H), 7.20 (d, J = 2.3 Hz, 1H), 6.75 (s, 2H), 6.55-6.49 (m, 1H), 5.11 (dd, J = 13.3, 5.1 Hz, 1H), 4.39-4.19 (m, 2H), 3.89-3.83 (m, 2H), 3.81 (s, 6H), 3.48 (s, 3H), 3.45-3.37 (m, 2H), 3.08 (s, 6H), 2.99-2.86 (m, 1H), 2.82-2.70 (m, 2H), 2.65-2.56 (m, 1H), 2.47-2.35 (m, 2H), 2.06-1.96 (m, 1H), 1.61-1.53 (m, 2H). |
| D48 | 707.20 | ¹H NMR (300 MHz, Methanol-d4) δ 9.48 (s, 1H), 8.55 (s, 1H, FA), 7.85-7.69 (m, 2H), 7.34 (d, J = 8.6 Hz, 1H), 7.08-6.93 (m, 2H), 6.86 (s, 2H), 5.24-5.06 (m, 1H), 4.82 (s, 2H), 4.63 (d, J = 8.0 Hz, 2H), 4.46-4.26 (m, 2H), 3.92-3.83 (m, 6H), 3.76-3.69 (m, 4H), 3.65 (d, J = 20.3 Hz, 3H), 3.56-3.46 (m, 2H), 3.29-3.17 (m, 2H), 2.97-2.73 (m, 2H), 2.60-2.41 (m, 1H), 2.39-2.12 (m, 3H), 2.03-1.85 (m, 2H). |
| D49 | 694.35 | ¹H NMR (400 MHz, Methanol-d4) δ 9.15 (d, J = 0.8 Hz, 1H), 8.48 (s, 0.2H, FA), 7.73 (d, J = 8.5 Hz, 1H), 7.42 (s, 1H), 7.19 (d, J = 2.3 Hz, 1H), 7.06 (dd, J = 8.5, 2.4 Hz, 1H), 6.90-6.83 (m, 2H), 6.48 (s, 1H), 5.10 (dd, J = 12.5, 5.4 Hz, 1H), 4.38-4.17 (m, 4H), 4.08-3.77 (m, 8H), 3.67-3.54 (m, 3H), 3.22-2.96 (m, 9H), 2.95-2.67 (m, 4H), 2.16-2.07 (m, 1H). |
| D50 | 711.20 | ¹H NMR (400 MHz, DMSO-d6) δ 10.96 (s, 1H), 9.03 (s, 1H), 7.59 (s, 1H), 7.40 (d, J = 8.4 Hz, 1H), 7.22 (dd, J = 8.5, 2.4 Hz, 1H), 7.13 (d, J = 2.3 Hz, 1H), 6.75 (s, 2H), 6.49 (s, 1H), 5.09 (dd, J = 13.3, 5.1 Hz, 1H), 4.37-4.15 (m, 2H), 3.91 (d, J = 12.1 Hz, 1H), 3.83 (s, 6H), 3.53 (d, J = 12.9 Hz, 1H), 3.15 (d, J = 10.9 Hz, 2H), 3.07 (s, 6H), 3.04-2.98 (m, 2H), 2.96-2.84 (m, 3H), 2.69-2.54 (m, 1H), 2.45-2.30 (m, 1H), 2.04-1.92 (m, 1H), 1.22 (d, J = 6.1 Hz, 6H). |
| D51 | 756.35 | ¹H NMR (300 MHz, DMSO-d6) δ 10.97 (s, 1H), 9.10 (s, 1H), 7.69 (s, 1H), 7.41 (d, J = 8.4 Hz, 1H), 7.31-7.18 (m, 1H), 7.14 (d, J = 2.3 Hz, 1H), 6.75 (s, 2H), 6.49 (s, 1H), 5.10 (dd, J = 13.3, 5.1 Hz, 1H), 4.49 (t, J = 12.3 Hz, 4H), 4.41-4.12 (m, 2H), 3.83 (s, 6H), 3.58 (s, 2H), 3.51 (s, 3H), 3.02 (d, J = 23.7 Hz, 5H), 2.63 (s, 3H), 2.46-2.24 (m, 1H), 2.10-1.91 (m, 1H), 1.25 (s, 6H). |
| D52 | 694.40 | ¹H NMR (400 MHz, DMSO-d6) δ 10.97 (s, 1H), 8.99 (s, 1H), 8.13 (s, 0.2H, FA), 7.45-7.38 (m, 2H), 7.28 (dd, J = 8.6, 2.5 Hz, 1H), 7.18 (d, J = 2.4 Hz, 1H), 6.83 (s, 1H), 6.72 (s, 1H), 5.97 (s, 1H), 5.20-5.03 (m, 1H), 4.41-4.15 (m, 2H), 3.85 (d, J = 11.8 Hz, 2H), 3.76 (s, 3H), 3.66 (s, 3H), 3.51 (s, 1H), 3.44 (s, 3H), 3.01 (s, 6H), 5.23-4.94 (m, 1H), 2.82-2.68 (m, 5H), 2.65-2.55 (m, 1H), 2.45-2.30 (m, 1H), 7.31-7.25 (m, 1H), 1.81 (s, 4H). |
| D53 | 679.30 | ¹H NMR (400 MHz, DMSO-d6) δ 10.98 (s, 1H), 9.02 (s, 1H), 7.58 (s, 1H), 7.55-7.51 (m, 1H), 7.47 (s, 2H), 6.76 (s, 2H), 6.51 (s, 1H), 5.10 (dd, J = 13.3, 5.1 Hz, 1H), 4.39 (d, J = 17.1 Hz, 1H), 4.26 (d, J = 17.1 Hz, 1H), 3.83 (s, 6H), 3.70 (d, J = 11.9 Hz, 2H), 3.48 (s, 3H), 3.08 (s, 6H), 3.03-2.83 (m, 3H), 2.65-2.56 (m, 3H), 2.47-2.32 (m, 1H), 2.06-1.94 (m, 1H), 1.82 (s, 1H), 1.72 (d, J = 12.8 Hz, 2H), 1.54-1.47 (m, 2H). |

TABLE 4-continued

| Compound No. | LCMS | ¹H NMR |
|---|---|---|
| D54 | 695.50 | ¹H NMR (400 MHz, Methanol-d4) δ 9.27 (s, 1H), 7.59 (s, 1H), 7.53 (d, J = 8.3 Hz, 1H), 7.39 (d, J = 9.7 Hz, 2H), 6.89 (s, 2H), 6.83 (s, 1H), 5.17 (dd, J = 13.3, 5.2 Hz, 1H), 4.63 (d, J = 20.8 Hz, 1H), 4.57-4.38 (m, 3H), 4.01 (d, J = 5.1 Hz, 10H), 3.96-3.85 (m, 3H), 3.65 (s, 3H), 3.60-3.44 (m, 1H), 2.99-2.87 (m, 1H), 2.86-2.75 (m, 1H), 2.59-2.45 (m, 1H), 2.25-2.13 (m, 1H), 1.74-1.51 (m, 7H). |
| D55 | 666.25 | ¹H NMR (300 MHz, Methanol-d4) δ 9.25 (s, 1H), 8.56 (d, 1H), 7.79 (d, J = 7.9 Hz, 1H), 7.58 (s, 1H), 7.54 (s, 1H), 7.48 (d, J = 8.1 Hz, 1H), 6.94-6.78 (m, 3H), 5.17 (dd, J = 13.3, 5.1 Hz, 1H), 4.51 (d, J = 5.0 Hz, 2H), 4.37-4.24 (m, 2H), 4.01 (s, 3H), 3.97 (s, 6H), 3.65 (s, 3H), 3.57 (d, J = 12.0 Hz, 2H), 3.16-2.97 (m, 3H), 2.97-2.86 (m, 1H), 2.86-2.75 (m, 1H), 2.51 (qd, J = 13.1, 4.7 Hz, 1H), 2.27-2.15 (m, 1H), 2.15-2.03 (m, 4H). |
| D56 | 720.40 | ¹H NMR (300 MHz, Methanol-d4) δ 9.10 (s, 1H), 8.51 (s, 0.2H, FA), 7.46 (d, J = 11.0 Hz, 2H), 7.31 (d, J = 9.3 Hz, 2H), 6.80 (s, 2H), 6.23 (s, 1H), 5.21-5.09 (m, 1H), 4.51-4.33 (m, 2H), 4.14-4.03 (m, 4H), 3.93 (s, 8H), 3.59 (s, 3H), 3.20-3.14 (m, 5H), 2.96-2.70 (m, 3H), 2.56-2.37 (m, 3H), 2.24-2.13 (m, 1H), 1.49 (s, 6H). |
| D57 | 681.40 | ¹H NMR (300 MHz, DMSO-d6) δ 10.97 (s, 1H), 9.16 (s, 1H), 7.74 (s, 1H), 7.42 (d, J = 8.4 Hz, 1H), 7.32-7.21 (m, 1H), 7.16 (d, J = 2.3 Hz, 1H), 6.78 (s, 1H), 6.74 (s, 2H), 5.10 (dd, J = 13.2, 5.0 Hz, 1H), 4.40-4.13 (m, 2H), 4.09-3.98 (m, 1H), 3.94 (s, 3H), 3.83 (s, 6H), 3.64-3.46 (m, 5H), 3.00-2.68 (m, 4H), 2.67-2.53 (m, 3H), 2.46-2.25 (m, 2H), 2.07-1.90 (m, 1H), 1.30 (d, J = 5.0 Hz, 3H). |
| D58 | 677.45 | ¹H NMR (400 MHz, Methanol-d4) δ 8.91 (s, 1H), 7.95 (d, J = 2.2 Hz, 1H), 7.85 (dd, J = 8.3, 2.3 Hz, 1H), 7.76 (d, J = 8.3 Hz, 1H), 7.54 (s, 1H), 6.75 (s, 2H), 6.43 (s, 1H), 5.18 (dd, J = 13.3, 5.1 Hz, 1H), 4.63-4.47 (m, 2H), 4.24 (t, J = 7.6 Hz, 4H), 3.89 (s, 6H), 3.87-3.73 (m, 3H), 3.63 (t, J = 12.1 Hz, 2H), 3.57 (s, 3H), 2.99-2.74 (m, 4H), 2.60-2.44 (m, 3H), 2.21 (ddd, J = 9.7, 5.3, 2.7 Hz, 1H), 1.86 (d, J = 13.8 Hz, 2H). |
| D59 | 652.40 | ¹H NMR (400 MHz, Methanol-d4) δ 9.23 (s, 1H), 8.09 (d, J = 2.2 Hz, 1H), 7.97 (dd, J = 8.3, 2.3 Hz, 1H), 7.84 (d, J = 8.3 Hz, 1H), 7.51 (s, 1H), 6.80 (s, 1H), 6.74 (s, 2H), 5.19 (dd, J = 13.3, 5.1 Hz, 1H), 4.67-4.49 (m, 2H), 3.99 (s, 3H), 3.90 (s, 6H), 3.88-3.76 (m, 5H), 3.62 (s, 3H), 3.03-2.86 (m, 3H), 2.80 (ddd, J = 17.5, 4.8, 2.4 Hz, 1H), 2.53 (qd, J = 13.2, 4.7 Hz, 1H), 2.21 (ddd, J = 10.9, 5.4, 3.0 Hz, 1H), 1.95 (d, J = 13.5 Hz, 2H). |

Example 9—Preparation of 4-(6-(dimethylamino)-2-methyl-1-oxo-1,2-dihydro-2,7-naphthyridin-4-yl)-2,6-dimethoxybenzaldehyde

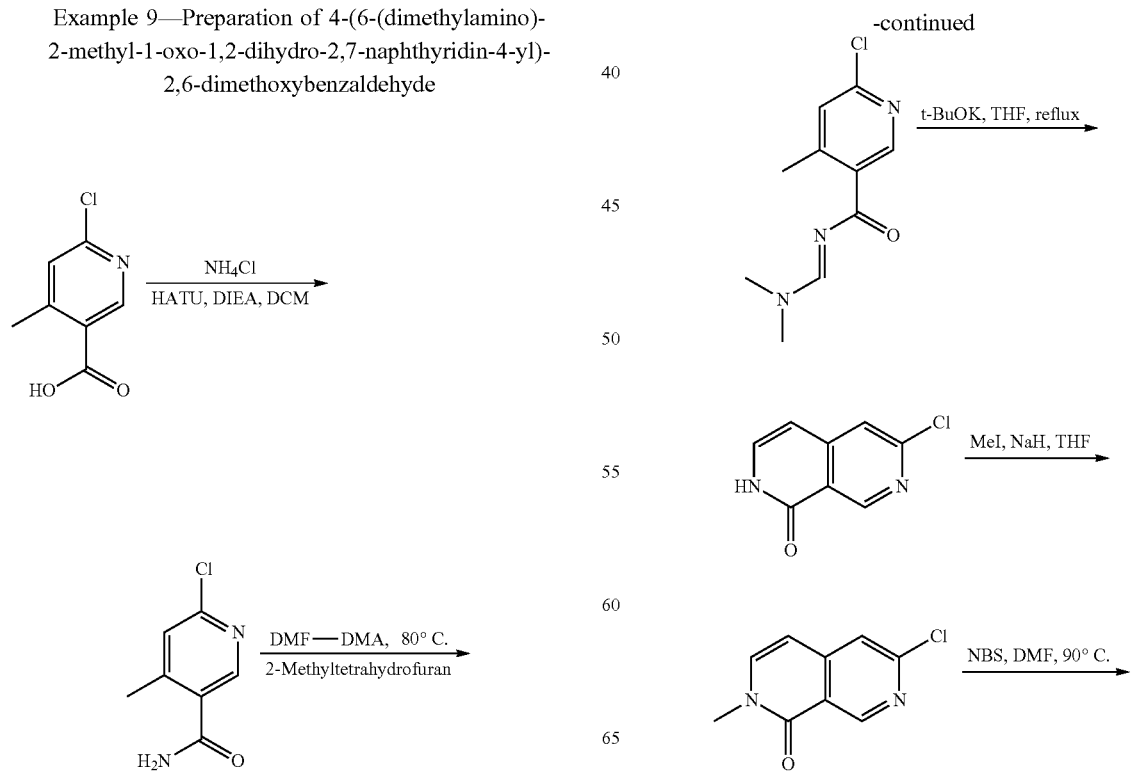

-continued

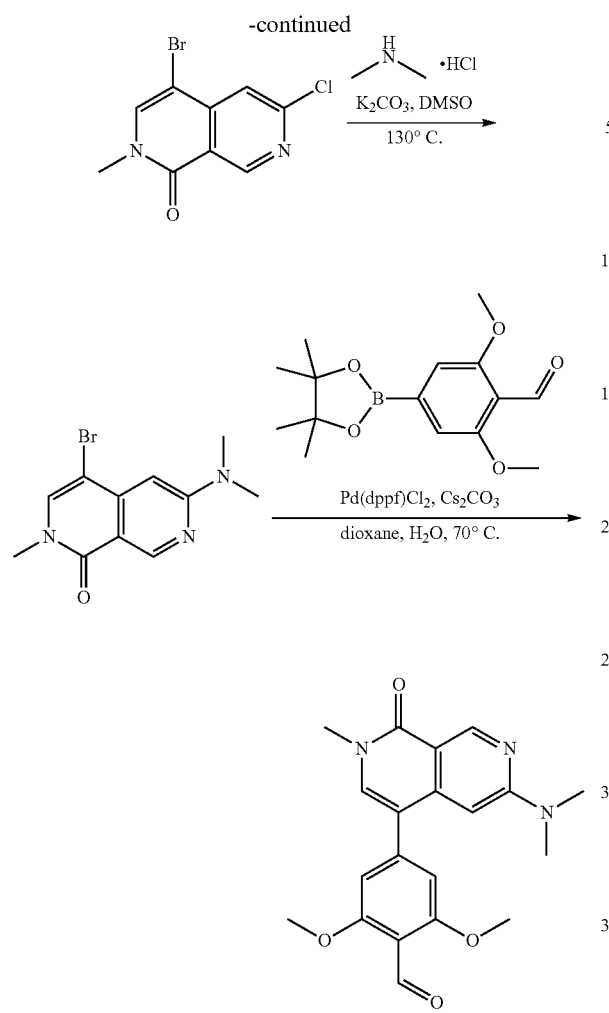

Step 1: Preparation of 6-chloro-4-methylpyridine-3-carboxamide

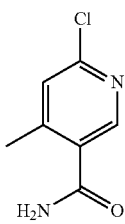

To a stirred mixture of 6-chloro-4-methylpyridine-3-carboxylic acid (20.00 g, 116.564 mmol, 1.00 equivalent) and NH$_4$Cl (62.35 g, 1.17 mol, 10.00 equivalent) in DCM (400 mL) was added DIEA (22.60 g, 174.846 mmol, 3.00 equivalent). After stirring for 5 min, HATU (66.48 g, 174.846 mmol, 1.50 equivalent) was added in portions. The resulting mixture was stirred for 3 hours at room temperature. The resulting mixture was concentrated under reduced pressure, and the residue was purified by silica gel column chromatography, eluted with PE/EtOAc from 1/1 to 3/2 to afford 6-chloro-4-methylpyridine-3-carboxamide (18.30 g, 61.3%) as a yellow solid. LCMS (ESI) m/z: [M+H]$^+$=171.

Step 2: Preparation of 6-chloro-N-[(1E)-(dimethylamino)methylidene]-4-methylpyridine-3-carboxamide

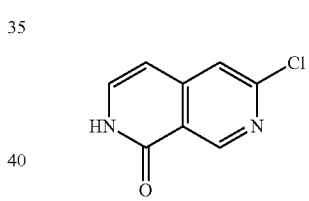

To a stirred mixture of 6-chloro-4-methylpyridine-3-carboxamide (18.30 g, 107.268 mmol, 1.00 equivalent) and in 2-methyltetrahydrofuran (100 mL) was added DMF-DMA (19.17 g, 160.903 mmol, 1.50 equivalent) at 80° C. under nitrogen atmosphere and stirred for additional 1 hour. Then the mixture was cooled and concentrated to afford 6-chloro-N-[(1E)-(dimethylamino)methylidene]-4-methylpyridine-3-carboxamide (26.3 g, 91.3%) as a yellow crude solid, that was used directly without further purification. LCMS (ESI) m/z: [M+H]$^+$=226.

Step 3: Preparation of 6-chloro-2H-2,7-naphthyridin-1-one

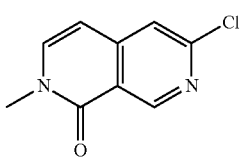

To a stirred mixture of 6-chloro-N-[(1E)-(dimethylamino)methylidene]-4-methylpyridine-3-carboxamide (26.30 g) in THF (170.00 mL) was added t-BuOK (174.00 mL, 1 mol/L in THF), the resulting solution was stirred at 60° C. under nitrogen atmosphere for 30 min. Then the mixture was cooled and concentrated under reduced pressure, the crude solid was washed with saturated NaHCO$_3$ solution (100 mL) and collected to give 6-chloro-2H-2,7-naphthyridin-1-one (14.1 g, 67.0%) as a pink solid, that was used directly without further purification. LCMS (ESI) m/z: [M+H]$^+$=181.

Step 4: Preparation of 6-chloro-2-methyl-2,7-naphthyridin-1-one

To a stirred mixture of 6-chloro-2H-2, 7-naphthyridin-1-one (14.10 g, 78.077 mmol, 1.00 equivalent) in anhydrous THF (280.00 mL) was added NaH (9.37 g, 234.232 mmol, 3.00 equivalent, 60%) in portions at 0° C. After 10 min, to above mixture was added MeI (33.25 g, 234.232 mmol, 3.00 equivalent) at 0° C., the mixture was allowed to stir for 10 min at 0 degrees. Then the mixture was allowed to stir for 12 h at room temperature. The resulting mixture was concentrated under reduced pressure. The crude solid was slurried with water (100 mL), and the solid was filtered and collected to give the 6-chloro-2-methyl-2,7-naphthyridin-1-one (14.6 g, 94.1%) as a yellow solid, that was used directly without further purification. LCMS (ESI) m/z: [M+H]$^+$=195.

Step 5: Preparation of 4-bromo-6-chloro-2-methyl-2,7-naphthyridin-1-one

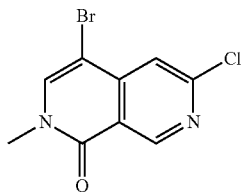

To a stirred mixture of 6-chloro-2-methyl-2,7-naphthyridin-1-one (8.00 g, 41.106 mmol, 1.00 equivalent) in DMF (160.00 mL) was added NBS (8.78 g, 49.327 mmol, 1.20 equivalent), the resulting mixture was stirred for 2 h at 90° C. The reaction mixture was cooled and diluted with DCM (150 mL), and washed with water (3×100 mL), the organic layers were dried and concentrated. Then the residue was slurried with EtOAc (20 mL), the slurry was filtered, the filter cake was washed with EtOAc (20 mL) to give 4-bromo-6-chloro-2-methyl-2,7-naphthyridin-1-one (6.32 g, 55.7%) as a white solid, that was used directly without further purification. LCMS (ESI) m/z: [M+H]$^+$=273.

Step 6: Preparation of 4-bromo-6-(dimethylamino)-2-methyl-2,7-naphthyridin-1-one

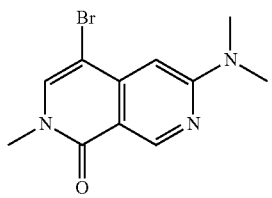

A stirred mixture of 4-bromo-6-chloro-2-methyl-2,7-naphthyridin-1-one (6.00 g, 21.937 mmol, 1.00 equivalent), dimethylamine hydrochloride (5.37 g, 65.811 mmol, 3.00 equivalent) and K$_2$CO$_3$ (15.16 g, 109.685 mmol, 5.00 equivalent) in DMSO (60.00 mL) was heated at 130° C. under nitrogen atmosphere. After 3 h, the resulting mixture was cooled and diluted with water (100 mL), and then extracted with EtOAc (3×100 mL). The combined organic layers were washed with saturated NaCl solution (3×50 mL), dried over anhydrous Na$_2$SO$_4$, concentrated under reduced pressure to afford 4-bromo-6-(dimethylamino)-2-methyl-2,7-naphthyridin-1-one (5.91 g, 93.6%) as a yellow solid, that was used directly without further purification. LCMS (ESI) m/z: [M+H]$^+$=282.

Step 7: Preparation of (4-[6-(dimethylamino)-2-methyl-1-oxo-2,7-naphthyridin-4-yl]-2,6-dimethoxy benzaldehyde

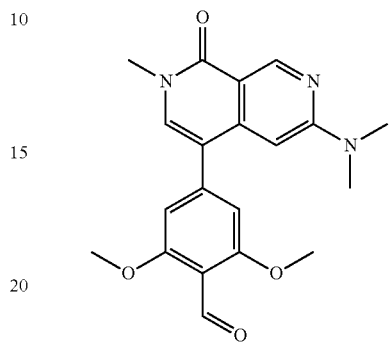

To a stirred mixture of 4-bromo-6-(dimethylamino)-2-methyl-2,7-naphthyridin-1-one (5.70 g, 20.203 mmol, 1.00 equivalent) and 2,6-dimethoxy-4-(4,4,5,5-tetramethyl-1,3,2-dioxaborolan-2-yl)benzaldehyde (8.26 g, 28.284 mmol, 1.40 equivalent) in dioxane (100.00 mL) and H$_2$O (10.00 mL) was added Pd(dppf)Cl$_2$·CH$_2$Cl$_2$ (1.65 g, 2.020 mmol, 0.10 equivalent) and Cs$_2$CO$_3$ (13.16 g, 40.405 mmol, 2.00 equivalent), then the mixture was allowed to stir for 4 h at 70° C. under nitrogen atmosphere. The resulting mixture was cooled and concentrated under reduced pressure, the residue was slurried with water (100 mL) and filtered, the filter cake was collected. And this solid was further slurried with MeOH (100 mL) and filtered, the solid was collected to afford product to afford 4-[6-(dimethylamino)-2-methyl-1-oxo-2,7-naphthyridin-4-yl]-2,6-dimethoxybenzaldehyde (6.10 g, 77.6%) as a brown solid. LCMS (ESI) m/z: [M+H]$^+$=368.

Example 10—Preparation of 3-(6-(1-(4-(6-(dimethylamino)-2-methyl-1-oxo-1,2-dihydro-2,7-naphthyridin-4-yl)-2,6-dimethoxybenzyl)piperidin-4-yl)-1-oxoisoindolin-2-yl)piperidine-2,6-dione formic acid; and 3-(5-(1-(4-(6-(dimethylamino)-2-methyl-1-oxo-1,2-dihydro-2,7-naphthyridin-4-yl)-2,6-dimethoxybenzyl)piperidin-4-yl)-1-oxoisoindolin-2-yl)piperidine-2,6-dione formic acid

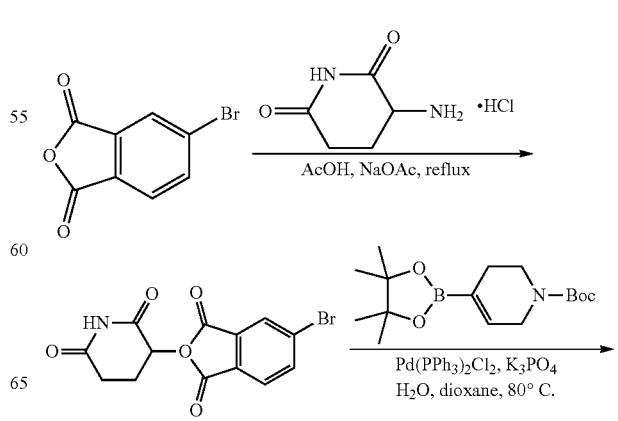

175
-continued

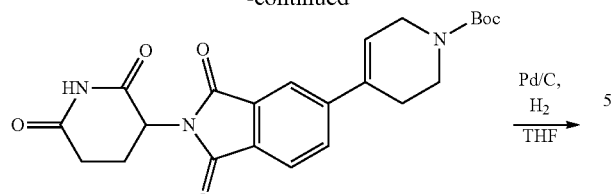

Pd/C, H₂
THF

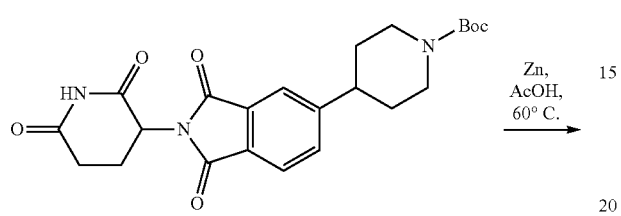

Zn, AcOH, 60° C.

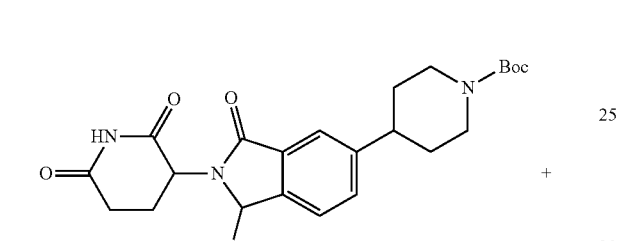

TES, TFA, DCM

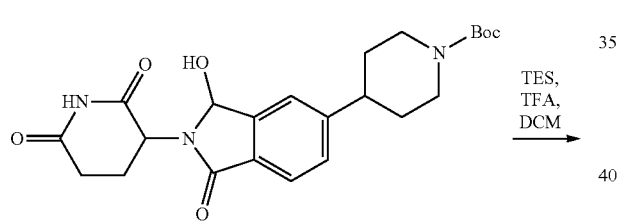

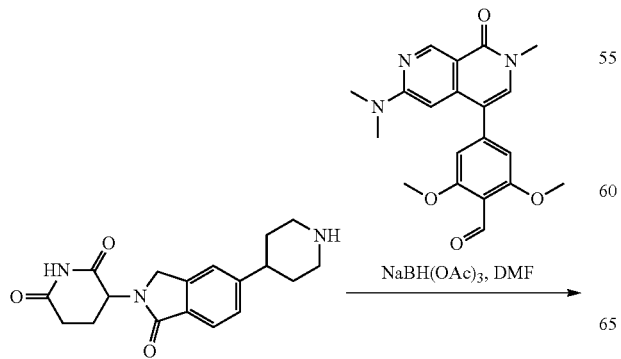

NaBH(OAc)₃, DMF

176
-continued

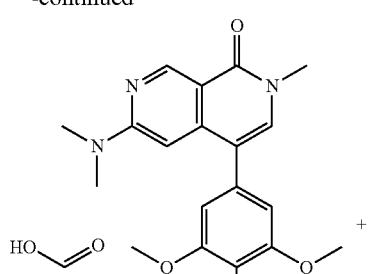

+

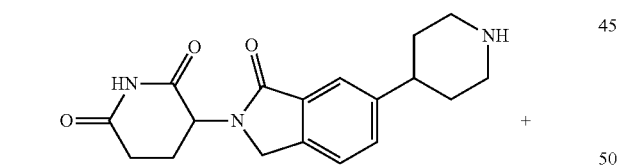

Step 1: Preparation of 5-bromo-2-(2,6-dioxopiperidin-3-yl)isoindole-1,3-dione

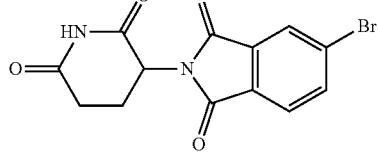

To a stirred solution of 5-bromo-2-benzofuran-1,3-dione (10.00 g, 44.050 mmol, 1.00 equivalent), NaOAc (7.23 mg, 88.134 mmol, 2.00 equivalent) and 3-aminopiperidine-2,6-dione (11.29 g, 88.113 mmol, 2.00 equivalent) in AcOH (80.00 mL) at room temperature. The resulting mixture was stirred for 16 h at 115° C. The resulting mixture was concentrated under reduced pressure. The residue was purified by silica gel column chromatography, eluted with petroleum ether/EtOAc (10:1) to afford 5-bromo-2-(2,6-dioxopiperidin-3-yl)isoindole-1,3-dione (13.6 g, 91.6%) as a dark brown solid. LCMS (ESI) m/z: [M+H]⁺=337.

Step 2: Preparation of tert-butyl 4-[2-(2,6-dioxopiperidin-3-yl)-1,3-dioxoisoindol-5-yl]-3,6-dihydro-2H-pyridine-1-carboxylate

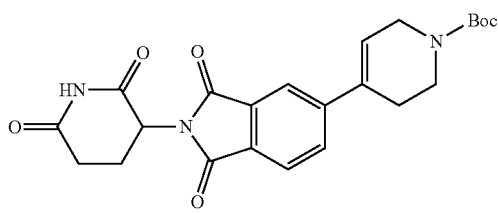 [SMILES: CC(C)(C)OC(=O)N1CC=C(c2ccc3c(c2)C(=O)N(C2CCC(=O)NC2=O)C3=O)CC1]

To a stirred solution of 5-bromo-2-(2,6-dioxopiperidin-3-yl)isoindole-1,3-dione (3.00 g, 8.899 mmol, 1.00 equivalent), tert-butyl4-(4,4,5,5-tetramethyl-1,3,2-dioxaborolan-2-yl)-3,6-dihydro-2H-pyridine-1-carboxylate (3.30 g, 10.672 mmol, 1.20 equivalent), K$_3$PO$_4$ (5.67 g, 26.712 mmol, 3.00 equivalent) in dioxane (20.00 mL) and H$_2$O (4.00 mL) was added Pd(PPh$_3$)$_2$Cl$_2$ (0.62 g, 0.883 mmol, 0.10 equivalent) at room temperature under nitrogen atmosphere. The resulting mixture was stirred for 16 h at 80° C. under nitrogen atmosphere. The resulting mixture was concentrated under reduced pressure. The residue was purified by silica gel column chromatography, eluted with PE/EtOAc (8/1) to afford tert-butyl 4-[2-(2,6-dioxopiperidin-3-yl)-1,3-dioxoisoindol-5-yl]-3,6-dihydro-2H-pyridine-1-carboxylate (0.8 g, 20.5%) as a colorless oil. LCMS (ESI) m/z: [M+H]$^+$=440.

Step 3: Preparation of tert-butyl 4-[2-(2,6-dioxopiperidin-3-yl)-1,3-dioxoisoindol-5-yl]piperidine-1-carboxylate

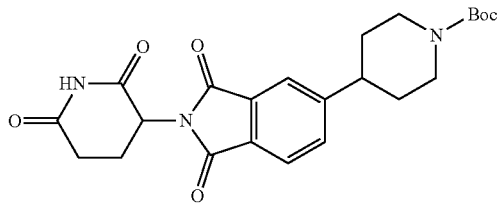 [SMILES: CC(C)(C)OC(=O)N1CCC(c2ccc3c(c2)C(=O)N(C2CCC(=O)NC2=O)C3=O)CC1]

To a stirred solution of tert-butyl 4-[2-(2,6-dioxopiperidin-3-yl)-1,3-dioxoisoindol-5-yl]-3,6-dihydro-2H-pyridine-1-carboxylate (0.80 g) in THF (20.00 mL) was added 10% Pd/C (500.0 mg) under nitrogen atmosphere in a 100 mL round-bottom flask. The mixture was hydrogenated at room temperature for 12 h under hydrogen atmosphere using a hydrogen balloon, filtered through a Celite pad and concentrated under reduced pressure. This resulted in tert-butyl 4-[2-(2,6-dioxopiperidin-3-yl)-1,3-dioxoisoindol-5-yl]piperidine-1-carboxylate (0.73 g, crude) as a white solid that was used in the next step directly without further purification. LCMS (ESI) m/z: [M+H]$^+$=442.

Step 4: Preparation of tert-butyl 4-(2-(2,6-dioxopiperidin-3-yl)-1-hydroxy-3-oxoisoindolin-5-yl)piperidine-1-carboxylate; tert-butyl 4-(2-(2,6-dioxo piperidin-3-yl)-3-hydroxy-1-oxoisoindolin-5-yl)piperidine-1-carboxylate

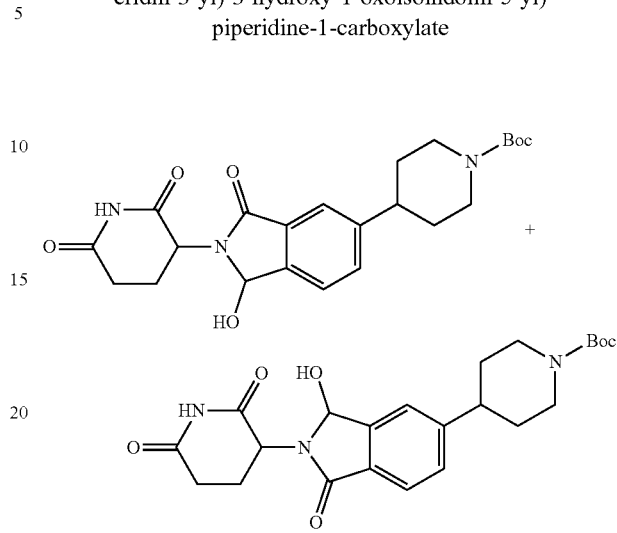

To a stirred solution of tert-butyl 4-[2-(2,6-dioxopiperidin-3-yl)-1,3-dioxoisoindol-5-yl]piperidine-1-carboxylate (0.73 g, 16.55 mmol, 1.00 equivalent) and Zn (1.08 g, 1.65 mmol, 10.00 equivalent) in AcOH (10.00 mL) at room temperature. The resulting mixture was stirred for 2 h at 60° C. The resulting mixture was concentrated under reduced pressure. The residue was purified by silica gel column chromatography, eluted with PE/EtOAc (2:1) to afford tert-butyl 4-(2-(2,6-dioxopiperidin-3-yl)-1-hydroxy-3-oxoisoindolin-5-yl)piperidine-1-carboxylate; tert-butyl 4-(2-(2,6-dioxopiperidin-3-yl)-3-hydroxy-1-oxoisoindolin-5-yl)piperidine-1-carboxylate (0.546 g, 74.8%, mixture of two regio-isomers) as a colorless solid. LCMS (ESI) m/z: [M+H]$^+$=444.

Step 5: Preparation of 3-(1-oxo-6-(piperidin-4-yl)isoindolin-2-yl)piperidine-2,6-dione; 3-(1-oxo-5-(piperidin-4-yl)isoindolin-2-yl)piperidine-2,6-dione

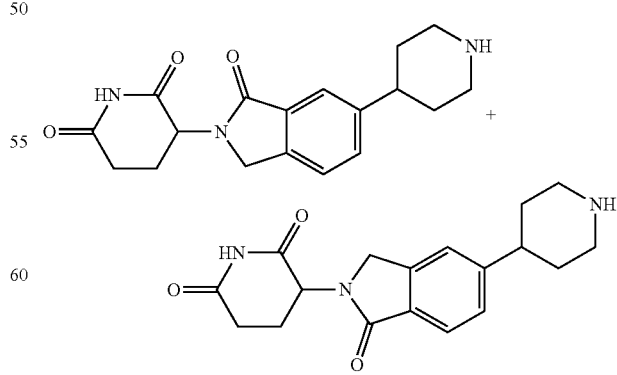

To a stirred solution of tert-butyl 4-(2-(2,6-dioxopiperidin-3-yl)-1-hydroxy-3-oxoisoindolin-5-yl)piperidine-1-carboxylate; tert-butyl 4-(2-(2,6-dioxopiperidin-3-yl)-3-hydroxy-1-oxoisoindolin-5-yl)piperidine-1-carboxylate (mixture of two regio-isomers, 573.00 mg, 1.00 equivalent) and TFA (3.00 mL) in DCM (9.00 mL) was added TES (450.7 mg, 3.876 mmol, 3.00 equivalent) at room temperature. The resulting mixture was stirred for 2 h at room temperature. The resulting mixture was concentrated under reduced pressure, This was used directly without further purification, to afford 3-(1-oxo-6-(piperidin-4-yl)isoindolin-2-yl)piperidine-2,6-dione; 3-(1-oxo-5-(piperidin-4-yl)isoindolin-2-yl)piperidine-2,6-dione (200 mg 36.6% mixture of two regio-isomers) as an off-white oil. LCMS (ESI) m/z: [M+H]$^+$=328.

Step 6: Preparation of 3-(6-(1-(4-(6-(dimethylamino)-2-methyl-1-oxo-1,2-dihydro-2,7-naphthyridin-4-yl)-2,6-dimethoxybenzyl)piperidin-4-yl)-1-oxoisoindolin-2-yl)piperidine-2,6-dione formic acid; and 3-(5-(1-(4-(6-(dimethylamino)-2-methyl-1-oxo-1,2-dihydro-2,7-naphthyridin-4-yl)-2,6-dimethoxybenzyl)piperidin-4-yl)-1-oxoisoindolin-2-yl)piperidine-2,6-dione formic acid 1.00 equivalent), and 3-(1-oxo-6-(piperidin-4-yl)isoindolin-2-yl)piperidine-2,6-dione; 3-(1-oxo-5-(piperidin-4-yl)isoindolin-2-yl)piperidine-2,6-dione (mixture of two regio-isomers, 222.2 mg, 0.605 mmol, 1.20 equivalent) in DMF (4.00 mL) was added NaBH(OAc)$_3$ (427.3 mg, 2.016 mmol, 4.00 equivalent) at room temperature. The resulting mixture was stirred for 16 h at room temperature. The residue was purified by reverse flash chromatography with the following conditions: column, C18 silica gel; mobile phase, CH$_3$CN in water (0.05% FA), 0% to 50% gradient in 30 min; detector, UV 254 nm. The crude product was purified by Prep-HPLC with the following conditions: Column, Sunfire Prep C18 OBD Column, 10 μm, 19*250 mm; mobile phase, water (0.05% FA) and CH$_3$CN (15% to 22% CH$_3$CN in 15 min); Detector, UV 254 nm. This resulted in 3-[6-[1-([4-[6-(dimethylamino)-2-methyl-1-oxo-2,7-naphthyridin-4-yl]-2,6-dimethoxyphenyl]methyl)piperidin-4-yl]-1-oxo-3H-isoindol-2-yl]piperidine-2,6-dione; formic acid (52.5 mg, 26.3%) as a white solid and 3-[5-[1-([4-[6-(dimethylamino)-2-methyl-1-oxo-2,7-naphthyridin-4-yl]-2,6-dimethoxyphenyl]methyl)piperidin-4-yl]-1-oxo-3H-isoindol-2-yl]piperidine-2,6-dione; formic acid (68.4 mg, 34.2%) as a yellow solid.

For 3-[6-[1-([4-[6-(dimethylamino)-2-methyl-1-oxo-2,7-naphthyridin-4-yl]-2,6-dimethoxyphenyl]methyl)piperidin-4-yl]-1-oxo-3H-isoindol-2-yl]piperidine-2,6-dione; formic acid: $^1$H NMR (400 MHz, DMSO-d$_6$) δ 10.97 (s, 1H), 9.04 (s, 1H), 8.20 (s, 1H, FA), 7.58 (d, J=14.5 Hz, 2H), 7.52 (s, 2H), 6.79 (s, 2H), 6.50 (s, 1H), 5.10 (dd, J=13.4, 5.1 Hz, 1H), 4.41 (d, J=17.1 Hz, 1H), 4.28 (d, J=17.0 Hz, 1H), 3.84 (s, 6H), 3.68 (s, 2H), 3.49 (s, 3H), 3.08-3.05 (m, 8H), 2.91-2.89 (m, 1H), 2.66-2.56 (m, 2H), 2.40-2.35 (m, 1H), 2.30 (t, J=11.3 Hz, 2H), 2.03-1.95 (m, 1H), 1.88-1.57 (m, 4H). LCMS (ESI) m/z: [M+H]$^+$=679.32.

For 3-[5-[1-([4-[6-(dimethylamino)-2-methyl-1-oxo-2,7-naphthyridin-4-yl]-2,6-dimethoxyphenyl]methyl)piperidin-4-yl]-1-oxo-3H-isoindol-2-yl]piperidine-2,6-dione; formic acid: 1H NMR (400 MHz, DMSO-d$_6$) δ 10.98 (s, 1H), 9.05 (s, 1H), 8.15 (s, 1H, FA), 7.69 (d, J=7.8 Hz, 1H), 7.60 (s, 1H), 7.48 (s, 1H), 7.40 (d, J=7.9 Hz, 1H), 6.87 (s, 2H), 6.51 (s, 1H), 5.11 (dd, J=13.3, 5.1 Hz, 1H), 4.44 (d, J=17.3 Hz, 1H), 4.31 (d, J=17.3 Hz, 1H), 4.05 (s, 2H), 3.90 (s, 6H), 3.49 (s, 3H), 3.31 (d, J=11.7 Hz, 2H), 3.09 (s, 6H), 2.99-2.71 (m, 4H), 2.65-2.56 (m, 1H), 2.47-2.33 (m, 1H), 2.04-1.96 (m, 1H), 1.92 (m, 4H). LCMS (ESI) m/z: [M+H]$^+$=679.32.

Example 11—Preparation 4-(6-cyclopropyl-2-methyl-1-oxo-1,2-dihydro-2,7-naphthyridin-4-yl)-2,6-dimethoxybenzaldehyde

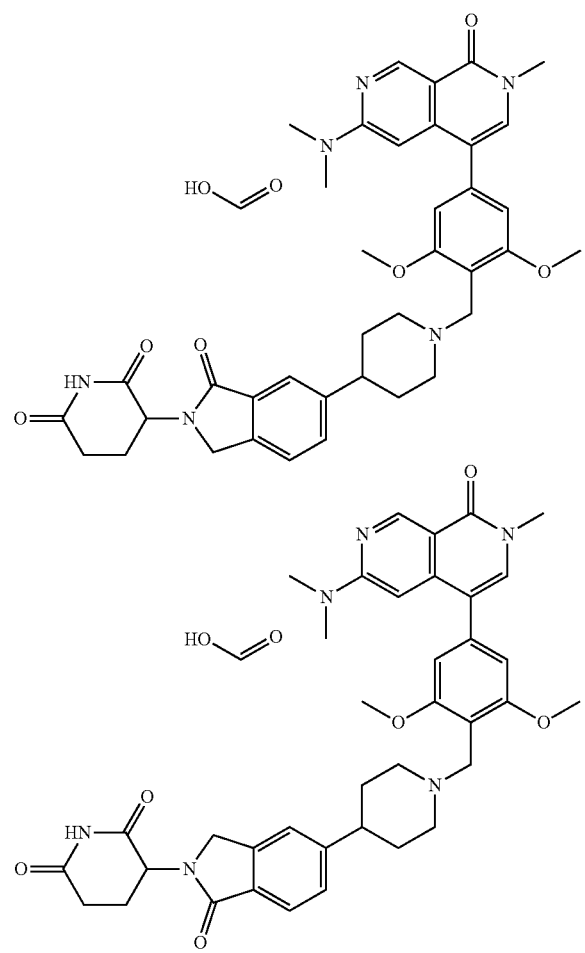

To a stirred solution of 3-[1-oxo-6-(piperidin-4-yl)-3H-isoindol-2-yl]piperidine-2,6-dione (165.0 mg, 0.504 mmol,

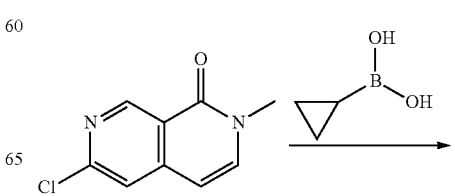

Step 2: Preparation of 4-bromo-6-cyclopropyl-2-methyl-2,7-naphthyridin-1-one

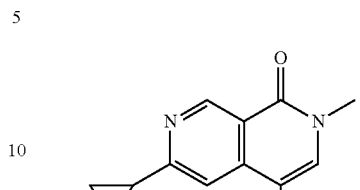

To a stirred solution of 6-cyclopropyl-2-methyl-2,7-naphthyridin-1-one (100.00 mg, 0.499 mmol, 1.00 equivalent) in DMF (4.00 mL) was added NBS (106.66 mg, 0.599 mmol, 1.20 equivalent) at room temperature under nitrogen atmosphere. The resulting mixture was stirred for 2 h at 90° C. The resulting mixture was diluted with water (12 mL), extracted with EtOAc (3×100 mL). The combined organic layers were washed with brine (2×50 mL), dried over anhydrous $Na_2SO_4$. After filtration, the filtrate was concentrated under reduced pressure to afford 4-bromo-6-cyclopropyl-2-methyl-2,7-naphthyridin-1-one (400 mg, 75.96%) as a brown solid. That was used directly without further purification. LCMS (ESI) m/z: $[M+H]^+=279$.

Step 3: Preparation of 4-(6-cyclopropyl-2-methyl-1-oxo-2,7-naphthyridin-4-yl)-2,6-dimethoxybenzaldehyde

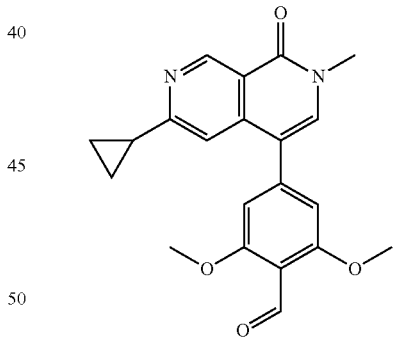

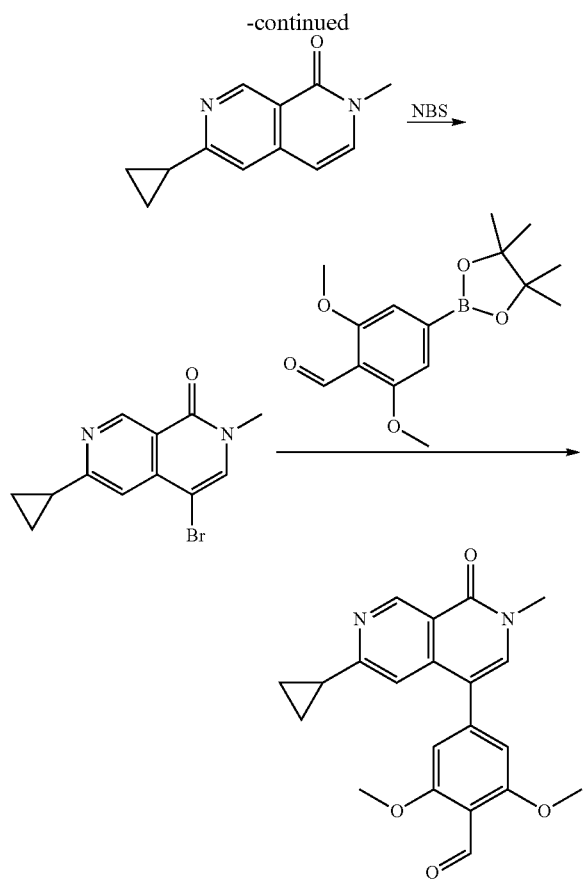

Step 1: Preparation of 6-cyclopropyl-2-methyl-2,7-naphthyridin-1-one

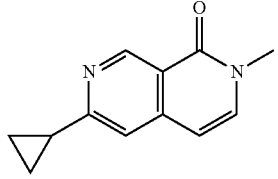

To a stirred solution of 6-chloro-2-methyl-2,7-naphthyridin-1-one (500.00 mg, 2.569 mmol, 1.00 equivalent) and cyclopropylboronic acid (441.37 mg, 5.138 mmol, 2 equivalent) in toluene (20.00 mL) and water (1.00 mL) was added tricyclohexylphosphane (144.09 mg, 0.514 mmol, 0.20 equivalent), Pd(AcO)$_2$ (57.68 mg, 0.257 mmol, 0.10 equivalent) and K$_3$PO$_4$ (1636.01 mg, 7.707 mmol, 3.00 equivalent) at room temperature under nitrogen atmosphere. The resulting mixture was stirred for 1 h at 110° C. The mixture was concentrated under reduced pressure. The residue was purified by silica gel column chromatography, eluted with CH$_2$Cl$_2$/MeOH (50:1) to afford 6-cyclopropyl-2-methyl-2,7-naphthyridin-1-one (340 mg, 59.48%) as a brown solid. LCMS (ESI) m/z: $[M+H]^+=201$.

To a stirred solution of 4-bromo-6-cyclopropyl-2-methyl-2,7-naphthyridin-1-one (420.00 mg, 1.505 mmol, 1.00 equivalent) and 2,6-dimethoxy-4-(4,4,5,5-tetramethyl-1,3,2-dioxaborolan-2-yl)benzaldehyde (527.48 mg, 1.806 mmol, 1.2 equivalent) in dioxane (10.00 mL) and water (2.00 mL) was added Pd(dppf)Cl$_2$ (110.09 mg, 0.150 mmol, 0.10 equivalent) and K$_2$CO$_3$ (415.90 mg, 3.009 mmol, 2.00 equivalent) at room temperature under nitrogen atmosphere. The resulting mixture was stirred for overnight at 80° C. The mixture was concentrated under reduced pressure. The residue was purified by Prep-TLC (CH$_2$Cl$_2$/MeOH 50:1) to afford 4-(6-cyclopropyl-2-methyl-1-oxo-2,7-naphthyridin- 4-yl)-2,6-dimethoxybenzaldehyde (440 mg, 72.22%) as a yellow solid. LCMS (ESI) m/z: [M+H]$^+$=365.

Example 12—Preparation of 3-[6-[(1-[[4-(6-cyclopropyl-2-methyl-1-oxo-2,7-naphthyridin-4-yl)-2,6-dimethoxyphenyl]methyl]135zetidine-3-yl)oxy]-1-oxo-3H-isoindol-2-yl]piperidine-2,6-dione

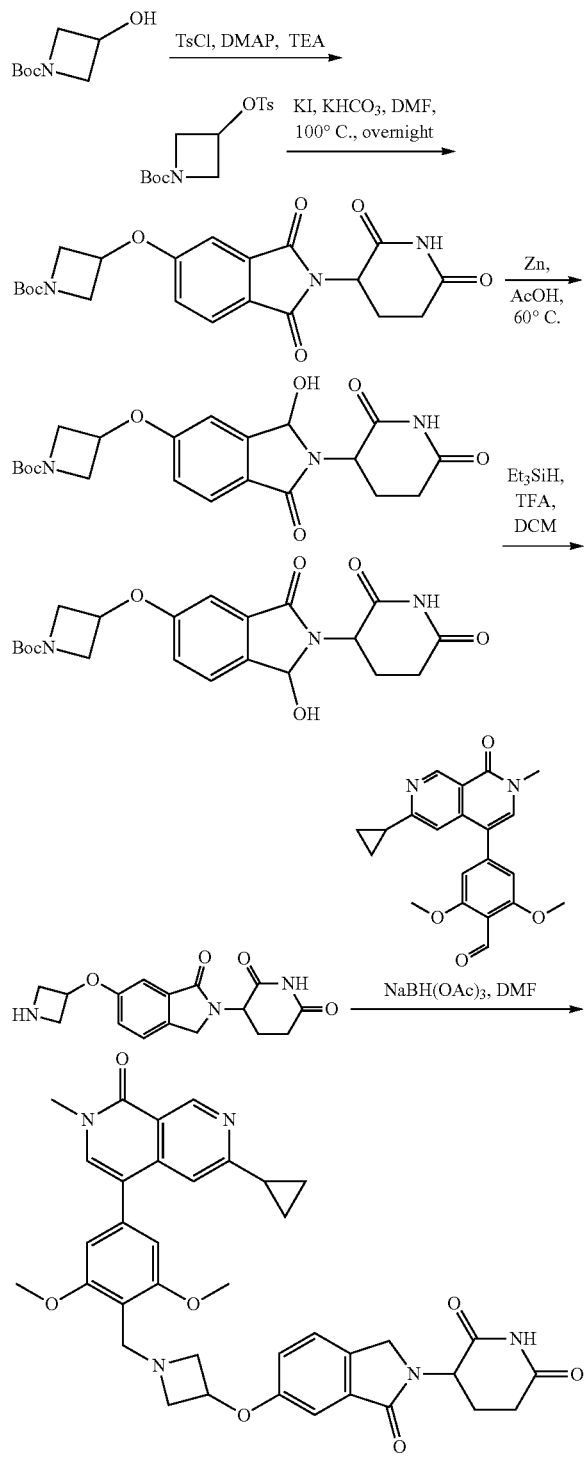

Step 1: Preparation of tert-butyl 3-[(4-methylbenzenesulfonyl)oxy]azetidine-1-carboxylate (25)

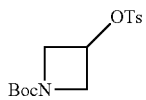

To a stirred solution of tert-butyl 3-hydroxyazetidine-1-carboxylate (2.50 g, 14.433 mmol, 1.00 equivalent) and TsCl (4.13 g, 21.650 mmol, 1.50 equivalent) in DCM were added DMAP (264.49 mg, 2.165 mmol, 0.15 equivalent) and TEA (4.38 g, 43.300 mmol, 3.00 equivalent) in portions at 0° C. under air atmosphere. The resulting mixture was concentrated under reduced pressure. The residue was purified by silica gel column chromatography, eluted with Petroleum ether/EtOAc (1:1) to afford tert-butyl 3-[(4-methylbenzenesulfonyl)oxy]azetidine-1-carboxylate (4.4 g, 93.11%) as a brown oil. LCMS (ESI) m/z: [M+H]$^+$=328.

Step 2: Preparation of tert-butyl 3-[[2-(2,6-dioxopiperidin-3-yl)-1,3-dioxoisoindol-5-yl]oxy] azetidine-1-carboxylate

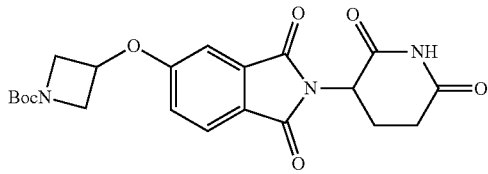 [SMILES: CC(C)(C)OC(=O)N1CC(Oc2ccc3c(c2)C(=O)N(C2CCC(=O)NC2=O)C3=O)C1]

To a solution of tert-butyl 3-[(4-methylbenzenesulfonyl)oxy]azetidine-1-carboxylate (4.40 g, 13.439 mmol, 1.00 equivalent) and KI (0.22 g, 1.344 mmol, 0.10 equivalent) in DMF was added KHCO$_3$ (4.04 g, 40.318 mmol, 3.00 equivalent) in portions at 100° C. under air atmosphere. The resulting mixture was washed with 3×150 mL of EtOAc. The resulting mixture was concentrated under reduced pressure. The residue was purified by reverse flash chromatography with the following conditions: column, C18 silica gel; mobile phase, MeCN in water, 0% to 100% gradient in 40 min; detector, UV 254 nm. This resulted in tert-butyl 3-[[2-(2,6-dioxopiperidin-3-yl)-1,3-dioxoisoindol-5-yl]oxy]azetidine-1-carboxylate (1.73 g, 29.98%) as an off-white solid. LCMS (ESI) m/z: [M+H]$^+$=430.

Step 3: Preparation of tert-butyl 3-[[2-(2,6-dioxopiperidin-3-yl)-1-hydroxy-3-oxo-1H-isoindol-5-yl]oxy]azetidine-1-carboxylate, and tert-butyl 3-[[2-(2,6-dioxopiperidin-3-yl)-3-hydroxy-1-oxo-3H-isoindol-5-yl]oxy]azetidine-1-carboxylate

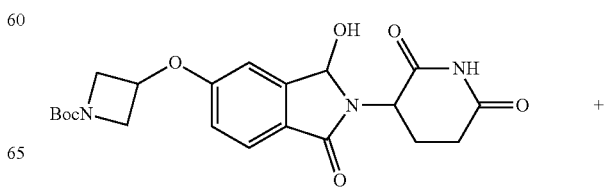

+

-continued

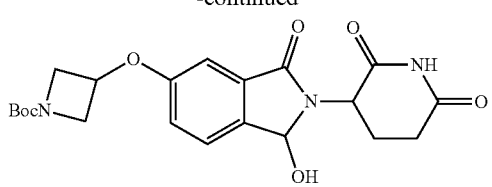

A solution of tert-butyl 3-[[2-(2,6-dioxopiperidin-3-yl)-1,3-dioxoisoindol-5-yl]oxy] azetidine-1-carboxylate (1.73 g, 4.029 mmol, 1.00 equivalent) and Zn (2.64 g, 40.286 mmol, 10.00 equivalent) in AcOH was stirred for 2 h at 60° C. under air atmosphere. The resulting mixture was washed with 3×100 mL of ethyl acetate. The resulting mixture was concentrated under reduced pressure. The crude product was used in the next step directly without further purification to afford tert-butyl 3-[[2-(2,6-dioxopiperidin-3-yl)-1-hydroxy-3-oxo-1H-isoindol-5-yl] oxy]azetidine-1-carboxylate and tert-butyl 3-[[2-(2,6-dioxopiperidin-3-yl)-3-hydroxy-1-oxo-3H-isoindol-5-yl]oxy]azetidine-1-carboxylate (2.73 g, 78.53%) as an off-white solid. LCMS (ESI) m/z: [M+H]$^+$=432.

Step 4: Preparation of 3-[6-(137zetidine-3-yloxy)-1-oxo-3H-isoindol-2-yl]piperidine-2,6-dione

To a solution of tert-butyl 3-[[2-(2,6-dioxopiperidin-3-yl)-1-hydroxy-3-oxo-1H-isoindol-5-yl]oxy]azetidine-1-carboxylate and tert-butyl 3-[[2-(2,6-dioxopiperidin-3-yl)-3-hydroxy-1-oxo-3H-isoindol-5-yl]oxy]azetidine-1-carboxylate (2.73 g, 3.164 mmol, 1.00 equivalent) and TFA (1.50 mL, 20.195 mmol, 6.38 equivalent) in DCM was added Et$_3$SiH (3.68 g, 31.638 mmol, 10.00 equivalent) in portions at room temperature under air atmosphere. The resulting mixture was concentrated under reduced pressure. The crude product (mg) was purified by Prep-HPLC with the following conditions (Column: Xcelect CSH F-pheny OBD Column, 19*250 mm, 5 μm; Mobile Phase A:Water (0.05% TFA), Mobile Phase B: can; Flow rate: 30 mL/min; Gradient: 5 B to 21 B in 10 min; 254/220 nm; RT1: 7.20/8.67 min) to afford 3-[6-(azetidin-3-yloxy)-1-oxo-3H-isoindol-2-yl]piperidine-2,6-dione (165 mg, 8.27%) as an off-white solid. LCMS (ESI) m/z: [M+H]$^+$=316.

Step 5: Preparation of 3-[6-[(1-[[4-(6-cyclopropyl-2-methyl-1-oxo-2,7-naphthyridin-4-yl)-2,6-dimethoxyphenyl]methyl]azetidin-3-yl)oxy]-1-oxo-3H-isoindol-2-yl]piperidine-2,6-dione

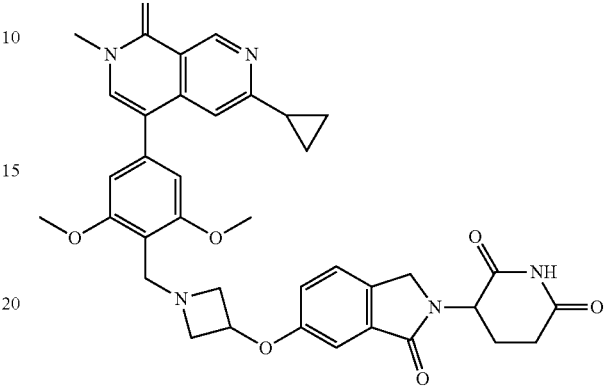

To a stirred solution of 3-[6-(azetidin-3-yloxy)-1-oxo-3H-isoindol-2-yl piperidine-2,6-dione (75.00 mg, 0.238 mmol, 1.00 equivalent) and 4-(6-cyclopropyl-2-methyl-1-oxo-2,7-naphthyridin-4-yl)-2,6-dimethoxybenzaldehyde (86.67 mg, 0.238 mmol, 1.00 equivalent) in DMF was added NaBH(OAc)$_3$ (100.82 mg, 0.476 mmol, 2.00 equivalent) dropwise at room temperature under air atmosphere for 2 hours. The crude product (mg) was purified by Prep-HPLC with the following conditions (Column: XSelect CSH Prep C18 OBD Column, 19*250 mm, 5 μm; Mobile Phase A:Water (0.05% TFA), Mobile Phase B:ACN; Flow rate: 25 mL/min; Gradient: 15 B to 23 B in 12 min; 254/220 nm; RT1: 10.38 min) to afford 3-[6-[(1-[[4-(6-cyclopropyl-2-methyl-1-oxo-2,7-naphthyridin-4-yl)-2,6-dimethoxyphenyl] methyl]azetidin-3-yl)oxy]-1-oxo-3H-isoindol-2-yl]piperidine-2,6-dione (18.9 mg, 11.69%) as an off-white solid. $^1$H NMR (400 MHz, Methanol-d4) δ 9.39 (d, J=0.8 Hz, 1H), 7.80 (d, J=4.5 Hz, 1H), 7.60 (t, J=7.2 Hz, 1H), 7.42 (d, J=5.4 Hz, 1H), 7.32-7.24 (m, 1H), 7.22 (d, J=3.2 Hz, 1H), 6.89 (s, 2H), 5.35-5.19 (m, 1H), 5.16 (dd, J=13.3, 5.2 Hz, 1H), 4.84-4.69 (m, 2H), 4.65 (s, 2H), 4.48 (d, J=10.6 Hz, 2H), 4.42 (s, 2H), 3.98 (d, J=22.6 Hz, 6H), 3.69 (s, 3H), 2.93 (ddd, J=17.6, 13.5, 5.4 Hz, 1H), 2.80 (ddd, J=17.6, 4.7, 2.4 Hz, 1H), 2.52 (qd, J=13.2, 4.7 Hz, 1H), 2.21 (dddd, J=14.5, 10.7, 6.9, 3.9 Hz, 2H), 1.23-1.12 (m, 2H), 1.09 (d, J=4.4 Hz, 2H). LCMS (ESI) m/z: [M+H]$^+$=664.

Example 13—Preparation of 4-(6-cyclopropyl-2-(methyl-d3)-1-oxo-1,2-dihydro-2,7-naphthyridin-4-yl)-2,6-dimethoxybenzaldehyde

-continued

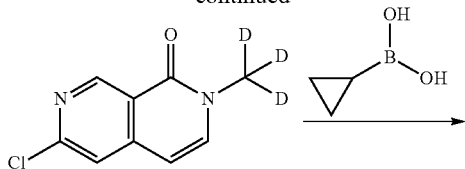

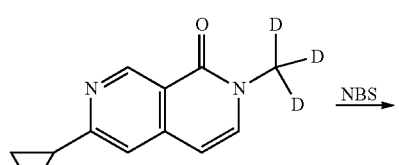

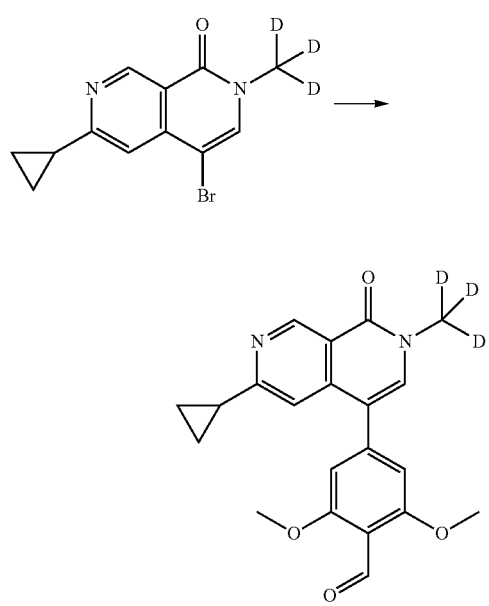

Step 1: Preparation of 6-chloro-2-(2H3)methyl-2,7-naphthyridin-1-one

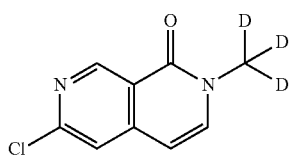 [SMILES: [2H]C([2H])([2H])n1ccc2cc(Cl)ncc2c1=O]

A solution of 6-chloro-2H-2,7-naphthyridin-1-one (500.00 mg, 2.769 mmol, 1.00 equivalent) in THF (5.00 mL) was treated with NaH (132.89 mg, 5.537 mmol, 2.00 equivalent) for 5 min at 0° C. followed by the addition of CD3I (802.69 mg, 5.537 mmol, 2.00 equivalent) in portions at 0° C. After stirring at 0° C. for 1 h, the reaction mixture was poured into ice-water (50 mL), the precipitated solids were collected by filtration and washed with water (3×50 mL), then the solid was dried under vacuum to afford 6-chloro-2-(2H3)methyl-2,7-naphthyridin-1-one (500 mg, 91.37%) as a light yellow solid that was used directly without further purification. LCMS (ESI) m/z: [M+H]$^+$=198.

Step 2: Preparation of 6-cyclopropyl-2-(2H3)methyl-2,7-naphthyridin-1-one

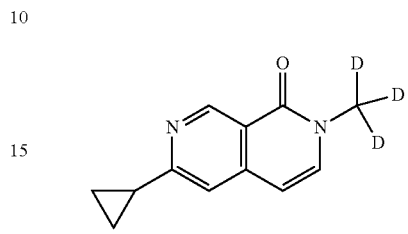

A mixture of 6-chloro-2-(2H3)methyl-2,7-naphthyridin-1-one (400.00 mg, 2.024 mmol, 1.00 equivalent), cyclopropylboronic acid (260.78 mg, 3.036 mmol, 1.50 equivalent), $K_3PO_4$ (1288.81 mg, 6.072 mmol, 3.00 equivalent), $PCy_3$ (113.51 mg, 0.405 mmol, 0.20 equivalent) and Pd(AcO)$_2$ (45.44 mg, 0.202 mmol, 0.10 equivalent) in Toluene (20.00 mL) and H$_2$O (1.00 mL) was stirred for 2 h at 110° C. under nitrogen atmosphere. The resulting mixture was concentrated under reduced pressure. The residue was purified by silica gel column chromatography, eluted with CH$_2$Cl$_2$/MeOH (10:1) to afford 6-cyclopropyl-2-(2H3)methyl-2,7-naphthyridin-1-one (350 mg, 85.08%) as a white solid. LCMS (ESI) m/z: [M+H]$^+$=204

Step 3: Preparation of 4-bromo-6-cyclopropyl-2-(2H3)methyl-2,7-naphthyridin-1-one

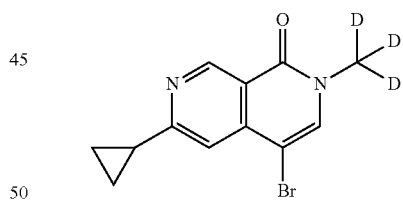

A mixture of 6-cyclopropyl-2-(2H3)methyl-2,7-naphthyridin-1-one (300.00 mg, 1.476 mmol, 1.00 equivalent) and NBS (315.23 mg, 1.771 mmol, 1.20 equivalent) in ACN (3.00 mL) was stirred for 2 h at 90° C. The resulting mixture was diluted with 1×50 mL of water. The resulting mixture was extracted with EtOAc (3×50 mL). The combined organic layers were washed with water (3×50 mL), dried over anhydrous Na$_2$SO$_4$. After filtration, the filtrate was concentrated under reduced pressure. The resulting mixture was concentrated under reduced pressure to afford 4-bromo-6-cyclopropyl-2-(2H3)methyl-2,7-naphthyridin-1-one (350 mg, 84.04%) as a yellow solid that was used directly without further purification. LCMS (ESI) m/z: [M+H]$^+$=282.

Step 4: Preparation of 4-[6-cyclopropyl-2-(2H3) methyl-1-oxo-2,7-naphthyridin-4-yl]-2,6-dimethoxy-benzaldehyde

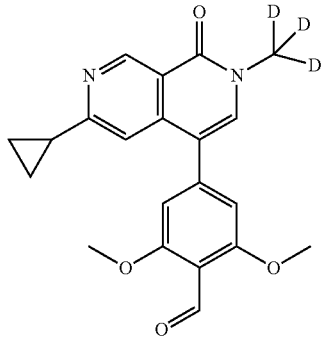 [SMILES: [2H]C([2H])([2H])n1cc(-c2cc(OC)c(C=O)c(OC)c2)c2cc(C3CC3)ncc2c1=O]

A mixture of 4-bromo-6-cyclopropyl-2-(2H3)methyl-2,7-naphthyridin-1-one (350.00 mg, 1.240 mmol, 1.00 equivalent), 2,6-dimethoxy-4-(4,4,5,5-tetramethyl-1,3,2-dioxaborolan-2-yl)benzaldehyde (434.86 mg, 1.489 mmol, 1.20 equivalent), Cs$_2$CO$_3$ (808.33 mg, 2.481 mmol, 2.00 equivalent) and Pd(dppf)Cl$_2$ (90.76 mg, 0.124 mmol, 0.10 equivalent) in dioxane (3.00 mL) and H$_2$O (1.00 mL) was stirred for 3 hours at 90° C. under nitrogen atmosphere. The resulting mixture was concentrated under reduced pressure. The residue was purified by silica gel column chromatography, eluted with CH$_2$Cl$_2$/MeOH (10:1) to afford 4-[6-cyclopropyl-2 (2H3) methyl-1-oxo-2,7-naphthyridin-4-yl]-2,6-dimethoxybenzaldehyde (200 mg, 43.88%) as an orange solid. LCMS (ESI) m/z: [M+H]$^+$=368.

Example 14—Preparation of 3-[5-[7-([4-[6-(azetidin-1-yl)-2-methyl-1-oxo-2,7-naphthyridin-4-yl]-2, 6-dimethoxyphenyl]methyl)-2,7-diazaspiro[3.5] nonan-2-yl]-1-oxo-3H-isoindol-2-yl]piperidine-2,6-dione formic acid

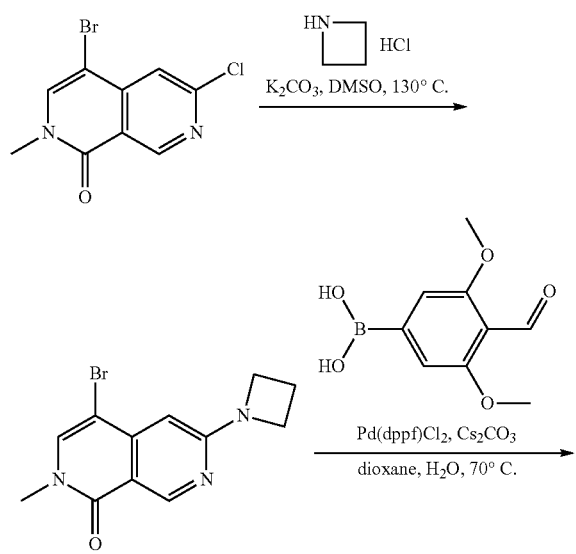

Step 1: Preparation of 6-(azetidin-1-yl)-4-bromo-2-methyl-2, 7-naphthyridin-1-one

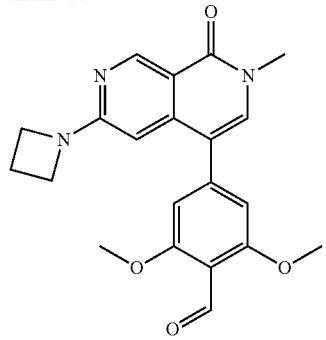

To a solution of 4-bromo-6-chloro-2-methyl-2,7-naphthyridin-1-one (5.00 g, 18.281 mmol, 1.00 equivalent) and azetidine hydrochloride (3.2 g, 54.843 mmol, 3 equivalent) in DMSO (50.00 mL) was added K$_2$CO$_3$ (12.6 g, 91.404 mmol, 5 equivalent). The resulting solution was stirred at 130° C. for 2 hours. The resulting mixture was cooled and diluted with water (100 mL), and then extracted with EtOAc (3×100 mL). The combined organic layers were washed with saturated NaCl solution (3×50 mL), dried over anhydrous Na$_2$SO$_4$, concentrated under reduced pressure to afford 6-(azetidin-1-yl)-4-bromo-2-methyl-2,7-naphthyridin-1-one (3.7 g, 68.8%) as a grey solid, that was used directly without further purification. LCMS (ESI) m/z: [M+H]$^+$=294.

Step 2: Preparation of 4-[6-(azetidin-1-yl)-2-methyl-1-oxo-2,7-naphthyridin-4-yl]-2,6-dimethoxy-benzaldehyde

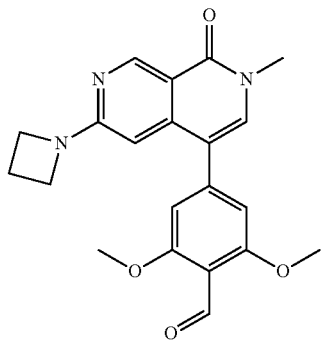 [SMILES: COc1cc(-c2cn(C)c(=O)c3cnc(N4CCC4)cc23)cc(OC)c1C=O]

To a solution of 6-(azetidin-1-yl)-4-bromo-2-methyl-2,7-naphthyridin-1-one (1.42 g, 4.827 mmol, 1.00 equivalent) and 4-formyl-3,5-dimethoxyphenylboronic acid (1.52 g, 7.241 mmol, 1.5 equivalent) in dioxane (16.00 mL) and H$_2$O (4.00 mL) were added Pd(dppf)Cl$_2$ (353.2 mg, 0.483 mmol, 0.1 equivalent) and Cs$_2$CO$_3$ (3.15 g, 9.655 mmol, 2 equivalent), and the resulting solution was stirred at 70° C. for 2 hours. The resulting mixture was cooled and concentrated under reduced pressure. The residue was slurried with water (30 mL) and filtered, the filter cake was collected. And this solid was further slurried with MeOH (30 mL) and filtered. The solid was collected to afford product to afford 4-[6-(azetidin-1-yl)-2-methyl-1-oxo-2,7-naphthyridin-4-yl]-2,6-dimethoxybenzaldehyde (1.42 g, 77.5%) as a grey and solid. LCMS (ESI) m/z: [M+H]$^+$=380.

Example 15—Preparation of 3-[5-[7-([4-[6-(azetidin-1-yl)-2-methyl-1-oxo-2,7-naphthyridin-4-yl]-2,6-dimethoxyphenyl]methyl)-2,7-diazaspiro[3.5]nonan-2-yl]-1-oxo-3H-isoindol-2-yl]piperidine-2,6-dione formic acid

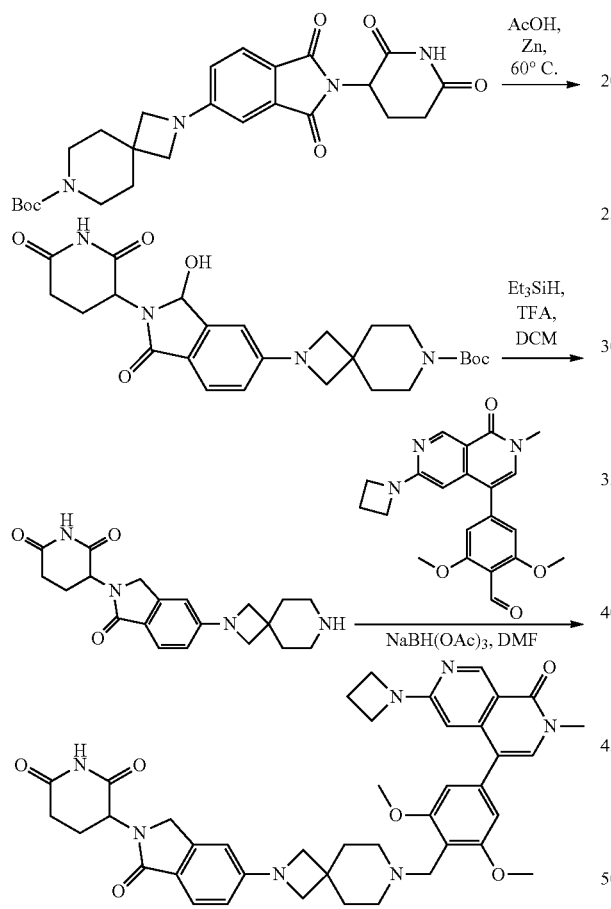

Step 1: Preparation of tert-butyl 2-[2-(2,6-dioxopiperidin-3-yl)-3-hydroxy-1-oxo-3H-isoindol-5-yl]-2,7-diaza spiro[3.5]nonane-7-carboxylate

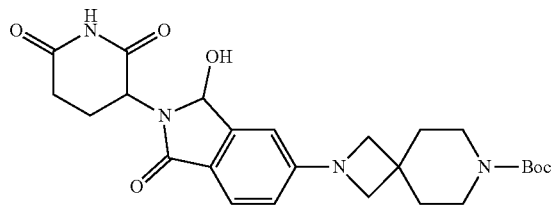 [SMILES: CC(C)(C)OC(=O)N1CCC2(CC1)CN(c1ccc3c(c1)C(O)N(C1CCC(=O)NC1=O)C3=O)C2]

To a stirred solution of tert-butyl 2-[2-(2,6-dioxopiperidin-3-yl)-1,3-dioxoisoindol-5-yl]-2,7-diazaspiro[3.5]nonane-7-carboxylate (500.0 mg, 1.036 mmol, 1.00 equivalent) in AcOH (4.00 mL) was added Zn (677.7 mg, 10.362 mmol, 10.00 equivalent). The resulting mixture was stirred at 60° C. for 2 h. The reaction mixture was filtered, and the filtrate was evaporated to afford crude product. The crude product was purified by reverse phase column, elution gradient 0 to 30% MeCN in water (containing 0.1% formic acid). Pure fractions were evaporated to dryness to afford tert-butyl 2-[2-(2,6-dioxopiperidin-3-yl)-3-hydroxy-1-oxo-3H-isoindol-5-yl]-2,7-diaza spiro[3.5]nonane-7-carboxylate (277.3 mg, 55.2%) as a yellow solid. LCMS (ESI) m/z: [M+H]$^+$=485.

Step 2: Preparation of 3-(5-[2,7-diazaspiro[3.5]nonan-2-yl]-1-oxo-3H-isoindol-2-yl)piperidine-2,6-dione

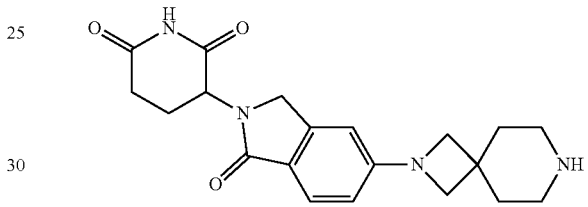

To a stirred solution of tert-butyl 2-[2-(2,6-dioxopiperidin-3-yl)-3-hydroxy-1-oxo-3H-isoindol-5-yl]-2,7-diazaspiro[3.5]nonane-7-carboxylate (250.0 mg, 0.516 mmol, 1.00 equivalent) in DCM (2.00 mL) were added TFA (0.50 mL) and Et$_3$SiH (0.20 mL). The resulting mixture was stirred at room temperature for 1 hour. The resulting mixture was concentrated under reduced pressure. This resulted in 3-(5-[2,7-diazaspiro[3.5]nonan-2-yl]-1-oxo-3H-isoindol-2-yl)piperidine-2,6-dione (267.5 mg, crude) as a yellow gum. The crude product was used in the next step directly without further purification. LCMS (ESI) m/z: [M+H]$^+$=369.

Step 3: Preparation of 3-[5-[7-([4-[6-(azetidin-1-yl)-2-methyl-1-oxo-2,7-naphthyridin-4-yl]-2,6-dimethoxyphenyl]methyl)-2,7-diazaspiro[3.5]nonan-2-yl]-1-oxo-3H-isoindol-2-yl]piperidine-2,6-dione; formic acid

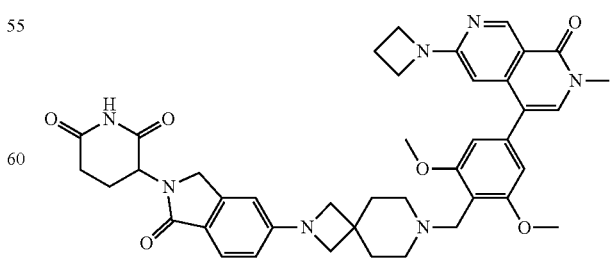

To a stirred solution of 3-(5-[2,7-diazaspiro[3.5]nonan-2-yl]-1-oxo-3H-isoindol-2-yl)piperidine-2,6-dione (400.0 mg, 1.086 mmol, 1.00 equivalent) and 4-[6-(azetidin-1-yl)-2-methyl-1-oxo-2,7-naphthyridin-4-yl]-2,6-dimethoxybenzaldehyde (494.3 mg, 1.303 mmol, 1.20 equivalent) in DMF (3.00 mL) was added NaBH(OAc)₃ (920.4 mg, 4.343 mmol, 4.00 equivalent) at room temperature. The resulting mixture was stirred at room temperature for 2 hours. The crude reaction solution was directly purified by Prep-HPLC with the following conditions (Column: XSelect CSH Prep C18 OBD Column, 5 μm, 19*150 mm; Mobile Phase A: Water (0.05% FA), Mobile Phase B: ACN; Flow rate: 25 mL/min; Gradient: 14 B to 22 B in 15 min; 254/220 nm; RT1: 11.72 min) to afford 3-[6-[7-([4-[6-(azetidin-1-yl)-2-methyl-1-oxo-2,7-naphthyridin-4-yl]-2,6-dimethoxyphenyl]methyl)-2,7-diazaspiro[3.5]nonan-2-yl]-1-oxo-3H-isoindol-2-yl]piperidine-2,6-dione; formic acid (99.2 mg, 12.5%) as a white solid. ¹H NMR (400 MHz, DMSO-d6) δ 10.94 (s, 1H), 9.02 (s, 1H), 8.15 (s, 1H, FA), 7.61 (s, 1H), 7.48 (d, J=8.2 Hz, 1H), 6.75 (s, 2H), 6.53-6.44 (m, 2H), 6.21 (s, 1H), 5.04 (dd, J=13.3, 5.2 Hz, 1H), 4.30 (d, J=17.0 Hz, 1H), 4.17 (d, J=16.9 Hz, 1H), 4.01 (t, J=7.4 Hz, 4H), 3.83 (s, 6H), 3.61 (d, J=13.2 Hz, 6H), 3.48 (s, 3H), 2.96-2.84 (m, 1H), 2.63-2.54 (m, 3H), 2.51-2.45 (m, 2H), 2.35 (q, J=6.6 Hz, 3H), 1.95 (d, J=12.9 Hz, 1H), 1.75 (s, 4H). LCMS (ESI) m/z: [M+H]⁺=732.45.

Example 16—Preparation of 3-[5-[1-([4-[6-(azetidin-1-yl)-2-methyl-1-oxo-2,7-naphthyridin-4-yl]-2,6-dimethoxy phenyl]methyl)piperidin-4-yl]-1-oxo-3H-isoindol-2-yl]piperidine-2,6-dione formic acid; and 3-[6-[1-([4-[6-(azetidin-1-yl)-2-methyl-1-oxo-2,7-naphthyridin-4-yl]-2,6-dimethoxyphenyl] methyl)piperidin-4-yl]-1-oxo-3H-isoindol-2-yl]piperidine-2,6-dione formic acid

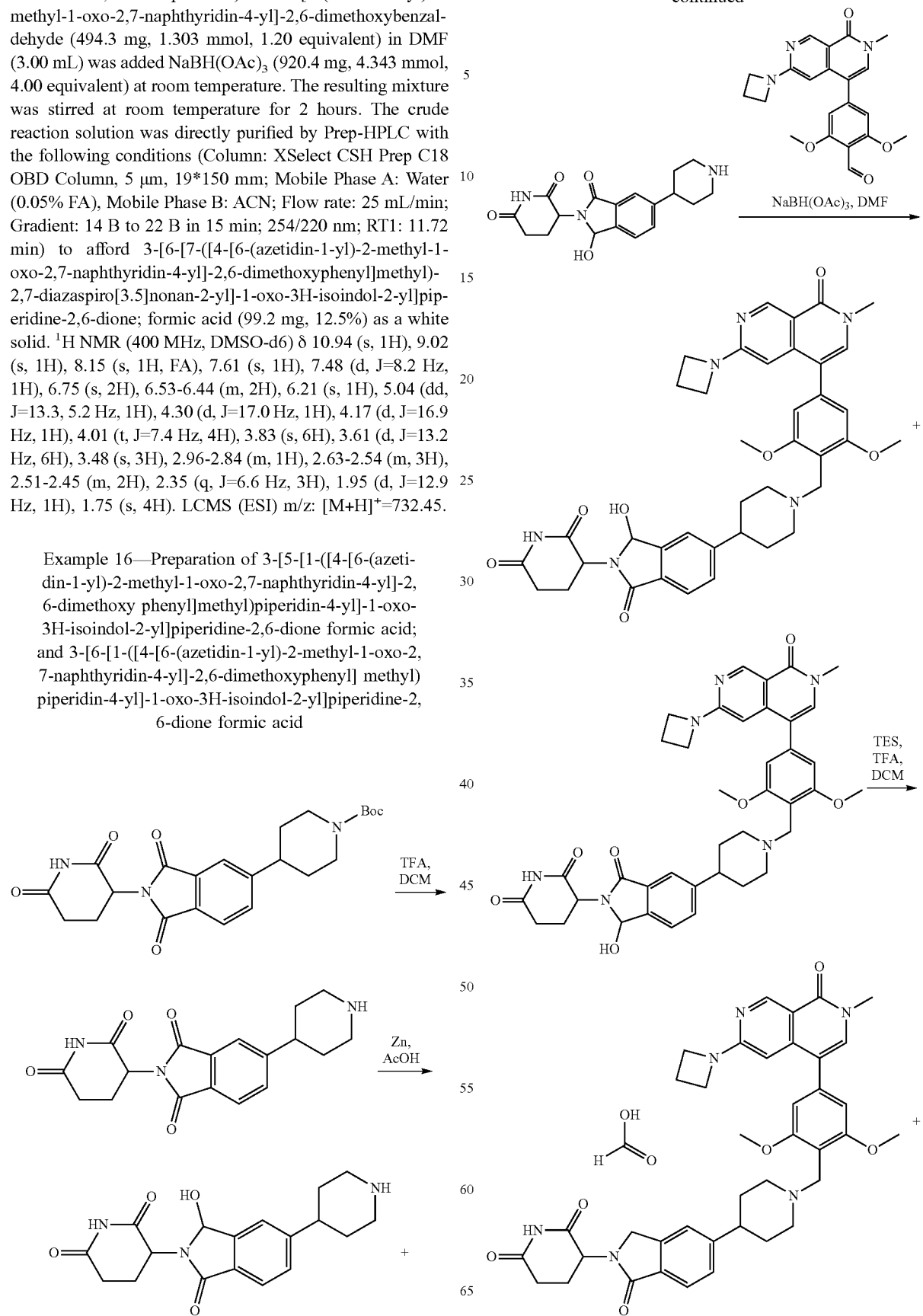

Step 1: Preparation of 2-(2,6-dioxopiperidin-3-yl)-5-(piperidin-4-yl)isoindole-1,3-dione

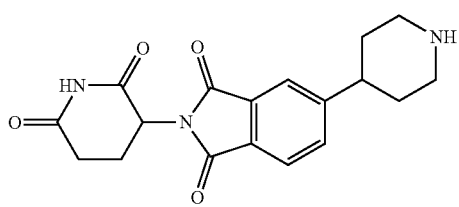 [SMILES: O=C1CCC(N2C(=O)c3ccc(C4CCNCC4)cc3C2=O)C(=O)N1]

To a stirred solution of tert-butyl 4-[2-(2, 6-dioxopiperidin-3-yl)-1,3-dioxoisoindol-5-yl]piperidine-1-carboxylate (1.00 g, 2.265 mmol, 1.00 equivalent) in DCM (8 mL) was added TFA (2.00 mL) at room temperature. The resulting mixture was stirred for 2 h at room temperature. The resulting mixture was concentrated under reduced pressure. This resulted in 2-(2,6-dioxopiperidin-3-yl)-5-(piperidin-4-yl)isoindole-1,3-dione (1.23 g, crude) as a white solid that was used in the next step directly without further purification. LCMS (ESI) m/z: [M+H]$^+$=342.

Step 2: Preparation of 3-[3-hydroxy-1-oxo-5-(piperidin-4-yl)-3H-isoindol-2-yl]piperidine-2,6-dione and 3-[1-hydroxy-3-oxo-5-(piperidin-4-yl)-1H-isoindol-2-yl]piperidine-2,6-dione

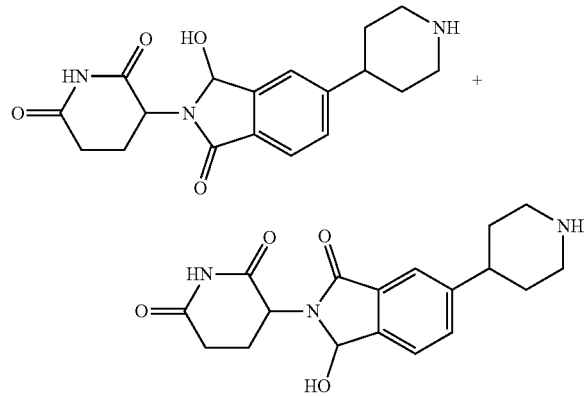

To a solution of 2-(2,6-dioxopiperidin-3-yl)-5-(piperidin-4-yl)isoindole-1,3-dione (300.0 mg, 0.879 mmol, 1.00 equivalent) in AcOH (5.00 mL) was added Zn (574.9 mg, 8.788 mmol, 10 equivalent), and the resulting solution was stirred at 25° C. for 2 hours. The mixture was diluted with EtOAc (30 mL) and washed with water (30 mL×3). The organic layers were combined and dried over anhydrous sodium sulfate, filtered and concentrated to give a crude product. The crude product was purified by flash C18 chromatography (elution gradient 0 to 11% ACN in H$_2$O) to give 3-[3-hydroxy-1-oxo-5-(piperidin-4-yl)-3H-isoindol-2-yl]piperidine-2,6-dione and 3-[1-hydroxy-3-oxo-5-(piperidin-4-yl)-1H-isoindol-2-yl]piperidine-2,6-dione (280 mg, mixture of two regio-isomers, 92.8%) as a white solid. LCMS (ESI) m/z: [M+H]$^+$=344.

Step 3: Preparation of 3-[5-[1-([4-[6-(azetidin-1-yl)-2-methyl-1-oxo-2,7-naphthyridin-4-yl]-2,6-dimethoxyphenyl]methyl)piperidin-4-yl]-3-hydroxy-1-oxo-3H-isoindol-2-yl]piperidine-2,6-dione and 3-[5-[1-([4-[6-(azetidin-1-yl)-2-methyl-1-oxo-2,7-naphthyridin-4-yl]-2,6-dimethoxyphenyl]methyl)piperidin-4-yl]-1-hydroxy-3-oxo-1H-isoindol-2-yl]piperidine-2,6-dione

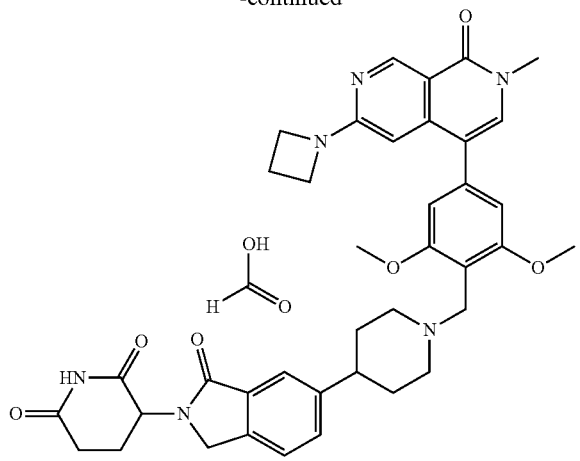

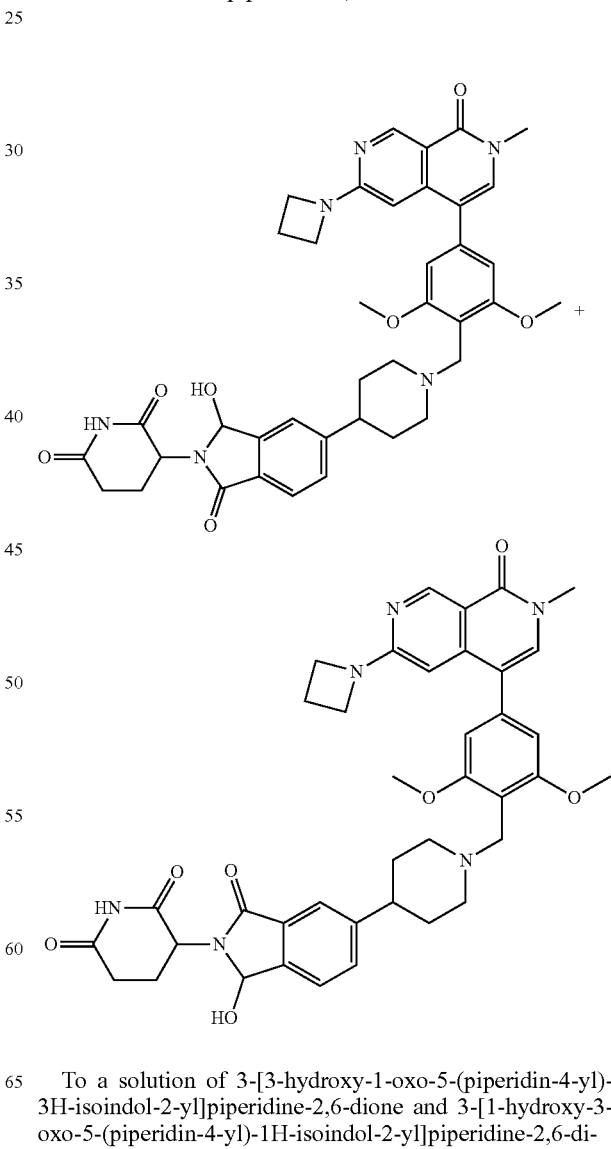

To a solution of 3-[3-hydroxy-1-oxo-5-(piperidin-4-yl)-3H-isoindol-2-yl]piperidine-2,6-dione and 3-[1-hydroxy-3-oxo-5-(piperidin-4-yl)-1H-isoindol-2-yl]piperidine-2,6-dione (mixture of two regio-isomers, 260.0 mg, 0.757 mmol, 1.00 equivalent), 4-[6-(azetidin-1-yl)-2-methyl-1-oxo-2,7-naphthyridin-4-yl]-2,6-dimethoxybenzaldehyde (287.3 mg, 0.757 mmol, 1 equivalent) in DMF (3 mL) was added NaBH(OAc)$_3$ (321.0 mg, 1.514 mmol, 2 equivalent), and the resulting solution was stirred at 25° C. for 4 hours. The mixture was diluted with EtOAc (20 mL) and washed with water (20 mL×3). The organic layers were combined and dried over anhydrous sodium sulfate, filtered and concentrated to give a crude product. The crude product was purified by Prep-TLC (CH$_2$Cl$_2$/MeOH 10:1) to give 3-[5-[1-([4-[6-(azetidin-1-yl)-2-methyl-1-oxo-2,7-naphthyridin-4-yl]-2,6-dimethoxyphenyl]methyl)piperidin-4-yl]-3-hydroxy-1-oxo-3H-isoindol-2-yl]piperidine-2,6-dione and 3-[5-[1-([4-[6-(azetidin-1-yl)-2-methyl-1-oxo-2,7-naphthyridin-4-yl]-2,6-dimethoxyphenyl]methyl)piperidin-4-yl]-1-hydroxy-3-oxo-1H-isoindol-2-yl]piperidine-2,6-dione (208 mg, mixture of two regio-isomers, 38.9%) as a white solid. LCMS (ESI) m/z: [M+H]$^+$=707.

Step 4: Preparation of 3-[5-[1-([4-[6-(azetidin-1-yl)-2-methyl-1-oxo-2,7-naphthyridin-4-yl]-2,6-dimethoxy phenyl]methyl) piperidin-4-yl]-1-oxo-3H-isoindol-2-yl]piperidine-2,6-dione formic acid; and 3-[6-[1-([4-[6-(azetidin-1-yl)-2-methyl-1-oxo-2,7-naphthyridin-4-yl]-2,6-dimethoxyphenyl]methyl) piperidin-4-yl]-1-oxo-3H-isoindol-2-yl]piperidine-2,6-dione formic acid To a solution of 3-[5-[1-([4-[6-(azetidin-1-yl)-2-methyl-1-oxo-2,7-naphthyridin-4-yl]-2,6-dimethoxyphenyl]methyl) piperidin-4-yl]-3-hydroxy-1-oxo-3H-isoindol-2-yl]piperidine-2,6-dione and 3-[5-[1-([4-[6-(azetidin-1-yl)-2-methyl-1-oxo-2,7-naphthyridin-4-yl]-2,6-dimethoxyphenyl]methyl) piperidin-4-yl]-1-hydroxy-3-oxo-1H-isoindol-2-yl] piperidine-2,6-dione (mixture of two regio-isomers, 200.0 mg, 0.141 mmol, 1.00 equivalent) in DCM (3.00 mL) was added TFA (2.00 mL, 26.926 mmol, 95.16 equivalent) and triethylsilane (1.00 mL, 6.192 mmol, 21.88 equivalent), and the resulting solution was stirred at 25° C. for 1 hour. The crude product was purified by Prep-HPLC (Column: XSelect CSH Prep C18 OBD Column, 5 μm, 19*150 mm; Mobile Phase A: Water (0.05% FA), Mobile Phase B: ACN; Flow rate: 25 mL/min; Gradient: 3 B to 26 B in 14 minutes; 254 nm; RT1: 13.32 min) to afford 3-[5-[1-([4-[6-(azetidin-1-yl)-2-methyl-1-oxo-2,7-naphthyridin-4-yl]-2,6-dimethoxyphenyl]methyl) piperidin-4-yl]-1-oxo-3H-isoindol-2-yl]piperidine-2,6-dione (39.5 mg, 39.1%) and 3-[6-[1-([4-[6-(azetidin-1-yl)-2-methyl-1-oxo-2,7-naphthyridin-4-yl]-2,6-dimethoxyphenyl] methyl)piperidin-4-yl]-1-oxo-3H-isoindol-2-yl]piperidine-2,6-dione; formic acid (24.8 mg, 22.7%) both as a white solid.

For 3-[5-[1-([4-[6-(azetidin-1-yl)-2-methyl-1-oxo-2,7-naphthyridin-4-yl]-2,6-dimethoxyphenyl]methyl) piperidin-4-yl]-1-oxo-3H-isoindol-2-yl]piperidine-2,6-dione: $^1$H NMR (400 MHz, DMSO-d6) δ 10.99 (s, 1H), 9.02 (s, 1H), 8.16 (s, 1H, FA), 7.68-7.60 (m, 2H), 7.49 (s, 1H), 7.39 (dd, J=7.8, 1.4 Hz, 1H), 6.76 (s, 2H), 6.22 (s, 1H), 5.10 (dd, J=13.3, 5.1 Hz, 1H), 4.42 (d, J=17.3 Hz, 1H), 4.28 (d, J=17.3 Hz, 1H), 4.01 (t, J=7.4 Hz, 4H), 3.84 (s, 6H), 3.69 (s, 2H), 3.49 (s, 3H), 3.05 (d, J=11.2 Hz, 2H), 2.92 (ddd, J=17.3, 13.6, 5.4 Hz, 1H), 2.66-2.60 (m, 1H), 2.60-2.55 (m, 1H), 2.46-2.38 (m, 1H), 2.37-2.28 (m, 4H), 2.04-1.95 (m, 1H), 1.78-1.65 (m, 4H). LCMS (ESI) m/z: [M+H]$^+$=691.35.

For 3-[6-[1-([4-[6-(azetidin-1-yl)-2-methyl-1-oxo-2,7-naphthyridin-4-yl]-2,6-dimethoxyphenyl]methyl)piperidin-4-yl]-1-oxo-3H-isoindol-2-yl]piperidine-2,6-dione; formic acid: $^1$H NMR (400 MHz, DMSO-d6) δ 10.99 (s, 1H), 9.02 (s, 1H), 8.18 (s, FA), 7.62 (s, 1H), 7.58-7.48 (m, 3H), 6.75 (s, 2H), 6.22 (s, 1H), 5.10 (dd, J=13.3, 5.1 Hz, 1H), 4.41 (d, J=17.1 Hz, 1H), 4.27 (d, J=17.1 Hz, 1H), 4.01 (t, J=7.4 Hz, 4H), 3.84 (s, 6H), 3.63 (s, 2H), 3.48 (s, 3H), 3.00 (d, J=11.0 Hz, 2H), 2.97-2.85 (m, 1H), 2.65-2.60 (m, 1H), 2.60-2.56 (m, 1H), 2.45-2.37 (m, 1H), 2.37-2.30 (m, 1H), 2.24 (t, J=11.3 Hz, 2H), 2.03-1.96 (m, 1H), 1.80-1.73 (m, 2H), 1.73-1.62 (m, 2H). LCMS (ESI) m/z: [M+H]$^+$=691.55.

Example 17—Preparation of 3-(5-[[1-([2,6-dimethoxy-4-[2-methyl-6-(morpholin-4-yl)-1-oxo-2,7-naphthyridin-4-yl]phenyl]methyl)azetidin-3-yl]oxy]-1-oxo-3H-isoindol-2-yl)piperidine-2,6-dione

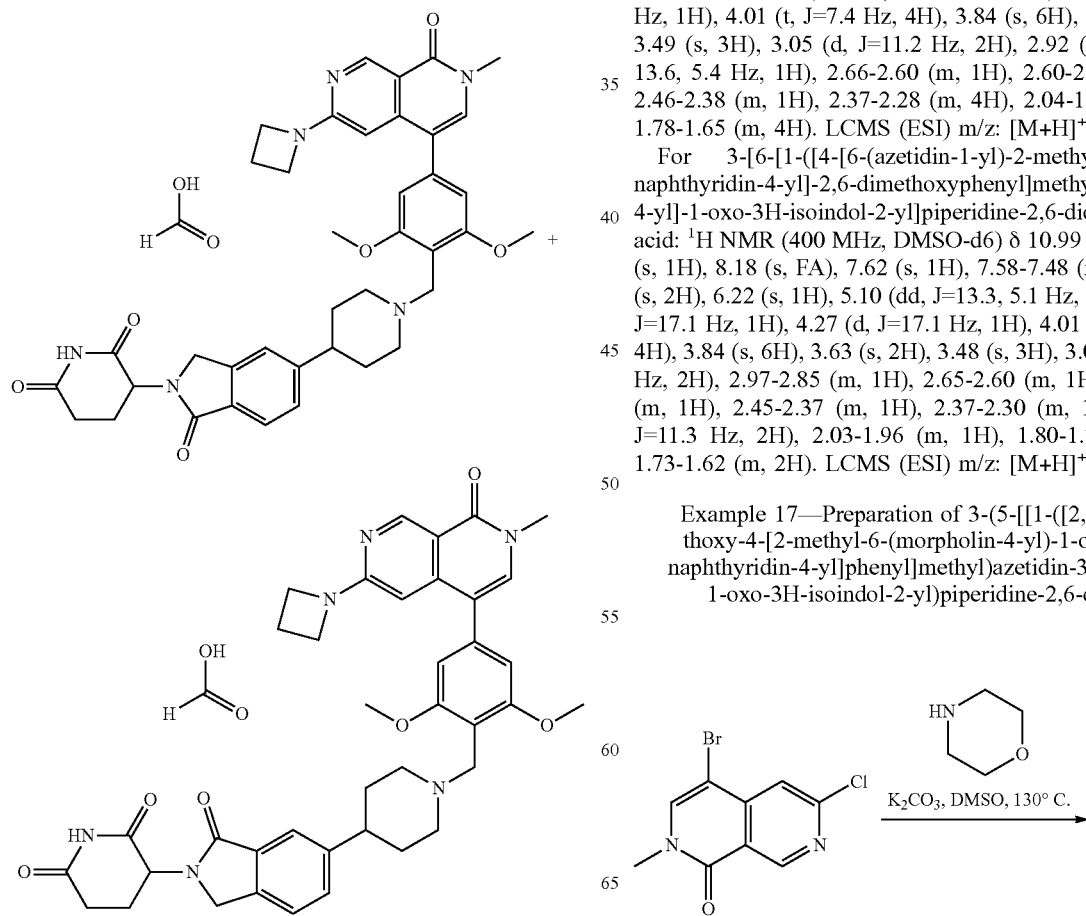

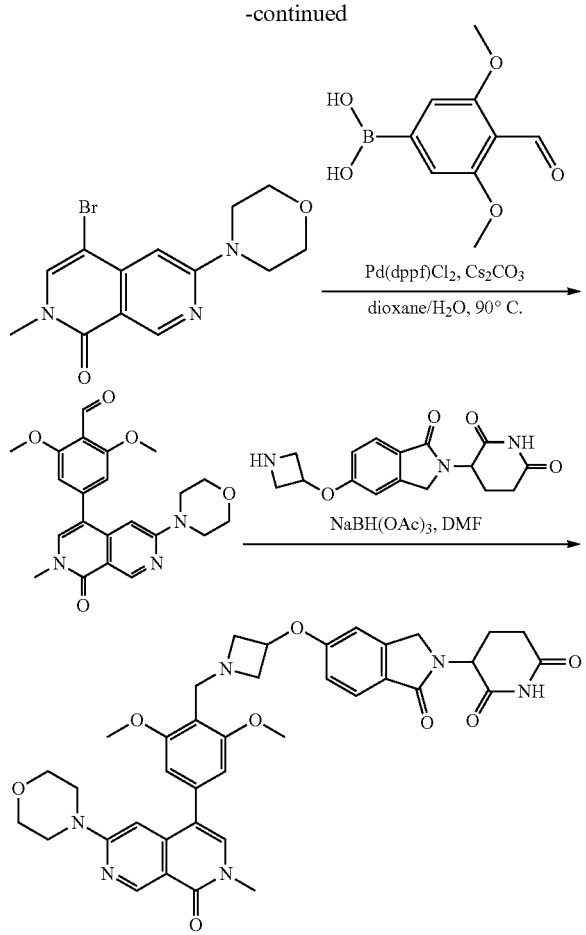

Step 1: preparation of 4-bromo-2-methyl-6-(morpholin-4-yl)-2,7-naphthyridin-1-one

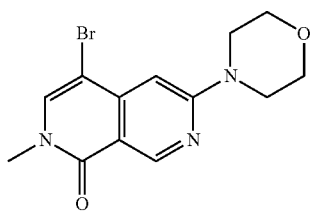 [SMILES: Cn1cc(Br)c2cc(N3CCOCC3)ncc2c1=O]

To a stirred solution of 4-bromo-6-chloro-2-methyl-2,7-naphthyridin-1-one (547.00 mg, 2.000 mmol, 1.00 equivalent) and morpholine (522.71 mg, 6.000 mmol, 3.00 equivalent) in DMSO (6.00 mL) was added K$_2$CO$_3$ (1382.00 mg, 10.000 mmol, 5.00 equivalent). The resulting mixture was stirred for 1 h at 130° C. under nitrogen atmosphere. The reaction mixture was diluted with EA (100 mL).

The resulting mixture was washed with 3×100 mL of water and 1×100 mL saturated brine. The organic layer was dried over Na$_2$SO$_4$, filtered and evaporated to afford crude product. The residue was purified by silica gel column chromatography, elution gradient 0 to 10% MeOH in DCM. Pure fractions were evaporated to dryness to afford 4-bromo-2-methyl-6-(morpholin-4-yl)-2,7-naphthyridin-1-one (541 mg, 83.44%) as a light yellow solid. LCMS (ESI) m/z: [M+H]$^+$=324.

Step 2: Preparation of 2,6-dimethoxy-4-[2-methyl-6-(morpholin-4-yl)-1-oxo-2,7-naphthyridin-4-yl]benzaldehyde

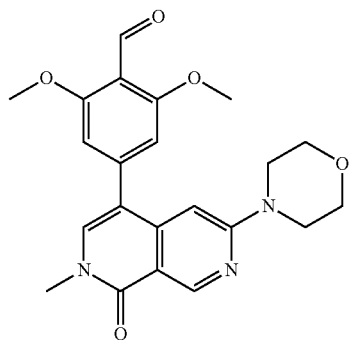 [SMILES: COc1cc(-c2cn(C)c(=O)c3cnc(N4CCOCC4)cc23)cc(OC)c1C=O]

To a solution of 4-bromo-2-methyl-6-(morpholin-4-yl)-2,7-naphthyridin-1-one (540.00 mg, 1.666 mmol, 1.00 equivalent) and 4-formyl-3,5-dimethoxyphenylboronic acid (454.73 mg, 2.165 mmol, 1.30 equivalent), Cs$_2$CO$_3$ (1628.20 mg, 4.997 mmol, 3.00 equivalent) in H$_2$O (1.00 mL) and dioxane (5.00 mL) was added Pd(dppf)Cl$_2$CH$_2$Cl$_2$ (136.03 mg, 0.167 mmol, 0.10 equivalent) under nitrogen. After stirring for 1 h at 90° C. under a nitrogen atmosphere, the resulting mixture was concentrated under reduced pressure. The residue was purified by silica gel column chromatography, elution gradient 0 to 10% MeOH in DCM. Pure fractions were evaporated to dryness to afford 2,6-dimethoxy-4-[2-methyl-6-(morpholin-4-yl)-1-oxo-2,7 naphthyridin-4-yl] benzaldehyde (356 mg, 52.20%) as a yellow solid. LCMS (ESI) m/z: [M+H]$^+$=410.

Step 3: Preparation of 3-(5-[[1-([2,6-dimethoxy-4-[2-methyl-6-(morpholin-4-yl)-1-oxo-2,7-naphthyridin-4-yl]phenyl]methyl)azetidin-3-yl]oxy]-1-oxo-3H-isoindol-2-yl)piperidine-2,6-dione

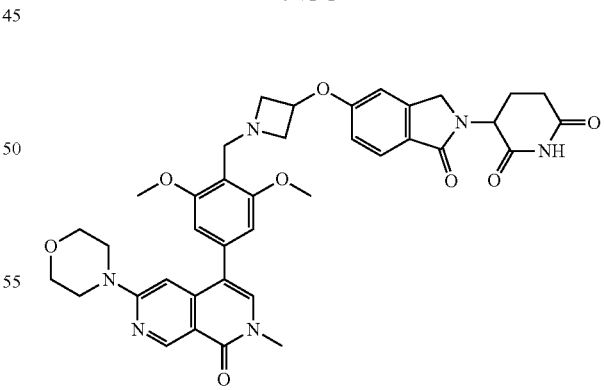

To a stirred solution of 3-[5-(azetidin-3-yloxy)-1-oxo-3H-isoindol-2-yl]piperidine-2,6-dione (100.00 mg, 0.317 mmol, 1.00 equivalent) and 2,6-dimethoxy-4-[2-methyl-6-(morpholin-4-yl)-1-oxo-2,7-naphthyridin-4-yl]benzaldehyde (129.85 mg, 0.317 mmol, 1.00 equivalent) in DMF was added NaBH(OAc)$_3$ (134.43 mg, 0.634 mmol, 2.00 equivalent) dropwise at room temperature under air atmosphere for 2 hours. The residue was purified by reverse flash chromatography with the following conditions: column, C18 silica gel; mobile phase, MeCN in water, 0% to 100% gradient in 45 min; detector, UV 254 nm. The crude product was purified by Prep-HPLC with the following conditions (Column: Xcelect CSH F-pheny OBD Column, 19*250 mm, 5 μm; Mobile Phase A: Water (0.05% FA); Mobile Phase B: ACN; Flow rate: 30 mL/min; Gradient: 13 B to 33 B in 14 min; 254/220 nm; RT1: 12.85 min) to afford 3-(5-[[1-([2,6-dimethoxy-4-[2-methyl-6-(morpholin-4-yl)-1-oxo-2,7-naphthyridin-4-yl]phenyl]methyl)azetidin-3-yl]oxy]-1-oxo-3H-isoindol-2-yl)piperidine-2,6-dione (100 mg, 44.15%) as a yellow solid. $^1$H NMR (400 MHz, Methanol-d4) δ 9.18 (s, 1H), 7.80 (t, J=6.7 Hz, 1H), 7.49 (s, 1H), 7.09 (t, J=7.3 Hz, 2H), 6.88 (s, 2H), 6.63 (d, J=4.9 Hz, 1H), 5.40-5.20 (m, 1H), 5.15 (dd, J=13.3, 5.2 Hz, 1H), 4.77 (ddd, J=24.3, 12.5, 6.8 Hz, 2H), 4.65 (d, J=22.0 Hz, 2H), 4.48 (d, J=6.3 Hz, 2H), 4.44-4.28 (m, 2H), 3.96 (d, J=23.6 Hz, 6H), 3.78 (t, J=4.8 Hz, 4H), 3.61 (s, 3H), 3.56 (d, J=4.7 Hz, 4H), 2.93 (ddd, J=18.5, 13.5, 5.3 Hz, 1H), 2.80 (ddd, J=17.5, 4.6, 2.3 Hz, 1H), 2.49 (qd, J=13.2, 4.7 Hz, 1H), 2.23-2.14 (m, 1H). LCMS (ESI) m/z: $[M+H]^+$=709.

Example 18—SYO1 BRD9 NanoLuc Degradation Assay

This example demonstrates the ability of the compounds of the disclosure to degrade a Nanoluciferase-BRD9 fusion protein in a cell-based degradation assay.

Procedure: A stable SYO-1 cell line expressing 3×FLAG-NLuc-BRD9 was generated. On day 0 cells were seeded in 30 μL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 μM as final top dose). Subsequently plates were incubated for 6 hours in a standard tissue culture incubator and equilibrated at room temperature for 15 minutes. Nanoluciferase activity was measured by adding 15 μL of freshly prepared Nano-Glo Luciferase Assay Reagent (Promega N1130), shaking the plates for 10 minutes and reading the bioluminescence using an EnVision reader.

Results: The Inhibition % was calculated using the following formula: % Inhibition=100×($Lum_{HC}$−$Lum_{Sample}$)/($Lum_{HC}$−$Lum_{LC}$). DMSO treated cells are employed as High Control (HC) and 1 μM of a known BRD9 degrader standard treated cells are employed as Low Control (LC). The data was fit to a four parameter, non-linear curve fit to calculate $IC_{50}$ (μM) values as shown in Table 4. As shown by the results in Table 4, a number of compounds of the present disclosure exhibit an $IC_{50}$ value of <1 μM for the degradation of BRD9, indicating their use as compounds for reducing the levels and/or activity of BRD9 and their potential for treating BRD9-related disorders.

TABLE 4

| SYO1 BRD9-NanoLuc Degradation | |
|---|---|
| Compound No. | SYO1 BRD9-NanoLuc degradation $IC_{50}$ (nM) |
| D1 | ++++ |
| D2 | ++++ |
| D3 | ++++ |
| D4 | ++++ |
| D5 | ++++ |
| D6 | ++++ |
| D7 | ++++ |
| D8 | ++++ |
| D9 | ++++ |
| D10 | ++++ |
| D11 | ++++ |
| D12 | ++++ |
| D13 | ++++ |
| D14 | ++++ |
| D15 | ++++ |
| D16 | ++++ |
| D17 | ++++ |
| D18 | ++++ |
| D19 | ++++ |
| D20 | ++++ |
| D21 | ++++ |
| D22 | ++++ |
| D23 | ++++ |
| D24 | ++++ |
| D25 | ++++ |
| D26 | ++++ |
| D27 | ++++ |
| D28 | ++++ |
| D29 | ++++ |
| D30 | ++++ |
| D31 | ++++ |
| D32 | ++++ |
| D33 | ++++ |
| D34 | ++++ |
| D35 | ++++ |
| D36 | ++++ |
| D37 | ++++ |
| D38 | ++++ |
| D39 | ++++ |
| D40 | ++++ |
| D41 | ++++ |
| D42 | ++++ |
| D43 | ++++ |
| D44 | ++++ |
| D45 | ++++ |
| D46 | ++++ |
| D47 | ++++ |
| D48 | ++ |
| D49 | ++++ |
| D50 | ++++ |
| D51 | ++++ |
| D52 | ++++ |
| D53 | ++++ |
| D54 | ++++ |
| D55 | ++++ |
| D56 | ++++ |
| D57 | ++++ |
| D58 | ++++ |
| D59 | ++++ |
| D60 | ++++ |
| D61 | ++++ |
| D62 | ++++ |
| D63 | ++++ |
| D64 | ++++ |
| D65 | ++++ |
| D66 | ++++ |

"+" indicates inhibitory effect of ≥1000 nM;
"++" indicates inhibitory effect of ≥100 nM;
"+++" indicates inhibitory effect of ≥10 nM;
"++++" indicates inhibitory effect of <10 nM;
"NT" indicates not tested

OTHER EMBODIMENTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:
1. A compound having the structure of Formula I:

A-L-B          Formula I, where
  L has the structure of Formula II:

A¹-E¹-F-E²-A²,          Formula II

A¹ is a bond between the linker and A;
A² is a bond between B and the linker;
each of E¹ and E² is, independently, absent, CH₂, O, or NCH₃; and
F is optionally substituted $C_{2-10}$ heterocyclylene;
B is a degradation moiety that has the structure of Formula A:

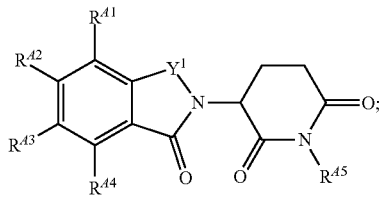

Formula A and
A has the structure of Formula III:

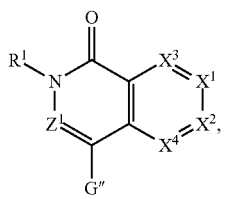

Formula III wherein
$R^1$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;
$Z^1$ is $CR^2$;
$R^2$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;
$X^1$ is N, and $X^2$ is C—$R^{7"}$;
$R^{7"}$ is

optionally substituted $C_1$-$C_6$ alkyl, optionally substituted $C_1$-$C_6$ heteroalkyl, optionally substituted $C_1$-$C_6$ alkoxy, optionally substituted amino, optionally substituted sulfone, optionally substituted sulfonamide, optionally substituted carbocyclyl having 3 to 6 atoms, or optionally substituted heterocyclyl having 3 to 6 atoms;

$R^{7'}$ is H, optionally substituted $C_1$-$C_6$ alkyl, optionally substituted $C_1$-$C_6$ heteroalkyl, or optionally substituted $C_3$-$C_{10}$ carbocycylyl;
$X^3$ is CH;
$X^4$ is CH;
G" is

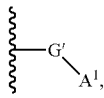

optionally substituted $C_3$-$C_{10}$ carbocyclyl, $C_2$-$C_9$ heterocyclyl, optionally substituted $C_6$-$C_{10}$ aryl, or optionally substituted $C_2$-$C_9$ heteroaryl;
  G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and
  A¹ is a bond between A and the linker,
  where G" is

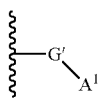

or $R^{7"}$ is

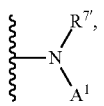

Y¹ is

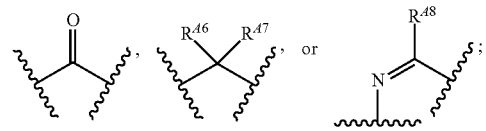

$R^{A5}$ is H, optionally substituted $C_1$-$C_6$ alkyl, or optionally substituted $C_1$-$C_6$ heteroalkyl;
$R^{A6}$ is H or optionally substituted $C_1$-$C_6$ alkyl; and
$R^{A7}$ is H or optionally substituted $C_1$-$C_6$ alkyl;
or $R^{A6}$ and $R^{A7}$, together with the carbon atom to which each is bound, combine to form optionally substituted $C_3$-$C_6$ carbocyclyl or optionally substituted $C_2$-$C_5$ heterocyclyl; or $R^{A6}$ and $R^{A7}$, together with the carbon atom to which each is bound, combine to form optionally substituted $C_3$-$C_6$ carbocyclyl or optionally substituted $C_2$-$C_5$ heterocyclyl;
$R^{A8}$ is H, optionally substituted $C_1$-$C_6$ alkyl, or optionally substituted $C_1$-$C_6$ heteroalkyl; and
each of $R^{A1}$, $R^{A2}$, $R^{A3}$, and $R^{A4}$ is, independently, H, A², halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

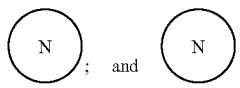

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$, or

is substituted with $A^2$, or a pharmaceutically acceptable salt thereof.

2. The compound of claim 1, wherein $R^1$ is optionally substituted $C_1$-$C_6$ alkyl.

3. The compound of claim 2, wherein $R^1$ is

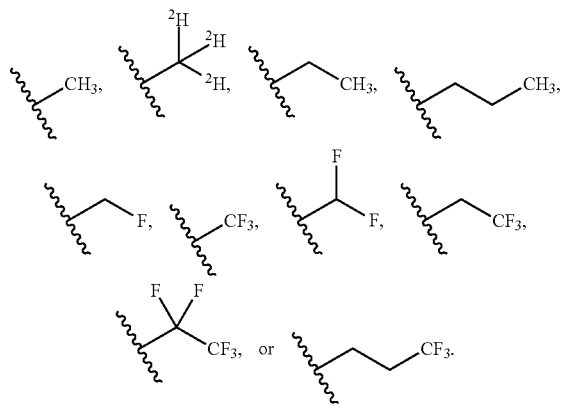

4. The compound of claim 3, wherein $R^1$ is

5. The compound of claim 1, wherein $Z^1$ is $CR^2$.

6. The compound of claim 5, wherein $R^2$ is H, F, or

7. The compound of claim 1, wherein $X^1$ is N and $X^2$ is C—$R^{7\prime\prime}$.

8. The compound of claim 7, wherein $R^{7\prime\prime}$ is optionally substituted $C_1$-$C_6$ alkyl, optionally substituted $C_1$-$C_6$ heteroalkyl, optionally substituted carbocyclyl having 3 to 6 atoms, or optionally substituted heterocyclyl having 3 to 6 atoms.

9. The compound of claim 8, wherein $R^{7\prime\prime}$ is optionally substituted $C_1$-$C_6$ heteroalkyl.

10. The compound of claim 9, wherein $R^{7\prime\prime}$ is —$NR^3R^4$.

11. The compound of claim 8, wherein $R^{7\prime\prime}$ is optionally substituted heterocyclyl having 3 to 6 atoms.

12. The compound of claim 11, wherein $R^{7\prime\prime}$ is

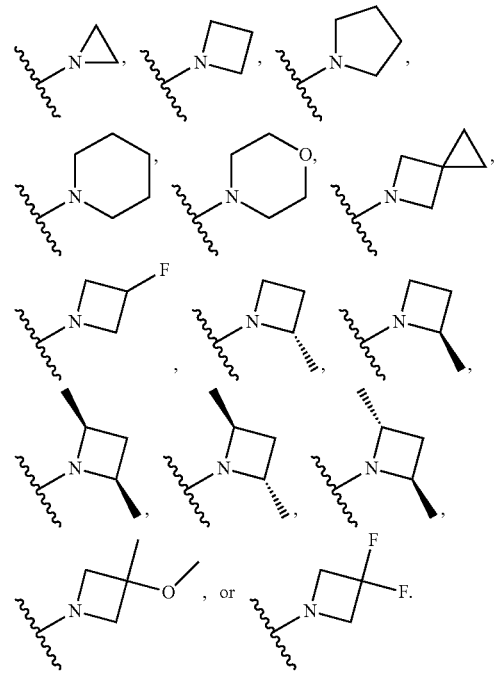

13. The compound of claim 1, wherein G" is optionally substituted $C_5$-$C_{10}$ aryl.

14. The compound of claim 13, wherein G" is

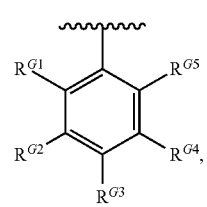

wherein each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, optionally substituted —$C_1$-$C_3$ alkyl-$C_3$-$C_6$ carbocyclyl, optionally substituted —$C_1$-$C_3$ alkyl-$C_2$-$C_5$ heterocyclyl, hydroxyl, thiol, or optionally substituted amino; or $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl.

15. The compound of claim 14, wherein each of $R^{G1}$, $R^{G2}$, $R^{G3}$, $R^{G4}$, and $R^{G5}$ is, independently, H, halogen, optionally substituted $C_1$-$C_6$ alkyl, optionally substituted $C_1$-$C_6$ heteroalkyl, optionally substituted —O—$C_3$-$C_5$ carbocyclyl, or optionally substituted —$C_1$-$C_3$ alkyl-$C_2$-$C_5$ heterocyclyl.

16. The compound of claim 15, wherein each of $R^{G1}$, $R^{G2}$, $R^{G3}$, $R^{G4}$, and $R^{G5}$ is, independently, H, F, Cl

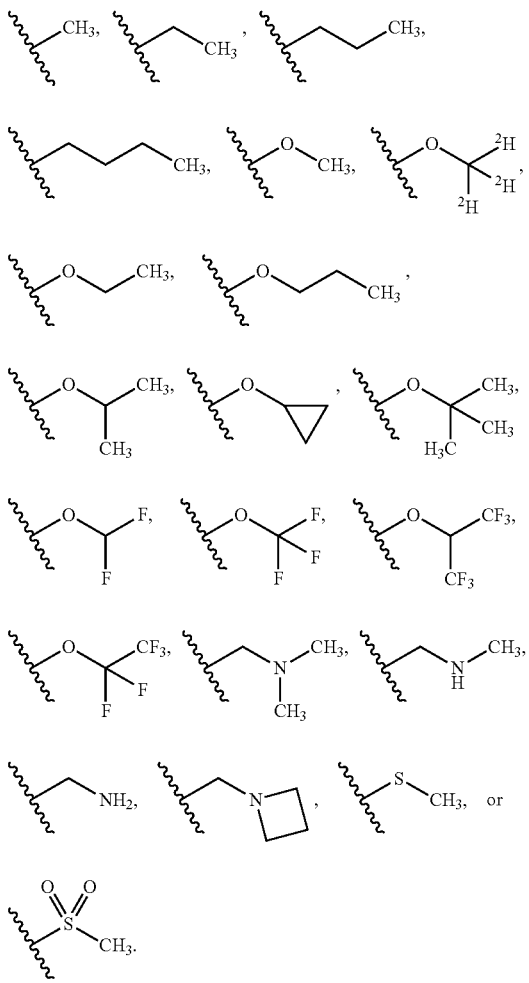

17. The compound of claim 1, wherein A has the structure of Formula IIIa:

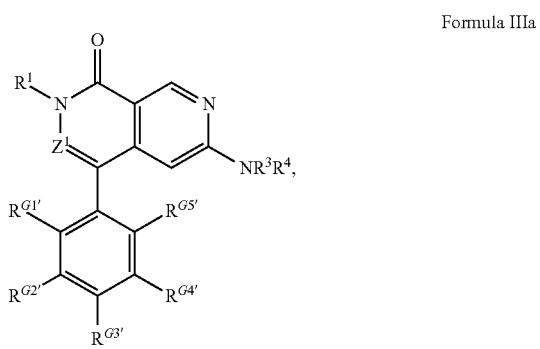

Formula IIIa or a pharmaceutically acceptable salt thereof.

18. The compound of claim 1, wherein A has the structure of Formula IIIu:

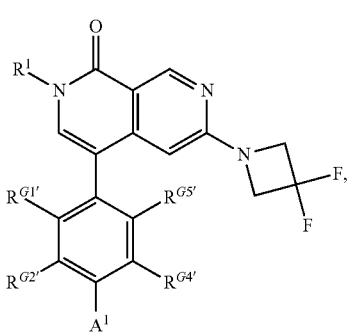

Formula IIIu or a pharmaceutically acceptable salt thereof.

19. The compound of claim 1, wherein the structure of Formula A has the structure of Formula A6:

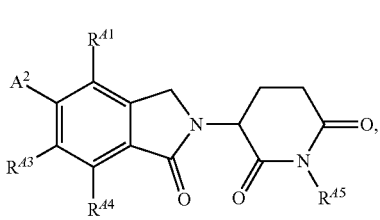

Formula A6 or a pharmaceutically acceptable salt thereof.

20. The compound of claim 19, wherein the structure of Formula A6 is

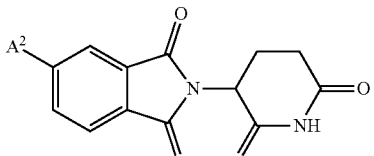

21. The compound of claim 1, wherein the linker has the structure of Formula II:

$$A^1\text{-}E^1\text{-}F\text{-}E^2\text{-}A^2,$$ Formula II $A^1$ is a bond between the linker and A;
$A^2$ is a bond between B and the linker;
each of $E^1$ and $E^2$ is, independently, absent, $CH_2$, O, or $NCH_3$; and
F has the structure:

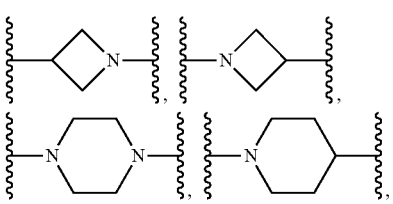

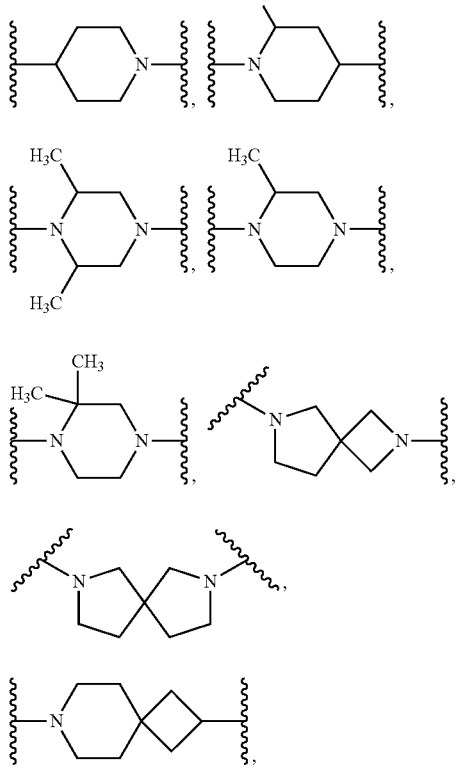

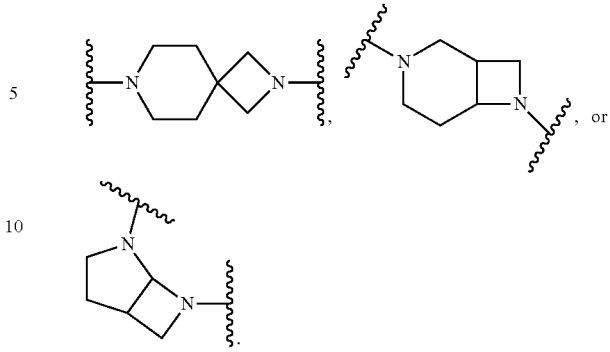

22. A pharmaceutical composition comprising the compound of claim 1 and a pharmaceutically acceptable excipient.

23. A method of inhibiting the level and/or activity of BRD9 in a subject in need thereof, the method including administering to the subject an effective amount of a compound of claim 1, or a pharmaceutically acceptable salt thereof, wherein BRD9 is a protein having at least 85% identity to an amino acid sequence encoded by the nucleic acid sequence of the BRD9 gene.

24. The method of claim 23, wherein the compound, or a pharmaceutically acceptable salt thereof, or the pharmaceutical composition is administered orally.

* * * * *

```
                            SEQUENCE LISTING

<160> NUMBER OF SEQ ID NOS: 673

<210> SEQ ID NO 1
<211> LENGTH: 141
<212> TYPE: PRT
<213> ORGANISM: Artificial Sequence
<220> FEATURE:
<223> OTHER INFORMATION: Synthetic Construct

<400> SEQUENCE: 1

Met Gly Ser Ser His His His His His Glu Asn Leu Tyr Phe Gln
1               5                   10                  15

Gly Asp Tyr Lys Asp Asp Asp Lys Gly Ser Leu Glu Val Leu Phe
            20                  25                  30

Gln Gly Pro Ala Glu Asn Glu Ser Thr Pro Ile Gln Gln Leu Leu Glu
        35                  40                  45

His Phe Leu Arg Gln Leu Gln Arg Lys Asp Pro His Gly Phe Phe Ala
    50                  55                  60

Phe Pro Val Thr Asp Ala Ile Ala Pro Gly Tyr Ser Met Ile Ile Lys
65                  70                  75                  80

His Pro Met Asp Phe Gly Thr Met Lys Asp Lys Ile Val Ala Asn Glu
                85                  90                  95

Tyr Lys Ser Val Thr Glu Phe Lys Ala Asp Phe Lys Leu Met Cys Asp
            100                 105                 110

Asn Ala Met Thr Tyr Asn Arg Pro Asp Thr Val Tyr Tyr Lys Leu Ala
        115                 120                 125

Lys Lys Ile Leu His Ala Gly Phe Lys Met Met Ser Lys
    130                 135                 140

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000
```

-continued

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17

```
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
```

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

-continued

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

-continued

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

```
<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107
```

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

```
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
```

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

```
<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000
```

```
<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
```

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203
<211> LENGTH: 20
<212> TYPE: DNA
<213> ORGANISM: Artificial Sequence
<220> FEATURE:
<223> OTHER INFORMATION: Synthetic Construct

<400> SEQUENCE: 203
caagaagcac aagaagcaca                                           20

<210> SEQ ID NO 204
<211> LENGTH: 20
<212> TYPE: DNA
<213> ORGANISM: Artificial Sequence
<220> FEATURE:
<223> OTHER INFORMATION: Synthetic Construct

<400> SEQUENCE: 204
cttgtgcttc ttgcccatgg                                           20

<210> SEQ ID NO 205
<211> LENGTH: 20
<212> TYPE: DNA
<213> ORGANISM: Artificial Sequence
<220> FEATURE:
<223> OTHER INFORMATION: Synthetic Construct

<400> SEQUENCE: 205
cttcttgtgc ttcttgccca                                           20

<210> SEQ ID NO 206
<211> LENGTH: 20
<212> TYPE: DNA
<213> ORGANISM: Artificial Sequence
<220> FEATURE:
<223> OTHER INFORMATION: Synthetic Construct

<400> SEQUENCE: 206
acaagaagca caaggccgag                                              20

<210> SEQ ID NO 207
<211> LENGTH: 20
<212> TYPE: DNA
<213> ORGANISM: Artificial Sequence
<220> FEATURE:
<223> OTHER INFORMATION: Synthetic Construct

<400> SEQUENCE: 207
ctcgtaggac gagcgccact                                              20

<210> SEQ ID NO 208
<211> LENGTH: 20
<212> TYPE: DNA
<213> ORGANISM: Artificial Sequence
<220> FEATURE:
<223> OTHER INFORMATION: Synthetic Construct

<400> SEQUENCE: 208
cgagtggcgc tcgtcctacg                                              20

<210> SEQ ID NO 209
<211> LENGTH: 20
<212> TYPE: DNA
<213> ORGANISM: Artificial Sequence
<220> FEATURE:
<223> OTHER INFORMATION: Synthetic Construct

<400> SEQUENCE: 209
gagtggcgct cgtcctacga                                              20

<210> SEQ ID NO 210
<211> LENGTH: 20
<212> TYPE: DNA
<213> ORGANISM: Artificial Sequence
<220> FEATURE:
<223> OTHER INFORMATION: Synthetic Construct

<400> SEQUENCE: 210
aggcttctcc aggggcttgt                                              20

<210> SEQ ID NO 211
<211> LENGTH: 20
<212> TYPE: DNA
<213> ORGANISM: Artificial Sequence
<220> FEATURE:
<223> OTHER INFORMATION: Synthetic Construct

<400> SEQUENCE: 211
agattatgcc gacaagcccc                                              20

<210> SEQ ID NO 212
<211> LENGTH: 20
<212> TYPE: DNA
<213> ORGANISM: Artificial Sequence
<220> FEATURE:
<223> OTHER INFORMATION: Synthetic Construct

<400> SEQUENCE: 212
accttcagga ctagctttag                                              20

<210> SEQ ID NO 213
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 213
agctttagag gcttctccag                                            20

<210> SEQ ID NO 214
<211> LENGTH: 20
<212> TYPE: DNA
<213> ORGANISM: Artificial Sequence
<220> FEATURE:
<223> OTHER INFORMATION: Synthetic Construct

<400> SEQUENCE: 214
ctagctttag aggcttctcc                                            20

<210> SEQ ID NO 215
<211> LENGTH: 20
<212> TYPE: DNA
<213> ORGANISM: Artificial Sequence
<220> FEATURE:
<223> OTHER INFORMATION: Synthetic Construct

<400> SEQUENCE: 215
tagctttaga ggcttctcca                                            20

<210> SEQ ID NO 216
<211> LENGTH: 20
<212> TYPE: DNA
<213> ORGANISM: Artificial Sequence
<220> FEATURE:
<223> OTHER INFORMATION: Synthetic Construct

<400> SEQUENCE: 216
ctaaagctag tcctgaaggt                                            20

<210> SEQ ID NO 217
<211> LENGTH: 20
<212> TYPE: DNA
<213> ORGANISM: Artificial Sequence
<220> FEATURE:
<223> OTHER INFORMATION: Synthetic Construct

<400> SEQUENCE: 217
gcctctaaag ctagtcctga                                            20

<210> SEQ ID NO 218
<211> LENGTH: 20
<212> TYPE: DNA
<213> ORGANISM: Artificial Sequence
<220> FEATURE:
<223> OTHER INFORMATION: Synthetic Construct

<400> SEQUENCE: 218
cttcacttcc tccgaccttc                                            20

<210> SEQ ID NO 219
<211> LENGTH: 20
<212> TYPE: DNA
<213> ORGANISM: Artificial Sequence
<220> FEATURE:
<223> OTHER INFORMATION: Synthetic Construct

<400> SEQUENCE: 219
```
aagctagtcc tgaaggtcgg                                               20

<210> SEQ ID NO 220
<211> LENGTH: 20
<212> TYPE: DNA
<213> ORGANISM: Artificial Sequence
<220> FEATURE:
<223> OTHER INFORMATION: Synthetic Construct

<400> SEQUENCE: 220
agtgaagtga ctgaactctc                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic Construct

<400> SEQUENCE: 221
gtgactgaac tctcaggatc                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic Construct

<400> SEQUENCE: 222
atagtaactg gagtcgtggc                                               20

<210> SEQ ID NO 223
<211> LENGTH: 20
<212> TYPE: DNA
<213> ORGANISM: Artificial Sequence
<220> FEATURE:
<223> OTHER INFORMATION: Synthetic Construct

<400> SEQUENCE: 223
catcatagta actggagtcg                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic Construct

<400> SEQUENCE: 224
tgacctgtca tcatagtaac                                               20

<210> SEQ ID NO 225
<211> LENGTH: 20
<212> TYPE: DNA
<213> ORGANISM: Artificial Sequence
<220> FEATURE:
<223> OTHER INFORMATION: Synthetic Construct

<400> SEQUENCE: 225
actccagtta ctatgatgac                                               20

<210> SEQ ID NO 226
<211> LENGTH: 20
<212> TYPE: DNA
<213> ORGANISM: Artificial Sequence
<220> FEATURE:
<223> OTHER INFORMATION: Synthetic Construct

<400> SEQUENCE: 226
ctttgtgcct ctctcgctca                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic Construct

<400> SEQUENCE: 227
ggtcagacca tgagcgagag                                              20

<210> SEQ ID NO 228
<211> LENGTH: 20
<212> TYPE: DNA
<213> ORGANISM: Artificial Sequence
<220> FEATURE:
<223> OTHER INFORMATION: Synthetic Construct

<400> SEQUENCE: 228
gaagaagaag aagtccgaga                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic Construct

<400> SEQUENCE: 229
gtccagatgc ttctccttct                                              20

<210> SEQ ID NO 230
<211> LENGTH: 20
<212> TYPE: DNA
<213> ORGANISM: Artificial Sequence
<220> FEATURE:
<223> OTHER INFORMATION: Synthetic Construct

<400> SEQUENCE: 230
gtccgagaag gagaagcatc                                              20

<210> SEQ ID NO 231
<211> LENGTH: 20
<212> TYPE: DNA
<213> ORGANISM: Artificial Sequence
<220> FEATURE:
<223> OTHER INFORMATION: Synthetic Construct

<400> SEQUENCE: 231
ggagaagcat ctggacgatg                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic Construct

<400> SEQUENCE: 232
tgaggaaaga aggaagcgaa                                              20

<210> SEQ ID NO 233
<211> LENGTH: 20
<212> TYPE: DNA
<213> ORGANISM: Artificial Sequence
<220> FEATURE:
<223> OTHER INFORMATION: Synthetic Construct

<400> SEQUENCE: 233
atctggacga tgaggaaaga                                          20

<210> SEQ ID NO 234
<211> LENGTH: 20
<212> TYPE: DNA
<213> ORGANISM: Artificial Sequence
<220> FEATURE:
<223> OTHER INFORMATION: Synthetic Construct

<400> SEQUENCE: 234
agaagaagcg gaagcgagag                                          20

<210> SEQ ID NO 235
<211> LENGTH: 20
<212> TYPE: DNA
<213> ORGANISM: Artificial Sequence
<220> FEATURE:
<223> OTHER INFORMATION: Synthetic Construct

<400> SEQUENCE: 235
gaagaagcgg aagcgagaga                                          20

<210> SEQ ID NO 236
<211> LENGTH: 20
<212> TYPE: DNA
<213> ORGANISM: Artificial Sequence
<220> FEATURE:
<223> OTHER INFORMATION: Synthetic Construct

<400> SEQUENCE: 236
ccgcccagga agagaagaag                                          20

<210> SEQ ID NO 237
<211> LENGTH: 20
<212> TYPE: DNA
<213> ORGANISM: Artificial Sequence
<220> FEATURE:
<223> OTHER INFORMATION: Synthetic Construct

<400> SEQUENCE: 237
agagagggag cactgtgaca                                          20

<210> SEQ ID NO 238
<211> LENGTH: 20
<212> TYPE: DNA
<213> ORGANISM: Artificial Sequence
<220> FEATURE:
<223> OTHER INFORMATION: Synthetic Construct

<400> SEQUENCE: 238
agggagcact gtgacacgga                                          20

<210> SEQ ID NO 239
<211> LENGTH: 20
<212> TYPE: DNA
<213> ORGANISM: Artificial Sequence
<220> FEATURE:
<223> OTHER INFORMATION: Synthetic Construct

```
<400> SEQUENCE: 239
gagggagcac tgtgacacgg                                           20

<210> SEQ ID NO 240
<211> LENGTH: 20
<212> TYPE: DNA
<213> ORGANISM: Artificial Sequence
<220> FEATURE:
<223> OTHER INFORMATION: Synthetic Construct

<400> SEQUENCE: 240
gcactgtgac acggagggag                                           20

<210> SEQ ID NO 241
<211> LENGTH: 20
<212> TYPE: DNA
<213> ORGANISM: Artificial Sequence
<220> FEATURE:
<223> OTHER INFORMATION: Synthetic Construct

<400> SEQUENCE: 241
gaggctgacg actttgatcc                                           20

<210> SEQ ID NO 242
<211> LENGTH: 20
<212> TYPE: DNA
<213> ORGANISM: Artificial Sequence
<220> FEATURE:
<223> OTHER INFORMATION: Synthetic Construct

<400> SEQUENCE: 242
aggctgacga ctttgatcct                                           20

<210> SEQ ID NO 243
<211> LENGTH: 20
<212> TYPE: DNA
<213> ORGANISM: Artificial Sequence
<220> FEATURE:
<223> OTHER INFORMATION: Synthetic Construct

<400> SEQUENCE: 243
tccacctcca ccttcttccc                                           20

<210> SEQ ID NO 244
<211> LENGTH: 20
<212> TYPE: DNA
<213> ORGANISM: Artificial Sequence
<220> FEATURE:
<223> OTHER INFORMATION: Synthetic Construct

<400> SEQUENCE: 244
cgactttgat cctgggaaga                                           20

<210> SEQ ID NO 245
<211> LENGTH: 20
<212> TYPE: DNA
<213> ORGANISM: Artificial Sequence
<220> FEATURE:
<223> OTHER INFORMATION: Synthetic Construct

<400> SEQUENCE: 245
ctttgatcct gggaagaagg                                           20

<210> SEQ ID NO 246
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 246
tgatcctggg aagaaggtgg                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic Construct

<400> SEQUENCE: 247
tcctgggaag aaggtggagg                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic Construct

<400> SEQUENCE: 248
cggactggcc gatctggggg                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic Construct

<400> SEQUENCE: 249
acgctcggac tggccgatct                                              20

<210> SEQ ID NO 250
<211> LENGTH: 20
<212> TYPE: DNA
<213> ORGANISM: Artificial Sequence
<220> FEATURE:
<223> OTHER INFORMATION: Synthetic Construct

<400> SEQUENCE: 250
aggtggagcc gcccccagat                                              20

<210> SEQ ID NO 251
<211> LENGTH: 20
<212> TYPE: DNA
<213> ORGANISM: Artificial Sequence
<220> FEATURE:
<223> OTHER INFORMATION: Synthetic Construct

<400> SEQUENCE: 251
cgctcggact ggccgatctg                                              20

<210> SEQ ID NO 252
<211> LENGTH: 20
<212> TYPE: DNA
<213> ORGANISM: Artificial Sequence
<220> FEATURE:
<223> OTHER INFORMATION: Synthetic Construct

<400> SEQUENCE: 252
```
gctcggactg gccgatctgg                                              20

<210> SEQ ID NO 253
<211> LENGTH: 20
<212> TYPE: DNA
<213> ORGANISM: Artificial Sequence
<220> FEATURE:
<223> OTHER INFORMATION: Synthetic Construct

<400> SEQUENCE: 253
cacgctcgga ctggccgatc                                              20

<210> SEQ ID NO 254
<211> LENGTH: 20
<212> TYPE: DNA
<213> ORGANISM: Artificial Sequence
<220> FEATURE:
<223> OTHER INFORMATION: Synthetic Construct

<400> SEQUENCE: 254
tgtgtccggc acgctcggac                                              20

<210> SEQ ID NO 255
<211> LENGTH: 20
<212> TYPE: DNA
<213> ORGANISM: Artificial Sequence
<220> FEATURE:
<223> OTHER INFORMATION: Synthetic Construct

<400> SEQUENCE: 255
ctggctgtgt ccggcacgct                                              20

<210> SEQ ID NO 256
<211> LENGTH: 20
<212> TYPE: DNA
<213> ORGANISM: Artificial Sequence
<220> FEATURE:
<223> OTHER INFORMATION: Synthetic Construct

<400> SEQUENCE: 256
atcggccagt ccgagcgtgc                                              20

<210> SEQ ID NO 257
<211> LENGTH: 20
<212> TYPE: DNA
<213> ORGANISM: Artificial Sequence
<220> FEATURE:
<223> OTHER INFORMATION: Synthetic Construct

<400> SEQUENCE: 257 caccettgcc tggctgtgtc                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic Construct

<400> SEQUENCE: 258
cgagcgtgcc ggacacagcc                                              20

<210> SEQ ID NO 259
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 259
tgttccagga gttgctgaat                                               20

<210> SEQ ID NO 260
<211> LENGTH: 20
<212> TYPE: DNA
<213> ORGANISM: Artificial Sequence
<220> FEATURE:
<223> OTHER INFORMATION: Synthetic Construct

<400> SEQUENCE: 260
cacacctatt cagcaactcc                                               20

<210> SEQ ID NO 261
<211> LENGTH: 20
<212> TYPE: DNA
<213> ORGANISM: Artificial Sequence
<220> FEATURE:
<223> OTHER INFORMATION: Synthetic Construct

<400> SEQUENCE: 261
gctggcggag gaagtgttcc                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic Construct

<400> SEQUENCE: 262
tttacctctg aagctggcgg                                               20

<210> SEQ ID NO 263
<211> LENGTH: 20
<212> TYPE: DNA
<213> ORGANISM: Artificial Sequence
<220> FEATURE:
<223> OTHER INFORMATION: Synthetic Construct

<400> SEQUENCE: 263
ccccggttta cctctgaagc                                               20

<210> SEQ ID NO 264
<211> LENGTH: 20
<212> TYPE: DNA
<213> ORGANISM: Artificial Sequence
<220> FEATURE:
<223> OTHER INFORMATION: Synthetic Construct

<400> SEQUENCE: 264
acttcctccg ccagcttcag                                               20

<210> SEQ ID NO 265
<211> LENGTH: 20
<212> TYPE: DNA
<213> ORGANISM: Artificial Sequence
<220> FEATURE:
<223> OTHER INFORMATION: Synthetic Construct

<400> SEQUENCE: 265
caggaaaagc aaaaaatcca                                               20
```

```
<210> SEQ ID NO 266
<211> LENGTH: 20
<212> TYPE: DNA
<213> ORGANISM: Artificial Sequence
<220> FEATURE:
<223> OTHER INFORMATION: Synthetic Construct

<400> SEQUENCE: 266
gctttcagaa aagatcccca                                              20

<210> SEQ ID NO 267
<211> LENGTH: 20
<212> TYPE: DNA
<213> ORGANISM: Artificial Sequence
<220> FEATURE:
<223> OTHER INFORMATION: Synthetic Construct

<400> SEQUENCE: 267
aggaaaagca aaaatccat                                               20

<210> SEQ ID NO 268
<211> LENGTH: 20
<212> TYPE: DNA
<213> ORGANISM: Artificial Sequence
<220> FEATURE:
<223> OTHER INFORMATION: Synthetic Construct

<400> SEQUENCE: 268
ggaaaagcaa aaatccatg                                               20

<210> SEQ ID NO 269
<211> LENGTH: 20
<212> TYPE: DNA
<213> ORGANISM: Artificial Sequence
<220> FEATURE:
<223> OTHER INFORMATION: Synthetic Construct

<400> SEQUENCE: 269
ggagcaattg catccgtgac                                              20

<210> SEQ ID NO 270
<211> LENGTH: 20
<212> TYPE: DNA
<213> ORGANISM: Artificial Sequence
<220> FEATURE:
<223> OTHER INFORMATION: Synthetic Construct

<400> SEQUENCE: 270
gtcacggatg caattgctcc                                              20

<210> SEQ ID NO 271
<211> LENGTH: 20
<212> TYPE: DNA
<213> ORGANISM: Artificial Sequence
<220> FEATURE:
<223> OTHER INFORMATION: Synthetic Construct

<400> SEQUENCE: 271
tttattatca ttgaatatcc                                              20

<210> SEQ ID NO 272
<211> LENGTH: 20
<212> TYPE: DNA
<213> ORGANISM: Artificial Sequence
<220> FEATURE:
```

```
<223> OTHER INFORMATION: Synthetic Construct

<400> SEQUENCE: 272
aatgataata aaacatccca                                              20

<210> SEQ ID NO 273
<211> LENGTH: 20
<212> TYPE: DNA
<213> ORGANISM: Artificial Sequence
<220> FEATURE:
<223> OTHER INFORMATION: Synthetic Construct

<400> SEQUENCE: 273
ataaaacatc ccatggattt                                              20

<210> SEQ ID NO 274
<211> LENGTH: 20
<212> TYPE: DNA
<213> ORGANISM: Artificial Sequence
<220> FEATURE:
<223> OTHER INFORMATION: Synthetic Construct

<400> SEQUENCE: 274
ttcatggtgc caaaatccat                                              20

<210> SEQ ID NO 275
<211> LENGTH: 20
<212> TYPE: DNA
<213> ORGANISM: Artificial Sequence
<220> FEATURE:
<223> OTHER INFORMATION: Synthetic Construct

<400> SEQUENCE: 275
tttcatggtg ccaaaatcca                                              20

<210> SEQ ID NO 276
<211> LENGTH: 20
<212> TYPE: DNA
<213> ORGANISM: Artificial Sequence
<220> FEATURE:
<223> OTHER INFORMATION: Synthetic Construct

<400> SEQUENCE: 276
taatgaatac aagtcagtta                                              20

<210> SEQ ID NO 277
<211> LENGTH: 20
<212> TYPE: DNA
<213> ORGANISM: Artificial Sequence
<220> FEATURE:
<223> OTHER INFORMATION: Synthetic Construct

<400> SEQUENCE: 277
caagtcagtt acggaattta                                              20

<210> SEQ ID NO 278
<211> LENGTH: 20
<212> TYPE: DNA
<213> ORGANISM: Artificial Sequence
<220> FEATURE:
<223> OTHER INFORMATION: Synthetic Construct

<400> SEQUENCE: 278
ataatgcaat gacatacaat                                              20
```

```
<210> SEQ ID NO 279
<211> LENGTH: 20
<212> TYPE: DNA
<213> ORGANISM: Artificial Sequence
<220> FEATURE:
<223> OTHER INFORMATION: Synthetic Construct

<400> SEQUENCE: 279
aacttgtagt acacggtatc                                               20

<210> SEQ ID NO 280
<211> LENGTH: 20
<212> TYPE: DNA
<213> ORGANISM: Artificial Sequence
<220> FEATURE:
<223> OTHER INFORMATION: Synthetic Construct

<400> SEQUENCE: 280
cttcgccaac ttgtagtaca                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic Construct

<400> SEQUENCE: 281
agataccgtg tactacaagt                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic Construct

<400> SEQUENCE: 282
gcgaagaaga tccttcacgc                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic Construct

<400> SEQUENCE: 283
tcatcttaaa gcctgcgtga                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic Construct

<400> SEQUENCE: 284
ttctcagcag gcagctcttt                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 285
caatgaagat acagctgttg                                               20

<210> SEQ ID NO 286
<211> LENGTH: 20
<212> TYPE: DNA
<213> ORGANISM: Artificial Sequence
<220> FEATURE:
<223> OTHER INFORMATION: Synthetic Construct

<400> SEQUENCE: 286
actggtacaa cttcagggac                                               20

<210> SEQ ID NO 287
<211> LENGTH: 20
<212> TYPE: DNA
<213> ORGANISM: Artificial Sequence
<220> FEATURE:
<223> OTHER INFORMATION: Synthetic Construct

<400> SEQUENCE: 287
cttgtactgg tacaacttca                                               20

<210> SEQ ID NO 288
<211> LENGTH: 20
<212> TYPE: DNA
<213> ORGANISM: Artificial Sequence
<220> FEATURE:
<223> OTHER INFORMATION: Synthetic Construct

<400> SEQUENCE: 288
acttgtactg gtacaacttc                                               20

<210> SEQ ID NO 289
<211> LENGTH: 20
<212> TYPE: DNA
<213> ORGANISM: Artificial Sequence
<220> FEATURE:
<223> OTHER INFORMATION: Synthetic Construct

<400> SEQUENCE: 289
ttggcagttt ctacttgtac                                               20

<210> SEQ ID NO 290
<211> LENGTH: 20
<212> TYPE: DNA
<213> ORGANISM: Artificial Sequence
<220> FEATURE:
<223> OTHER INFORMATION: Synthetic Construct

<400> SEQUENCE: 290
tacctgataa cttctctact                                               20

<210> SEQ ID NO 291
<211> LENGTH: 20
<212> TYPE: DNA
<213> ORGANISM: Artificial Sequence
<220> FEATURE:
<223> OTHER INFORMATION: Synthetic Construct

<400> SEQUENCE: 291
agccgagtag agaagttatc                                               20

<210> SEQ ID NO 292
<211> LENGTH: 20

<212> TYPE: DNA
<213> ORGANISM: Artificial Sequence
<220> FEATURE:
<223> OTHER INFORMATION: Synthetic Construct

<400> SEQUENCE: 292
agctgcatgt ttgagcctga                                        20

<210> SEQ ID NO 293
<211> LENGTH: 20
<212> TYPE: DNA
<213> ORGANISM: Artificial Sequence
<220> FEATURE:
<223> OTHER INFORMATION: Synthetic Construct

<400> SEQUENCE: 293
gctgcatgtt tgagcctgaa                                        20

<210> SEQ ID NO 294
<211> LENGTH: 20
<212> TYPE: DNA
<213> ORGANISM: Artificial Sequence
<220> FEATURE:
<223> OTHER INFORMATION: Synthetic Construct

<400> SEQUENCE: 294
aagctgcagg cattcccttc                                        20

<210> SEQ ID NO 295
<211> LENGTH: 20
<212> TYPE: DNA
<213> ORGANISM: Artificial Sequence
<220> FEATURE:
<223> OTHER INFORMATION: Synthetic Construct

<400> SEQUENCE: 295
ggtactgtcc gtcaagctgc                                        20

<210> SEQ ID NO 296
<211> LENGTH: 20
<212> TYPE: DNA
<213> ORGANISM: Artificial Sequence
<220> FEATURE:
<223> OTHER INFORMATION: Synthetic Construct

<400> SEQUENCE: 296
agggaatgcc tgcagcttga                                        20

<210> SEQ ID NO 297
<211> LENGTH: 20
<212> TYPE: DNA
<213> ORGANISM: Artificial Sequence
<220> FEATURE:
<223> OTHER INFORMATION: Synthetic Construct

<400> SEQUENCE: 297
cttgacggac agtaccgcag                                        20

<210> SEQ ID NO 298
<211> LENGTH: 20
<212> TYPE: DNA
<213> ORGANISM: Artificial Sequence
<220> FEATURE:
<223> OTHER INFORMATION: Synthetic Construct

<400> SEQUENCE: 298
cgccagcacg tgctcctctg                                          20

<210> SEQ ID NO 299
<211> LENGTH: 20
<212> TYPE: DNA
<213> ORGANISM: Artificial Sequence
<220> FEATURE:
<223> OTHER INFORMATION: Synthetic Construct

<400> SEQUENCE: 299
taccgcagag gagcacgtgc                                          20

<210> SEQ ID NO 300
<211> LENGTH: 20
<212> TYPE: DNA
<213> ORGANISM: Artificial Sequence
<220> FEATURE:
<223> OTHER INFORMATION: Synthetic Construct

<400> SEQUENCE: 300
agaggagcac gtgctggcgc                                          20

<210> SEQ ID NO 301
<211> LENGTH: 20
<212> TYPE: DNA
<213> ORGANISM: Artificial Sequence
<220> FEATURE:
<223> OTHER INFORMATION: Synthetic Construct

<400> SEQUENCE: 301
ggagcacgtg ctggcgctgg                                          20

<210> SEQ ID NO 302
<211> LENGTH: 20
<212> TYPE: DNA
<213> ORGANISM: Artificial Sequence
<220> FEATURE:
<223> OTHER INFORMATION: Synthetic Construct

<400> SEQUENCE: 302
agcacgcagc tgacgaagct                                          20

<210> SEQ ID NO 303
<211> LENGTH: 20
<212> TYPE: DNA
<213> ORGANISM: Artificial Sequence
<220> FEATURE:
<223> OTHER INFORMATION: Synthetic Construct

<400> SEQUENCE: 303
gcacgcagct gacgaagctc                                          20

<210> SEQ ID NO 304
<211> LENGTH: 20
<212> TYPE: DNA
<213> ORGANISM: Artificial Sequence
<220> FEATURE:
<223> OTHER INFORMATION: Synthetic Construct

<400> SEQUENCE: 304
cagctgacga agctcgggac                                          20

<210> SEQ ID NO 305
<211> LENGTH: 20
<212> TYPE: DNA
<213> ORGANISM: Artificial Sequence
<220> FEATURE:
<223> OTHER INFORMATION: Synthetic Construct

<400> SEQUENCE: 305
aagctcggga caggatcaac                                                    20

<210> SEQ ID NO 306
<211> LENGTH: 20
<212> TYPE: DNA
<213> ORGANISM: Artificial Sequence
<220> FEATURE:
<223> OTHER INFORMATION: Synthetic Construct

<400> SEQUENCE: 306
ccttgccgcc tgggaggaac                                                    20

<210> SEQ ID NO 307
<211> LENGTH: 20
<212> TYPE: DNA
<213> ORGANISM: Artificial Sequence
<220> FEATURE:
<223> OTHER INFORMATION: Synthetic Construct

<400> SEQUENCE: 307
aggatcaacc ggttcctccc                                                    20

<210> SEQ ID NO 308
<211> LENGTH: 20
<212> TYPE: DNA
<213> ORGANISM: Artificial Sequence
<220> FEATURE:
<223> OTHER INFORMATION: Synthetic Construct

<400> SEQUENCE: 308
atcaaccggt tcctcccagg                                                    20

<210> SEQ ID NO 309
<211> LENGTH: 20
<212> TYPE: DNA
<213> ORGANISM: Artificial Sequence
<220> FEATURE:
<223> OTHER INFORMATION: Synthetic Construct

<400> SEQUENCE: 309
gcactacctt gccgcctggg                                                    20

<210> SEQ ID NO 310
<211> LENGTH: 20
<212> TYPE: DNA
<213> ORGANISM: Artificial Sequence
<220> FEATURE:
<223> OTHER INFORMATION: Synthetic Construct

<400> SEQUENCE: 310
agagcactac cttgccgcct                                                    20

<210> SEQ ID NO 311
<211> LENGTH: 20
<212> TYPE: DNA
<213> ORGANISM: Artificial Sequence
<220> FEATURE:
<223> OTHER INFORMATION: Synthetic Construct

<400> SEQUENCE: 311
ccggttcctc ccaggcggca                                                    20

<210> SEQ ID NO 312
<211> LENGTH: 20
<212> TYPE: DNA
<213> ORGANISM: Artificial Sequence
<220> FEATURE:
<223> OTHER INFORMATION: Synthetic Construct

<400> SEQUENCE: 312
tcctcttcag atagcccatc                                           20

<210> SEQ ID NO 313
<211> LENGTH: 20
<212> TYPE: DNA
<213> ORGANISM: Artificial Sequence
<220> FEATURE:
<223> OTHER INFORMATION: Synthetic Construct

<400> SEQUENCE: 313
atgggctatc tgaagaggaa                                           20

<210> SEQ ID NO 314
<211> LENGTH: 20
<212> TYPE: DNA
<213> ORGANISM: Artificial Sequence
<220> FEATURE:
<223> OTHER INFORMATION: Synthetic Construct

<400> SEQUENCE: 314
gggctatctg aagaggaacg                                           20

<210> SEQ ID NO 315
<211> LENGTH: 20
<212> TYPE: DNA
<213> ORGANISM: Artificial Sequence
<220> FEATURE:
<223> OTHER INFORMATION: Synthetic Construct

<400> SEQUENCE: 315
tgggctatct gaagaggaac                                           20

<210> SEQ ID NO 316
<211> LENGTH: 20
<212> TYPE: DNA
<213> ORGANISM: Artificial Sequence
<220> FEATURE:
<223> OTHER INFORMATION: Synthetic Construct

<400> SEQUENCE: 316
tatctgaaga ggaacgggga                                           20

<210> SEQ ID NO 317
<211> LENGTH: 20
<212> TYPE: DNA
<213> ORGANISM: Artificial Sequence
<220> FEATURE:
<223> OTHER INFORMATION: Synthetic Construct

<400> SEQUENCE: 317
atctgaagag gaacggggac                                           20

<210> SEQ ID NO 318
<211> LENGTH: 20
<212> TYPE: DNA
<213> ORGANISM: Artificial Sequence
<220> FEATURE:
<223> OTHER INFORMATION: Synthetic Construct

```
<400> SEQUENCE: 318
tgttgaccac gctgtagagc                                               20

<210> SEQ ID NO 319
<211> LENGTH: 20
<212> TYPE: DNA
<213> ORGANISM: Artificial Sequence
<220> FEATURE:
<223> OTHER INFORMATION: Synthetic Construct

<400> SEQUENCE: 319
gctctacagc gtggtcaaca                                               20

<210> SEQ ID NO 320
<211> LENGTH: 20
<212> TYPE: DNA
<213> ORGANISM: Artificial Sequence
<220> FEATURE:
<223> OTHER INFORMATION: Synthetic Construct

<400> SEQUENCE: 320
cgggagcctg ctctacagcg                                               20

<210> SEQ ID NO 321
<211> LENGTH: 20
<212> TYPE: DNA
<213> ORGANISM: Artificial Sequence
<220> FEATURE:
<223> OTHER INFORMATION: Synthetic Construct

<400> SEQUENCE: 321
cgtggtcaac acggccgagc                                               20

<210> SEQ ID NO 322
<211> LENGTH: 20
<212> TYPE: DNA
<213> ORGANISM: Artificial Sequence
<220> FEATURE:
<223> OTHER INFORMATION: Synthetic Construct

<400> SEQUENCE: 322
cccaccatca gcgtccggct                                               20

<210> SEQ ID NO 323
<211> LENGTH: 20
<212> TYPE: DNA
<213> ORGANISM: Artificial Sequence
<220> FEATURE:
<223> OTHER INFORMATION: Synthetic Construct

<400> SEQUENCE: 323
acggccgagc cggacgctga                                               20

<210> SEQ ID NO 324
<211> LENGTH: 20
<212> TYPE: DNA
<213> ORGANISM: Artificial Sequence
<220> FEATURE:
<223> OTHER INFORMATION: Synthetic Construct

<400> SEQUENCE: 324
gggcacccac catcagcgtc                                               20

<210> SEQ ID NO 325
```

<211> LENGTH: 20
<212> TYPE: DNA
<213> ORGANISM: Artificial Sequence
<220> FEATURE:
<223> OTHER INFORMATION: Synthetic Construct

<400> SEQUENCE: 325
gccgagccgg acgctgatgg                                           20

<210> SEQ ID NO 326
<211> LENGTH: 20
<212> TYPE: DNA
<213> ORGANISM: Artificial Sequence
<220> FEATURE:
<223> OTHER INFORMATION: Synthetic Construct

<400> SEQUENCE: 326
ccatgtccgt gttgcagagg                                           20

<210> SEQ ID NO 327
<211> LENGTH: 20
<212> TYPE: DNA
<213> ORGANISM: Artificial Sequence
<220> FEATURE:
<223> OTHER INFORMATION: Synthetic Construct

<400> SEQUENCE: 327
ccgagccgga cgctgatggt                                           20

<210> SEQ ID NO 328
<211> LENGTH: 20
<212> TYPE: DNA
<213> ORGANISM: Artificial Sequence
<220> FEATURE:
<223> OTHER INFORMATION: Synthetic Construct

<400> SEQUENCE: 328
cgagctcaag tccaccgggt                                           20

<210> SEQ ID NO 329
<211> LENGTH: 20
<212> TYPE: DNA
<213> ORGANISM: Artificial Sequence
<220> FEATURE:
<223> OTHER INFORMATION: Synthetic Construct

<400> SEQUENCE: 329
gcgagctcaa gtccaccggg                                           20

<210> SEQ ID NO 330
<211> LENGTH: 20
<212> TYPE: DNA
<213> ORGANISM: Artificial Sequence
<220> FEATURE:
<223> OTHER INFORMATION: Synthetic Construct

<400> SEQUENCE: 330
agagcgagct caagtccacc                                           20

<210> SEQ ID NO 331
<211> LENGTH: 20
<212> TYPE: DNA
<213> ORGANISM: Artificial Sequence
<220> FEATURE:
<223> OTHER INFORMATION: Synthetic Construct

<400> SEQUENCE: 331
gagagcgagc tcaagtccac                                                       20

<210> SEQ ID NO 332
<211> LENGTH: 20
<212> TYPE: DNA
<213> ORGANISM: Artificial Sequence
<220> FEATURE:
<223> OTHER INFORMATION: Synthetic Construct

<400> SEQUENCE: 332
gaagcctggg agtagcttac                                                       20

<210> SEQ ID NO 333
<211> LENGTH: 20
<212> TYPE: DNA
<213> ORGANISM: Artificial Sequence
<220> FEATURE:
<223> OTHER INFORMATION: Synthetic Construct

<400> SEQUENCE: 333
ctctccagta agctactccc                                                       20

<210> SEQ ID NO 334
<211> LENGTH: 20
<212> TYPE: DNA
<213> ORGANISM: Artificial Sequence
<220> FEATURE:
<223> OTHER INFORMATION: Synthetic Construct

<400> SEQUENCE: 334
agcccagcgt ggtgaagcct                                                       20

<210> SEQ ID NO 335
<211> LENGTH: 20
<212> TYPE: DNA
<213> ORGANISM: Artificial Sequence
<220> FEATURE:
<223> OTHER INFORMATION: Synthetic Construct

<400> SEQUENCE: 335
aagcccagcg tggtgaagcc                                                       20

<210> SEQ ID NO 336
<211> LENGTH: 20
<212> TYPE: DNA
<213> ORGANISM: Artificial Sequence
<220> FEATURE:
<223> OTHER INFORMATION: Synthetic Construct

<400> SEQUENCE: 336
actcccaggc ttcaccacgc                                                       20

<210> SEQ ID NO 337
<211> LENGTH: 20
<212> TYPE: DNA
<213> ORGANISM: Artificial Sequence
<220> FEATURE:
<223> OTHER INFORMATION: Synthetic Construct

<400> SEQUENCE: 337
ctcccaggct tcaccacgct                                                       20

<210> SEQ ID NO 338
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 338
ctcgtctttg aagcccagcg                                               20

<210> SEQ ID NO 339
<211> LENGTH: 20
<212> TYPE: DNA
<213> ORGANISM: Artificial Sequence
<220> FEATURE:
<223> OTHER INFORMATION: Synthetic Construct

<400> SEQUENCE: 339
cactggagag aaaggtgact                                               20

<210> SEQ ID NO 340
<211> LENGTH: 20
<212> TYPE: DNA
<213> ORGANISM: Artificial Sequence
<220> FEATURE:
<223> OTHER INFORMATION: Synthetic Construct

<400> SEQUENCE: 340
gcactggaga gaaaggtgac                                               20

<210> SEQ ID NO 341
<211> LENGTH: 20
<212> TYPE: DNA
<213> ORGANISM: Artificial Sequence
<220> FEATURE:
<223> OTHER INFORMATION: Synthetic Construct

<400> SEQUENCE: 341
agtagtggca ctggagagaa                                               20

<210> SEQ ID NO 342
<211> LENGTH: 20
<212> TYPE: DNA
<213> ORGANISM: Artificial Sequence
<220> FEATURE:
<223> OTHER INFORMATION: Synthetic Construct

<400> SEQUENCE: 342
cgaaagcgca gtagtggcac                                               20

<210> SEQ ID NO 343
<211> LENGTH: 20
<212> TYPE: DNA
<213> ORGANISM: Artificial Sequence
<220> FEATURE:
<223> OTHER INFORMATION: Synthetic Construct

<400> SEQUENCE: 343
ctgcatcgaa agcgcagtag                                               20

<210> SEQ ID NO 344
<211> LENGTH: 20
<212> TYPE: DNA
<213> ORGANISM: Artificial Sequence
<220> FEATURE:
<223> OTHER INFORMATION: Synthetic Construct

<400> SEQUENCE: 344
atgcagaata attcagtatt                                               20
```

```
<210> SEQ ID NO 345
<211> LENGTH: 20
<212> TYPE: DNA
<213> ORGANISM: Artificial Sequence
<220> FEATURE:
<223> OTHER INFORMATION: Synthetic Construct

<400> SEQUENCE: 345
agtatttggc gacttgaagt                                              20

<210> SEQ ID NO 346
<211> LENGTH: 20
<212> TYPE: DNA
<213> ORGANISM: Artificial Sequence
<220> FEATURE:
<223> OTHER INFORMATION: Synthetic Construct

<400> SEQUENCE: 346
cgacttgaag tcggacgaga                                              20

<210> SEQ ID NO 347
<211> LENGTH: 20
<212> TYPE: DNA
<213> ORGANISM: Artificial Sequence
<220> FEATURE:
<223> OTHER INFORMATION: Synthetic Construct

<400> SEQUENCE: 347
gagctgctct actcagccta                                              20

<210> SEQ ID NO 348
<211> LENGTH: 20
<212> TYPE: DNA
<213> ORGANISM: Artificial Sequence
<220> FEATURE:
<223> OTHER INFORMATION: Synthetic Construct

<400> SEQUENCE: 348
cacgcctgtc tcatctccgt                                              20

<210> SEQ ID NO 349
<211> LENGTH: 20
<212> TYPE: DNA
<213> ORGANISM: Artificial Sequence
<220> FEATURE:
<223> OTHER INFORMATION: Synthetic Construct

<400> SEQUENCE: 349
tcagcctacg gagatgagac                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic Construct

<400> SEQUENCE: 350
caggcgtgca gtgtgcgctg                                              20

<210> SEQ ID NO 351
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 351
ccgcggcccc tctagcctgc                                           20

<210> SEQ ID NO 352
<211> LENGTH: 20
<212> TYPE: DNA
<213> ORGANISM: Artificial Sequence
<220> FEATURE:
<223> OTHER INFORMATION: Synthetic Construct

<400> SEQUENCE: 352
catccttcac aaactcctgc                                           20

<210> SEQ ID NO 353
<211> LENGTH: 20
<212> TYPE: DNA
<213> ORGANISM: Artificial Sequence
<220> FEATURE:
<223> OTHER INFORMATION: Synthetic Construct

<400> SEQUENCE: 353
tagcctgcag gagtttgtga                                           20

<210> SEQ ID NO 354
<211> LENGTH: 20
<212> TYPE: DNA
<213> ORGANISM: Artificial Sequence
<220> FEATURE:
<223> OTHER INFORMATION: Synthetic Construct

<400> SEQUENCE: 354
caggagtttg tgaaggatgc                                           20

<210> SEQ ID NO 355
<211> LENGTH: 20
<212> TYPE: DNA
<213> ORGANISM: Artificial Sequence
<220> FEATURE:
<223> OTHER INFORMATION: Synthetic Construct

<400> SEQUENCE: 355
aggagtttgt gaaggatgct                                           20

<210> SEQ ID NO 356
<211> LENGTH: 20
<212> TYPE: DNA
<213> ORGANISM: Artificial Sequence
<220> FEATURE:
<223> OTHER INFORMATION: Synthetic Construct

<400> SEQUENCE: 356
tgggagctac agcaagaaag                                           20

<210> SEQ ID NO 357
<211> LENGTH: 20
<212> TYPE: DNA
<213> ORGANISM: Artificial Sequence
<220> FEATURE:
<223> OTHER INFORMATION: Synthetic Construct

<400> SEQUENCE: 357
gagctacagc aagaaagtgg                                           20

```
<210> SEQ ID NO 358
<211> LENGTH: 20
<212> TYPE: DNA
<213> ORGANISM: Artificial Sequence
<220> FEATURE:
<223> OTHER INFORMATION: Synthetic Construct

<400> SEQUENCE: 358
gaaagtggtg gacgacctcc                                              20

<210> SEQ ID NO 359
<211> LENGTH: 20
<212> TYPE: DNA
<213> ORGANISM: Artificial Sequence
<220> FEATURE:
<223> OTHER INFORMATION: Synthetic Construct

<400> SEQUENCE: 359
cgcctgtgat ctggtccagg                                              20

<210> SEQ ID NO 360
<211> LENGTH: 20
<212> TYPE: DNA
<213> ORGANISM: Artificial Sequence
<220> FEATURE:
<223> OTHER INFORMATION: Synthetic Construct

<400> SEQUENCE: 360
ctccgcctgt gatctggtcc                                              20

<210> SEQ ID NO 361
<211> LENGTH: 20
<212> TYPE: DNA
<213> ORGANISM: Artificial Sequence
<220> FEATURE:
<223> OTHER INFORMATION: Synthetic Construct

<400> SEQUENCE: 361
gacctcctgg accagatcac                                              20

<210> SEQ ID NO 362
<211> LENGTH: 20
<212> TYPE: DNA
<213> ORGANISM: Artificial Sequence
<220> FEATURE:
<223> OTHER INFORMATION: Synthetic Construct

<400> SEQUENCE: 362
ctcctggacc agatcacagg                                              20

<210> SEQ ID NO 363
<211> LENGTH: 20
<212> TYPE: DNA
<213> ORGANISM: Artificial Sequence
<220> FEATURE:
<223> OTHER INFORMATION: Synthetic Construct

<400> SEQUENCE: 363
gctggaagag cgtcctagag                                              20

<210> SEQ ID NO 364
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 364
tgcagcccac ctgcttcagc                                               20

<210> SEQ ID NO 365
<211> LENGTH: 20
<212> TYPE: DNA
<213> ORGANISM: Artificial Sequence
<220> FEATURE:
<223> OTHER INFORMATION: Synthetic Construct

<400> SEQUENCE: 365
gacgctcttc cagctgaagc                                               20

<210> SEQ ID NO 366
<211> LENGTH: 20
<212> TYPE: DNA
<213> ORGANISM: Artificial Sequence
<220> FEATURE:
<223> OTHER INFORMATION: Synthetic Construct

<400> SEQUENCE: 366
ctcttccagc tgaagcaggt                                               20

<210> SEQ ID NO 367
<211> LENGTH: 20
<212> TYPE: DNA
<213> ORGANISM: Artificial Sequence
<220> FEATURE:
<223> OTHER INFORMATION: Synthetic Construct

<400> SEQUENCE: 367
gctcttccag ctgaagcagg                                               20

<210> SEQ ID NO 368
<211> LENGTH: 20
<212> TYPE: DNA
<213> ORGANISM: Artificial Sequence
<220> FEATURE:
<223> OTHER INFORMATION: Synthetic Construct

<400> SEQUENCE: 368
cctccagatg aagccaaggt                                               20

<210> SEQ ID NO 369
<211> LENGTH: 20
<212> TYPE: DNA
<213> ORGANISM: Artificial Sequence
<220> FEATURE:
<223> OTHER INFORMATION: Synthetic Construct

<400> SEQUENCE: 369
gcttcatctg gaggcttcat                                               20

<210> SEQ ID NO 370
<211> LENGTH: 20
<212> TYPE: DNA
<213> ORGANISM: Artificial Sequence
<220> FEATURE:
<223> OTHER INFORMATION: Synthetic Construct

<400> SEQUENCE: 370
ggcttcatct ggaggcttca                                               20

<210> SEQ ID NO 371
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 371
cttaccttgg cttcatctgg                                              20

<210> SEQ ID NO 372
<211> LENGTH: 20
<212> TYPE: DNA
<213> ORGANISM: Artificial Sequence
<220> FEATURE:
<223> OTHER INFORMATION: Synthetic Construct

<400> SEQUENCE: 372
aaacttacct tggcttcatc                                              20

<210> SEQ ID NO 373
<211> LENGTH: 20
<212> TYPE: DNA
<213> ORGANISM: Artificial Sequence
<220> FEATURE:
<223> OTHER INFORMATION: Synthetic Construct

<400> SEQUENCE: 373
gaagcctcca gatgaagcca                                              20

<210> SEQ ID NO 374
<211> LENGTH: 20
<212> TYPE: DNA
<213> ORGANISM: Artificial Sequence
<220> FEATURE:
<223> OTHER INFORMATION: Synthetic Construct

<400> SEQUENCE: 374
tcctagggtg tccccaacct                                              20

<210> SEQ ID NO 375
<211> LENGTH: 20
<212> TYPE: DNA
<213> ORGANISM: Artificial Sequence
<220> FEATURE:
<223> OTHER INFORMATION: Synthetic Construct

<400> SEQUENCE: 375
cctagggtgt ccccaacctg                                              20

<210> SEQ ID NO 376
<211> LENGTH: 20
<212> TYPE: DNA
<213> ORGANISM: Artificial Sequence
<220> FEATURE:
<223> OTHER INFORMATION: Synthetic Construct

<400> SEQUENCE: 376
gtgtctgtct ccacaggttg                                              20

<210> SEQ ID NO 377
<211> LENGTH: 20
<212> TYPE: DNA
<213> ORGANISM: Artificial Sequence
<220> FEATURE:
<223> OTHER INFORMATION: Synthetic Construct

<400> SEQUENCE: 377
```

```
tgtgtctgtc tccacaggtt                                              20

<210> SEQ ID NO 378
<211> LENGTH: 20
<212> TYPE: DNA
<213> ORGANISM: Artificial Sequence
<220> FEATURE:
<223> OTHER INFORMATION: Synthetic Construct

<400> SEQUENCE: 378
ccacaggttg gggacaccct                                              20

<210> SEQ ID NO 379
<211> LENGTH: 20
<212> TYPE: DNA
<213> ORGANISM: Artificial Sequence
<220> FEATURE:
<223> OTHER INFORMATION: Synthetic Construct

<400> SEQUENCE: 379
agagctgctg ctgtctccta                                              20

<210> SEQ ID NO 380
<211> LENGTH: 20
<212> TYPE: DNA
<213> ORGANISM: Artificial Sequence
<220> FEATURE:
<223> OTHER INFORMATION: Synthetic Construct

<400> SEQUENCE: 380
cagagctgct gctgtctcct                                              20

<210> SEQ ID NO 381
<211> LENGTH: 20
<212> TYPE: DNA
<213> ORGANISM: Artificial Sequence
<220> FEATURE:
<223> OTHER INFORMATION: Synthetic Construct

<400> SEQUENCE: 381
agacagcagc agctctgttc                                              20

<210> SEQ ID NO 382
<211> LENGTH: 20
<212> TYPE: DNA
<213> ORGANISM: Artificial Sequence
<220> FEATURE:
<223> OTHER INFORMATION: Synthetic Construct

<400> SEQUENCE: 382
atccacagaa acgtcgggat                                              20

<210> SEQ ID NO 383
<211> LENGTH: 20
<212> TYPE: DNA
<213> ORGANISM: Artificial Sequence
<220> FEATURE:
<223> OTHER INFORMATION: Synthetic Construct

<400> SEQUENCE: 383
gagatatcca cagaaacgtc                                              20

<210> SEQ ID NO 384
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 384
ggagatatcc acagaaacgt                                              20

<210> SEQ ID NO 385
<211> LENGTH: 20
<212> TYPE: DNA
<213> ORGANISM: Artificial Sequence
<220> FEATURE:
<223> OTHER INFORMATION: Synthetic Construct

<400> SEQUENCE: 385
gtcctatccc gacgtttctg                                              20

<210> SEQ ID NO 386
<211> LENGTH: 20
<212> TYPE: DNA
<213> ORGANISM: Artificial Sequence
<220> FEATURE:
<223> OTHER INFORMATION: Synthetic Construct

<400> SEQUENCE: 386
tctccatgct cagctctctg                                              20

<210> SEQ ID NO 387
<211> LENGTH: 20
<212> TYPE: DNA
<213> ORGANISM: Artificial Sequence
<220> FEATURE:
<223> OTHER INFORMATION: Synthetic Construct

<400> SEQUENCE: 387
ctcacccaga gagctgagca                                              20

<210> SEQ ID NO 388
<211> LENGTH: 20
<212> TYPE: DNA
<213> ORGANISM: Artificial Sequence
<220> FEATURE:
<223> OTHER INFORMATION: Synthetic Construct

<400> SEQUENCE: 388
atctccatgc tcagctctct                                              20

<210> SEQ ID NO 389
<211> LENGTH: 20
<212> TYPE: DNA
<213> ORGANISM: Artificial Sequence
<220> FEATURE:
<223> OTHER INFORMATION: Synthetic Construct

<400> SEQUENCE: 389
tatctccatg ctcagctctc                                              20

<210> SEQ ID NO 390
<211> LENGTH: 20
<212> TYPE: DNA
<213> ORGANISM: Artificial Sequence
<220> FEATURE:
<223> OTHER INFORMATION: Synthetic Construct

<400> SEQUENCE: 390
atgtcctgtt tacacaggga                                              20
```

<210> SEQ ID NO 391
<211> LENGTH: 20
<212> TYPE: DNA
<213> ORGANISM: Artificial Sequence
<220> FEATURE:
<223> OTHER INFORMATION: Synthetic Construct

<400> SEQUENCE: 391
ttacacaggg aaggtgaaga                                       20

<210> SEQ ID NO 392
<211> LENGTH: 20
<212> TYPE: DNA
<213> ORGANISM: Artificial Sequence
<220> FEATURE:
<223> OTHER INFORMATION: Synthetic Construct

<400> SEQUENCE: 392
agttcaaatg gctgtcgtca                                       20

<210> SEQ ID NO 393
<211> LENGTH: 20
<212> TYPE: DNA
<213> ORGANISM: Artificial Sequence
<220> FEATURE:
<223> OTHER INFORMATION: Synthetic Construct

<400> SEQUENCE: 393
tgacgacagc catttgaact                                       20

<210> SEQ ID NO 394
<211> LENGTH: 20
<212> TYPE: DNA
<213> ORGANISM: Artificial Sequence
<220> FEATURE:
<223> OTHER INFORMATION: Synthetic Construct

<400> SEQUENCE: 394
aagttcaaat ggctgtcgtc                                       20

<210> SEQ ID NO 395
<211> LENGTH: 20
<212> TYPE: DNA
<213> ORGANISM: Artificial Sequence
<220> FEATURE:
<223> OTHER INFORMATION: Synthetic Construct

<400> SEQUENCE: 395
tcgtctcatc caagttcaaa                                       20

<210> SEQ ID NO 396
<211> LENGTH: 20
<212> TYPE: DNA
<213> ORGANISM: Artificial Sequence
<220> FEATURE:
<223> OTHER INFORMATION: Synthetic Construct

<400> SEQUENCE: 396
tgagacgacg aagctcctgc                                       20

<210> SEQ ID NO 397
<211> LENGTH: 20
<212> TYPE: DNA
<213> ORGANISM: Artificial Sequence
<220> FEATURE:
<223> OTHER INFORMATION: Synthetic Construct

<400> SEQUENCE: 397
gtgcttcgtg caggtcctgc                                               20

<210> SEQ ID NO 398
<211> LENGTH: 20
<212> TYPE: DNA
<213> ORGANISM: Artificial Sequence
<220> FEATURE:
<223> OTHER INFORMATION: Synthetic Construct

<400> SEQUENCE: 398
gcaggacctg cacgaagcac                                               20

<210> SEQ ID NO 399
<211> LENGTH: 20
<212> TYPE: DNA
<213> ORGANISM: Artificial Sequence
<220> FEATURE:
<223> OTHER INFORMATION: Synthetic Construct

<400> SEQUENCE: 399
gctccgcctg tgcttcgtgc                                               20

<210> SEQ ID NO 400
<211> LENGTH: 20
<212> TYPE: DNA
<213> ORGANISM: Artificial Sequence
<220> FEATURE:
<223> OTHER INFORMATION: Synthetic Construct

<400> SEQUENCE: 400
ggacctgcac gaagcacagg                                               20

<210> SEQ ID NO 401
<211> LENGTH: 20
<212> TYPE: DNA
<213> ORGANISM: Artificial Sequence
<220> FEATURE:
<223> OTHER INFORMATION: Synthetic Construct

<400> SEQUENCE: 401
cacgaagcac aggcggagcg                                               20

<210> SEQ ID NO 402
<211> LENGTH: 20
<212> TYPE: DNA
<213> ORGANISM: Artificial Sequence
<220> FEATURE:
<223> OTHER INFORMATION: Synthetic Construct

<400> SEQUENCE: 402
aggcggagcg cggcggctct                                               20

<210> SEQ ID NO 403
<211> LENGTH: 20
<212> TYPE: DNA
<213> ORGANISM: Artificial Sequence
<220> FEATURE:
<223> OTHER INFORMATION: Synthetic Construct

<400> SEQUENCE: 403
agggagctga ggttggacga                                               20

<210> SEQ ID NO 404

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 404
gttggacagg gagctgaggt                                              20

<210> SEQ ID NO 405
<211> LENGTH: 20
<212> TYPE: DNA
<213> ORGANISM: Artificial Sequence
<220> FEATURE:
<223> OTHER INFORMATION: Synthetic Construct

<400> SEQUENCE: 405
aggcgttgga cagggagctg                                              20

<210> SEQ ID NO 406
<211> LENGTH: 20
<212> TYPE: DNA
<213> ORGANISM: Artificial Sequence
<220> FEATURE:
<223> OTHER INFORMATION: Synthetic Construct

<400> SEQUENCE: 406
ccctctcgga ggcgttggac                                              20

<210> SEQ ID NO 407
<211> LENGTH: 20
<212> TYPE: DNA
<213> ORGANISM: Artificial Sequence
<220> FEATURE:
<223> OTHER INFORMATION: Synthetic Construct

<400> SEQUENCE: 407
cctctcggag gcgttggaca                                              20

<210> SEQ ID NO 408
<211> LENGTH: 20
<212> TYPE: DNA
<213> ORGANISM: Artificial Sequence
<220> FEATURE:
<223> OTHER INFORMATION: Synthetic Construct

<400> SEQUENCE: 408
ctggtccctc tcggaggcgt                                              20

<210> SEQ ID NO 409
<211> LENGTH: 20
<212> TYPE: DNA
<213> ORGANISM: Artificial Sequence
<220> FEATURE:
<223> OTHER INFORMATION: Synthetic Construct

<400> SEQUENCE: 409
ccctgtccaa cgcctccgag                                              20

<210> SEQ ID NO 410
<211> LENGTH: 20
<212> TYPE: DNA
<213> ORGANISM: Artificial Sequence
<220> FEATURE:
<223> OTHER INFORMATION: Synthetic Construct

<400> SEQUENCE: 410
```
cctgtccaac gcctccgaga                                              20

<210> SEQ ID NO 411
<211> LENGTH: 20
<212> TYPE: DNA
<213> ORGANISM: Artificial Sequence
<220> FEATURE:
<223> OTHER INFORMATION: Synthetic Construct

<400> SEQUENCE: 411
gtggtgctgg tccctctcgg                                              20

<210> SEQ ID NO 412
<211> LENGTH: 20
<212> TYPE: DNA
<213> ORGANISM: Artificial Sequence
<220> FEATURE:
<223> OTHER INFORMATION: Synthetic Construct

<400> SEQUENCE: 412
caggtggtgc tggtccctct                                              20

<210> SEQ ID NO 413
<211> LENGTH: 20
<212> TYPE: DNA
<213> ORGANISM: Artificial Sequence
<220> FEATURE:
<223> OTHER INFORMATION: Synthetic Construct

<400> SEQUENCE: 413
gcatctcacc caggtggtgc                                              20

<210> SEQ ID NO 414
<211> LENGTH: 20
<212> TYPE: DNA
<213> ORGANISM: Artificial Sequence
<220> FEATURE:
<223> OTHER INFORMATION: Synthetic Construct

<400> SEQUENCE: 414
cgagagggac cagcaccacc                                              20

<210> SEQ ID NO 415
<211> LENGTH: 20
<212> TYPE: DNA
<213> ORGANISM: Artificial Sequence
<220> FEATURE:
<223> OTHER INFORMATION: Synthetic Construct

<400> SEQUENCE: 415
gagagggacc agcaccacct                                              20

<210> SEQ ID NO 416
<211> LENGTH: 20
<212> TYPE: DNA
<213> ORGANISM: Artificial Sequence
<220> FEATURE:
<223> OTHER INFORMATION: Synthetic Construct

<400> SEQUENCE: 416
gtgggggcat ctcacccagg                                              20

<210> SEQ ID NO 417
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 417
ccccgacact caggcgagaa                                                  20

<210> SEQ ID NO 418
<211> LENGTH: 20
<212> TYPE: DNA
<213> ORGANISM: Artificial Sequence
<220> FEATURE:
<223> OTHER INFORMATION: Synthetic Construct

<400> SEQUENCE: 418
tccccgacac tcaggcgaga                                                  20

<210> SEQ ID NO 419
<211> LENGTH: 20
<212> TYPE: DNA
<213> ORGANISM: Artificial Sequence
<220> FEATURE:
<223> OTHER INFORMATION: Synthetic Construct

<400> SEQUENCE: 419
agcccttctc gcctgagtgt                                                  20

<210> SEQ ID NO 420
<211> LENGTH: 20
<212> TYPE: DNA
<213> ORGANISM: Artificial Sequence
<220> FEATURE:
<223> OTHER INFORMATION: Synthetic Construct

<400> SEQUENCE: 420
ctggctgctc cccgacactc                                                  20

<210> SEQ ID NO 421
<211> LENGTH: 20
<212> TYPE: DNA
<213> ORGANISM: Artificial Sequence
<220> FEATURE:
<223> OTHER INFORMATION: Synthetic Construct

<400> SEQUENCE: 421
cccttctcgc ctgagtgtcg                                                  20

<210> SEQ ID NO 422
<211> LENGTH: 20
<212> TYPE: DNA
<213> ORGANISM: Artificial Sequence
<220> FEATURE:
<223> OTHER INFORMATION: Synthetic Construct

<400> SEQUENCE: 422
gcccttctcg cctgagtgtc                                                  20

<210> SEQ ID NO 423
<211> LENGTH: 20
<212> TYPE: DNA
<213> ORGANISM: Artificial Sequence
<220> FEATURE:
<223> OTHER INFORMATION: Synthetic Construct

<400> SEQUENCE: 423 tagggtcgt gggtgacgtc                                                   20
```

<210> SEQ ID NO 424
<211> LENGTH: 20
<212> TYPE: DNA
<213> ORGANISM: Artificial Sequence
<220> FEATURE:
<223> OTHER INFORMATION: Synthetic Construct

<400> SEQUENCE: 424
aagaaactca tagggtcgt                                                    20

<210> SEQ ID NO 425
<211> LENGTH: 20
<212> TYPE: DNA
<213> ORGANISM: Artificial Sequence
<220> FEATURE:
<223> OTHER INFORMATION: Synthetic Construct

<400> SEQUENCE: 425
gaagaaactc atagggtcg                                                    20

<210> SEQ ID NO 426
<211> LENGTH: 20
<212> TYPE: DNA
<213> ORGANISM: Artificial Sequence
<220> FEATURE:
<223> OTHER INFORMATION: Synthetic Construct

<400> SEQUENCE: 426
gagactgaag aaactcatag                                                   20

<210> SEQ ID NO 427
<211> LENGTH: 20
<212> TYPE: DNA
<213> ORGANISM: Artificial Sequence
<220> FEATURE:
<223> OTHER INFORMATION: Synthetic Construct

<400> SEQUENCE: 427
ggagactgaa gaaactcata                                                   20

<210> SEQ ID NO 428
<211> LENGTH: 20
<212> TYPE: DNA
<213> ORGANISM: Artificial Sequence
<220> FEATURE:
<223> OTHER INFORMATION: Synthetic Construct

<400> SEQUENCE: 428
tggagactga agaaactcat                                                   20

<210> SEQ ID NO 429
<211> LENGTH: 20
<212> TYPE: DNA
<213> ORGANISM: Artificial Sequence
<220> FEATURE:
<223> OTHER INFORMATION: Synthetic Construct

<400> SEQUENCE: 429
tcttcagtct ccagagcctg                                                   20

<210> SEQ ID NO 430
<211> LENGTH: 20
<212> TYPE: DNA
<213> ORGANISM: Artificial Sequence
<220> FEATURE:

<223> OTHER INFORMATION: Synthetic Construct

<400> SEQUENCE: 430
ttggcagagg ccgcaggctc                                          20

<210> SEQ ID NO 431
<211> LENGTH: 20
<212> TYPE: DNA
<213> ORGANISM: Artificial Sequence
<220> FEATURE:
<223> OTHER INFORMATION: Synthetic Construct

<400> SEQUENCE: 431
taggtcttgg cagaggccgc                                          20

<210> SEQ ID NO 432
<211> LENGTH: 20
<212> TYPE: DNA
<213> ORGANISM: Artificial Sequence
<220> FEATURE:
<223> OTHER INFORMATION: Synthetic Construct

<400> SEQUENCE: 432
ctagagttag gtcttggcag                                          20

<210> SEQ ID NO 433
<211> LENGTH: 20
<212> TYPE: DNA
<213> ORGANISM: Artificial Sequence
<220> FEATURE:
<223> OTHER INFORMATION: Synthetic Construct

<400> SEQUENCE: 433
ggtggtctag agttaggtct                                          20

<210> SEQ ID NO 434
<211> LENGTH: 20
<212> TYPE: DNA
<213> ORGANISM: Artificial Sequence
<220> FEATURE:
<223> OTHER INFORMATION: Synthetic Construct

<400> SEQUENCE: 434
gtagcgaacg tgtccggcgt                                          20

<210> SEQ ID NO 435
<211> LENGTH: 20
<212> TYPE: DNA
<213> ORGANISM: Artificial Sequence
<220> FEATURE:
<223> OTHER INFORMATION: Synthetic Construct

<400> SEQUENCE: 435
gaccggaacg atctcgcgta                                          20

<210> SEQ ID NO 436
<211> LENGTH: 20
<212> TYPE: DNA
<213> ORGANISM: Artificial Sequence
<220> FEATURE:
<223> OTHER INFORMATION: Synthetic Construct

<400> SEQUENCE: 436
ggcagtcgtt cggttgatat                                          20

```
<210> SEQ ID NO 437
<211> LENGTH: 20
<212> TYPE: DNA
<213> ORGANISM: Artificial Sequence
<220> FEATURE:
<223> OTHER INFORMATION: Synthetic Construct

<400> SEQUENCE: 437
gcttgagcac atacgcgaat                                              20

<210> SEQ ID NO 438
<211> LENGTH: 20
<212> TYPE: DNA
<213> ORGANISM: Artificial Sequence
<220> FEATURE:
<223> OTHER INFORMATION: Synthetic Construct

<400> SEQUENCE: 438
gtggtagaat aacgtattac                                              20

<210> SEQ ID NO 439
<211> LENGTH: 20
<212> TYPE: DNA
<213> ORGANISM: Artificial Sequence
<220> FEATURE:
<223> OTHER INFORMATION: Synthetic Construct

<400> SEQUENCE: 439
gtcatacatg gataaggcta                                              20

<210> SEQ ID NO 440
<211> LENGTH: 20
<212> TYPE: DNA
<213> ORGANISM: Artificial Sequence
<220> FEATURE:
<223> OTHER INFORMATION: Synthetic Construct

<400> SEQUENCE: 440
gatacacgaa gcatcactag                                              20

<210> SEQ ID NO 441
<211> LENGTH: 20
<212> TYPE: DNA
<213> ORGANISM: Artificial Sequence
<220> FEATURE:
<223> OTHER INFORMATION: Synthetic Construct

<400> SEQUENCE: 441
gaacgttggc actacttcac                                              20

<210> SEQ ID NO 442
<211> LENGTH: 20
<212> TYPE: DNA
<213> ORGANISM: Artificial Sequence
<220> FEATURE:
<223> OTHER INFORMATION: Synthetic Construct

<400> SEQUENCE: 442
gatccatgta atgcgttcga                                              20

<210> SEQ ID NO 443
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 443
gtcgtgaagt gcattcgatc                                               20

<210> SEQ ID NO 444
<211> LENGTH: 20
<212> TYPE: DNA
<213> ORGANISM: Artificial Sequence
<220> FEATURE:
<223> OTHER INFORMATION: Synthetic Construct

<400> SEQUENCE: 444
gttcgactcg cgtgaccgta                                               20

<210> SEQ ID NO 445
<211> LENGTH: 20
<212> TYPE: DNA
<213> ORGANISM: Artificial Sequence
<220> FEATURE:
<223> OTHER INFORMATION: Synthetic Construct

<400> SEQUENCE: 445
gaatctaccg cagcggttcg                                               20

<210> SEQ ID NO 446
<211> LENGTH: 20
<212> TYPE: DNA
<213> ORGANISM: Artificial Sequence
<220> FEATURE:
<223> OTHER INFORMATION: Synthetic Construct

<400> SEQUENCE: 446
gaagtgacgt cgattcgata                                               20

<210> SEQ ID NO 447
<211> LENGTH: 20
<212> TYPE: DNA
<213> ORGANISM: Artificial Sequence
<220> FEATURE:
<223> OTHER INFORMATION: Synthetic Construct

<400> SEQUENCE: 447
gcggtgtatg acaaccgccg                                               20

<210> SEQ ID NO 448
<211> LENGTH: 20
<212> TYPE: DNA
<213> ORGANISM: Artificial Sequence
<220> FEATURE:
<223> OTHER INFORMATION: Synthetic Construct

<400> SEQUENCE: 448
gtaccgcgcc tgaagttcgc                                               20

<210> SEQ ID NO 449
<211> LENGTH: 20
<212> TYPE: DNA
<213> ORGANISM: Artificial Sequence
<220> FEATURE:
<223> OTHER INFORMATION: Synthetic Construct

<400> SEQUENCE: 449
gcagctcgtg tgtcgtactc                                               20

<210> SEQ ID NO 450
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 450
gcgccttaag agtactcatc                                               20

<210> SEQ ID NO 451
<211> LENGTH: 20
<212> TYPE: DNA
<213> ORGANISM: Artificial Sequence
<220> FEATURE:
<223> OTHER INFORMATION: Synthetic Construct

<400> SEQUENCE: 451
gagtgtcgtc gttgctccta                                               20

<210> SEQ ID NO 452
<211> LENGTH: 20
<212> TYPE: DNA
<213> ORGANISM: Artificial Sequence
<220> FEATURE:
<223> OTHER INFORMATION: Synthetic Construct

<400> SEQUENCE: 452
gcagctcgac ctcaagccgt                                               20

<210> SEQ ID NO 453
<211> LENGTH: 20
<212> TYPE: DNA
<213> ORGANISM: Artificial Sequence
<220> FEATURE:
<223> OTHER INFORMATION: Synthetic Construct

<400> SEQUENCE: 453
gtatcctgac ctacgcgctg                                               20

<210> SEQ ID NO 454
<211> LENGTH: 20
<212> TYPE: DNA
<213> ORGANISM: Artificial Sequence
<220> FEATURE:
<223> OTHER INFORMATION: Synthetic Construct

<400> SEQUENCE: 454
gtgtatctca gcacgctaac                                               20

<210> SEQ ID NO 455
<211> LENGTH: 20
<212> TYPE: DNA
<213> ORGANISM: Artificial Sequence
<220> FEATURE:
<223> OTHER INFORMATION: Synthetic Construct

<400> SEQUENCE: 455
gtcgtcatac aacggcaacg                                               20

<210> SEQ ID NO 456
<211> LENGTH: 20
<212> TYPE: DNA
<213> ORGANISM: Artificial Sequence
<220> FEATURE:
<223> OTHER INFORMATION: Synthetic Construct

<400> SEQUENCE: 456
```
gtcgtgcgct tccggcggta                                        20

<210> SEQ ID NO 457
<211> LENGTH: 20
<212> TYPE: DNA
<213> ORGANISM: Artificial Sequence
<220> FEATURE:
<223> OTHER INFORMATION: Synthetic Construct

<400> SEQUENCE: 457
gcggtcctca gtaagcgcgt                                        20

<210> SEQ ID NO 458
<211> LENGTH: 20
<212> TYPE: DNA
<213> ORGANISM: Artificial Sequence
<220> FEATURE:
<223> OTHER INFORMATION: Synthetic Construct

<400> SEQUENCE: 458
gctctgctgc ggaaggattc                                        20

<210> SEQ ID NO 459
<211> LENGTH: 20
<212> TYPE: DNA
<213> ORGANISM: Artificial Sequence
<220> FEATURE:
<223> OTHER INFORMATION: Synthetic Construct

<400> SEQUENCE: 459
gcatggagga gcgtcgcaga                                        20

<210> SEQ ID NO 460
<211> LENGTH: 20
<212> TYPE: DNA
<213> ORGANISM: Artificial Sequence
<220> FEATURE:
<223> OTHER INFORMATION: Synthetic Construct

<400> SEQUENCE: 460
gtagcgcgcg taggagtggc                                        20

<210> SEQ ID NO 461
<211> LENGTH: 20
<212> TYPE: DNA
<213> ORGANISM: Artificial Sequence
<220> FEATURE:
<223> OTHER INFORMATION: Synthetic Construct

<400> SEQUENCE: 461
gatcacctgc attcgtacac                                        20

<210> SEQ ID NO 462
<211> LENGTH: 20
<212> TYPE: DNA
<213> ORGANISM: Artificial Sequence
<220> FEATURE:
<223> OTHER INFORMATION: Synthetic Construct

<400> SEQUENCE: 462
gcacacctag atatcgaatg                                        20

<210> SEQ ID NO 463
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 463
gttgatcaac gcgcttcgcg                                                    20

<210> SEQ ID NO 464
<211> LENGTH: 20
<212> TYPE: DNA
<213> ORGANISM: Artificial Sequence
<220> FEATURE:
<223> OTHER INFORMATION: Synthetic Construct

<400> SEQUENCE: 464
gcgtctcact cactccatcg                                                    20

<210> SEQ ID NO 465
<211> LENGTH: 20
<212> TYPE: DNA
<213> ORGANISM: Artificial Sequence
<220> FEATURE:
<223> OTHER INFORMATION: Synthetic Construct

<400> SEQUENCE: 465
gccgaccaac gtcagcggta                                                    20

<210> SEQ ID NO 466
<211> LENGTH: 20
<212> TYPE: DNA
<213> ORGANISM: Artificial Sequence
<220> FEATURE:
<223> OTHER INFORMATION: Synthetic Construct

<400> SEQUENCE: 466
ggatacggtg cgtcaatcta                                                    20

<210> SEQ ID NO 467
<211> LENGTH: 20
<212> TYPE: DNA
<213> ORGANISM: Artificial Sequence
<220> FEATURE:
<223> OTHER INFORMATION: Synthetic Construct

<400> SEQUENCE: 467
gaatccagtg gcggcgacaa                                                    20

<210> SEQ ID NO 468
<211> LENGTH: 20
<212> TYPE: DNA
<213> ORGANISM: Artificial Sequence
<220> FEATURE:
<223> OTHER INFORMATION: Synthetic Construct

<400> SEQUENCE: 468
gcactgtcag tgcaacgata                                                    20

<210> SEQ ID NO 469
<211> LENGTH: 20
<212> TYPE: DNA
<213> ORGANISM: Artificial Sequence
<220> FEATURE:
<223> OTHER INFORMATION: Synthetic Construct

<400> SEQUENCE: 469
gcgatcctca agtatgctca                                                    20
```

<210> SEQ ID NO 470
<211> LENGTH: 20
<212> TYPE: DNA
<213> ORGANISM: Artificial Sequence
<220> FEATURE:
<223> OTHER INFORMATION: Synthetic Construct

<400> SEQUENCE: 470
gctaatatcg acacggccgc                                                   20

<210> SEQ ID NO 471
<211> LENGTH: 20
<212> TYPE: DNA
<213> ORGANISM: Artificial Sequence
<220> FEATURE:
<223> OTHER INFORMATION: Synthetic Construct

<400> SEQUENCE: 471
ggagatgcat cgaagtcgat                                                   20

<210> SEQ ID NO 472
<211> LENGTH: 20
<212> TYPE: DNA
<213> ORGANISM: Artificial Sequence
<220> FEATURE:
<223> OTHER INFORMATION: Synthetic Construct

<400> SEQUENCE: 472
ggatgcactc catctcgtct                                                   20

<210> SEQ ID NO 473
<211> LENGTH: 20
<212> TYPE: DNA
<213> ORGANISM: Artificial Sequence
<220> FEATURE:
<223> OTHER INFORMATION: Synthetic Construct

<400> SEQUENCE: 473
gtgccgagta ataacgcgag                                                   20

<210> SEQ ID NO 474
<211> LENGTH: 20
<212> TYPE: DNA
<213> ORGANISM: Artificial Sequence
<220> FEATURE:
<223> OTHER INFORMATION: Synthetic Construct

<400> SEQUENCE: 474
gagattccga tgtaacgtac                                                   20

<210> SEQ ID NO 475
<211> LENGTH: 20
<212> TYPE: DNA
<213> ORGANISM: Artificial Sequence
<220> FEATURE:
<223> OTHER INFORMATION: Synthetic Construct

<400> SEQUENCE: 475
gtcgtcacga gcaggattgc                                                   20

<210> SEQ ID NO 476
<211> LENGTH: 20
<212> TYPE: DNA
<213> ORGANISM: Artificial Sequence
<220> FEATURE:
<223> OTHER INFORMATION: Synthetic Construct

```
<400> SEQUENCE: 476
gcgttagtca cttagctcga                                                    20

<210> SEQ ID NO 477
<211> LENGTH: 20
<212> TYPE: DNA
<213> ORGANISM: Artificial Sequence
<220> FEATURE:
<223> OTHER INFORMATION: Synthetic Construct

<400> SEQUENCE: 477
gttcacacgg tgtcggatag                                                    20

<210> SEQ ID NO 478
<211> LENGTH: 20
<212> TYPE: DNA
<213> ORGANISM: Artificial Sequence
<220> FEATURE:
<223> OTHER INFORMATION: Synthetic Construct

<400> SEQUENCE: 478
ggataggtga ccttagtacg                                                    20

<210> SEQ ID NO 479
<211> LENGTH: 20
<212> TYPE: DNA
<213> ORGANISM: Artificial Sequence
<220> FEATURE:
<223> OTHER INFORMATION: Synthetic Construct

<400> SEQUENCE: 479
gtatgagtca agctaatgcg                                                    20

<210> SEQ ID NO 480
<211> LENGTH: 20
<212> TYPE: DNA
<213> ORGANISM: Artificial Sequence
<220> FEATURE:
<223> OTHER INFORMATION: Synthetic Construct

<400> SEQUENCE: 480
gcaactattg gaatacgtga                                                    20

<210> SEQ ID NO 481
<211> LENGTH: 20
<212> TYPE: DNA
<213> ORGANISM: Artificial Sequence
<220> FEATURE:
<223> OTHER INFORMATION: Synthetic Construct

<400> SEQUENCE: 481
gttaccttcg ctcgtctata                                                    20

<210> SEQ ID NO 482
<211> LENGTH: 20
<212> TYPE: DNA
<213> ORGANISM: Artificial Sequence
<220> FEATURE:
<223> OTHER INFORMATION: Synthetic Construct

<400> SEQUENCE: 482
gtaccgagca ccacaggccg                                                    20

<210> SEQ ID NO 483
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 483
gtcagccatc ggatagagat                                              20

<210> SEQ ID NO 484
<211> LENGTH: 20
<212> TYPE: DNA
<213> ORGANISM: Artificial Sequence
<220> FEATURE:
<223> OTHER INFORMATION: Synthetic Construct

<400> SEQUENCE: 484
gtacggcact cctagccgct                                              20

<210> SEQ ID NO 485
<211> LENGTH: 20
<212> TYPE: DNA
<213> ORGANISM: Artificial Sequence
<220> FEATURE:
<223> OTHER INFORMATION: Synthetic Construct

<400> SEQUENCE: 485
ggtcctgtcg tatgcttgca                                              20

<210> SEQ ID NO 486
<211> LENGTH: 20
<212> TYPE: DNA
<213> ORGANISM: Artificial Sequence
<220> FEATURE:
<223> OTHER INFORMATION: Synthetic Construct

<400> SEQUENCE: 486
gccgcaatat atgcggtaag                                              20

<210> SEQ ID NO 487
<211> LENGTH: 20
<212> TYPE: DNA
<213> ORGANISM: Artificial Sequence
<220> FEATURE:
<223> OTHER INFORMATION: Synthetic Construct

<400> SEQUENCE: 487
gcgcacgtat aatcctgcgt                                              20

<210> SEQ ID NO 488
<211> LENGTH: 20
<212> TYPE: DNA
<213> ORGANISM: Artificial Sequence
<220> FEATURE:
<223> OTHER INFORMATION: Synthetic Construct

<400> SEQUENCE: 488
gtgcacaaca cgatccacga                                              20

<210> SEQ ID NO 489
<211> LENGTH: 20
<212> TYPE: DNA
<213> ORGANISM: Artificial Sequence
<220> FEATURE:
<223> OTHER INFORMATION: Synthetic Construct

<400> SEQUENCE: 489
```
gcacaatgtt gacgtaagtg                                              20

<210> SEQ ID NO 490
<211> LENGTH: 20
<212> TYPE: DNA
<213> ORGANISM: Artificial Sequence
<220> FEATURE:
<223> OTHER INFORMATION: Synthetic Construct

<400> SEQUENCE: 490
gtaagatgct gctcaccgtg                                              20

<210> SEQ ID NO 491
<211> LENGTH: 20
<212> TYPE: DNA
<213> ORGANISM: Artificial Sequence
<220> FEATURE:
<223> OTHER INFORMATION: Synthetic Construct

<400> SEQUENCE: 491
gtcggtgatc caacgtatcg                                              20

<210> SEQ ID NO 492
<211> LENGTH: 20
<212> TYPE: DNA
<213> ORGANISM: Artificial Sequence
<220> FEATURE:
<223> OTHER INFORMATION: Synthetic Construct

<400> SEQUENCE: 492
gagctagtag gacgcaagac                                              20

<210> SEQ ID NO 493
<211> LENGTH: 20
<212> TYPE: DNA
<213> ORGANISM: Artificial Sequence
<220> FEATURE:
<223> OTHER INFORMATION: Synthetic Construct

<400> SEQUENCE: 493
gtacgtggaa gcttgtggcc                                              20

<210> SEQ ID NO 494
<211> LENGTH: 20
<212> TYPE: DNA
<213> ORGANISM: Artificial Sequence
<220> FEATURE:
<223> OTHER INFORMATION: Synthetic Construct

<400> SEQUENCE: 494
gagaactgcc agttctcgat                                              20

<210> SEQ ID NO 495
<211> LENGTH: 20
<212> TYPE: DNA
<213> ORGANISM: Artificial Sequence
<220> FEATURE:
<223> OTHER INFORMATION: Synthetic Construct

<400> SEQUENCE: 495
gccattcggc gcggcacttc                                              20

<210> SEQ ID NO 496
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 496
gcacacgacc aatccgcttc                                               20

<210> SEQ ID NO 497
<211> LENGTH: 20
<212> TYPE: DNA
<213> ORGANISM: Artificial Sequence
<220> FEATURE:
<223> OTHER INFORMATION: Synthetic Construct

<400> SEQUENCE: 497
gaggtgatcg attaagtaca                                               20

<210> SEQ ID NO 498
<211> LENGTH: 20
<212> TYPE: DNA
<213> ORGANISM: Artificial Sequence
<220> FEATURE:
<223> OTHER INFORMATION: Synthetic Construct

<400> SEQUENCE: 498
gtcactcgca gacgcctaac                                               20

<210> SEQ ID NO 499
<211> LENGTH: 20
<212> TYPE: DNA
<213> ORGANISM: Artificial Sequence
<220> FEATURE:
<223> OTHER INFORMATION: Synthetic Construct

<400> SEQUENCE: 499
gcgctacgga atcatacgtt                                               20

<210> SEQ ID NO 500
<211> LENGTH: 20
<212> TYPE: DNA
<213> ORGANISM: Artificial Sequence
<220> FEATURE:
<223> OTHER INFORMATION: Synthetic Construct

<400> SEQUENCE: 500
ggtaggacct cacggcgcgc                                               20

<210> SEQ ID NO 501
<211> LENGTH: 20
<212> TYPE: DNA
<213> ORGANISM: Artificial Sequence
<220> FEATURE:
<223> OTHER INFORMATION: Synthetic Construct

<400> SEQUENCE: 501
gaactgcatc ttgttgtagt                                               20

<210> SEQ ID NO 502
<211> LENGTH: 20
<212> TYPE: DNA
<213> ORGANISM: Artificial Sequence
<220> FEATURE:
<223> OTHER INFORMATION: Synthetic Construct

<400> SEQUENCE: 502
gatcctgatc cggcggcgcg                                               20
```

<210> SEQ ID NO 503
<211> LENGTH: 20
<212> TYPE: DNA
<213> ORGANISM: Artificial Sequence
<220> FEATURE:
<223> OTHER INFORMATION: Synthetic Construct

<400> SEQUENCE: 503
ggtatgcgcg atcctgagtt                                          20

<210> SEQ ID NO 504
<211> LENGTH: 20
<212> TYPE: DNA
<213> ORGANISM: Artificial Sequence
<220> FEATURE:
<223> OTHER INFORMATION: Synthetic Construct

<400> SEQUENCE: 504
gcggagctag agagcggtca                                          20

<210> SEQ ID NO 505
<211> LENGTH: 20
<212> TYPE: DNA
<213> ORGANISM: Artificial Sequence
<220> FEATURE:
<223> OTHER INFORMATION: Synthetic Construct

<400> SEQUENCE: 505
gaatggcaat tacggctgat                                          20

<210> SEQ ID NO 506
<211> LENGTH: 20
<212> TYPE: DNA
<213> ORGANISM: Artificial Sequence
<220> FEATURE:
<223> OTHER INFORMATION: Synthetic Construct

<400> SEQUENCE: 506
gtatggtgag tagtcgcttg                                          20

<210> SEQ ID NO 507
<211> LENGTH: 20
<212> TYPE: DNA
<213> ORGANISM: Artificial Sequence
<220> FEATURE:
<223> OTHER INFORMATION: Synthetic Construct

<400> SEQUENCE: 507
gtgtaattgc gtctagtcgg                                          20

<210> SEQ ID NO 508
<211> LENGTH: 20
<212> TYPE: DNA
<213> ORGANISM: Artificial Sequence
<220> FEATURE:
<223> OTHER INFORMATION: Synthetic Construct

<400> SEQUENCE: 508
ggtcctggcg aggagccttg                                          20

<210> SEQ ID NO 509
<211> LENGTH: 20
<212> TYPE: DNA
<213> ORGANISM: Artificial Sequence
<220> FEATURE:

<223> OTHER INFORMATION: Synthetic Construct

<400> SEQUENCE: 509
gaagataagt cgctgtctcg                                           20

<210> SEQ ID NO 510
<211> LENGTH: 20
<212> TYPE: DNA
<213> ORGANISM: Artificial Sequence
<220> FEATURE:
<223> OTHER INFORMATION: Synthetic Construct

<400> SEQUENCE: 510
gtcggcgttc tgttgtgact                                           20

<210> SEQ ID NO 511
<211> LENGTH: 20
<212> TYPE: DNA
<213> ORGANISM: Artificial Sequence
<220> FEATURE:
<223> OTHER INFORMATION: Synthetic Construct

<400> SEQUENCE: 511
gaggcaagcc gttaggtgta                                           20

<210> SEQ ID NO 512
<211> LENGTH: 20
<212> TYPE: DNA
<213> ORGANISM: Artificial Sequence
<220> FEATURE:
<223> OTHER INFORMATION: Synthetic Construct

<400> SEQUENCE: 512
gcggatccag atctcattcg                                           20

<210> SEQ ID NO 513
<211> LENGTH: 20
<212> TYPE: DNA
<213> ORGANISM: Artificial Sequence
<220> FEATURE:
<223> OTHER INFORMATION: Synthetic Construct

<400> SEQUENCE: 513
ggaacatagg agcacgtagt                                           20

<210> SEQ ID NO 514
<211> LENGTH: 20
<212> TYPE: DNA
<213> ORGANISM: Artificial Sequence
<220> FEATURE:
<223> OTHER INFORMATION: Synthetic Construct

<400> SEQUENCE: 514
gtcatcatta tggcgtaagg                                           20

<210> SEQ ID NO 515
<211> LENGTH: 20
<212> TYPE: DNA
<213> ORGANISM: Artificial Sequence
<220> FEATURE:
<223> OTHER INFORMATION: Synthetic Construct

<400> SEQUENCE: 515
gcgactagcg ccatgagcgg                                           20

```
<210> SEQ ID NO 516
<211> LENGTH: 20
<212> TYPE: DNA
<213> ORGANISM: Artificial Sequence
<220> FEATURE:
<223> OTHER INFORMATION: Synthetic Construct

<400> SEQUENCE: 516
ggcgaagttc gacatgacac                                               20

<210> SEQ ID NO 517
<211> LENGTH: 20
<212> TYPE: DNA
<213> ORGANISM: Artificial Sequence
<220> FEATURE:
<223> OTHER INFORMATION: Synthetic Construct

<400> SEQUENCE: 517
gctgtcgtgt ggaggctatg                                               20

<210> SEQ ID NO 518
<211> LENGTH: 20
<212> TYPE: DNA
<213> ORGANISM: Artificial Sequence
<220> FEATURE:
<223> OTHER INFORMATION: Synthetic Construct

<400> SEQUENCE: 518
gcggagagca ttgacctcat                                               20

<210> SEQ ID NO 519
<211> LENGTH: 20
<212> TYPE: DNA
<213> ORGANISM: Artificial Sequence
<220> FEATURE:
<223> OTHER INFORMATION: Synthetic Construct

<400> SEQUENCE: 519
gactaatgga ccaagtcagt                                               20

<210> SEQ ID NO 520
<211> LENGTH: 20
<212> TYPE: DNA
<213> ORGANISM: Artificial Sequence
<220> FEATURE:
<223> OTHER INFORMATION: Synthetic Construct

<400> SEQUENCE: 520
gcggattaga ggtaatgcgg                                               20

<210> SEQ ID NO 521
<211> LENGTH: 20
<212> TYPE: DNA
<213> ORGANISM: Artificial Sequence
<220> FEATURE:
<223> OTHER INFORMATION: Synthetic Construct

<400> SEQUENCE: 521
gccgacggca atcagtacgc                                               20

<210> SEQ ID NO 522
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 522
gtaacctctc gagcgataga                                                   20

<210> SEQ ID NO 523
<211> LENGTH: 20
<212> TYPE: DNA
<213> ORGANISM: Artificial Sequence
<220> FEATURE:
<223> OTHER INFORMATION: Synthetic Construct

<400> SEQUENCE: 523
gacttgtatg tggcttacgg                                                   20

<210> SEQ ID NO 524
<211> LENGTH: 20
<212> TYPE: DNA
<213> ORGANISM: Artificial Sequence
<220> FEATURE:
<223> OTHER INFORMATION: Synthetic Construct

<400> SEQUENCE: 524
gtcactgtgg tcgaacatgt                                                   20

<210> SEQ ID NO 525
<211> LENGTH: 20
<212> TYPE: DNA
<213> ORGANISM: Artificial Sequence
<220> FEATURE:
<223> OTHER INFORMATION: Synthetic Construct

<400> SEQUENCE: 525
gtactccaat ccgcgatgac                                                   20

<210> SEQ ID NO 526
<211> LENGTH: 20
<212> TYPE: DNA
<213> ORGANISM: Artificial Sequence
<220> FEATURE:
<223> OTHER INFORMATION: Synthetic Construct

<400> SEQUENCE: 526
gcgttggcac gatgttacgg                                                   20

<210> SEQ ID NO 527
<211> LENGTH: 20
<212> TYPE: DNA
<213> ORGANISM: Artificial Sequence
<220> FEATURE:
<223> OTHER INFORMATION: Synthetic Construct

<400> SEQUENCE: 527
gaaccagccg gctagtatga                                                   20

<210> SEQ ID NO 528
<211> LENGTH: 20
<212> TYPE: DNA
<213> ORGANISM: Artificial Sequence
<220> FEATURE:
<223> OTHER INFORMATION: Synthetic Construct

<400> SEQUENCE: 528
gtatactagc taaccacacg                                                   20

<210> SEQ ID NO 529
<211> LENGTH: 20
```

-continued

```
<212> TYPE: DNA
<213> ORGANISM: Artificial Sequence
<220> FEATURE:
<223> OTHER INFORMATION: Synthetic Construct

<400> SEQUENCE: 529
gaatcggaat agttgattcg                                          20

<210> SEQ ID NO 530
<211> LENGTH: 20
<212> TYPE: DNA
<213> ORGANISM: Artificial Sequence
<220> FEATURE:
<223> OTHER INFORMATION: Synthetic Construct

<400> SEQUENCE: 530
gagcacttgc atgaggcggt                                          20

<210> SEQ ID NO 531
<211> LENGTH: 20
<212> TYPE: DNA
<213> ORGANISM: Artificial Sequence
<220> FEATURE:
<223> OTHER INFORMATION: Synthetic Construct

<400> SEQUENCE: 531
gaacggcgat gaagccagcc                                          20

<210> SEQ ID NO 532
<211> LENGTH: 20
<212> TYPE: DNA
<213> ORGANISM: Artificial Sequence
<220> FEATURE:
<223> OTHER INFORMATION: Synthetic Construct

<400> SEQUENCE: 532
gcaaccgaga tgagaggttc                                          20

<210> SEQ ID NO 533
<211> LENGTH: 20
<212> TYPE: DNA
<213> ORGANISM: Artificial Sequence
<220> FEATURE:
<223> OTHER INFORMATION: Synthetic Construct

<400> SEQUENCE: 533
gcaagatcaa tatgcgtgat                                          20

<210> SEQ ID NO 534
<211> LENGTH: 20
<212> TYPE: DNA
<213> ORGANISM: Artificial Sequence
<220> FEATURE:
<223> OTHER INFORMATION: Synthetic Construct

<400> SEQUENCE: 534
acggaggcta agcgtcgcaa                                          20

<210> SEQ ID NO 535
<211> LENGTH: 20
<212> TYPE: DNA
<213> ORGANISM: Artificial Sequence
<220> FEATURE:
<223> OTHER INFORMATION: Synthetic Construct

<400> SEQUENCE: 535
```
cgcttccgcg gcccgttcaa                                                20

<210> SEQ ID NO 536
<211> LENGTH: 20
<212> TYPE: DNA
<213> ORGANISM: Artificial Sequence
<220> FEATURE:
<223> OTHER INFORMATION: Synthetic Construct

<400> SEQUENCE: 536
atcgtttccg cttaacggcg                                                20

<210> SEQ ID NO 537
<211> LENGTH: 20
<212> TYPE: DNA
<213> ORGANISM: Artificial Sequence
<220> FEATURE:
<223> OTHER INFORMATION: Synthetic Construct

<400> SEQUENCE: 537
gtaggcgcgc cgctctctac                                                20

<210> SEQ ID NO 538
<211> LENGTH: 20
<212> TYPE: DNA
<213> ORGANISM: Artificial Sequence
<220> FEATURE:
<223> OTHER INFORMATION: Synthetic Construct

<400> SEQUENCE: 538
ccatatcggg gcgagacatg                                                20

<210> SEQ ID NO 539
<211> LENGTH: 20
<212> TYPE: DNA
<213> ORGANISM: Artificial Sequence
<220> FEATURE:
<223> OTHER INFORMATION: Synthetic Construct

<400> SEQUENCE: 539
tactaacgcc gctcctacag                                                20

<210> SEQ ID NO 540
<211> LENGTH: 20
<212> TYPE: DNA
<213> ORGANISM: Artificial Sequence
<220> FEATURE:
<223> OTHER INFORMATION: Synthetic Construct

<400> SEQUENCE: 540
tgaggatcat gtcgagcgcc                                                20

<210> SEQ ID NO 541
<211> LENGTH: 20
<212> TYPE: DNA
<213> ORGANISM: Artificial Sequence
<220> FEATURE:
<223> OTHER INFORMATION: Synthetic Construct

<400> SEQUENCE: 541
gggcccgcat aggatatcgc                                                20

<210> SEQ ID NO 542
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 542
tagacaaccg cggagaatgc                                               20

<210> SEQ ID NO 543
<211> LENGTH: 20
<212> TYPE: DNA
<213> ORGANISM: Artificial Sequence
<220> FEATURE:
<223> OTHER INFORMATION: Synthetic Construct

<400> SEQUENCE: 543
acgggcggct atcgctgact                                               20

<210> SEQ ID NO 544
<211> LENGTH: 20
<212> TYPE: DNA
<213> ORGANISM: Artificial Sequence
<220> FEATURE:
<223> OTHER INFORMATION: Synthetic Construct

<400> SEQUENCE: 544
cgcggaaatt ttaccgacga                                               20

<210> SEQ ID NO 545
<211> LENGTH: 20
<212> TYPE: DNA
<213> ORGANISM: Artificial Sequence
<220> FEATURE:
<223> OTHER INFORMATION: Synthetic Construct

<400> SEQUENCE: 545
cttacaatcg tcggtccaat                                               20

<210> SEQ ID NO 546
<211> LENGTH: 20
<212> TYPE: DNA
<213> ORGANISM: Artificial Sequence
<220> FEATURE:
<223> OTHER INFORMATION: Synthetic Construct

<400> SEQUENCE: 546
gcgtgcgtcc cgggttaccc                                               20

<210> SEQ ID NO 547
<211> LENGTH: 20
<212> TYPE: DNA
<213> ORGANISM: Artificial Sequence
<220> FEATURE:
<223> OTHER INFORMATION: Synthetic Construct

<400> SEQUENCE: 547
cggagtaaca agcggacgga                                               20

<210> SEQ ID NO 548
<211> LENGTH: 20
<212> TYPE: DNA
<213> ORGANISM: Artificial Sequence
<220> FEATURE:
<223> OTHER INFORMATION: Synthetic Construct

<400> SEQUENCE: 548
cgagtgttat acgcaccgtt                                               20
```

<210> SEQ ID NO 549
<211> LENGTH: 20
<212> TYPE: DNA
<213> ORGANISM: Artificial Sequence
<220> FEATURE:
<223> OTHER INFORMATION: Synthetic Construct

<400> SEQUENCE: 549
cgactaaccg gaaactttt                                                    20

<210> SEQ ID NO 550
<211> LENGTH: 20
<212> TYPE: DNA
<213> ORGANISM: Artificial Sequence
<220> FEATURE:
<223> OTHER INFORMATION: Synthetic Construct

<400> SEQUENCE: 550
caacgggttc tcccggctac                                                   20

<210> SEQ ID NO 551
<211> LENGTH: 20
<212> TYPE: DNA
<213> ORGANISM: Artificial Sequence
<220> FEATURE:
<223> OTHER INFORMATION: Synthetic Construct

<400> SEQUENCE: 551
caggagtcgc cgatacgcgt                                                   20

<210> SEQ ID NO 552
<211> LENGTH: 20
<212> TYPE: DNA
<213> ORGANISM: Artificial Sequence
<220> FEATURE:
<223> OTHER INFORMATION: Synthetic Construct

<400> SEQUENCE: 552
ttcacgtcgt ctcgcgacca                                                   20

<210> SEQ ID NO 553
<211> LENGTH: 20
<212> TYPE: DNA
<213> ORGANISM: Artificial Sequence
<220> FEATURE:
<223> OTHER INFORMATION: Synthetic Construct

<400> SEQUENCE: 553
gtgtcggatt ccgccgctta                                                   20

<210> SEQ ID NO 554
<211> LENGTH: 20
<212> TYPE: DNA
<213> ORGANISM: Artificial Sequence
<220> FEATURE:
<223> OTHER INFORMATION: Synthetic Construct

<400> SEQUENCE: 554
cacgaactca caccgcgcga                                                   20

<210> SEQ ID NO 555
<211> LENGTH: 20
<212> TYPE: DNA
<213> ORGANISM: Artificial Sequence
<220> FEATURE:
<223> OTHER INFORMATION: Synthetic Construct -continued

```
<400> SEQUENCE: 555
cgctagtacg ctcctctata                                              20

<210> SEQ ID NO 556
<211> LENGTH: 20
<212> TYPE: DNA
<213> ORGANISM: Artificial Sequence
<220> FEATURE:
<223> OTHER INFORMATION: Synthetic Construct

<400> SEQUENCE: 556
tcgcgcttgg gttatacgct                                              20

<210> SEQ ID NO 557
<211> LENGTH: 20
<212> TYPE: DNA
<213> ORGANISM: Artificial Sequence
<220> FEATURE:
<223> OTHER INFORMATION: Synthetic Construct

<400> SEQUENCE: 557
ctatctcgag tggtaatgcg                                              20

<210> SEQ ID NO 558
<211> LENGTH: 20
<212> TYPE: DNA
<213> ORGANISM: Artificial Sequence
<220> FEATURE:
<223> OTHER INFORMATION: Synthetic Construct

<400> SEQUENCE: 558
aatcgactcg aacttcgtgt                                              20

<210> SEQ ID NO 559
<211> LENGTH: 20
<212> TYPE: DNA
<213> ORGANISM: Artificial Sequence
<220> FEATURE:
<223> OTHER INFORMATION: Synthetic Construct

<400> SEQUENCE: 559
cccgatggac tataccgaac                                              20

<210> SEQ ID NO 560
<211> LENGTH: 20
<212> TYPE: DNA
<213> ORGANISM: Artificial Sequence
<220> FEATURE:
<223> OTHER INFORMATION: Synthetic Construct

<400> SEQUENCE: 560
acgttcgagt acgaccagct                                              20

<210> SEQ ID NO 561
<211> LENGTH: 20
<212> TYPE: DNA
<213> ORGANISM: Artificial Sequence
<220> FEATURE:
<223> OTHER INFORMATION: Synthetic Construct

<400> SEQUENCE: 561
cgcgacgact caacctagtc                                              20

<210> SEQ ID NO 562
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 562
ggtcaccgat cgagagctag                                               20

<210> SEQ ID NO 563
<211> LENGTH: 20
<212> TYPE: DNA
<213> ORGANISM: Artificial Sequence
<220> FEATURE:
<223> OTHER INFORMATION: Synthetic Construct

<400> SEQUENCE: 563
ctcaaccgac cgtatggtca                                               20

<210> SEQ ID NO 564
<211> LENGTH: 20
<212> TYPE: DNA
<213> ORGANISM: Artificial Sequence
<220> FEATURE:
<223> OTHER INFORMATION: Synthetic Construct

<400> SEQUENCE: 564
cgtattcgac tctcaacgcg                                               20

<210> SEQ ID NO 565
<211> LENGTH: 20
<212> TYPE: DNA
<213> ORGANISM: Artificial Sequence
<220> FEATURE:
<223> OTHER INFORMATION: Synthetic Construct

<400> SEQUENCE: 565
ctagccgccc agatcgagcc                                               20

<210> SEQ ID NO 566
<211> LENGTH: 20
<212> TYPE: DNA
<213> ORGANISM: Artificial Sequence
<220> FEATURE:
<223> OTHER INFORMATION: Synthetic Construct

<400> SEQUENCE: 566
gaatcgaccg acactaatgt                                               20

<210> SEQ ID NO 567
<211> LENGTH: 20
<212> TYPE: DNA
<213> ORGANISM: Artificial Sequence
<220> FEATURE:
<223> OTHER INFORMATION: Synthetic Construct

<400> SEQUENCE: 567
acttcagttc ggcgtagtca                                               20

<210> SEQ ID NO 568
<211> LENGTH: 20
<212> TYPE: DNA
<213> ORGANISM: Artificial Sequence
<220> FEATURE:
<223> OTHER INFORMATION: Synthetic Construct

<400> SEQUENCE: 568
```
gtgcgatgtc gcttcaacgt 20

<210> SEQ ID NO 569
<211> LENGTH: 20
<212> TYPE: DNA
<213> ORGANISM: Artificial Sequence
<220> FEATURE:
<223> OTHER INFORMATION: Synthetic Construct

<400> SEQUENCE: 569
cgcctaattt ccggatcaat 20

<210> SEQ ID NO 570
<211> LENGTH: 20
<212> TYPE: DNA
<213> ORGANISM: Artificial Sequence
<220> FEATURE:
<223> OTHER INFORMATION: Synthetic Construct

<400> SEQUENCE: 570
cgtggccgga accgtcatag 20

<210> SEQ ID NO 571
<211> LENGTH: 20
<212> TYPE: DNA
<213> ORGANISM: Artificial Sequence
<220> FEATURE:
<223> OTHER INFORMATION: Synthetic Construct

<400> SEQUENCE: 571
accctccgaa tcgtaacgga 20

<210> SEQ ID NO 572
<211> LENGTH: 20
<212> TYPE: DNA
<213> ORGANISM: Artificial Sequence
<220> FEATURE:
<223> OTHER INFORMATION: Synthetic Construct

<400> SEQUENCE: 572
aaacggtacg acagcgtgtg 20

<210> SEQ ID NO 573
<211> LENGTH: 20
<212> TYPE: DNA
<213> ORGANISM: Artificial Sequence
<220> FEATURE:
<223> OTHER INFORMATION: Synthetic Construct

<400> SEQUENCE: 573
acatagtcga cggctcgatt 20

<210> SEQ ID NO 574
<211> LENGTH: 20
<212> TYPE: DNA
<213> ORGANISM: Artificial Sequence
<220> FEATURE:
<223> OTHER INFORMATION: Synthetic Construct

<400> SEQUENCE: 574
gatggcgctt cagtcgtcgg 20

<210> SEQ ID NO 575
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 575
ataatccgga aacgctcgac                                               20

<210> SEQ ID NO 576
<211> LENGTH: 20
<212> TYPE: DNA
<213> ORGANISM: Artificial Sequence
<220> FEATURE:
<223> OTHER INFORMATION: Synthetic Construct

<400> SEQUENCE: 576
cgccgggctg acaattaacg                                               20

<210> SEQ ID NO 577
<211> LENGTH: 20
<212> TYPE: DNA
<213> ORGANISM: Artificial Sequence
<220> FEATURE:
<223> OTHER INFORMATION: Synthetic Construct

<400> SEQUENCE: 577
cgtcgccata tgccggtggc                                               20

<210> SEQ ID NO 578
<211> LENGTH: 20
<212> TYPE: DNA
<213> ORGANISM: Artificial Sequence
<220> FEATURE:
<223> OTHER INFORMATION: Synthetic Construct

<400> SEQUENCE: 578
cgggcctata acaccatcga                                               20

<210> SEQ ID NO 579
<211> LENGTH: 20
<212> TYPE: DNA
<213> ORGANISM: Artificial Sequence
<220> FEATURE:
<223> OTHER INFORMATION: Synthetic Construct

<400> SEQUENCE: 579
cgccgttccg agatacttga                                               20

<210> SEQ ID NO 580
<211> LENGTH: 20
<212> TYPE: DNA
<213> ORGANISM: Artificial Sequence
<220> FEATURE:
<223> OTHER INFORMATION: Synthetic Construct

<400> SEQUENCE: 580
cgggacgtcg cgaaaatgta                                               20

<210> SEQ ID NO 581
<211> LENGTH: 20
<212> TYPE: DNA
<213> ORGANISM: Artificial Sequence
<220> FEATURE:
<223> OTHER INFORMATION: Synthetic Construct

<400> SEQUENCE: 581
tcggcatacg ggacacacgc                                               20
```

```
<210> SEQ ID NO 582
<211> LENGTH: 20
<212> TYPE: DNA
<213> ORGANISM: Artificial Sequence
<220> FEATURE:
<223> OTHER INFORMATION: Synthetic Construct

<400> SEQUENCE: 582
agctccatcg ccgcgataat                                              20

<210> SEQ ID NO 583
<211> LENGTH: 20
<212> TYPE: DNA
<213> ORGANISM: Artificial Sequence
<220> FEATURE:
<223> OTHER INFORMATION: Synthetic Construct

<400> SEQUENCE: 583
atcgtatcat cagctagcgc                                              20

<210> SEQ ID NO 584
<211> LENGTH: 20
<212> TYPE: DNA
<213> ORGANISM: Artificial Sequence
<220> FEATURE:
<223> OTHER INFORMATION: Synthetic Construct

<400> SEQUENCE: 584
tcgatcgagg ttgcattcgg                                              20

<210> SEQ ID NO 585
<211> LENGTH: 20
<212> TYPE: DNA
<213> ORGANISM: Artificial Sequence
<220> FEATURE:
<223> OTHER INFORMATION: Synthetic Construct

<400> SEQUENCE: 585
ctcgacagtt cgtcccgagc                                              20

<210> SEQ ID NO 586
<211> LENGTH: 20
<212> TYPE: DNA
<213> ORGANISM: Artificial Sequence
<220> FEATURE:
<223> OTHER INFORMATION: Synthetic Construct

<400> SEQUENCE: 586
cggtagtatt aatcgctgac                                              20

<210> SEQ ID NO 587
<211> LENGTH: 20
<212> TYPE: DNA
<213> ORGANISM: Artificial Sequence
<220> FEATURE:
<223> OTHER INFORMATION: Synthetic Construct

<400> SEQUENCE: 587
tgaacgcgtg tttccttgca                                              20

<210> SEQ ID NO 588
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 588
cgacgctagg taacgtagag                                        20

<210> SEQ ID NO 589
<211> LENGTH: 20
<212> TYPE: DNA
<213> ORGANISM: Artificial Sequence
<220> FEATURE:
<223> OTHER INFORMATION: Synthetic Construct

<400> SEQUENCE: 589
cattgttgag cgggcgcgct                                        20

<210> SEQ ID NO 590
<211> LENGTH: 20
<212> TYPE: DNA
<213> ORGANISM: Artificial Sequence
<220> FEATURE:
<223> OTHER INFORMATION: Synthetic Construct

<400> SEQUENCE: 590
ccgctattga aaccgcccac                                        20

<210> SEQ ID NO 591
<211> LENGTH: 20
<212> TYPE: DNA
<213> ORGANISM: Artificial Sequence
<220> FEATURE:
<223> OTHER INFORMATION: Synthetic Construct

<400> SEQUENCE: 591
agacacgtca ccggtcaaaa                                        20

<210> SEQ ID NO 592
<211> LENGTH: 20
<212> TYPE: DNA
<213> ORGANISM: Artificial Sequence
<220> FEATURE:
<223> OTHER INFORMATION: Synthetic Construct

<400> SEQUENCE: 592
tttacgatct agcggcgtag                                        20

<210> SEQ ID NO 593
<211> LENGTH: 20
<212> TYPE: DNA
<213> ORGANISM: Artificial Sequence
<220> FEATURE:
<223> OTHER INFORMATION: Synthetic Construct

<400> SEQUENCE: 593
ttcgcacgat tgcaccttgg                                        20

<210> SEQ ID NO 594
<211> LENGTH: 20
<212> TYPE: DNA
<213> ORGANISM: Artificial Sequence
<220> FEATURE:
<223> OTHER INFORMATION: Synthetic Construct

<400> SEQUENCE: 594
ggttagagac taggcgcgcg                                        20

```
<210> SEQ ID NO 595
<211> LENGTH: 20
<212> TYPE: DNA
<213> ORGANISM: Artificial Sequence
<220> FEATURE:
<223> OTHER INFORMATION: Synthetic Construct

<400> SEQUENCE: 595
cctccgtgct aacgcggacg                                           20

<210> SEQ ID NO 596
<211> LENGTH: 20
<212> TYPE: DNA
<213> ORGANISM: Artificial Sequence
<220> FEATURE:
<223> OTHER INFORMATION: Synthetic Construct

<400> SEQUENCE: 596
ttatcgcgta gtgctgacgt                                           20

<210> SEQ ID NO 597
<211> LENGTH: 20
<212> TYPE: DNA
<213> ORGANISM: Artificial Sequence
<220> FEATURE:
<223> OTHER INFORMATION: Synthetic Construct

<400> SEQUENCE: 597
tacgcttgcg tttagcgtcc                                           20

<210> SEQ ID NO 598
<211> LENGTH: 20
<212> TYPE: DNA
<213> ORGANISM: Artificial Sequence
<220> FEATURE:
<223> OTHER INFORMATION: Synthetic Construct

<400> SEQUENCE: 598
cgcggcccac gcgtcatcgc                                           20

<210> SEQ ID NO 599
<211> LENGTH: 20
<212> TYPE: DNA
<213> ORGANISM: Artificial Sequence
<220> FEATURE:
<223> OTHER INFORMATION: Synthetic Construct

<400> SEQUENCE: 599
agctcgccat gtcggttctc                                           20

<210> SEQ ID NO 600
<211> LENGTH: 20
<212> TYPE: DNA
<213> ORGANISM: Artificial Sequence
<220> FEATURE:
<223> OTHER INFORMATION: Synthetic Construct

<400> SEQUENCE: 600
aactagcccg agcagcttcg                                           20

<210> SEQ ID NO 601
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 601
cgcaaggtgt cggtaaccct                                               20

<210> SEQ ID NO 602
<211> LENGTH: 20
<212> TYPE: DNA
<213> ORGANISM: Artificial Sequence
<220> FEATURE:
<223> OTHER INFORMATION: Synthetic Construct

<400> SEQUENCE: 602
cttcgacgcc atcgtgctca                                               20

<210> SEQ ID NO 603
<211> LENGTH: 20
<212> TYPE: DNA
<213> ORGANISM: Artificial Sequence
<220> FEATURE:
<223> OTHER INFORMATION: Synthetic Construct

<400> SEQUENCE: 603
tcctggatac cgcgtggtta                                               20

<210> SEQ ID NO 604
<211> LENGTH: 20
<212> TYPE: DNA
<213> ORGANISM: Artificial Sequence
<220> FEATURE:
<223> OTHER INFORMATION: Synthetic Construct

<400> SEQUENCE: 604
atagccgccg ctcattactt                                               20

<210> SEQ ID NO 605
<211> LENGTH: 20
<212> TYPE: DNA
<213> ORGANISM: Artificial Sequence
<220> FEATURE:
<223> OTHER INFORMATION: Synthetic Construct

<400> SEQUENCE: 605
gtcgtccggg attacaaaat                                               20

<210> SEQ ID NO 606
<211> LENGTH: 20
<212> TYPE: DNA
<213> ORGANISM: Artificial Sequence
<220> FEATURE:
<223> OTHER INFORMATION: Synthetic Construct

<400> SEQUENCE: 606
taatgctgca cacgccgaat                                               20

<210> SEQ ID NO 607
<211> LENGTH: 20
<212> TYPE: DNA
<213> ORGANISM: Artificial Sequence
<220> FEATURE:
<223> OTHER INFORMATION: Synthetic Construct

<400> SEQUENCE: 607
tatcgcttcc gattagtccg                                               20

<210> SEQ ID NO 608
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 608
gtaccatacc gcgtaccctt                                              20

<210> SEQ ID NO 609
<211> LENGTH: 20
<212> TYPE: DNA
<213> ORGANISM: Artificial Sequence
<220> FEATURE:
<223> OTHER INFORMATION: Synthetic Construct

<400> SEQUENCE: 609
taagatccgc gggtggcaac                                              20

<210> SEQ ID NO 610
<211> LENGTH: 20
<212> TYPE: DNA
<213> ORGANISM: Artificial Sequence
<220> FEATURE:
<223> OTHER INFORMATION: Synthetic Construct

<400> SEQUENCE: 610
gtagacgtcg tgagcttcac                                              20

<210> SEQ ID NO 611
<211> LENGTH: 20
<212> TYPE: DNA
<213> ORGANISM: Artificial Sequence
<220> FEATURE:
<223> OTHER INFORMATION: Synthetic Construct

<400> SEQUENCE: 611
tcgcggacat agggctctaa                                              20

<210> SEQ ID NO 612
<211> LENGTH: 20
<212> TYPE: DNA
<213> ORGANISM: Artificial Sequence
<220> FEATURE:
<223> OTHER INFORMATION: Synthetic Construct

<400> SEQUENCE: 612
agcgcagata gcgcgtatca                                              20

<210> SEQ ID NO 613
<211> LENGTH: 20
<212> TYPE: DNA
<213> ORGANISM: Artificial Sequence
<220> FEATURE:
<223> OTHER INFORMATION: Synthetic Construct

<400> SEQUENCE: 613
gttcgcttcg taacgaggaa                                              20

<210> SEQ ID NO 614
<211> LENGTH: 20
<212> TYPE: DNA
<213> ORGANISM: Artificial Sequence
<220> FEATURE:
<223> OTHER INFORMATION: Synthetic Construct

<400> SEQUENCE: 614
``` gaccccgat aacttttgac                                                    20

<210> SEQ ID NO 615
<211> LENGTH: 20
<212> TYPE: DNA
<213> ORGANISM: Artificial Sequence
<220> FEATURE:
<223> OTHER INFORMATION: Synthetic Construct

<400> SEQUENCE: 615
acgtccatac tgtcggctac                                                   20

<210> SEQ ID NO 616
<211> LENGTH: 20
<212> TYPE: DNA
<213> ORGANISM: Artificial Sequence
<220> FEATURE:
<223> OTHER INFORMATION: Synthetic Construct

<400> SEQUENCE: 616
gtaccattgc cggctcccta                                                   20

<210> SEQ ID NO 617
<211> LENGTH: 20
<212> TYPE: DNA
<213> ORGANISM: Artificial Sequence
<220> FEATURE:
<223> OTHER INFORMATION: Synthetic Construct

<400> SEQUENCE: 617
tggttccgta ggtcggtata                                                   20

<210> SEQ ID NO 618
<211> LENGTH: 20
<212> TYPE: DNA
<213> ORGANISM: Artificial Sequence
<220> FEATURE:
<223> OTHER INFORMATION: Synthetic Construct

<400> SEQUENCE: 618
tctggcttga cacgaccgtt                                                   20

<210> SEQ ID NO 619
<211> LENGTH: 20
<212> TYPE: DNA
<213> ORGANISM: Artificial Sequence
<220> FEATURE:
<223> OTHER INFORMATION: Synthetic Construct

<400> SEQUENCE: 619
cgctaggtcc ggtaagtgcg                                                   20

<210> SEQ ID NO 620
<211> LENGTH: 20
<212> TYPE: DNA
<213> ORGANISM: Artificial Sequence
<220> FEATURE:
<223> OTHER INFORMATION: Synthetic Construct

<400> SEQUENCE: 620
agcacgtaat gtccgtggat                                                   20

<210> SEQ ID NO 621
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 621
aaggcgcgcg aatgtggcag                                          20

<210> SEQ ID NO 622
<211> LENGTH: 20
<212> TYPE: DNA
<213> ORGANISM: Artificial Sequence
<220> FEATURE:
<223> OTHER INFORMATION: Synthetic Construct

<400> SEQUENCE: 622
actgcggagc gcccaatatc                                          20

<210> SEQ ID NO 623
<211> LENGTH: 20
<212> TYPE: DNA
<213> ORGANISM: Artificial Sequence
<220> FEATURE:
<223> OTHER INFORMATION: Synthetic Construct

<400> SEQUENCE: 623
cgtcgagtgc tcgaactcca                                          20

<210> SEQ ID NO 624
<211> LENGTH: 20
<212> TYPE: DNA
<213> ORGANISM: Artificial Sequence
<220> FEATURE:
<223> OTHER INFORMATION: Synthetic Construct

<400> SEQUENCE: 624
tcgcagcggc gtgggatcgg                                          20

<210> SEQ ID NO 625
<211> LENGTH: 20
<212> TYPE: DNA
<213> ORGANISM: Artificial Sequence
<220> FEATURE:
<223> OTHER INFORMATION: Synthetic Construct

<400> SEQUENCE: 625
atctgtccta attcggatcg                                          20

<210> SEQ ID NO 626
<211> LENGTH: 20
<212> TYPE: DNA
<213> ORGANISM: Artificial Sequence
<220> FEATURE:
<223> OTHER INFORMATION: Synthetic Construct

<400> SEQUENCE: 626
tgcggcgtaa tgcttgaaag                                          20

<210> SEQ ID NO 627
<211> LENGTH: 20
<212> TYPE: DNA
<213> ORGANISM: Artificial Sequence
<220> FEATURE:
<223> OTHER INFORMATION: Synthetic Construct

<400> SEQUENCE: 627
cgaacttaat cccgtggcaa                                          20
```

```
<210> SEQ ID NO 628
<211> LENGTH: 20
<212> TYPE: DNA
<213> ORGANISM: Artificial Sequence
<220> FEATURE:
<223> OTHER INFORMATION: Synthetic Construct

<400> SEQUENCE: 628
gccgtgttgc tggatacgcc                                              20

<210> SEQ ID NO 629
<211> LENGTH: 20
<212> TYPE: DNA
<213> ORGANISM: Artificial Sequence
<220> FEATURE:
<223> OTHER INFORMATION: Synthetic Construct

<400> SEQUENCE: 629
taccctccgg atacggactg                                              20

<210> SEQ ID NO 630
<211> LENGTH: 20
<212> TYPE: DNA
<213> ORGANISM: Artificial Sequence
<220> FEATURE:
<223> OTHER INFORMATION: Synthetic Construct

<400> SEQUENCE: 630
ccgttggact atggcgggtc                                              20

<210> SEQ ID NO 631
<211> LENGTH: 20
<212> TYPE: DNA
<213> ORGANISM: Artificial Sequence
<220> FEATURE:
<223> OTHER INFORMATION: Synthetic Construct

<400> SEQUENCE: 631
gtacggggcg atcatccaca                                              20

<210> SEQ ID NO 632
<211> LENGTH: 20
<212> TYPE: DNA
<213> ORGANISM: Artificial Sequence
<220> FEATURE:
<223> OTHER INFORMATION: Synthetic Construct

<400> SEQUENCE: 632
aagagtagta gacgcccggg                                              20

<210> SEQ ID NO 633
<211> LENGTH: 20
<212> TYPE: DNA
<213> ORGANISM: Artificial Sequence
<220> FEATURE:
<223> OTHER INFORMATION: Synthetic Construct

<400> SEQUENCE: 633
aagagcgaat cgatttcgtg                                              20

<210> SEQ ID NO 634
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 634
tcaacaccag tgcctgacgg                                         20

<210> SEQ ID NO 635
<211> LENGTH: 20
<212> TYPE: DNA
<213> ORGANISM: Artificial Sequence
<220> FEATURE:
<223> OTHER INFORMATION: Synthetic Construct

<400> SEQUENCE: 635
aaagtagctt cactctctcg                                         20

<210> SEQ ID NO 636
<211> LENGTH: 20
<212> TYPE: DNA
<213> ORGANISM: Artificial Sequence
<220> FEATURE:
<223> OTHER INFORMATION: Synthetic Construct

<400> SEQUENCE: 636
gagccaacca atagatgtcc                                         20

<210> SEQ ID NO 637
<211> LENGTH: 20
<212> TYPE: DNA
<213> ORGANISM: Artificial Sequence
<220> FEATURE:
<223> OTHER INFORMATION: Synthetic Construct

<400> SEQUENCE: 637
gcgccgccat gaacctagag                                         20

<210> SEQ ID NO 638
<211> LENGTH: 20
<212> TYPE: DNA
<213> ORGANISM: Artificial Sequence
<220> FEATURE:
<223> OTHER INFORMATION: Synthetic Construct

<400> SEQUENCE: 638
acaaaggttg gaacagaacc                                         20

<210> SEQ ID NO 639
<211> LENGTH: 20
<212> TYPE: DNA
<213> ORGANISM: Artificial Sequence
<220> FEATURE:
<223> OTHER INFORMATION: Synthetic Construct

<400> SEQUENCE: 639
ggtgaccggg ttattgatgt                                         20

<210> SEQ ID NO 640
<211> LENGTH: 20
<212> TYPE: DNA
<213> ORGANISM: Artificial Sequence
<220> FEATURE:
<223> OTHER INFORMATION: Synthetic Construct

<400> SEQUENCE: 640
ttagtggagg actacagagc                                         20

<210> SEQ ID NO 641

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 641
acatatagcc cgtaaagctg                                              20

<210> SEQ ID NO 642
<211> LENGTH: 20
<212> TYPE: DNA
<213> ORGANISM: Artificial Sequence
<220> FEATURE:
<223> OTHER INFORMATION: Synthetic Construct

<400> SEQUENCE: 642
cgttggcgat gatctccacg                                              20

<210> SEQ ID NO 643
<211> LENGTH: 20
<212> TYPE: DNA
<213> ORGANISM: Artificial Sequence
<220> FEATURE:
<223> OTHER INFORMATION: Synthetic Construct

<400> SEQUENCE: 643
tggccttttc tacctcgcgc                                              20

<210> SEQ ID NO 644
<211> LENGTH: 20
<212> TYPE: DNA
<213> ORGANISM: Artificial Sequence
<220> FEATURE:
<223> OTHER INFORMATION: Synthetic Construct

<400> SEQUENCE: 644
aatggagata ctcatctggg                                              20

<210> SEQ ID NO 645
<211> LENGTH: 20
<212> TYPE: DNA
<213> ORGANISM: Artificial Sequence
<220> FEATURE:
<223> OTHER INFORMATION: Synthetic Construct

<400> SEQUENCE: 645
gaagcccgtc cagaaagtgt                                              20

<210> SEQ ID NO 646
<211> LENGTH: 20
<212> TYPE: DNA
<213> ORGANISM: Artificial Sequence
<220> FEATURE:
<223> OTHER INFORMATION: Synthetic Construct

<400> SEQUENCE: 646
caatctgagg aactccacga                                              20

<210> SEQ ID NO 647
<211> LENGTH: 20
<212> TYPE: DNA
<213> ORGANISM: Artificial Sequence
<220> FEATURE:
<223> OTHER INFORMATION: Synthetic Construct

<400> SEQUENCE: 647
```
aggctgcggc gcccacgaga                                           20

<210> SEQ ID NO 648
<211> LENGTH: 20
<212> TYPE: DNA
<213> ORGANISM: Artificial Sequence
<220> FEATURE:
<223> OTHER INFORMATION: Synthetic Construct

<400> SEQUENCE: 648
actttgacca ggccttgcta                                           20

<210> SEQ ID NO 649
<211> LENGTH: 20
<212> TYPE: DNA
<213> ORGANISM: Artificial Sequence
<220> FEATURE:
<223> OTHER INFORMATION: Synthetic Construct

<400> SEQUENCE: 649
accttccata actgccacgc                                           20

<210> SEQ ID NO 650
<211> LENGTH: 20
<212> TYPE: DNA
<213> ORGANISM: Artificial Sequence
<220> FEATURE:
<223> OTHER INFORMATION: Synthetic Construct

<400> SEQUENCE: 650
cgaggcgtac atacccaagg                                           20

<210> SEQ ID NO 651
<211> LENGTH: 20
<212> TYPE: DNA
<213> ORGANISM: Artificial Sequence
<220> FEATURE:
<223> OTHER INFORMATION: Synthetic Construct

<400> SEQUENCE: 651
atggtacggc caaatcaaga                                           20

<210> SEQ ID NO 652
<211> LENGTH: 20
<212> TYPE: DNA
<213> ORGANISM: Artificial Sequence
<220> FEATURE:
<223> OTHER INFORMATION: Synthetic Construct

<400> SEQUENCE: 652
tcttgtaatc ccatacgcgt                                           20

<210> SEQ ID NO 653
<211> LENGTH: 20
<212> TYPE: DNA
<213> ORGANISM: Artificial Sequence
<220> FEATURE:
<223> OTHER INFORMATION: Synthetic Construct

<400> SEQUENCE: 653
attcacagga cacagagaat                                           20

<210> SEQ ID NO 654
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 654
ccagggctcc atcctcaaga                                              20

<210> SEQ ID NO 655
<211> LENGTH: 20
<212> TYPE: DNA
<213> ORGANISM: Artificial Sequence
<220> FEATURE:
<223> OTHER INFORMATION: Synthetic Construct

<400> SEQUENCE: 655
tgagctgcac caaagagacg                                              20

<210> SEQ ID NO 656
<211> LENGTH: 20
<212> TYPE: DNA
<213> ORGANISM: Artificial Sequence
<220> FEATURE:
<223> OTHER INFORMATION: Synthetic Construct

<400> SEQUENCE: 656
atgtctgcag atgtacccct                                              20

<210> SEQ ID NO 657
<211> LENGTH: 20
<212> TYPE: DNA
<213> ORGANISM: Artificial Sequence
<220> FEATURE:
<223> OTHER INFORMATION: Synthetic Construct

<400> SEQUENCE: 657
cgaagataac gcggatacct                                              20

<210> SEQ ID NO 658
<211> LENGTH: 20
<212> TYPE: DNA
<213> ORGANISM: Artificial Sequence
<220> FEATURE:
<223> OTHER INFORMATION: Synthetic Construct

<400> SEQUENCE: 658
gctgcaggcc gagtacaccg                                              20

<210> SEQ ID NO 659
<211> LENGTH: 20
<212> TYPE: DNA
<213> ORGANISM: Artificial Sequence
<220> FEATURE:
<223> OTHER INFORMATION: Synthetic Construct

<400> SEQUENCE: 659
acaagtggga ggcttacctg                                              20

<210> SEQ ID NO 660
<211> LENGTH: 20
<212> TYPE: DNA
<213> ORGANISM: Artificial Sequence
<220> FEATURE:
<223> OTHER INFORMATION: Synthetic Construct

<400> SEQUENCE: 660
gcagcgtaca gggatgatca                                              20
```

```
<210> SEQ ID NO 661
<211> LENGTH: 20
<212> TYPE: DNA
<213> ORGANISM: Artificial Sequence
<220> FEATURE:
<223> OTHER INFORMATION: Synthetic Construct

<400> SEQUENCE: 661
gcagtagcgc ttcaggccca                                               20

<210> SEQ ID NO 662
<211> LENGTH: 20
<212> TYPE: DNA
<213> ORGANISM: Artificial Sequence
<220> FEATURE:
<223> OTHER INFORMATION: Synthetic Construct

<400> SEQUENCE: 662
caaatggtgg ggtaacagaa                                               20

<210> SEQ ID NO 663
<211> LENGTH: 20
<212> TYPE: DNA
<213> ORGANISM: Artificial Sequence
<220> FEATURE:
<223> OTHER INFORMATION: Synthetic Construct

<400> SEQUENCE: 663
gaaaggaact ggctaccgtt                                               20

<210> SEQ ID NO 664
<211> LENGTH: 20
<212> TYPE: DNA
<213> ORGANISM: Artificial Sequence
<220> FEATURE:
<223> OTHER INFORMATION: Synthetic Construct

<400> SEQUENCE: 664
agggcttccg ttacaagatg                                               20

<210> SEQ ID NO 665
<211> LENGTH: 20
<212> TYPE: DNA
<213> ORGANISM: Artificial Sequence
<220> FEATURE:
<223> OTHER INFORMATION: Synthetic Construct

<400> SEQUENCE: 665
gaacaagcaa cacctaaaag                                               20

<210> SEQ ID NO 666
<211> LENGTH: 20
<212> TYPE: DNA
<213> ORGANISM: Artificial Sequence
<220> FEATURE:
<223> OTHER INFORMATION: Synthetic Construct

<400> SEQUENCE: 666
tgaggagaag gaacggctca                                               20

<210> SEQ ID NO 667
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 667
ggaagaatgc agagtataag                                              20

<210> SEQ ID NO 668
<211> LENGTH: 20
<212> TYPE: DNA
<213> ORGANISM: Artificial Sequence
<220> FEATURE:
<223> OTHER INFORMATION: Synthetic Construct

<400> SEQUENCE: 668
ggaatttgag gaactcctga                                              20

<210> SEQ ID NO 669
<211> LENGTH: 20
<212> TYPE: DNA
<213> ORGANISM: Artificial Sequence
<220> FEATURE:
<223> OTHER INFORMATION: Synthetic Construct

<400> SEQUENCE: 669
gctcaccggc catccaggaa                                              20

<210> SEQ ID NO 670
<211> LENGTH: 20
<212> TYPE: DNA
<213> ORGANISM: Artificial Sequence
<220> FEATURE:
<223> OTHER INFORMATION: Synthetic Construct

<400> SEQUENCE: 670
actggccagg aacgatgcga                                              20

<210> SEQ ID NO 671
<211> LENGTH: 20
<212> TYPE: DNA
<213> ORGANISM: Artificial Sequence
<220> FEATURE:
<223> OTHER INFORMATION: Synthetic Construct

<400> SEQUENCE: 671
gcagctccaa gatcttccca                                              20

<210> SEQ ID NO 672
<211> LENGTH: 20
<212> TYPE: DNA
<213> ORGANISM: Artificial Sequence
<220> FEATURE:
<223> OTHER INFORMATION: Synthetic Construct

<400> SEQUENCE: 672
gaatgagtac acagaacgga                                              20

<210> SEQ ID NO 673
<211> LENGTH: 20
<212> TYPE: DNA
<213> ORGANISM: Artificial Sequence
<220> FEATURE:
<223> OTHER INFORMATION: Synthetic Construct

<400> SEQUENCE: 673
ggagcaggac aaggtcgggg                                              20
```